(12) United States Patent
Cutler et al.

(10) Patent No.: US 10,704,056 B2
(45) Date of Patent: Jul. 7, 2020

(54) CONSTITUTIVELY ACTIVE ABA RECEPTOR MUTANTS

(75) Inventors: Sean R. Cutler, Riverside, CA (US); Assaf Mosquna, Rehovot (IL)

(73) Assignee: The Regents of the University of California, Oakland, CA (US)

( * ) Notice: Subject to any disclaimer, the term of this patent is extended or adjusted under 35 U.S.C. 154(b) by 1475 days.

(21) Appl. No.: 14/126,774

(22) PCT Filed: Jun. 19, 2012

(86) PCT No.: PCT/US2012/043121
§ 371 (c)(1),
(2), (4) Date: May 22, 2014

(87) PCT Pub. No.: WO2013/006263
PCT Pub. Date: Jan. 10, 2013

(65) Prior Publication Data
US 2014/0259226 A1 Sep. 11, 2014

Related U.S. Application Data

(60) Provisional application No. 61/503,816, filed on Jul. 1, 2011, provisional application No. 61/512,280, filed on Jul. 27, 2011.

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01)

(58) Field of Classification Search
None
See application file for complete search history.

(56) References Cited

U.S. PATENT DOCUMENTS

| | | | |
|---|---|---|---|
| 5,625,130 | A | 4/1997 | Grant et al. |
| 7,214,786 | B2 | 5/2007 | Kovalic et al. |
| 7,569,389 | B2 | 8/2009 | Feldmann et al. |
| 7,847,156 | B2 | 2/2010 | Inze et al. |
| 2004/0148654 | A1 | 7/2004 | Helentjaris |
| 2004/0214272 | A1 | 10/2004 | La Rosa et al. |
| 2005/0244971 | A1 | 11/2005 | Kim |
| 2006/0150283 | A1 | 7/2006 | Alexandrov |
| 2006/0179518 | A1 | 8/2006 | Hill et al. |
| 2007/0039067 | A1 | 2/2007 | Feldmann et al. |
| 2009/0105238 | A1 | 4/2009 | Filippini et al. |
| 2009/0320152 | A1 | 12/2009 | Steber et al. |
| 2010/0216643 | A1 | 8/2010 | Cutler et al. |
| 2011/0271408 | A1 | 11/2011 | Cutler et al. |

FOREIGN PATENT DOCUMENTS

| | | |
|---|---|---|
| CN | 101173287 A | 5/2008 |
| JP | 2007 222129 A | 9/2007 |
| WO | 2003/008540 A2 | 1/2003 |
| WO | 2004/035798 A2 | 4/2004 |
| WO | 2010/093954 A2 | 8/2010 |

OTHER PUBLICATIONS

Melcher et al. Nature 462.7273 (2009): 602-608.*
Melcher et al. Nature 462.7273 (2009): 602-608. (Year: 2009).*
Nishimura et al. Science 326.5958 (2009): 1373-1379. (Year: 2009).*
Santiago et al. Nature 462.7273 (2009): 665-668. (Year: 2009).*
Hao et al. (Molecular cell 42.5 (2011): 662-672). (Year: 2011).*
Chen, Inês, "ABA Receptor Diversity," SBKB, Nov. 2010 Featured Articles, Retrieved Jun. 2, 2014, 3 Pages [DOI:10.1038/SBKB.2010.49].
Cutler et al., *Annual Review of Plant Biology* 61:651-679 (2010).
EMBL accession No. AY042890, Feb. 26, 2010.
Fujii et al., "In vitro reconstitution of an abscisic acid signaling pathway," *Nature*, vol. 462, Dec. 2009, p. 660.
GenBank as accession No. NP_563626, Available online Jan. 28, 2002.
GenBank as accession No. NP_565887, Available online Jan. 28, 2002.
Gonzalez-Guzman M. et al. (2002) *Plant Cell* 14(8):1833-1846.
Gonzalez-Guzman et al., "*Arabidopsis* PYR-PYL/RCAR receptors play a major role in quantitative regulation of stomatal aperture and transcriptional response to abscisic acid," *The Plant Cell*, 2012, vol. 24, pp. 2483-2496.
Hao Q, et al., "The molecular basis of ABA-independent inhibition of PP2Cs by a subclass of PYL proteins," *Mol Cell* 42 (5):662-672 (2011).
Hauser, Felix et al., "Evolution of abscisic acid synthesis and signaling mechanisms," *Current Biology*, vol. 21, No. 9, May 2011, pp. R346-R355.
International Search Report dated Dec. 15, 2010, for International Application No. PCT/US2010/024139, 5pp.
Kline et al., "Abscisic Acid Receptors," *Plant Physiology*, Oct. 2010, vol. 154, No. 2, pp. 479-482.
Lee, Sung Chul et al., "Functional roles of the pepper antimicrobial protein gene, CaAMP1, in abscisic acid signaling, and salt and drought tolerance in *Arabidopsis*," *Planta* (2009) 229:383-391.
Li et al., (*Science in China Ser. C Life Sciences* 2005 vol. 48, No. 2, 181-186.).
Masgrau, Caries et al.; "Inducible overexpression of oat arginine decarboxylase in transgenic tobacco plants"; 1997, *The Plant Journal*, vol. 11, No. 3, pp. 465-473.
Melcher et al., *Nature* 462: 602-608, 2009.
Melcher K, et al. (2010) *Nature Stuctural and Molecular Biology* 17(9):1102-1108.
Mosquna et al., "Potent and selective activation of abscisic acid receptors in vivo by mutational stabilization of their agonist-bound conformation," *Proc Nat Acad Sci ePub*, Dec. 20, 2011, vol. 108, No. 51, pp. 20838-20843.

(Continued)

*Primary Examiner* — Charles Logsdon
(74) *Attorney, Agent, or Firm* — Kilpatrick Townsend & Stockton LLP

(57) ABSTRACT

The present invention provides for compositions comprising mutated PYR/PYL receptor polypeptides that bind to a type 2 protein phosphatase in the absence of abscisic acid. The present invention further provides for methods of making and using the mutated PYR/PYL receptor polypeptides.

18 Claims, 30 Drawing Sheets

Specification includes a Sequence Listing.

(56) References Cited

OTHER PUBLICATIONS

Nishimura et al., "Structural Mechanism of Abscisic Acid Binding and Signaling by Dimeric PYR1," *Science*, Dec. 2009, 326(5958):1373-1379.

Park, Sang-Youl et al., "Abscisic acid inhibits type 2C protein phosphatases via the PYR/PYL family of START proteins," *Science*, vol. 324, No. 5930, May 2009, pp. 1068-1071, XP002676971.

Peterson FC, et al. "Structural basis for selective activation of ABA receptors," *Nature Stuctural and Molecular Biology* 17(9):1109-1113 (2010).

Santiago et al., *The Plant Journal*, 60:575-588, 2009.

Santiago, Julia et al., "The Abscisic acid receptor PYR1 complex with abscisic acid," *Nature*, vol. 462, No. 7273, Nov. 8, 2009, pp. 665-668.

Spencer et al., "Segregation of transgenes in maize," *Plant Mol. Biol.*, 1992, vol. 18, pp. 201-210.

Supplementary European Search Report, dated Jul. 2, 2012, for European Application No. EP 10741826.1, 13 pages.

UniProtKP accession No. O49686, Mar. 2, 2010.

Wang et al., *Plant J.*, 2005, vol. 43, pp. 413-424.

Weiner et al., *Curr Opin Plant Biol* 13:495-502 (2010).

Williams, Robert W. et al.; "A Possible Role for Kinase-Associated Protein Phosphatase in the *Arabidopsis* Clavata1 Signaling Pathway"; 1997, Proc. Natl. Acad. Sci., vol. 94, pp. 10467-10472.

Xie, Chunzheng et al., "Cloning, sequence analysis and prokaryotic expression of pathogenesis-induced protein (PIP) gene from peanut," Crops Research Institute, Guangdong Academy of Agricultural Sciences, China, Jan. 2009, XP002676969, Database accession No. 153:424228, abstract.

\* cited by examiner

Wild Type Controls

| | HAB1 N Cntrl | SD | ABI1 N Cntrl | SD | ABI2 N Cntrl | SD |
|---|---|---|---|---|---|---|
| PYR1 | 99.6 | 7.6 | 92.8 | 4.5 | 101.4 | 3.4 |
| PYR1 +ABA | 4.6 | 1.9 | 7.0 | 0.8 | 13.3 | 2.6 |
| PYR2 | 101.0 | 5.0 | 100.3 | 2.2 | 118.8 | 2.7 |
| PYR2 +ABA | 4.1 | 0.1 | 2.6 | 0.7 | 7.1 | 0.7 |
| PYR6 | 69.4 | 1.9 | | | | |
| PYR6 +ABA | 1.3 | 0.5 | | | | |
| PYR9 | 96.0 | 0.6 | 89.8 | 3.5 | 96.4 | 3.7 |
| PYR9 +ABA | 10.1 | 2.8 | 16.9 | 0.5 | 10.9 | 0.6 |
| PYR10 | 47.5 | 2.9 | | | | |
| PYR10 +ABA | 2.6 | 0.2 | | | | |

PYR1 — Mutations Introduced / PP2C Activity

| H60P | V83F | I68Q | A89W | M158I | F159V | T162F | K170W | HAB1 | SD | ABI1 | SD | ABI2 | SD | Allele name |
|---|---|---|---|---|---|---|---|---|---|---|---|---|---|---|
| X | | | | | | | | 70.6 | 0.3 | | | | | |
| | X | | | | | | | 87.6 | 2.9 | | | | | |
| | | X | | | | | | 86.5 | 5.2 | | | | | |
| | X | | X | | | | | 84.8 | 2.5 | | | | | |
| | X | | | X | | | | 68.2 | 2.9 | | | | | |
| | X | | | | X | | | 66.4 | 4.5 | | | | | |
| | X | | | | | X | | 63.3 | 3.0 | | | | | |
| | X | | X | | | | X | 61.3 | 3.5 | | | | | |
| | X | | | | X | | | 83.3 | 2.2 | | | | | |
| | X | | X | | X | | | 23.9 | 2.5 | 31.9 | 1.2 | 41.1 | 1.1 | PYR1 CA3 |
| | X | | | X | X | | | 63.9 | 3.1 | | | | | |
| | X | | X | X | X | | | 42.6 | 1.4 | | | | | |
| | X | | X | X | X | X | | 13.0 | 0.0 | 14.4 | 1.0 | 26.5 | 1.4 | PYR1 CA4 |
| | X | | X | X | X | | X | 36.1 | 1.8 | | | | | PYR1 CA4C |
| | X | X | X | X | X | X | X | 71.9 | 0.7 | | | | | |
| | X | | X | X | X | X | X | 78.2 | 3.4 | | | | | |
| | X | | X | X | X | X | X | 5.1 | 2.4 | | | | | |
| | X | | X | X | X | X | X | 62.9 | 1.1 | | | | | PYR1 CA4B |

FIG. 17 (Continued)

PYR2

| H65P | V87F | I88Q | A93W | M164I | F165V | T168F | K176W | HAB1 | | ABI1 | | ABI2 | | |
|---|---|---|---|---|---|---|---|---|---|---|---|---|---|---|
|  | X |  |  |  |  |  |  | 45.2 | 4.8 |  |  |  |  |  |
| X | X |  |  |  |  |  |  | 46.0 | 2.6 |  |  |  |  |  |
| X |  |  |  |  |  |  |  | 115.7 | 6.0 |  |  |  |  |  |
|  | X |  |  |  | X |  |  | 69.8 | 2.5 |  |  |  |  |  |
|  |  |  |  |  |  |  |  | 71.2 | 1.9 |  |  |  |  |  |
| X | X |  | X |  | X |  |  | 94.6 | 5.8 |  |  |  |  |  |
|  | X |  |  | X |  |  |  | 61.9 | 3.9 |  |  |  |  |  |
| X | X |  |  |  | X |  |  | 91.0 | 5.6 |  |  |  |  |  |
|  |  |  |  |  |  |  |  | 16.1 | 1.7 |  |  |  |  |  |
| X | X |  | X |  |  | X |  | 10.5 | 0.5 | 13.7 | 0.8 | 22.5 | 0.8 | PYR2 CA3 |
|  |  |  |  |  |  |  |  | 48.8 | 5.3 |  |  |  |  |  |
| X | X |  | X |  |  | X | X | 18.2 | 1.2 |  |  |  |  |  |
| X | X |  |  |  | X | X | X | 23.5 | 3.3 |  |  |  |  |  |
| X | X |  | X |  | X | X | X | 6.3 | 0.5 | 8.0 | 0.2 | 13.5 | 1.3 | PYR2 CA4 |
| X |  |  |  |  |  |  |  | 14.0 | 0.3 |  |  |  |  | PYR2 CA4C |

PYL9

| P64 | V85F | K86Q | A91W | Y160I | F161V | A164F | S172W | HAB1 | | ABI1 | | ABI2 | | |
|---|---|---|---|---|---|---|---|---|---|---|---|---|---|---|
|  | X |  |  |  |  |  |  | 11.4 | 0.9 | 10.7 | 3.7 | 16.2 | 0.2 | PYL9 CA4 |
|  |  |  | X | X | X |  |  | 23.0 | 2.3 |  |  |  |  | PYR9 CA4C |

SEQUENCE LISTING

<160> NUMBER OF SEQ ID NOS: 454

<210> SEQ ID NO 1
<211> LENGTH: 191
<212> TYPE: PRT
<213> ORGANISM: Arabidopsis thaliana
<220> FEATURE:
<223> OTHER INFORMATION: thale cress PYR/PYL receptor, Pyrabactin
      resistance 1, abscisic acid receptor PYR1 (PYR1), ABI1-binding
      protein 6 (ABIP6), regulatory components of ABA receptor 11
      (RCAR11), At4g17870, T6K21.50

<400> SEQUENCE: 1

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
    50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 2
<211> LENGTH: 221
<212> TYPE: PRT
<213> ORGANISM: Arabidopsis thaliana
<220> FEATURE:
<223> OTHER INFORMATION: thale cress PYR/PYL receptor, abscisic acid
      receptor PYL1, PYR1-like protein 1 (PYL1), ABI1-binding protein 6
      (ABIP6), regulatory components of ABA receptor 9 (RCAR12),
      At5g46790, MZA15.21

<400> SEQUENCE: 2

Met Ala Asn Ser Glu Ser Ser Ser Ser Pro Val Asn Glu Glu Glu Asn
1               5                   10                  15

Ser Gln Arg Ile Ser Thr Leu His His Gln Thr Met Pro Ser Asp Leu
            20                  25                  30

Thr Gln Asp Glu Phe Thr Gln Leu Ser Gln Ser Ile Ala Glu Phe His
        35                  40                  45

Thr Tyr Gln Leu Gly Asn Gly Arg Cys Ser Ser Leu Leu Ala Gln Arg
    50                  55                  60

Ile His Ala Pro Pro Glu Thr Val Trp Ser Val Val Arg Arg Phe Asp
65                  70                  75                  80

Arg Pro Gln Ile Tyr Lys His Phe Ile Lys Ser Cys Asn Val Ser Glu
            85                  90                  95

Asp Phe Glu Met Arg Val Gly Cys Thr Arg Asp Val Asn Val Ile Ser
            100                 105                 110

Gly Leu Pro Ala Asn Thr Ser Arg Glu Arg Leu Asp Leu Leu Asp Asp
            115                 120                 125

Asp Arg Arg Val Thr Gly Phe Ser Ile Thr Gly Gly Glu His Arg Leu
    130                 135                 140

Arg Asn Tyr Lys Ser Val Thr Thr Val His Arg Phe Glu Lys Glu Glu
145                 150                 155                 160

Glu Glu Glu Arg Ile Trp Thr Val Val Leu Glu Ser Tyr Val Val Asp
                165                 170                 175

Val Pro Glu Gly Asn Ser Glu Glu Asp Thr Arg Leu Phe Ala Asp Thr
            180                 185                 190

Val Ile Arg Leu Asn Leu Gln Lys Leu Ala Ser Ile Thr Glu Ala Met
            195                 200                 205

Asn Arg Asn Asn Asn Asn Asn Ser Ser Gln Val Arg
            210                 215                 220

<210> SEQ ID NO 3
<211> LENGTH: 190
<212> TYPE: PRT
<213> ORGANISM: Arabidopsis thaliana
<220> FEATURE:
<223> OTHER INFORMATION: thale cress PYR/PYL receptor, abscisic acid
      receptor PYL2, PYR1-like protein 2 (PYL2), ABI1-binding protein 6
      (ABIP6), regulatory components of ABA receptor 14 (RCAR14), Bet v
      I allergen family protein, At2g26040, T19L18.15

<400> SEQUENCE: 3

Met Ser Ser Ser Pro Ala Val Lys Gly Leu Thr Asp Glu Glu Gln Lys
1               5                   10                  15

Thr Leu Glu Pro Val Ile Lys Thr Tyr His Gln Phe Glu Pro Asp Pro
            20                  25                  30

Thr Thr Cys Thr Ser Leu Ile Thr Gln Arg Ile His Ala Pro Ala Ser
        35                  40                  45

Val Val Trp Pro Leu Ile Arg Arg Phe Asp Asn Pro Glu Arg Tyr Lys
    50                  55                  60

His Phe Val Lys Arg Cys Arg Leu Ile Ser Gly Asp Gly Asp Val Gly
65                  70                  75                  80

Ser Val Arg Glu Val Thr Val Ile Ser Gly Leu Pro Ala Ser Thr Ser
                85                  90                  95

Thr Glu Arg Leu Glu Phe Val Asp Asp Asp His Arg Val Leu Ser Phe
            100                 105                 110

Arg Val Val Gly Gly Glu His Arg Leu Lys Asn Tyr Lys Ser Val Thr
        115                 120                 125

Ser Val Asn Glu Phe Leu Asn Gln Asp Ser Gly Lys Val Tyr Thr Val
    130                 135                 140

Val Leu Glu Ser Tyr Thr Val Asp Ile Pro Glu Gly Asn Thr Glu Glu
145                 150                 155                 160

Asp Thr Lys Met Phe Val Asp Thr Val Val Lys Leu Asn Leu Gln Lys
                165                 170                 175

Leu Gly Val Ala Ala Thr Ser Ala Pro Met His Asp Asp Glu
            180                 185                 190

<210> SEQ ID NO 4
<211> LENGTH: 209

```
<212> TYPE: PRT
<213> ORGANISM: Arabidopsis thaliana
<220> FEATURE:
<223> OTHER INFORMATION: thale cress PYR/PYL receptor, abscisic acid
      receptor PYL3,  PYR1-like protein 3 (PYL3), regulatory components
      of ABA receptor 13 (RCAR13), At1g73000, F3N23.20

<400> SEQUENCE: 4
```

Met Asn Leu Ala Pro Ile His Asp Pro Ser Ser Ser Thr Thr Thr
1               5                   10                  15

Thr Ser Ser Ser Thr Pro Tyr Gly Leu Thr Lys Asp Glu Phe Ser Thr
                20                  25                  30

Leu Asp Ser Ile Ile Arg Thr His His Thr Phe Pro Arg Ser Pro Asn
            35                  40                  45

Thr Cys Thr Ser Leu Ile Ala His Arg Val Asp Ala Pro Ala His Ala
    50                  55                  60

Ile Trp Arg Phe Val Arg Asp Phe Ala Asn Pro Asn Lys Tyr Lys His
65              70                  75                  80

Phe Ile Lys Ser Cys Thr Ile Arg Val Asn Gly Asn Gly Ile Lys Glu
                85                  90                  95

Ile Lys Val Gly Thr Ile Arg Glu Val Ser Val Val Ser Gly Leu Pro
            100                 105                 110

Ala Ser Thr Ser Val Glu Ile Leu Glu Val Leu Asp Glu Glu Lys Arg
        115                 120                 125

Ile Leu Ser Phe Arg Val Leu Gly Gly Glu His Arg Leu Asn Asn Tyr
130                 135                 140

Arg Ser Val Thr Ser Val Asn Glu Phe Val Val Leu Glu Lys Asp Lys
145                 150                 155                 160

Lys Lys Arg Val Tyr Ser Val Val Leu Glu Ser Tyr Ile Val Asp Ile
                165                 170                 175

Pro Gln Gly Asn Thr Glu Glu Asp Thr Arg Met Phe Val Asp Thr Val
            180                 185                 190

Val Lys Ser Asn Leu Gln Asn Leu Ala Val Ile Ser Thr Ala Ser Pro
        195                 200                 205

Thr

```
<210> SEQ ID NO 5
<211> LENGTH: 207
<212> TYPE: PRT
<213> ORGANISM: Arabidopsis thaliana
<220> FEATURE:
<223> OTHER INFORMATION: thale cress PYR/PYL receptor, abscisic acid
      receptor PYL4, PYR1-like protein 4 (PYL4), ABI1-binding protein 2
      (ABIP2), regulatory components of ABA receptor 10 (RCAR10),
      At2g38310, T19C21.20

<400> SEQUENCE: 5
```

Met Leu Ala Val His Arg Pro Ser Ser Ala Val Ser Asp Gly Asp Ser
1               5                   10                  15

Val Gln Ile Pro Met Met Ile Ala Ser Phe Gln Lys Arg Phe Pro Ser
                20                  25                  30

Leu Ser Arg Asp Ser Thr Ala Ala Arg Phe His Thr His Glu Val Gly
            35                  40                  45

Pro Asn Gln Cys Cys Ser Ala Val Ile Gln Glu Ile Ser Ala Pro Ile
        50                  55                  60

Ser Thr Val Trp Ser Val Val Arg Arg Phe Asp Asn Pro Gln Ala Tyr
65              70                  75                  80

Lys His Phe Leu Lys Ser Cys Ser Val Ile Gly Gly Asp Gly Asp Asn

```
                 85                  90                  95
Val Gly Ser Leu Arg Gln Val His Val Val Ser Gly Leu Pro Ala Ala
            100                 105                 110

Ser Ser Thr Glu Arg Leu Asp Ile Leu Asp Asp Glu Arg His Val Ile
            115                 120                 125

Ser Phe Ser Val Val Gly Asp His Arg Leu Ser Asn Tyr Arg Ser
            130                 135                 140

Val Thr Thr Leu His Pro Ser Pro Ile Ser Gly Thr Val Val Val Glu
145                 150                 155                 160

Ser Tyr Val Val Asp Val Pro Pro Gly Asn Thr Lys Glu Glu Thr Cys
                165                 170                 175

Asp Phe Val Asp Val Ile Val Arg Cys Asn Leu Gln Ser Leu Ala Lys
                180                 185                 190

Ile Ala Glu Asn Thr Ala Ala Glu Ser Lys Lys Lys Met Ser Leu
                195                 200                 205

<210> SEQ ID NO 6
<211> LENGTH: 203
<212> TYPE: PRT
<213> ORGANISM: Arabidopsis thaliana
<220> FEATURE:
<223> OTHER INFORMATION: thale cress PYR/PYL receptor, abscisic acid
      receptor PYL5, PYR1-like protein 5 (PYL5), ABI1-binding protein 3
      (ABIP3), regulatory components of ABA receptor 8 (RCAR8), Bet v I
      allergen family protein, At5g05440, K18I23.25

<400> SEQUENCE: 6

Met Arg Ser Pro Val Gln Leu Gln His Gly Ser Asp Ala Thr Asn Gly
1               5                   10                  15

Phe His Thr Leu Gln Pro His Asp Gln Thr Asp Gly Pro Ile Lys Arg
            20                  25                  30

Val Cys Leu Thr Arg Gly Met His Val Pro Glu His Val Ala Met His
        35                  40                  45

His Thr His Asp Val Gly Pro Asp Gln Cys Cys Ser Ser Val Val Gln
    50                  55                  60

Met Ile His Ala Pro Pro Glu Ser Val Trp Ala Leu Val Arg Arg Phe
65                  70                  75                  80

Asp Asn Pro Lys Val Tyr Lys Asn Phe Ile Arg Gln Cys Arg Ile Val
                85                  90                  95

Gln Gly Asp Gly Leu His Val Gly Asp Leu Arg Glu Val Met Val Val
            100                 105                 110

Ser Gly Leu Pro Ala Val Ser Ser Thr Glu Arg Leu Glu Ile Leu Asp
            115                 120                 125

Glu Glu Arg His Val Ile Ser Phe Ser Val Val Gly Gly Asp His Arg
        130                 135                 140

Leu Lys Asn Tyr Arg Ser Val Thr Thr Leu His Ala Ser Asp Asp Glu
145                 150                 155                 160

Gly Thr Val Val Val Glu Ser Tyr Ile Val Asp Val Pro Pro Gly Asn
                165                 170                 175

Thr Glu Glu Glu Thr Leu Ser Phe Val Asp Thr Ile Val Arg Cys Asn
            180                 185                 190

Leu Gln Ser Leu Ala Arg Ser Thr Asn Arg Gln
            195                 200

<210> SEQ ID NO 7
<211> LENGTH: 215
<212> TYPE: PRT
```

<213> ORGANISM: Arabidopsis thaliana
<220> FEATURE:
<223> OTHER INFORMATION: thale cress PYR/PYL receptor, abscisic acid
      receptor PYL6, PYR1-like protein 6 (PYL6), ABI1-binding protein 5
      (ABIP5), regulatory components of ABA receptor 9 (RCAR9), Bet v I
      allergen family protein, At2g40330, T7M7.15

<400> SEQUENCE: 7

```
Met Pro Thr Ser Ile Gln Phe Gln Arg Ser Ser Thr Ala Ala Glu Ala
1               5                   10                  15

Ala Asn Ala Thr Val Arg Asn Tyr Pro His His His Gln Lys Gln Val
            20                  25                  30

Gln Lys Val Ser Leu Thr Arg Gly Met Ala Asp Val Pro Glu His Val
        35                  40                  45

Glu Leu Ser His Thr His Val Val Gly Pro Ser Gln Cys Phe Ser Val
    50                  55                  60

Val Val Gln Asp Val Glu Ala Pro Val Ser Thr Val Trp Ser Ile Leu
65                  70                  75                  80

Ser Arg Phe Glu His Pro Gln Ala Tyr Lys His Phe Val Lys Ser Cys
                85                  90                  95

His Val Val Ile Gly Asp Gly Arg Glu Val Gly Ser Val Arg Glu Val
            100                 105                 110

Arg Val Val Ser Gly Leu Pro Ala Ala Phe Ser Leu Glu Arg Leu Glu
        115                 120                 125

Ile Met Asp Asp Asp Arg His Val Ile Ser Phe Ser Val Val Gly Gly
    130                 135                 140

Asp His Arg Leu Met Asn Tyr Lys Ser Val Thr Thr Val His Glu Ser
145                 150                 155                 160

Glu Glu Asp Ser Asp Gly Lys Lys Arg Thr Arg Val Val Glu Ser Tyr
                165                 170                 175

Val Val Asp Val Pro Ala Gly Asn Asp Lys Glu Glu Thr Cys Ser Phe
            180                 185                 190

Ala Asp Thr Ile Val Arg Cys Asn Leu Gln Ser Leu Ala Lys Leu Ala
        195                 200                 205

Glu Asn Thr Ser Lys Phe Ser
    210                 215
```

<210> SEQ ID NO 8
<211> LENGTH: 211
<212> TYPE: PRT
<213> ORGANISM: Arabidopsis thaliana
<220> FEATURE:
<223> OTHER INFORMATION: thale cress PYR/PYL receptor, abscisic acid
      receptor PYL7, PYR1-like protein 7 (PYL7), ABI1-binding protein 7
      (ABIP7), regulatory components of ABA receptor 2 (RCAR2),
      At4g01026

<400> SEQUENCE: 8

```
Met Glu Met Ile Gly Gly Asp Asp Thr Asp Thr Glu Met Tyr Gly Ala
1               5                   10                  15

Leu Val Thr Ala Gln Ser Leu Arg Leu Arg His Leu His His Cys Arg
            20                  25                  30

Glu Asn Gln Cys Thr Ser Val Leu Val Lys Tyr Ile Gln Ala Pro Val
        35                  40                  45

His Leu Val Trp Ser Leu Val Arg Arg Phe Asp Gln Pro Gln Lys Tyr
    50                  55                  60

Lys Pro Phe Ile Ser Arg Cys Thr Val Asn Gly Asp Pro Glu Ile Gly
65                  70                  75                  80
```

```
Cys Leu Arg Glu Val Asn Val Lys Ser Gly Leu Pro Ala Thr Thr Ser
                85                  90                  95

Thr Glu Arg Leu Glu Gln Leu Asp Asp Glu Glu His Ile Leu Gly Ile
            100                 105                 110

Asn Ile Ile Gly Gly Asp His Arg Leu Lys Asn Tyr Ser Ser Ile Leu
        115                 120                 125

Thr Val His Pro Glu Met Ile Asp Gly Arg Ser Gly Thr Met Val Met
    130                 135                 140

Glu Ser Phe Val Val Asp Val Pro Gln Gly Asn Thr Lys Asp Asp Thr
145                 150                 155                 160

Cys Tyr Phe Val Glu Ser Leu Ile Lys Cys Asn Leu Lys Ser Leu Ala
                165                 170                 175

Cys Val Ser Glu Arg Leu Ala Ala Gln Asp Ile Thr Asn Ser Ile Ala
            180                 185                 190

Thr Phe Cys Asn Ala Ser Asn Gly Tyr Arg Glu Lys Asn His Thr Glu
        195                 200                 205

Thr Asn Leu
    210
```

<210> SEQ ID NO 9
<211> LENGTH: 188
<212> TYPE: PRT
<213> ORGANISM: Arabidopsis thaliana
<220> FEATURE:
<223> OTHER INFORMATION: thale cress PYR/PYL receptor, abscisic acid
      receptor PYL8, PYR1-like protein 8 (PYL8), ABI1-binding protein 1
      (ABIP1), regulatory components of ABA receptor 3 (RCAR3),
      At5g53160, MFH8.10

<400> SEQUENCE: 9

```
Met Glu Ala Asn Gly Ile Glu Asn Leu Thr Asn Pro Asn Gln Glu Arg
1               5                   10                  15

Glu Phe Ile Arg Arg His His Lys His Glu Leu Val Asp Asn Gln Cys
            20                  25                  30

Ser Ser Thr Leu Val Lys His Ile Asn Ala Pro Val His Ile Val Trp
        35                  40                  45

Ser Leu Val Arg Arg Phe Asp Gln Pro Gln Lys Tyr Lys Pro Phe Ile
    50                  55                  60

Ser Arg Cys Val Val Lys Gly Asn Met Glu Ile Gly Thr Val Arg Glu
65                  70                  75                  80

Val Asp Val Lys Ser Gly Leu Pro Ala Thr Arg Ser Thr Glu Arg Leu
                85                  90                  95

Glu Leu Leu Asp Asp Asn Glu His Ile Leu Ser Ile Arg Ile Val Gly
            100                 105                 110

Gly Asp His Arg Leu Lys Asn Tyr Ser Ser Ile Ile Ser Leu His Pro
        115                 120                 125

Glu Thr Ile Glu Gly Arg Ile Gly Thr Leu Val Ile Glu Ser Phe Val
    130                 135                 140

Val Asp Val Pro Glu Gly Asn Thr Lys Asp Glu Thr Cys Tyr Phe Val
145                 150                 155                 160

Glu Ala Leu Ile Lys Cys Asn Leu Lys Ser Leu Ala Asp Ile Ser Glu
                165                 170                 175

Arg Leu Ala Val Gln Asp Thr Thr Glu Ser Arg Val
            180                 185
```

<210> SEQ ID NO 10
<211> LENGTH: 187

```
<212> TYPE: PRT
<213> ORGANISM: Arabidopsis thaliana
<220> FEATURE:
<223> OTHER INFORMATION: thale cress PYR/PYL receptor, abscisic acid
      receptor PYL9, PYR1-like protein 9 (PYL9), ABI1-binding protein 4
      (ABIP4), regulatory components of ABA receptor 1 (RCAR1),
      At1g01360, F6F3.16

<400> SEQUENCE: 10

Met Met Asp Gly Val Glu Gly Thr Ala Met Tyr Gly Gly Leu Glu
1               5                   10                  15

Thr Val Gln Tyr Val Arg Thr His His Gln His Leu Cys Arg Glu Asn
                20                  25                  30

Gln Cys Thr Ser Ala Leu Val Lys His Ile Lys Ala Pro Leu His Leu
            35                  40                  45

Val Trp Ser Leu Val Arg Arg Phe Asp Gln Pro Gln Lys Tyr Lys Pro
50                  55                  60

Phe Val Ser Arg Cys Thr Val Ile Gly Asp Pro Glu Ile Gly Ser Leu
65                  70                  75                  80

Arg Glu Val Asn Val Lys Ser Gly Leu Pro Ala Thr Thr Ser Thr Glu
                85                  90                  95

Arg Leu Glu Leu Leu Asp Asp Glu Glu His Ile Leu Gly Ile Lys Ile
            100                 105                 110

Ile Gly Gly Asp His Arg Leu Lys Asn Tyr Ser Ser Ile Leu Thr Val
        115                 120                 125

His Pro Glu Ile Ile Glu Gly Arg Ala Gly Thr Met Val Ile Glu Ser
130                 135                 140

Phe Val Asp Val Pro Gln Gly Asn Thr Lys Asp Glu Thr Cys Tyr
145                 150                 155                 160

Phe Val Glu Ala Leu Ile Arg Cys Asn Leu Lys Ser Leu Ala Asp Val
                165                 170                 175

Ser Glu Arg Leu Ala Ser Gln Asp Ile Thr Gln
            180                 185

<210> SEQ ID NO 11
<211> LENGTH: 183
<212> TYPE: PRT
<213> ORGANISM: Arabidopsis thaliana
<220> FEATURE:
<223> OTHER INFORMATION: thale cress PYR/PYL receptor, abscisic acid
      receptor PYL10, PYR1-like protein 10 (PYL10), ABI1-binding
      protein 8 (ABIP8), regulatory components of ABA receptor 4
      (RCAR4), At4g27920, T13J8.30

<400> SEQUENCE: 11

Met Asn Gly Asp Glu Thr Lys Lys Val Glu Ser Glu Tyr Ile Lys Lys
1               5                   10                  15

His His Arg His Glu Leu Val Glu Ser Gln Cys Ser Ser Thr Leu Val
                20                  25                  30

Lys His Ile Lys Ala Pro Leu His Leu Val Trp Ser Ile Val Arg Arg
            35                  40                  45

Phe Asp Glu Pro Gln Lys Tyr Lys Pro Phe Ile Ser Arg Cys Val Val
50                  55                  60

Gln Gly Lys Lys Leu Glu Val Gly Ser Val Arg Glu Val Asp Leu Lys
65                  70                  75                  80

Ser Gly Leu Pro Ala Thr Lys Ser Thr Glu Val Leu Glu Ile Leu Asp
                85                  90                  95

Asp Asn Glu His Ile Leu Gly Ile Arg Ile Val Gly Gly Asp His Arg
            100                 105                 110
```

```
Leu Lys Asn Tyr Ser Ser Thr Ile Ser Leu His Ser Glu Thr Ile Asp
        115                 120                 125

Gly Lys Thr Gly Thr Leu Ala Ile Glu Ser Phe Val Val Asp Val Pro
    130                 135                 140

Glu Gly Asn Thr Lys Glu Thr Cys Phe Phe Val Glu Ala Leu Ile
145                 150                 155                 160

Gln Cys Asn Leu Asn Ser Leu Ala Asp Val Thr Glu Arg Leu Gln Ala
                165                 170                 175

Glu Ser Met Glu Lys Lys Ile
            180
```

<210> SEQ ID NO 12
<211> LENGTH: 161
<212> TYPE: PRT
<213> ORGANISM: Arabidopsis thaliana
<220> FEATURE:
<223> OTHER INFORMATION: thale cress PYR/PYL receptor, abscisic acid
      receptor PYL11, PYR1-like protein 11 (PYL11), regulatory
      components of ABA receptor 5 (RCAR5), Bet v I allergen family
      protein, At5g45860, K15I22.6

<400> SEQUENCE: 12

```
Met Glu Thr Ser Gln Lys Tyr His Thr Cys Gly Ser Thr Leu Val Gln
1               5                   10                  15

Thr Ile Asp Ala Pro Leu Ser Leu Val Trp Ser Ile Leu Arg Arg Phe
            20                  25                  30

Asp Asn Pro Gln Ala Tyr Lys Gln Phe Val Lys Thr Cys Asn Leu Ser
        35                  40                  45

Ser Gly Asp Gly Gly Glu Gly Ser Val Arg Glu Val Thr Val Val Ser
    50                  55                  60

Gly Leu Pro Ala Glu Phe Ser Arg Glu Arg Leu Asp Glu Leu Asp Asp
65                  70                  75                  80

Glu Ser His Val Met Met Ile Ser Ile Ile Gly Gly Asp His Arg Leu
                85                  90                  95

Val Asn Tyr Arg Ser Lys Thr Met Ala Phe Val Ala Ala Asp Thr Glu
            100                 105                 110

Glu Lys Thr Val Val Val Glu Ser Tyr Val Val Asp Val Pro Glu Gly
        115                 120                 125

Asn Ser Glu Glu Glu Thr Thr Ser Phe Ala Asp Thr Ile Val Gly Phe
    130                 135                 140

Asn Leu Lys Ser Leu Ala Lys Leu Ser Glu Arg Val Ala His Leu Lys
145                 150                 155                 160

Leu
```

<210> SEQ ID NO 13
<211> LENGTH: 159
<212> TYPE: PRT
<213> ORGANISM: Arabidopsis thaliana
<220> FEATURE:
<223> OTHER INFORMATION: thale cress PYR/PYL receptor, abscisic acid
      receptor PYL12, PYR1-like protein 12 (PYL12), regulatory
      components of ABA receptor 6 (RCAR6), Bet v I allergen family
      protein, At5g45870, K15I22.7

<400> SEQUENCE: 13

```
Met Lys Thr Ser Gln Glu Gln His Val Cys Gly Ser Thr Val Val Gln
1               5                   10                  15

Thr Ile Asn Ala Pro Leu Pro Leu Val Trp Ser Ile Leu Arg Arg Phe
            20                  25                  30
```

Asp Asn Pro Lys Thr Phe Lys His Phe Val Lys Thr Cys Lys Leu Arg
            35                  40                  45

Ser Gly Asp Gly Gly Glu Gly Ser Val Arg Glu Val Thr Val Val Ser
 50                  55                  60

Asp Leu Pro Ala Ser Phe Ser Leu Glu Arg Leu Asp Glu Leu Asp Asp
65                  70                  75                  80

Glu Ser His Val Met Val Ile Ser Ile Ile Gly Gly Asp His Arg Leu
                85                  90                  95

Val Asn Tyr Gln Ser Lys Thr Thr Val Phe Val Ala Ala Glu Glu Glu
            100                 105                 110

Lys Thr Val Val Val Glu Ser Tyr Val Val Asp Val Pro Glu Gly Asn
        115                 120                 125

Thr Glu Glu Glu Thr Thr Leu Phe Ala Asp Thr Ile Val Gly Cys Asn
    130                 135                 140

Leu Arg Ser Leu Ala Lys Leu Ser Glu Lys Met Met Glu Leu Thr
145                 150                 155

<210> SEQ ID NO 14
<211> LENGTH: 164
<212> TYPE: PRT
<213> ORGANISM: Arabidopsis thaliana
<220> FEATURE:
<223> OTHER INFORMATION: thale cress PYR/PYL receptor, abscisic acid
      receptor PYL13, PYR1-like protein 13 (PYL13), regulatory
      components of ABA receptor 7 (RCAR7), At4g18620, F28A21.30

<400> SEQUENCE: 14

Met Glu Ser Ser Lys Gln Lys Arg Cys Arg Ser Ser Val Val Glu Thr
1               5                   10                  15

Ile Glu Ala Pro Leu Pro Leu Val Trp Ser Ile Leu Arg Ser Phe Asp
            20                  25                  30

Lys Pro Gln Ala Tyr Gln Arg Phe Val Lys Ser Cys Thr Met Arg Ser
        35                  40                  45

Gly Gly Gly Gly Gly Lys Gly Glu Gly Lys Gly Ser Val Arg Asp
 50                  55                  60

Val Thr Leu Val Ser Gly Phe Pro Ala Asp Phe Ser Thr Glu Arg Leu
65                  70                  75                  80

Glu Glu Leu Asp Asp Glu Ser His Val Met Val Val Ser Ile Ile Gly
                85                  90                  95

Gly Asn His Arg Leu Val Asn Tyr Lys Ser Lys Thr Lys Val Val Ala
            100                 105                 110

Ser Pro Glu Asp Met Ala Lys Lys Thr Val Val Val Glu Ser Tyr Val
        115                 120                 125

Val Asp Val Pro Glu Gly Thr Ser Glu Glu Asp Thr Ile Phe Phe Val
    130                 135                 140

Asp Asn Ile Ile Arg Tyr Asn Leu Thr Ser Leu Ala Lys Leu Thr Lys
145                 150                 155                 160

Lys Met Met Lys

<210> SEQ ID NO 15
<211> LENGTH: 191
<212> TYPE: PRT
<213> ORGANISM: Brassica oleracea
<220> FEATURE:
<223> OTHER INFORMATION: wild cabbage Streptomyces cyclase/dehydrase
      family protein, locus tag 40.t00062, GenBank Accession No.
      ABD65175.1

<400> SEQUENCE: 15

Met Pro Ser Gln Leu Thr Pro Glu Glu Arg Ser Glu Leu Ala Gln Ser
1               5                   10                  15

Ile Ala Glu Phe His Thr Tyr His Leu Gly Pro Gly Ser Cys Ser Ser
            20                  25                  30

Leu His Ala Gln Arg Ile His Ala Pro Pro Glu Ile Val Trp Ser Val
        35                  40                  45

Val Arg Arg Phe Asp Lys Pro Gln Thr Tyr Lys His Phe Ile Lys Ser
50                  55                  60

Cys Ser Val Glu Asp Gly Phe Glu Met Arg Val Gly Cys Thr Arg Ala
65                  70                  75                  80

Val Asn Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Arg Arg Ile Trp Thr Val Val Leu Glu Ser Tyr Val
130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Thr Glu
                165                 170                 175

Ala Met Ala Arg Asn Ala Gly Asp Gly Ser Gly Ala Gln Val Thr
            180                 185                 190

<210> SEQ ID NO 16
<211> LENGTH: 281
<212> TYPE: PRT
<213> ORGANISM: Brassica oleracea
<220> FEATURE:
<223> OTHER INFORMATION: wild cabbage Streptomyces cyclase/dehydrase
      family protein, locus tag 23.t00047, GenBank Accession No.
      ABD65631.1

<400> SEQUENCE: 16

Met Pro Ser Glu Leu Thr Gln Glu Glu Arg Ser Lys Leu Thr Gln Ser
1               5                   10                  15

Ile Ser Glu Phe His Thr Tyr His Leu Gly Pro Gly Ser Cys Ser Ser
            20                  25                  30

Leu His Ala Gln Arg Ile His Ala Pro Pro Glu Ile Val Trp Ser Val
        35                  40                  45

Val Arg Gln Phe Asp Lys Pro Gln Thr Tyr Lys His Phe Ile Lys Ser
50                  55                  60

Cys Ser Val Glu Glu Gly Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Met Leu Asp Asp Glu Arg Arg Val Thr Gly Phe Ser Ile Ile Gly
            100                 105                 110

Gly Glu His Arg Leu Lys Asn Tyr Lys Ser Val Thr Thr Val His Arg
        115                 120                 125

Phe Glu Arg Glu Arg Arg Ile Trp Thr Val Val Leu Glu Ser Tyr Val
130                 135                 140

Val Asp Met Pro Glu Gly Asn Ser Glu Asp Asp Thr Arg Met Phe Ala
145                 150                 155                 160

```
Asp Thr Val Val Lys Leu Asn Leu Gln Lys Leu Ala Thr Val Thr Glu
            165                 170                 175

Ala Met Ala Arg Asn Ala Gly Asp Gly Arg Gly Ser Arg Glu Thr Thr
            180                 185                 190

Cys Arg Glu Ser Phe His Leu Ile Thr Ala Phe Glu Lys Gln Arg Gln
            195                 200                 205

Ile Thr Glu Pro Thr Val Tyr Gln Asn Pro Tyr His Thr Gly Met
210                 215                 220

Thr Pro Glu Pro Arg Thr Ser Thr Val Phe Ile Glu Leu Glu Asp His
225                 230                 235                 240

Arg Thr Leu Pro Gly Asn Leu Thr Pro Thr Thr Glu Glu His Leu Gln
            245                 250                 255

Arg Met Tyr Gln Arg Phe Trp Gly Ile Arg Gln Leu Gln Arg Pro Arg
            260                 265                 270

Gln Ser Phe Gly Glu Arg Gln Ser Ile
            275                 280
```

<210> SEQ ID NO 17
<211> LENGTH: 453
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00015766001, GenBank Accession No.
      CAO63410.1

<400> SEQUENCE: 17

```
Met Gln Met Lys Tyr Leu Glu Gly Lys Gln Asn Leu Met Glu Glu Lys
1               5                   10                  15

Gly Glu Lys Gln Cys Ile Pro Met Asp Leu Ala Val Arg Glu Ala Gln
            20                  25                  30

Phe Lys Gly Ser Leu Leu Asp Arg Ile Thr Trp Leu Glu Gln Arg Leu
            35                  40                  45

His Lys Leu Ser Leu Gln Leu Glu Thr Arg Ser Lys Gln Gln Pro His
        50                  55                  60

Pro Ser Arg Met Gln Thr Ala Gly Glu Thr Ser Ser Arg His Gly Pro
65                  70                  75                  80

Lys Lys Glu Leu Ser Cys Ser Phe Pro Val Phe Ser Thr Arg Asn His
                85                  90                  95

Asn His Gly His Lys Gln Thr Ser Gln Phe His Val Pro Arg Phe Glu
            100                 105                 110

Tyr Gln Glu Gly Gly Arg Glu Asn Pro Ala Val Val Ile Thr Lys Leu
            115                 120                 125

Thr Pro Phe His His Pro Lys Ile Ile Thr Ile Leu Phe Pro Ile Ser
130                 135                 140

Asn Tyr Phe Ile Ile Phe Phe Phe Leu Thr Phe Asp Thr Lys Lys Gln
145                 150                 155                 160

Tyr Pro Leu Leu Phe Pro Ile Leu Pro Ser Arg Phe Leu Pro Ile Ser
                165                 170                 175

His Leu Ile Thr Gln Glu Ile Glu Lys Tyr Lys Thr Ser Ser His Phe
            180                 185                 190

Ser Ser Pro Ala Ser Leu Phe Ala Ala Met Asn Lys Ala Glu Thr Ser
            195                 200                 205

Ser Met Ala Glu Ala Glu Ser Glu Asp Ser Glu Thr Thr Thr Pro Thr
210                 215                 220
```

Thr His His Leu Thr Ile Pro Pro Gly Leu Thr Gln Pro Glu Phe Gln
225                 230                 235                 240

Glu Leu Ala His Ser Ile Ser Glu Phe His Thr Tyr Gln Val Gly Pro
            245                 250                 255

Gly Gln Cys Ser Ser Leu Leu Ala Gln Arg Val His Ala Pro Leu Pro
        260                 265                 270

Thr Val Trp Ser Val Val Arg Arg Phe Asp Lys Pro Gln Thr Tyr Lys
    275                 280                 285

His Phe Ile Lys Ser Cys His Val Glu Asp Gly Phe Glu Met Arg Val
290                 295                 300

Gly Cys Leu Arg Asp Val Asn Val Ile Ser Gly Leu Pro Ala Glu Thr
305                 310                 315                 320

Ser Thr Glu Arg Leu Asp Ile Leu Asp Asp Glu Arg His Val Thr Gly
            325                 330                 335

Phe Ser Ile Ile Gly Gly His Arg Leu Arg Asn Tyr Arg Ser Val
        340                 345                 350

Thr Thr Asn His Gly Gly Glu Ile Trp Thr Val Val Leu Glu Ser Tyr
            355                 360                 365

Val Val Asp Met Pro Glu Gly Asn Thr Glu Glu Asp Thr Arg Leu Phe
370                 375                 380

Ala Asp Thr Val Val Lys Leu Asn Leu Gln Lys Leu Ala Ser Val Thr
385                 390                 395                 400

Glu Val Ser Gln Ser Cys Asn Tyr Pro Cys Gln Phe His Ile Ile Glu
            405                 410                 415

Asn Glu Asp Ile Gln Pro Glu Glu Met Asn Leu Gly Val Leu Thr Thr
            420                 425                 430

Ser Ile Glu Glu Gln Arg Lys Lys Lys Arg Val Val Ala Met Lys Asp
        435                 440                 445

Gly Ser Thr Ser Ser
        450

<210> SEQ ID NO 18
<211> LENGTH: 195
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_033963, GenBank
      Accession No. CAN64657.1
<220> FEATURE:
<221> NAME/KEY: VARIANT
<222> LOCATION: (193)...(193)
<223> OTHER INFORMATION: Xaa = any amino acid

<400> SEQUENCE: 18

Met Ala Glu Ala Glu Ser Glu Asp Ser Glu Thr Thr Thr Pro Thr Thr
1               5                   10                  15

His His Leu Thr Ile Pro Pro Gly Leu Thr Gln Pro Glu Phe Gln Glu
            20                  25                  30

Leu Ala His Ser Ile Ser Glu Phe His Thr Tyr Gln Val Gly Pro Gly
        35                  40                  45

Gln Cys Ser Ser Leu Leu Ala Gln Arg Val His Ala Pro Leu Pro Thr
50                  55                  60

Val Trp Ser Val Val Arg Arg Phe Asp Lys Pro Gln Thr Tyr Lys His
65                  70                  75                  80

Phe Ile Lys Ser Cys His Val Glu Asp Gly Phe Glu Met Arg Val Gly
            85                  90                  95

Cys Leu Arg Asp Val Asn Val Ile Ser Gly Leu Pro Ala Glu Thr Ser
            100                 105                 110

Thr Glu Arg Leu Asp Ile Leu Asp Asp Glu Arg His Val Thr Gly Phe
        115                 120                 125

Ser Ile Ile Gly Gly Glu His Arg Leu Arg Asn Tyr Arg Ser Val Thr
    130                 135                 140

Thr Val His Glu Tyr Gln Asn His Gly Gly Glu Ile Trp Thr Val Val
145                 150                 155                 160

Leu Glu Ser Tyr Val Val Asp Met Pro Glu Gly Asn Thr Glu Glu Asp
                165                 170                 175

Thr Arg Leu Phe Ala Asp Thr Val Val Lys Leu Asn Leu Ser Glu Ala
            180                 185                 190

Xaa Arg Arg
    195

<210> SEQ ID NO 19
<211> LENGTH: 217
<212> TYPE: PRT
<213> ORGANISM: Medicago truncatula
<220> FEATURE:
<223> OTHER INFORMATION: barrel medic unknown protein, clone
      MTYFD_FE_FF_FG1G-N-24, GenBank Accession No. ACJ85026.1

<400> SEQUENCE: 19

Met Glu Lys Ala Glu Ser Ser Thr Ala Ser Thr Ser Asp Gln Asp Ser
1               5                   10                  15

Asp Glu Asn His Arg Thr Gln His Leu Thr Leu Pro Ser Gly Leu
                20                  25                  30

Arg Gln His Glu Phe Asp Ser Leu Ile Pro Phe Ile Asn Ser His His
            35                  40                  45

Thr Tyr Leu Ile Gly Pro Asn Gln Cys Ser Thr Leu Leu Ala Gln Arg
    50                  55                  60

Ile His Ala Pro Pro Gln Thr Val Trp Ser Val Val Arg Ser Phe Asp
65                  70                  75                  80

Lys Pro Gln Ile Tyr Lys His Ile Ile Lys Ser Cys Ser Leu Lys Glu
                85                  90                  95

Gly Phe Gln Met Lys Val Gly Cys Thr Arg Asp Val Asn Val Ile Ser
                100                 105                 110

Gly Leu Pro Ala Ala Thr Ser Thr Glu Arg Leu Asp Val Leu Asp Asp
            115                 120                 125

Glu Arg Arg Val Thr Gly Phe Ser Ile Ile Gly Gly Glu His Arg Leu
        130                 135                 140

Lys Asn Tyr Arg Ser Val Thr Ser Val His Gly Phe Gly Asp Gly Asp
145                 150                 155                 160

Asn Gly Gly Glu Ile Trp Thr Val Val Leu Glu Ser Tyr Val Val Asp
                165                 170                 175

Val Pro Glu Gly Asn Thr Glu Glu Asp Thr Arg Leu Phe Ala Asp Thr
            180                 185                 190

Val Val Lys Leu Asn Leu Gln Lys Leu Ala Ser Val Thr Glu Gly Lys
        195                 200                 205

Asn Arg Asp Gly Asp Gly Lys Ser His
    210                 215

<210> SEQ ID NO 20
<211> LENGTH: 212
<212> TYPE: PRT
<213> ORGANISM: Oryza sativa -continued

```
<220> FEATURE:
<223> OTHER INFORMATION: rice Japonica Group, cultivar Nipponbare,
      conserved hypothetical protein Os10g0573400, GenBank Accession
      No. NP_00106570.1

<400> SEQUENCE: 20

Met Glu Gln Gln Glu Glu Val Pro Pro Pro Ala Gly Leu Gly Leu
1               5                   10                  15

Thr Ala Glu Glu Tyr Ala Gln Val Arg Ala Thr Val Glu Ala His His
            20                  25                  30

Arg Tyr Ala Val Gly Pro Gly Gln Cys Ser Ser Leu Leu Ala Gln Arg
        35                  40                  45

Ile His Ala Pro Pro Ala Ala Val Trp Ala Val Val Arg Arg Phe Asp
50                  55                  60

Cys Pro Gln Val Tyr Lys His Phe Ile Arg Ser Cys Val Leu Arg Pro
65                  70                  75                  80

Asp Pro His His Asp Asp Asn Gly Asn Asp Leu Arg Pro Gly Arg Leu
                85                  90                  95

Arg Glu Val Ser Val Ile Ser Gly Leu Pro Ala Ser Thr Ser Thr Glu
            100                 105                 110

Arg Leu Asp Leu Leu Asp Asp Ala His Arg Val Phe Gly Phe Thr Ile
        115                 120                 125

Thr Gly Gly Glu His Arg Leu Arg Asn Tyr Arg Ser Val Thr Thr Val
130                 135                 140

Ser Gln Leu Asp Glu Ile Cys Thr Leu Val Leu Glu Ser Tyr Ile Val
145                 150                 155                 160

Asp Val Pro Asp Gly Asn Thr Glu Asp Thr Arg Leu Phe Ala Asp
                165                 170                 175

Thr Val Ile Arg Leu Asn Leu Gln Lys Leu Lys Ser Val Ser Glu Ala
            180                 185                 190

Asn Ala Asn Ala Ala Ala Ala Ala Ala Pro Pro Pro Pro Pro
        195                 200                 205

Ala Ala Ala Glu
    210

<210> SEQ ID NO 21
<211> LENGTH: 212
<212> TYPE: PRT
<213> ORGANISM: Zea mays
<220> FEATURE:
<223> OTHER INFORMATION: maize cyclase/dehydrase family protein, clone
      306819, GenBank Accession No. ACG40002.1

<400> SEQUENCE: 21

Met Asp Gln Gln Gly Ala Gly Gly Asp Ala Glu Val Pro Ala Gly Leu
1               5                   10                  15

Gly Leu Thr Ala Ala Glu Tyr Glu Gln Leu Arg Ser Thr Val Asp Ala
            20                  25                  30

His His Arg Tyr Ala Val Gly Glu Gly Gln Cys Ser Ser Leu Leu Ala
        35                  40                  45

Gln Arg Ile His Ala Pro Pro Glu Ala Val Trp Ala Val Val Arg Arg
50                  55                  60

Phe Asp Cys Pro Gln Val Tyr Lys His Phe Ile Arg Ser Cys Ala Leu
65                  70                  75                  80

Arg Pro Asp Pro Glu Ala Gly Asp Ala Leu Cys Pro Gly Arg Leu Arg
                85                  90                  95

Glu Val Ser Val Ile Ser Gly Leu Pro Ala Ser Thr Ser Thr Glu Arg
```

```
                        100                 105                 110
Leu Asp Leu Leu Asp Asp Ala Ala Arg Val Phe Gly Phe Ser Ile Thr
        115                 120                 125
Gly Gly Glu His Arg Leu Arg Asn Tyr Arg Ser Val Thr Thr Val Ser
        130                 135                 140
Glu Leu Ala Val Pro Ala Ile Cys Thr Val Val Leu Glu Ser Tyr Val
145                 150                 155                 160
Val Asp Val Pro Asp Gly Asn Thr Glu Asp Asp Thr Arg Leu Phe Ala
                165                 170                 175
Asp Thr Val Ile Arg Leu Asn Leu Gln Lys Leu Lys Ser Val Ala Glu
            180                 185                 190
Ala Asn Ala Ala Glu Ala Ala Ala Thr Thr Asn Ser Val Leu Leu Pro
        195                 200                 205
Arg Pro Ala Glu
        210

<210> SEQ ID NO 22
<211> LENGTH: 212
<212> TYPE: PRT
<213> ORGANISM: Zea mays
<220> FEATURE:
<223> OTHER INFORMATION: maize cyclase/dehydrase family protein, clone
      241996, GenBank Accession No. ACG34473.1
<220> FEATURE:
<221> NAME/KEY: VARIANT
<222> LOCATION: (11)...(11)
<223> OTHER INFORMATION: Xaa = any amino acid

<400> SEQUENCE: 22

Met Asp Gln Gln Gly Ala Gly Gly Asp Ala Xaa Val Pro Ala Gly Leu
1               5                   10                  15
Gly Leu Thr Ala Ala Glu Tyr Glu Gln Leu Arg Ser Thr Val Asp Ala
            20                  25                  30
His His Arg Tyr Ala Val Gly Glu Gly Gln Cys Ser Ser Leu Leu Ala
        35                  40                  45
Gln Arg Ile His Ala Pro Pro Glu Ala Val Trp Ala Val Val Arg Arg
    50                  55                  60
Phe Asp Cys Pro Gln Val Tyr Lys His Phe Ile Arg Ser Cys Ala Leu
65                  70                  75                  80
Arg Pro Asp Pro Glu Ala Gly Asp Ala Leu Cys Pro Gly Arg Leu Arg
                85                  90                  95
Glu Val Ser Val Ile Ser Gly Leu Pro Ala Ser Thr Ser Thr Glu Arg
            100                 105                 110
Leu Asp Leu Leu Asp Asp Ala Ala Arg Val Phe Gly Phe Ser Ile Thr
        115                 120                 125
Gly Gly Glu His Arg Leu Arg Asn Tyr Arg Ser Val Thr Thr Val Ser
        130                 135                 140
Glu Leu Ala Asp Pro Ala Ile Cys Thr Val Val Leu Glu Ser Tyr Val
145                 150                 155                 160
Val Asp Val Pro Asp Gly Asn Thr Glu Asp Asp Thr Arg Leu Phe Ala
                165                 170                 175
Asp Thr Val Ile Arg Leu Asn Leu Gln Lys Leu Lys Ser Val Thr Glu
            180                 185                 190
Ala Asn Ala Ala Glu Ala Ala Ala Thr Thr Asn Ser Val Leu Leu Pro
        195                 200                 205
Arg Pro Ala Glu
        210
```

<210> SEQ ID NO 23
<211> LENGTH: 233
<212> TYPE: PRT
<213> ORGANISM: Vitis vinifera
<220> FEATURE:
<223> OTHER INFORMATION: wine grape cultivar PN40024 unnamed protein
    product, locus tag GSVIVT00032173001, GenBank Accession No.
    CAO43790.1

<400> SEQUENCE: 23

Met Asp Pro His His His His Gly Leu Thr Glu Glu Phe Arg Ala
1               5                   10                  15

Leu Glu Pro Ile Ile Gln Asn Tyr His Thr Phe Glu Pro Ser Pro Asn
            20                  25                  30

Thr Cys Thr Ser Leu Ile Thr Gln Lys Ile Asp Ala Pro Ala Gln Val
        35                  40                  45

Val Trp Pro Phe Val Arg Ser Phe Glu Asn Pro Gln Lys Tyr Lys His
    50                  55                  60

Phe Ile Lys Asp Cys Thr Met Arg Gly Asp Gly Val Gly Ser Ile
65                  70                  75                  80

Arg Glu Val Thr Val Val Ser Gly Leu Pro Ala Ser Thr Ser Thr Glu
                85                  90                  95

Arg Leu Glu Ile Leu Asp Asp Glu Lys His Ile Leu Ser Phe Arg Val
            100                 105                 110

Val Gly Gly Glu His Arg Leu Asn Asn Tyr Arg Ser Val Thr Ser Val
        115                 120                 125

Asn Asp Phe Ser Lys Glu Gly Lys Asp Tyr Thr Ile Val Leu Glu Ser
    130                 135                 140

Tyr Ile Val Asp Ile Pro Glu Gly Asn Thr Gly Glu Asp Thr Lys Met
145                 150                 155                 160

Phe Val Asp Thr Val Val Lys Leu Asn Leu Gln Lys Leu Ala Val Val
                165                 170                 175

Ala Ile Thr Ser Leu His Glu Asn Glu Glu Ile Ala Asp Asn Glu Gly
            180                 185                 190

Pro Ser Arg Glu Ile Ser Leu Gln Ser Glu Thr Glu Ser Ala Glu Arg
        195                 200                 205

Gly Asp Glu Arg Arg Asp Gly Asp Gly Pro Ser Lys Ala Cys Asn Arg
    210                 215                 220

Asn Glu Trp His Cys Thr Thr Lys Glu
225                 230

<210> SEQ ID NO 24
<211> LENGTH: 207
<212> TYPE: PRT
<213> ORGANISM: Oryza sativa
<220> FEATURE:
<223> OTHER INFORMATION: rice Japonica Group, cultivar Nipponbare,
    Bet v I allergen-like protein, clone P0495C02.29, GenBank
    Accession No. BAD25659.1

<400> SEQUENCE: 24

Met Glu Pro His Met Glu Arg Ala Leu Arg Glu Ala Val Ala Ser Glu
1               5                   10                  15

Ala Glu Arg Arg Glu Leu Glu Gly Val Val Arg Ala His His Thr Phe
            20                  25                  30

Pro Ala Ala Glu Arg Ala Ala Gly Pro Gly Arg Arg Pro Thr Cys Thr
        35                  40                  45

```
Ser Leu Val Ala Gln Arg Val Asp Ala Pro Leu Ala Ala Val Trp Pro
    50                  55                  60

Ile Val Arg Gly Phe Ala Asn Pro Gln Arg Tyr Lys His Phe Ile Lys
 65                  70                  75                  80

Ser Cys Glu Leu Ala Ala Gly Asp Gly Ala Thr Val Gly Ser Val Arg
                 85                  90                  95

Glu Val Ala Val Val Ser Gly Leu Pro Ala Ser Thr Ser Thr Glu Arg
                100                 105                 110

Leu Glu Ile Leu Asp Asp Asp Arg His Val Leu Ser Phe Arg Val Val
                115                 120                 125

Gly Gly Asp His Arg Leu Arg Asn Tyr Arg Ser Val Thr Ser Val Thr
        130                 135                 140

Glu Phe Ser Ser Pro Ser Ser Pro Pro Arg Pro Tyr Cys Val Val Val
145                 150                 155                 160

Glu Ser Tyr Val Val Asp Val Pro Glu Gly Asn Thr Glu Glu Asp Thr
                    165                 170                 175

Arg Met Phe Thr Asp Thr Val Val Lys Leu Asn Leu Gln Lys Leu Ala
                180                 185                 190

Ala Val Ala Thr Ser Ser Ser Pro Pro Ala Ala Gly Asn His His
            195                 200                 205
```

<210> SEQ ID NO 25
<211> LENGTH: 210
<212> TYPE: PRT
<213> ORGANISM: Oryza sativa
<220> FEATURE:
<223> OTHER INFORMATION: rice Indica Group, cultivar 93-11, hypothetical
      protein OsI_06433, GenBank Accession No. EAY85077.1

<400> SEQUENCE: 25

```
Met Glu Pro His Met Glu Arg Ala Leu Arg Glu Ala Val Ala Ser Glu
 1               5                  10                  15

Ala Glu Arg Arg Glu Leu Glu Gly Val Val Arg Ala His His Thr Phe
                20                  25                  30

Pro Ala Ala Glu Arg Ala Ala Gly Pro Gly Arg Arg Pro Thr Cys Thr
            35                  40                  45

Ser Leu Val Ala Gln Arg Val Asp Ala Pro Leu Ala Ala Val Trp Pro
    50                  55                  60

Ile Val Arg Gly Phe Ala Asn Pro Gln Arg Tyr Lys His Phe Ile Lys
 65                  70                  75                  80

Ser Cys Glu Leu Ala Ala Gly Asp Gly Ala Thr Val Gly Ser Val Arg
                 85                  90                  95

Glu Val Ala Val Val Ser Gly Leu Pro Ala Ser Thr Ser Thr Glu Arg
                100                 105                 110

Leu Glu Ile Leu Asp Asp Asp Arg His Val Leu Ser Phe Arg Val Val
                115                 120                 125

Gly Gly Asp His Arg Leu Arg Asn Tyr Arg Ser Val Thr Ser Val Thr
        130                 135                 140

Glu Phe Ser Ser Pro Ser Ser Pro Ser Pro Arg Pro Tyr Cys
145                 150                 155                 160

Val Val Val Glu Ser Tyr Val Val Asp Val Pro Glu Gly Asn Thr Glu
                    165                 170                 175

Glu Asp Thr Arg Met Phe Thr Asp Thr Val Val Lys Leu Asn Leu Gln
                180                 185                 190

Lys Leu Ala Ala Val Ala Thr Ser Ser Ser Pro Pro Ala Ala Gly Asn
            195                 200                 205
```

His His
    210

<210> SEQ ID NO 26
<211> LENGTH: 200
<212> TYPE: PRT
<213> ORGANISM: Zea mays
<220> FEATURE:
<223> OTHER INFORMATION: maize strain B73 unknown protein, clone
      ZM_BFb0151H07, GenBank Accession No. ACF82013.1

<400> SEQUENCE: 26

Met Pro Tyr Thr Ala Pro Arg Pro Ser Pro Gln Gln His Ser Arg Val
1               5                   10                  15

Leu Ser Gly Gly Gly Ala Lys Ala Ala Ser His Gly Ala Ser Cys Ala
            20                  25                  30

Ala Val Pro Ala Glu Val Ala Arg His His Glu His Ala Ala Arg Ala
        35                  40                  45

Gly Gln Cys Cys Ser Ala Val Val Gln Ala Ile Ala Ala Pro Val Gly
    50                  55                  60

Ala Val Trp Ser Val Val Arg Arg Phe Asp Arg Pro Gln Ala Tyr Lys
65                  70                  75                  80

His Phe Ile Arg Ser Cys Arg Leu Val Gly Gly Asp Val Ala Val
                85                  90                  95

Gly Ser Val Arg Glu Val Arg Val Ser Gly Leu Pro Ala Thr Ser
            100                 105                 110

Ser Arg Glu Arg Leu Glu Ile Leu Asp Asp Glu Arg Arg Val Leu Ser
        115                 120                 125

Phe Arg Val Val Gly Gly Glu His Arg Leu Ala Asn Tyr Arg Ser Val
    130                 135                 140

Thr Thr Val His Glu Ala Gly Ala Gly Ala Gly Thr Gly Thr Val Val
145                 150                 155                 160

Val Glu Ser Tyr Val Val Asp Val Pro His Gly Asn Thr Ala Asp Glu
                165                 170                 175

Thr Arg Val Phe Val Asp Thr Ile Val Arg Cys Asn Leu Gln Ser Leu
            180                 185                 190

Ala Arg Thr Ala Glu Arg Leu Ala
        195                 200

<210> SEQ ID NO 27
<211> LENGTH: 215
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00037390001, GenBank Accession No.
      CAO48777.1

<400> SEQUENCE: 27

Met Pro Ser Asn Pro Pro Lys Ser Ser Leu Val Val His Arg Ile Asn
1               5                   10                  15

Ser Pro Asn Ser Ile Thr Thr Ala Thr Thr Ala Ser Ala Ala Ala Asn
            20                  25                  30

Asn His Asn Thr Ser Thr Met Pro Pro His Lys Gln Val Pro Asp Ala
        35                  40                  45

Val Ser Arg His His Thr His Val Val Gly Pro Asn Gln Cys Cys Ser
    50                  55                  60

Ala Val Val Gln Gln Ile Ala Ala Pro Val Ser Thr Val Trp Ser Val

```
                65                  70                  75                  80
Val Arg Arg Phe Asp Asn Pro Gln Ala Tyr Lys His Phe Val Lys Ser
                85                  90                  95

Cys His Val Val Gly Asp Gly Asp Val Gly Thr Leu Arg Glu Val
                100                 105                 110

His Val Ile Ser Gly Leu Pro Ala Ala Asn Ser Thr Glu Arg Leu Glu
                115                 120                 125

Ile Leu Asp Asp Glu Arg His Val Leu Ser Phe Ser Val Ile Gly Gly
    130                 135                 140

Asp His Arg Leu Ser Asn Tyr Arg Ser Val Thr Thr Leu His Pro Ser
145                 150                 155                 160

Pro Ser Ser Thr Gly Thr Val Val Leu Glu Ser Tyr Val Val Asp Ile
                165                 170                 175

Pro Pro Gly Asn Thr Lys Glu Asp Thr Cys Val Phe Val Asp Thr Ile
                180                 185                 190

Val Arg Cys Asn Leu Gln Ser Leu Ala Gln Ile Ala Glu Asn Ala Ala
                195                 200                 205

Gly Cys Lys Arg Ser Ser Ser
210                 215

<210> SEQ ID NO 28
<211> LENGTH: 213
<212> TYPE: PRT
<213> ORGANISM: Nicotiana tabacum
<220> FEATURE:
<223> OTHER INFORMATION: tobacco hypothetical protein, gene c17, GenBank
      Accession No. CAI84653.1

<400> SEQUENCE: 28

Met Pro Pro Ser Ser Pro Asp Ser Ser Val Leu Leu Gln Arg Ile Ser
1               5                   10                  15

Ser Asn Thr Thr Pro Asp Phe Ala Cys Lys Gln Ser Gln Gln Leu Gln
                20                  25                  30

Arg Arg Thr Met Pro Ile Pro Cys Thr Thr Gln Val Pro Asp Ser Val
                35                  40                  45

Val Arg Phe His Thr His Pro Val Gly Pro Asn Gln Cys Cys Ser Ala
    50                  55                  60

Val Ile Gln Arg Ile Ser Ala Pro Val Ser Thr Val Trp Ser Val Val
65                  70                  75                  80

Arg Arg Phe Asp Asn Pro Gln Ala Tyr Lys His Phe Val Lys Ser Cys
                85                  90                  95

His Val Ile Val Gly Asp Gly Asp Val Gly Thr Leu Arg Glu Val Arg
                100                 105                 110

Val Ile Ser Gly Leu Pro Ala Ala Ser Ser Thr Glu Arg Leu Glu Ile
                115                 120                 125

Leu Asp Asp Glu Arg His Val Ile Ser Phe Ser Val Val Gly Gly Asp
    130                 135                 140

His Arg Leu Ala Asn Tyr Arg Ser Val Thr Thr Leu His Pro Glu Pro
145                 150                 155                 160

Ser Gly Asp Gly Thr Thr Ile Val Val Glu Ser Tyr Val Val Asp Val
                165                 170                 175

Pro Pro Gly Asn Thr Arg Asp Glu Thr Cys Val Phe Val Asp Thr Ile
                180                 185                 190

Val Lys Cys Asn Leu Thr Ser Leu Ser Gln Ile Ala Val Asn Val Asn
                195                 200                 205
```

Arg Arg Lys Asp Ser
    210

<210> SEQ ID NO 29
<211> LENGTH: 208
<212> TYPE: PRT
<213> ORGANISM: Oryza sativa
<220> FEATURE:
<223> OTHER INFORMATION: rice Indica Group, cultivar 93-11, hypothetical
      protein OsI_04285, GenBank Accession No. EAY76350.1

<400> SEQUENCE: 29

Met Pro Tyr Ala Ala Val Arg Pro Ser Pro Pro Gln Leu Ser Arg
1               5                   10                  15

Pro Ile Gly Ser Gly Ala Gly Gly Gly Lys Ala Cys Pro Ala Val Pro
                20                  25                  30

Cys Glu Val Ala Arg Tyr His Glu His Ala Val Gly Ala Gly Gln Cys
                35                  40                  45

Cys Ser Thr Val Val Gln Ala Ile Ala Ala Pro Ala Asp Ala Val Trp
            50                  55                  60

Ser Val Val Arg Arg Phe Asp Arg Pro Gln Ala Tyr Lys Lys Phe Ile
65                  70                  75                  80

Lys Ser Cys Arg Leu Val Asp Gly Asp Gly Gly Glu Val Gly Ser Val
                85                  90                  95

Arg Glu Val Arg Val Val Ser Gly Leu Pro Ala Thr Ser Ser Arg Glu
                100                 105                 110

Arg Leu Glu Val Leu Asp Asp Arg Arg Val Leu Ser Phe Arg Ile
                115                 120                 125

Val Gly Gly Glu His Arg Leu Ala Asn Tyr Arg Ser Val Thr Thr Val
            130                 135                 140

His Glu Ala Ala Ala Pro Ala Met Ala Val Val Glu Ser Tyr Val
145                 150                 155                 160

Val Asp Val Pro Pro Gly Asn Thr Trp Glu Glu Thr Arg Val Phe Val
                165                 170                 175

Asp Thr Ile Val Arg Cys Asn Leu Gln Ser Leu Ala Arg Thr Val Glu
                180                 185                 190

Arg Leu Ala Pro Glu Ala Pro Arg Ala Asn Gly Ser Ile Asp His Ala
                195                 200                 205

<210> SEQ ID NO 30
<211> LENGTH: 208
<212> TYPE: PRT
<213> ORGANISM: Oryza sativa
<220> FEATURE:
<223> OTHER INFORMATION: rice Japonica Group, cultivar Nipponbare,
      Bet v I allergen-like protein, gene B1088C09.11, clone B1088C09,
      GenBank Accession No. BAB68102.1

<400> SEQUENCE: 30

Met Pro Tyr Ala Ala Val Arg Pro Ser Pro Pro Gln Leu Ser Arg
1               5                   10                  15

Pro Ile Gly Ser Gly Ala Gly Gly Gly Lys Ala Cys Pro Ala Val Pro
                20                  25                  30

Cys Glu Val Ala Arg Tyr His Glu His Ala Val Gly Ala Gly Gln Cys
                35                  40                  45

Phe Ser Thr Val Val Gln Ala Ile Ala Ala Pro Ala Asp Ala Val Trp
            50                  55                  60

Ser Val Val Arg Arg Phe Asp Arg Pro Gln Ala Tyr Lys Lys Phe Ile
65                  70                  75                  80

```
Lys Ser Cys Arg Leu Val Asp Gly Asp Gly Glu Val Gly Ser Val
             85                  90                  95

Arg Glu Val Arg Val Val Ser Gly Leu Pro Ala Thr Ser Ser Arg Glu
           100                 105                 110

Arg Leu Glu Val Leu Asp Asp Arg Arg Val Leu Ser Phe Arg Ile
           115                 120                 125

Val Gly Gly Glu His Arg Leu Ala Asn Tyr Arg Ser Val Thr Thr Val
130                 135                 140

His Glu Ala Ala Ala Pro Ala Met Ala Val Val Glu Ser Tyr Val
145                 150                 155                 160

Val Asp Val Pro Pro Gly Asn Thr Trp Glu Glu Thr Arg Val Phe Val
           165                 170                 175

Asp Thr Ile Val Arg Cys Asn Leu Gln Ser Leu Ala Arg Thr Val Glu
           180                 185                 190

Arg Leu Ala Pro Glu Ala Pro Arg Ala Asn Gly Ser Ile Asp His Ala
           195                 200                 205

<210> SEQ ID NO 31
<211> LENGTH: 213
<212> TYPE: PRT
<213> ORGANISM: Picea sitchensis
<220> FEATURE:
<223> OTHER INFORMATION: Sitka spruce cultivar FB3-425, unknown protein,
      clone WS0276_P02, GenBank Accession No. ABK22940.1

<400> SEQUENCE: 31

Met Asp Ile Ile Ala Gly Phe Asp Gln Leu Ser Phe Arg Leu Ser Gly
1               5                   10                  15

Ala Ser Lys Gln Ile Thr Lys Thr Gly Ala Val Gln Tyr Leu Lys Gly
            20                  25                  30

Glu Glu Gly Tyr Gly Glu Trp Leu Lys Glu Val Met Gly Arg Tyr His
        35                  40                  45

Tyr His Ser His Asp Gly Ala Arg Glu Cys Arg Cys Ser Ser Val Val
50                  55                  60

Val Gln Gln Val Glu Ala Pro Val Ser Val Val Trp Ser Leu Val Arg
65                  70                  75                  80

Arg Phe Asp Gln Pro Gln Val Tyr Lys His Phe Val Ser Asn Cys Phe
                85                  90                  95

Met Arg Gly Asp Leu Lys Val Gly Cys Leu Arg Glu Val Arg Val Val
            100                 105                 110

Ser Gly Leu Pro Ala Ala Thr Ser Thr Glu Arg Leu Asp Ile Leu Asp
        115                 120                 125

Glu Glu Arg His Ile Leu Ser Phe Ser Ile Val Gly Gly Asp His Arg
130                 135                 140

Leu Asn Asn Tyr Arg Ser Ile Thr Thr Leu His Glu Thr Leu Ile Asn
145                 150                 155                 160

Gly Lys Pro Gly Thr Ile Val Ile Glu Ser Tyr Val Leu Asp Val Pro
                165                 170                 175

His Gly Asn Thr Lys Glu Glu Thr Cys Leu Phe Val Asp Thr Ile Val
            180                 185                 190

Lys Cys Asn Leu Gln Ser Leu Ala His Val Ser Asn His Leu Asn Ser
        195                 200                 205

Thr His Arg Cys Leu
    210
```

<210> SEQ ID NO 32
<211> LENGTH: 207
<212> TYPE: PRT
<213> ORGANISM: Oryza sativa
<220> FEATURE:
<223> OTHER INFORMATION: rice Japonica Group, cultivar Nipponbare, hypothetical protein Os06g0562200, Bet v I allergen family protein, GenBank Accession No. NP_001057874.1

<400> SEQUENCE: 32

```
Met Glu Ala His Val Glu Arg Ala Leu Arg Glu Gly Leu Thr Glu Glu
1               5                   10                  15

Glu Arg Ala Ala Leu Glu Pro Ala Val Met Ala His His Thr Phe Pro
            20                  25                  30

Pro Ser Thr Thr Thr Ala Thr Thr Ala Ala Thr Cys Thr Ser Leu
        35                  40                  45

Val Thr Gln Arg Val Ala Ala Pro Val Arg Ala Val Trp Pro Ile Val
 50                  55                  60

Arg Ser Phe Gly Asn Pro Gln Arg Tyr Lys His Phe Val Arg Thr Cys
65                  70                  75                  80

Ala Leu Ala Ala Gly Asp Gly Ala Ser Val Gly Ser Val Arg Glu Val
                85                  90                  95

Thr Val Val Ser Gly Leu Pro Ala Ser Thr Ser Thr Glu Arg Leu Glu
            100                 105                 110

Met Leu Asp Asp Asp Arg His Ile Ile Ser Phe Arg Val Val Gly Gly
        115                 120                 125

Gln His Arg Leu Arg Asn Tyr Arg Ser Val Thr Ser Val Thr Glu Phe
    130                 135                 140

Gln Pro Pro Ala Ala Gly Pro Gly Pro Ala Pro Pro Tyr Cys Val Val
145                 150                 155                 160

Val Glu Ser Tyr Val Val Asp Val Pro Asp Gly Asn Thr Ala Glu Asp
                165                 170                 175

Thr Arg Met Phe Thr Asp Thr Val Val Lys Leu Asn Leu Gln Met Leu
            180                 185                 190

Ala Ala Val Ala Glu Asp Ser Ser Ser Ala Ser Arg Arg Arg Asp
        195                 200                 205
```

<210> SEQ ID NO 33
<211> LENGTH: 216
<212> TYPE: PRT
<213> ORGANISM: Oryza sativa
<220> FEATURE:
<223> OTHER INFORMATION: rice Japonica Group, cultivar Nipponbare, hypothetical protein Os05g0473000, Streptomyces cyclase/dehydrase family protein, GenBank Accession No. NP_001055819.1

<400> SEQUENCE: 33

```
Met Pro Tyr Thr Ala Pro Arg Pro Ser Pro Gln His Ser Arg Ile
1               5                   10                  15

Gly Gly Cys Gly Gly Gly Gly Val Leu Lys Ala Ala Gly Ala Ala Gly
            20                  25                  30

His Ala Ala Ser Cys Val Ala Val Pro Ala Glu Val Ala Arg His His
        35                  40                  45

Glu His Ala Ala Gly Val Gly Gln Cys Cys Ser Ala Val Val Gln Ala
    50                  55                  60

Ile Ala Ala Pro Val Asp Ala Val Trp Ser Val Val Arg Arg Phe Asp
65                  70                  75                  80

Arg Pro Gln Ala Tyr Lys His Phe Ile Arg Ser Cys Arg Leu Leu Asp
                85                  90                  95
```

```
Gly Asp Gly Asp Gly Ala Val Ala Val Gly Ser Val Arg Glu Val
            100                 105                 110

Arg Val Val Ser Gly Leu Pro Ala Thr Ser Ser Arg Glu Arg Leu Glu
        115                 120                 125

Ile Leu Asp Asp Glu Arg Arg Val Leu Ser Phe Arg Val Val Gly Gly
130                 135                 140

Glu His Arg Leu Ser Asn Tyr Arg Ser Val Thr Thr Val His Glu Thr
145                 150                 155                 160

Ala Ala Gly Ala Ala Ala Val Val Glu Ser Tyr Val Asp
                165                 170                 175

Val Pro His Gly Asn Thr Ala Asp Glu Thr Arg Met Phe Val Asp Thr
            180                 185                 190

Ile Val Arg Cys Asn Leu Gln Ser Leu Ala Arg Thr Ala Glu Gln Leu
        195                 200                 205

Ala Leu Ala Ala Pro Arg Ala Ala
    210                 215
```

<210> SEQ ID NO 34
<211> LENGTH: 212
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00029365001, GenBank Accession No.
      CAO41436.1

<400> SEQUENCE: 34

```
Met Pro Ser Ser Leu Gln Leu His Arg Ile Asn Asn Ile Asp Pro Thr
1               5                   10                  15

Thr Val Ala Val Ala Ala Thr Ala Ala Val Asn Cys His Lys Gln Ser
            20                  25                  30

Arg Thr Pro Leu Arg Cys Ala Thr Pro Val Pro Asp Ala Val Ala Ser
        35                  40                  45

Tyr His Ala His Ala Val Gly Pro His Gln Cys Cys Ser Met Val Val
    50                  55                  60

Gln Thr Thr Ala Ala Ala Leu Pro Thr Val Trp Ser Val Arg Arg
65                  70                  75                  80

Phe Asp Asn Pro Gln Ala Tyr Lys His Phe Leu Lys Ser Cys His Val
                85                  90                  95

Ile Phe Gly Asp Gly Asp Ile Gly Thr Leu Arg Glu Val His Val Val
            100                 105                 110

Ser Gly Leu Pro Ala Glu Ser Ser Thr Glu Arg Leu Glu Ile Leu Asp
        115                 120                 125

Asp Glu Arg His Val Leu Ser Phe Ser Val Val Gly Gly Asp His Arg
130                 135                 140

Leu Cys Asn Tyr Arg Ser Val Thr Thr Leu His Pro Ser Pro Thr Gly
145                 150                 155                 160

Thr Gly Thr Val Val Val Glu Ser Tyr Val Val Asp Ile Pro Pro Gly
                165                 170                 175

Asn Thr Lys Glu Asp Thr Cys Val Phe Val Asp Thr Ile Val Lys Cys
            180                 185                 190

Asn Leu Gln Ser Leu Ala Gln Met Ser Glu Lys Leu Thr Asn Asn Asn
        195                 200                 205

Arg Asn Ser Ser
    210
```

-continued

<210> SEQ ID NO 35
<211> LENGTH: 218
<212> TYPE: PRT
<213> ORGANISM: Zea mays
<220> FEATURE:
<223> OTHER INFORMATION: maize cyclase/dehydrase family protein, clone
      1678999, GenBank Accession No. ACG30334.1

<400> SEQUENCE: 35

Met Pro Cys Leu Gln Ala Ser Ser Pro Gly Ser Met Pro Tyr Gln His
1               5                   10                  15

His Gly Arg Gly Val Gly Cys Ala Ala Glu Ala Gly Ala Ala Val Gly
            20                  25                  30

Ala Ser Ala Gly Thr Gly Thr Arg Cys Gly Ala His Asp Gly Glu Val
        35                  40                  45

Pro Ala Glu Ala Ala Arg His His Glu His Ala Ala Pro Gly Pro Gly
    50                  55                  60

Arg Cys Cys Ser Ala Val Val Gln Arg Val Ala Ala Pro Ala Glu Ala
65                  70                  75                  80

Val Trp Ser Val Val Arg Arg Phe Asp Gln Pro Gln Ala Tyr Lys Arg
                85                  90                  95

Phe Val Arg Ser Cys Ala Leu Leu Ala Gly Asp Gly Val Gly Thr
            100                 105                 110

Leu Arg Glu Val Arg Val Val Ser Gly Leu Pro Ala Ala Ser Ser Arg
        115                 120                 125

Glu Arg Leu Glu Val Leu Asp Asp Glu Ser His Val Leu Ser Phe Arg
    130                 135                 140

Val Val Gly Gly Glu His Arg Leu Gln Asn Tyr Leu Ser Val Thr Thr
145                 150                 155                 160

Val His Pro Ser Pro Ala Ala Pro Asp Ala Ala Thr Val Val Val Glu
                165                 170                 175

Ser Tyr Val Val Asp Val Pro Pro Gly Asn Thr Pro Glu Asp Thr Arg
            180                 185                 190

Val Phe Val Asp Thr Ile Val Lys Cys Asn Leu Gln Ser Leu Ala Thr
        195                 200                 205

Thr Ala Glu Lys Leu Ala Leu Ala Ala Val
    210                 215

<210> SEQ ID NO 36
<211> LENGTH: 179
<212> TYPE: PRT
<213> ORGANISM: Physcomitrella patens
<220> FEATURE:
<223> OTHER INFORMATION: Physcomitrella patens subsp. patens moss,
      ecotype Gransden 2004, hypothetical protein, predicted protein,
      locus tag PHYPADRAFT_222359, GenBank Accession No. XP_001778048.1

<400> SEQUENCE: 36

Met Gln Thr Lys Gly Arg Gln Ala Asp Phe Gln Thr Leu Leu Glu Gly
1               5                   10                  15

Gln Gln Asp Leu Ile Cys Arg Phe His Arg His Glu Leu Gln Pro His
            20                  25                  30

Gln Cys Gly Ser Ile Leu Leu Gln Leu Ile Lys Ala Pro Val Glu Thr
        35                  40                  45

Val Trp Ser Val Ala Arg Ser Phe Asp Lys Pro Gln Val Tyr Lys Arg
    50                  55                  60

Phe Ile Gln Thr Cys Glu Ile Ile Glu Gly Asp Gly Gly Val Gly Ser
65                  70                  75                  80

```
Ile Arg Glu Val Arg Leu Val Ser Ser Ile Pro Ala Thr Ser Ser Ile
                85                  90                  95

Glu Arg Leu Glu Ile Leu Asp Asp Glu His Ile Ile Ser Phe Arg
            100                 105                 110

Val Leu Gly Gly Gly His Arg Leu Gln Asn Tyr Trp Ser Val Thr Ser
            115                 120                 125

Leu His Ser His Glu Ile Asp Gly Gln Met Gly Thr Leu Val Leu Glu
            130                 135                 140

Ser Tyr Val Val Asp Ile Pro Glu Gly Asn Thr Arg Glu Glu Thr His
145                 150                 155                 160

Met Phe Val Asp Thr Val Val Arg Cys Asn Leu Lys Ala Leu Ala Gln
                165                 170                 175

Val Ser Glu

<210> SEQ ID NO 37
<211> LENGTH: 229
<212> TYPE: PRT
<213> ORGANISM: Oryza sativa
<220> FEATURE:
<223> OTHER INFORMATION: rice Indica Group, cultivar 93-11, hypothetical
      protein OsI_11160, GenBank Accession No. EAY89631.1

<400> SEQUENCE: 37

Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys
            20                  25                  30

Ala Ala Glu Ala Ala Val Ala Ala Ala Gly Val Ala Gly Thr Arg Cys
            35                  40                  45

Gly Ala His Asp Gly Glu Val Pro Met Glu Val Ala Arg His His Glu
        50                  55                  60

His Ala Glu Pro Gly Ser Gly Arg Cys Cys Ser Ala Val Val Gln His
65                  70                  75                  80

Val Ala Ala Pro Ala Pro Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Val Gly Thr Leu Arg Glu Val Arg Val Val Ser Gly
            115                 120                 125

Leu Pro Ala Ala Ser Ser Arg Glu Arg Leu Glu Ile Leu Asp Asp Glu
            130                 135                 140

Ser His Val Leu Ser Phe Arg Val Val Gly Gly Glu His Arg Leu Lys
145                 150                 155                 160

Asn Tyr Leu Ser Val Thr Thr Val His Pro Ser Pro Ser Ala Pro Thr
                165                 170                 175

Ala Ala Thr Val Val Val Glu Ser Tyr Val Val Asp Val Pro Pro Gly
            180                 185                 190

Asn Thr Pro Glu Asp Thr Arg Val Phe Val Asp Thr Ile Val Lys Cys
            195                 200                 205

Asn Leu Gln Ser Leu Ala Lys Thr Ala Glu Lys Leu Ala Ala Gly Ala
            210                 215                 220

Arg Ala Ala Gly Ser
225

<210> SEQ ID NO 38
```

```
<211> LENGTH: 229
<212> TYPE: PRT
<213> ORGANISM: Oryza sativa
<220> FEATURE:
<223> OTHER INFORMATION: rice Japonica Group, cultivar Nipponbare,
      hypothetical protein Os03g0297600, Streptomyces cyclase/dehydrase
      family protein, GenBank Accession No. NP_001049838.1

<400> SEQUENCE: 38
```

Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys
            20                  25                  30

Ala Ala Glu Ala Ala Val Ala Ala Gly Val Ala Gly Thr Arg Cys
        35                  40                  45

Gly Ala His Asp Gly Glu Val Pro Met Glu Val Ala Arg His His Glu
    50                  55                  60

His Ala Glu Pro Gly Ser Gly Arg Cys Cys Ser Ala Val Val Gln His
65                  70                  75                  80

Val Ala Ala Pro Ala Ala Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Val Gly Thr Leu Arg Glu Val Arg Val Val Ser Gly
        115                 120                 125

Leu Pro Ala Ala Ser Ser Arg Glu Arg Leu Glu Ile Leu Asp Asp Glu
    130                 135                 140

Ser His Val Leu Ser Phe Arg Val Val Gly Glu His Arg Leu Lys
145                 150                 155                 160

Asn Tyr Leu Ser Val Thr Thr Val His Pro Ser Pro Ser Ala Pro Thr
                165                 170                 175

Ala Ala Thr Val Val Val Glu Ser Tyr Val Val Asp Val Pro Pro Gly
            180                 185                 190

Asn Thr Pro Glu Asp Thr Arg Val Phe Val Asp Thr Ile Val Lys Cys
        195                 200                 205

Asn Leu Gln Ser Leu Ala Lys Thr Ala Glu Lys Leu Ala Ala Gly Ala
    210                 215                 220

Arg Ala Ala Gly Ser
225

```
<210> SEQ ID NO 39
<211> LENGTH: 205
<212> TYPE: PRT
<213> ORGANISM: Medicago truncatula
<220> FEATURE:
<223> OTHER INFORMATION: barrel medic unknown protein, clone
      MTYFP_FQ_FR_FS1G-H-19, GenBank Accession No. ACJ85898.1

<400> SEQUENCE: 39
```

Met Pro Ser Pro Val Gln Phe Gln Arg Phe Asp Ser Asn Thr Ala Ile
1               5                   10                  15

Thr Asn Gly Val Asn Cys Pro Lys Gln Ile Gln Ala Cys Arg Tyr Ala
            20                  25                  30

Leu Ser Ser Leu Lys Pro Thr Val Ser Val Pro Glu Thr Val Val Asp
        35                  40                  45

His His Met His Val Val Gly Gln Asn Gln Cys Tyr Ser Val Val Ile
    50                  55                  60

Gln Thr Ile Asn Ala Ser Val Ser Thr Val Trp Ser Val Val Arg Arg

```
            65                  70                  75                  80
Phe Asp Tyr Pro Gln Gly Tyr Lys His Phe Val Lys Ser Cys Asn Val
                    85                  90                  95

Val Ala Ser Gly Asp Gly Ile Arg Val Gly Ala Leu Arg Glu Val Arg
                    100                 105                 110

Leu Val Ser Gly Leu Pro Ala Val Ser Ser Thr Glu Arg Leu Asp Ile
                    115                 120                 125

Leu Asp Glu Glu Arg His Val Ile Ser Phe Ser Val Val Gly Gly Val
                    130                 135                 140

His Arg Cys Arg Asn Tyr Arg Ser Val Thr Thr Leu His Gly Asp Gly
145                 150                 155                 160

Asn Gly Gly Thr Val Val Ile Glu Ser Tyr Val Val Asp Val Pro Gln
                    165                 170                 175

Gly Asn Thr Lys Glu Glu Thr Cys Ser Phe Ala Asp Thr Ile Val Arg
                    180                 185                 190

Cys Asn Leu Gln Ser Leu Val Gln Ile Ala Glu Lys Leu
                    195                 200                 205
```

<210> SEQ ID NO 40
<211> LENGTH: 212
<212> TYPE: PRT
<213> ORGANISM: Zea mays
<220> FEATURE:
<223> OTHER INFORMATION: maize AT-rich element binding factor 3, clone
      1458362, GenBank Accession No. ACG26321.1

<400> SEQUENCE: 40

```
Met Pro Phe Ala Ala Ser Arg Thr Ser Gln Gln Gln His Ser Arg Val
1               5                   10                  15

Ala Thr Asn Gly Arg Ala Val Ala Val Cys Ala Gly His Ala Gly Val
                20                  25                  30

Pro Asp Glu Val Ala Arg His His Glu His Ala Val Ala Ala Gly Gln
                35                  40                  45

Cys Cys Ala Ala Met Val Gln Ser Ile Ala Ala Pro Val Asp Ala Val
50                  55                  60

Trp Ser Leu Val Arg Arg Phe Asp Gln Pro Gln Arg Tyr Lys Arg Phe
65                  70                  75                  80

Ile Arg Ser Cys His Leu Val Asp Gly Asp Gly Ala Glu Val Gly Ser
                85                  90                  95

Val Arg Glu Leu Leu Leu Val Ser Gly Leu Pro Ala Glu Ser Ser Arg
                100                 105                 110

Glu Arg Leu Glu Ile Arg Asp Asp Glu Arg Arg Val Ile Ser Phe Arg
                115                 120                 125

Val Leu Gly Gly Asp His Arg Leu Ala Asn Tyr Arg Ser Val Thr Thr
                130                 135                 140

Val His Glu Ala Ala Pro Ser Gln Asp Gly Arg Pro Leu Thr Met Val
145                 150                 155                 160

Val Glu Ser Tyr Val Val Asp Val Pro Pro Gly Asn Thr Val Glu Glu
                165                 170                 175

Thr Arg Ile Phe Val Asp Thr Ile Val Arg Cys Asn Leu Gln Ser Leu
                180                 185                 190

Glu Gly Thr Val Ile Arg Gln Leu Glu Ile Ala Ala Met Pro His Asp
                195                 200                 205

Asp Asn Gln Asn
    210
```

-continued

```
<210> SEQ ID NO 41
<211> LENGTH: 233
<212> TYPE: PRT
<213> ORGANISM: Zea mays
<220> FEATURE:
<223> OTHER INFORMATION: maize strain B73 unknown protein, clone
      ZM_BFb0105O18, GenBank Accession No. ACF87013.1

<400> SEQUENCE: 41

Met Arg Glu Arg Asn Ser Ser Ile Asp Gln Glu His Gln Arg Gly Ser
1               5                   10                  15

Ser Ser Arg Ser Thr Met Pro Phe Ala Ala Ser Arg Thr Ser Gln Gln
            20                  25                  30

Gln His Ser Arg Val Ala Thr Asn Gly Arg Ala Val Ala Val Cys Ala
        35                  40                  45

Gly His Ala Gly Val Pro Asp Glu Val Ala Arg His His Glu His Ala
    50                  55                  60

Val Ala Ala Gly Gln Cys Cys Ala Ala Met Val Gln Ser Ile Ala Ala
65                  70                  75                  80

Pro Val Asp Ala Val Trp Ser Leu Val Arg Arg Phe Asp Gln Pro Gln
                85                  90                  95

Arg Tyr Lys Arg Phe Ile Arg Ser Cys His Leu Val Asp Gly Asp Gly
            100                 105                 110

Ala Glu Val Gly Ser Val Arg Glu Leu Leu Leu Val Ser Gly Leu Pro
        115                 120                 125

Ala Glu Ser Ser Arg Glu Arg Leu Glu Ile Arg Asp Asp Glu Arg Arg
    130                 135                 140

Val Ile Ser Phe Arg Val Leu Gly Gly Asp His Arg Leu Ala Asn Tyr
145                 150                 155                 160

Arg Ser Val Thr Thr Val His Glu Ala Ala Pro Ser Gln Asp Gly Arg
                165                 170                 175

Pro Leu Thr Met Val Val Glu Ser Tyr Val Val Asp Val Pro Pro Gly
            180                 185                 190

Asn Thr Val Glu Glu Thr Arg Ile Phe Val Asp Thr Ile Val Arg Cys
        195                 200                 205

Asn Leu Gln Ser Leu Glu Gly Thr Val Ile Arg Gln Leu Glu Ile Ala
    210                 215                 220

Ala Met Pro His Asp Asp Asn Gln Asn
225                 230

<210> SEQ ID NO 42
<211> LENGTH: 194
<212> TYPE: PRT
<213> ORGANISM: Physcomitrella patens
<220> FEATURE:
<223> OTHER INFORMATION: Physcomitrella patens subsp. patens moss,
      ecotype Gransden 2004, hypothetical protein, predicted protein,
      locus tag PHYPADRAFT_209242, GenBank Accession No. XP_001762113.1

<400> SEQUENCE: 42

Met Met Gln Glu Lys Gln Gly Arg Pro Asp Phe Gln Phe Leu Leu Glu
1               5                   10                  15

Gly Gln Gln Asp Leu Ile Cys Arg Phe His Lys His Glu Leu Leu Pro
            20                  25                  30

His Gln Cys Gly Ser Ile Leu Leu Gln Gln Ile Lys Ala Pro Val Gln
        35                  40                  45

Thr Val Trp Leu Ile Val Arg Arg Phe Asp Glu Pro Gln Val Tyr Lys
    50                  55                  60
```

-continued

```
Arg Phe Ile Gln Arg Cys Asp Ile Val Glu Gly Asp Gly Val Val Gly
 65                  70                  75                  80

Ser Ile Arg Glu Val Gln Leu Val Ser Ser Ile Pro Ala Thr Ser Ser
                 85                  90                  95

Ile Glu Arg Leu Glu Ile Leu Asp Asp Glu His Ile Ile Ser Phe
            100                 105                 110

Arg Val Leu Gly Gly Gly His Arg Leu Gln Asn Tyr Trp Ser Val Thr
            115                 120                 125

Ser Leu His Arg His Glu Ile Gln Gly Gln Met Gly Thr Leu Val Leu
        130                 135                 140

Glu Ser Tyr Val Val Asp Ile Pro Asp Gly Asn Thr Arg Glu Glu Thr
145                 150                 155                 160

His Thr Phe Val Asp Thr Val Val Arg Cys Asn Leu Lys Ala Leu Ala
                165                 170                 175

Gln Val Ser Glu Gln Lys His Leu Leu Asn Ser Asn Glu Lys Pro Ala
            180                 185                 190

Ala Pro
```

<210> SEQ ID NO 43
<211> LENGTH: 191
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00035869001, GenBank Accession No.
      CAO48052.1

<400> SEQUENCE: 43

```
Met Lys Val Tyr Ser Pro Ser Gln Ile Leu Ala Glu Arg Gly Pro Arg
 1                5                  10                  15

Ala Gln Ala Met Gly Asn Leu Tyr His Thr His Leu Leu Pro Asn
             20                  25                  30

Gln Cys Ser Ser Leu Val Val Gln Thr Thr Asp Ala Pro Leu Pro Gln
         35                  40                  45

Val Trp Ser Met Val Arg Arg Phe Asp Arg Pro Gln Ser Tyr Lys Arg
 50                  55                  60

Phe Val Arg Gly Cys Thr Leu Arg Arg Gly Lys Gly Val Gly Ser
 65                  70                  75                  80

Val Arg Glu Val Asn Ile Val Ser Gly Leu Pro Ala Glu Ile Ser Leu
                 85                  90                  95

Glu Arg Leu Asp Lys Leu Asp Asp Leu His Val Met Arg Phe Thr
            100                 105                 110

Val Ile Gly Gly Asp His Arg Leu Ala Asn Tyr His Ser Thr Leu Thr
            115                 120                 125

Leu His Glu Asp Glu Glu Asp Gly Val Arg Lys Thr Val Val Met Glu
        130                 135                 140

Ser Tyr Val Val Asp Val Pro Gly Gly Asn Ser Ala Gly Glu Thr Cys
145                 150                 155                 160

Tyr Phe Ala Asn Thr Ile Ile Gly Phe Asn Leu Lys Ala Leu Ala Ala
                165                 170                 175

Val Thr Glu Thr Met Ala Leu Lys Ala Asn Ile Pro Ser Gly Phe
            180                 185                 190
```

<210> SEQ ID NO 44
<211> LENGTH: 217
<212> TYPE: PRT

```
<213> ORGANISM: Physcomitrella patens
<220> FEATURE:
<223> OTHER INFORMATION: Physcomitrella patens subsp. patens moss,
      ecotype Gransden 2004, hypothetical protein, predicted protein,
      locus tag PHYPADRAFT_132509, GenBank Accession No. XP_001767821.1

<400> SEQUENCE: 44

Met Gln Gln Val Lys Gly Arg Gln Asp Phe Gln Arg Leu Leu Glu Ala
1               5                   10                  15

Gln Gln Asp Leu Ile Cys Arg Tyr His Thr His Glu Leu Lys Ala His
                20                  25                  30

Gln Cys Gly Ser Ile Leu Leu Gln Gln Ile Lys Val Pro Leu Pro Ile
            35                  40                  45

Val Trp Ala Ile Val Arg Ser Phe Asp Lys Pro Gln Val Tyr Lys Arg
    50                  55                  60

Phe Ile Gln Thr Cys Lys Ile Thr Glu Gly Asp Gly Gly Val Gly Ser
65                  70                  75                  80

Ile Arg Glu Val His Leu Val Ser Ser Val Pro Ala Thr Cys Ser Ile
                85                  90                  95

Glu Arg Leu Glu Ile Leu Asp Asp Gly Lys His Ile Ile Ser Phe Arg
                100                 105                 110

Val Leu Gly Gly Gly His Arg Leu Gln Asn Tyr Ser Ser Val Ser Ser
            115                 120                 125

Leu His Glu Leu Glu Val Glu Gly His Pro Cys Thr Leu Val Leu Glu
    130                 135                 140

Ser Tyr Met Val Asp Ile Pro Asp Gly Asn Thr Arg Glu Glu Thr His
145                 150                 155                 160

Met Phe Val Asp Thr Val Arg Cys Asn Leu Lys Ser Leu Ala Gln
                165                 170                 175

Ile Ser Glu Gln Gln Tyr Asn Lys Asp Cys Leu Gln Lys Gln His
            180                 185                 190

Asp Gln Gln Gln Met Tyr Gln Gln Arg His Pro Pro Leu Pro Pro Ile
        195                 200                 205

Pro Ile Thr Asp Lys Asn Met Glu Arg
    210                 215

<210> SEQ ID NO 45
<211> LENGTH: 195
<212> TYPE: PRT
<213> ORGANISM: Physcomitrella patens
<220> FEATURE:
<223> OTHER INFORMATION: Physcomitrella patens subsp. patens moss,
      ecotype Gransden 2004, hypothetical protein, predicted protein,
      locus tag PHYPADRAFT_213389, GenBank Accession No. XP_001767012.1

<400> SEQUENCE: 45

Met Arg Phe Asp Ile Gly His Asn Asp Val Arg Gly Phe Phe Thr Cys
1               5                   10                  15

Glu Glu Glu His Ala Tyr Ala Leu His Ser Gln Thr Val Glu Leu Asn
                20                  25                  30

Gln Cys Gly Ser Ile Leu Met Gln Gln Ile His Ala Pro Ile Glu Val
            35                  40                  45

Val Trp Ser Ile Val Arg Ser Phe Gly Ser Pro Gln Ile Tyr Lys Lys
    50                  55                  60

Phe Ile Gln Ala Cys Ile Leu Thr Val Gly Asp Gly Gly Val Gly Ser
65                  70                  75                  80

Ile Arg Glu Val Phe Leu Val Ser Gly Val Pro Ala Thr Ser Ser Ile
                85                  90                  95
```

```
Glu Arg Leu Glu Ile Leu Asp Asp Glu Lys His Val Phe Ser Phe Arg
                100                 105                 110

Val Leu Lys Gly Gly His Arg Leu Gln Asn Tyr Arg Ser Val Thr Thr
            115                 120                 125

Leu His Glu Gln Glu Val Asn Gly Arg Gln Thr Thr Thr Val Leu Glu
        130                 135                 140

Ser Tyr Val Val Asp Val Pro Asp Gly Asn Thr Arg Glu Glu Thr His
145                 150                 155                 160

Met Phe Ala Asp Thr Val Val Met Cys Asn Leu Lys Ser Leu Ala Gln
                165                 170                 175

Val Ala Glu Trp Arg Ala Met Gln Gly Ile Thr Gln Gln Leu Ser Thr
            180                 185                 190

Ser Ser Leu
        195

<210> SEQ ID NO 46
<211> LENGTH: 172
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_004947, GenBank
      Accession No. CAN72620.1

<400> SEQUENCE: 46

Met Gly Asn Leu Tyr His Thr His Leu Leu Pro Asn Gln Cys Ser
1               5                   10                  15

Ser Leu Val Val Gln Thr Thr Asp Ala Pro Leu Pro Gln Val Trp Ser
                20                  25                  30

Met Val Arg Arg Phe Asp Arg Pro Gln Ser Tyr Lys Arg Phe Val Arg
            35                  40                  45

Gly Cys Thr Leu Arg Arg Gly Lys Gly Gly Val Gly Ser Val Arg Glu
        50                  55                  60

Val Asn Ile Val Ser Gly Leu Pro Ala Glu Ile Ser Leu Glu Arg Leu
65                  70                  75                  80

Asp Lys Leu Asp Asp Leu His Val Met Arg Phe Thr Val Ile Gly
                85                  90                  95

Gly Asp His Arg Leu Ala Asn Tyr His Ser Thr Leu Thr Leu His Glu
                100                 105                 110

Asp Glu Glu Asp Gly Val Arg Lys Thr Val Val Met Glu Ser Tyr Val
            115                 120                 125

Val Asp Val Pro Gly Gly Asn Ser Ala Gly Glu Thr Cys Tyr Phe Ala
        130                 135                 140

Asn Thr Ile Ile Gly Phe Asn Leu Lys Ala Leu Ala Ala Val Thr Glu
145                 150                 155                 160

Thr Met Ala Leu Lys Ala Asn Ile Pro Ser Gly Phe
                165                 170

<210> SEQ ID NO 47
<211> LENGTH: 196
<212> TYPE: PRT
<213> ORGANISM: Picea sitchensis
<220> FEATURE:
<223> OTHER INFORMATION: Sitka spruce cultivar FB3-425, unknown protein,
      clone WS0281_I24, GenBank Accession No. ABK23752.1

<400> SEQUENCE: 47

Met Glu Asp Leu Ser Ser Trp Arg Glu Gly Arg Ala Met Trp Leu Gly
```

```
1               5                   10                  15
Asn Pro Pro Ser Glu Ser Glu Leu Val Cys Arg His His Arg His Glu
                20                  25                  30
Leu Gln Gly Asn Gln Cys Ser Ser Phe Leu Val Lys His Ile Arg Ala
                35                  40                  45
Pro Val His Leu Val Trp Ser Ile Val Arg Thr Phe Asp Gln Pro Gln
 50                  55                  60
Lys Tyr Lys Pro Phe Val His Ser Cys Ser Val Arg Gly Gly Ile Thr
 65                  70                  75                  80
Val Gly Ser Ile Arg Asn Val Asn Val Lys Ser Gly Leu Pro Ala Thr
                85                  90                  95
Ala Ser Glu Glu Arg Leu Glu Ile Leu Asp Asp Asn Glu His Val Phe
                100                 105                 110
Ser Ile Lys Ile Leu Gly Gly Asp His Arg Leu Gln Asn Tyr Ser Ser
                115                 120                 125
Ile Ile Thr Val His Pro Glu Ile Ile Asp Gly Arg Pro Gly Thr Leu
                130                 135                 140
Val Ile Glu Ser Tyr Val Val Asp Val Pro Glu Gly Asn Thr Arg Glu
145                 150                 155                 160
Glu Thr Arg Phe Phe Val Glu Ala Leu Val Lys Cys Asn Leu Lys Ser
                165                 170                 175
Leu Ala Asp Val Ser Glu Arg Leu Ala Ser Gln His His Thr Glu Leu
                180                 185                 190
Leu Glu Arg Thr
        195

<210> SEQ ID NO 48
<211> LENGTH: 185
<212> TYPE: PRT
<213> ORGANISM: Solanum tuberosum
<220> FEATURE:
<223> OTHER INFORMATION: potato cultivar Kuras, CAPIP1-like protein,
      clone 153D02, similar to Casicum annuum CAPIP1, GenBank Accession
      No. ABB29920.1

<400> SEQUENCE: 48

Met Asn Ala Asn Gly Phe Cys Gly Val Glu Lys Glu Tyr Ile Arg Lys
1               5                   10                  15
His His Leu His Glu Pro Lys Glu Asn Gln Cys Ser Ser Phe Leu Val
                20                  25                  30
Lys His Ile Arg Ala Pro Val His Leu Val Trp Ser Leu Val Arg Arg
                35                  40                  45
Phe Asp Gln Pro Gln Lys Tyr Lys Pro Phe Ile Ser Arg Cys Ile Val
 50                  55                  60
Gln Gly Asp Leu Glu Ile Gly Ser Leu Arg Glu Val Asp Val Lys Ser
 65                  70                  75                  80
Gly Leu Pro Ala Thr Thr Ser Thr Glu Arg Leu Glu Leu Leu Asp Asp
                85                  90                  95
Glu Glu His Ile Leu Ser Val Arg Ile Val Gly Gly Asp His Arg Leu
                100                 105                 110
Arg Asn Tyr Ser Ser Val Ile Ser Val His Pro Glu Val Ile Asp Gly
                115                 120                 125
Arg Pro Gly Thr Val Val Leu Glu Ser Phe Val Val Asp Val Pro Glu
                130                 135                 140
Gly Asn Thr Lys Asp Glu Thr Cys Tyr Phe Val Glu Ala Leu Ile Asn
145                 150                 155                 160
```

```
Cys Asn Leu Lys Ser Leu Ala Asp Ile Ser Glu Arg Val Ala Val Gln
            165                 170                 175

Asp Arg Thr Glu Pro Ile Asp Gln Val
            180                 185

<210> SEQ ID NO 49
<211> LENGTH: 190
<212> TYPE: PRT
<213> ORGANISM: Medicago truncatula
<220> FEATURE:
<223> OTHER INFORMATION: barrel medic unknown protein, clone
      MTYFP_FQ_FR_FS1G-E-17, GenBank Accession No. ACJ85952.1

<400> SEQUENCE: 49

Met Asn Asn Gly Cys Glu Gln Gln Gln Tyr Ser Val Ile Glu Thr Gln
1               5                   10                  15

Tyr Ile Arg Arg His His Lys His Asp Leu Arg Asp Asn Gln Cys Ser
            20                  25                  30

Ser Ala Leu Val Lys His Ile Lys Ala Pro Val His Leu Val Trp Ser
        35                  40                  45

Leu Val Arg Arg Phe Asp Gln Pro Gln Lys Tyr Lys Pro Phe Ile Ser
    50                  55                  60

Arg Cys Ile Met Gln Gly Asp Leu Ser Ile Gly Ser Val Arg Glu Val
65                  70                  75                  80

Asn Val Lys Ser Gly Leu Pro Ala Thr Thr Ser Thr Glu Arg Leu Glu
                85                  90                  95

Gln Leu Asp Asp Glu Glu His Ile Leu Gly Ile Arg Ile Val Gly Gly
            100                 105                 110

Asp His Arg Leu Arg Asn Tyr Ser Ser Ile Ile Thr Val His Pro Gly
        115                 120                 125

Val Ile Asp Gly Arg Pro Gly Thr Met Val Ile Glu Ser Phe Val Val
    130                 135                 140

Asp Val Pro Glu Gly Asn Thr Lys Asp Glu Thr Cys Tyr Phe Val Glu
145                 150                 155                 160

Ala Leu Ile Arg Tyr Asn Leu Ser Ser Leu Ala Asp Val Ser Glu Arg
                165                 170                 175

Met Ala Val Gln Gly Arg Thr Asp Pro Ile Asn Ile Asn Pro
            180                 185                 190

<210> SEQ ID NO 50
<211> LENGTH: 185
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00002440001, GenBank Accession No.
      CAO65816.1

<400> SEQUENCE: 50

Met Ser Gly Tyr Gly Cys Ile Lys Met Glu Asp Glu Tyr Ile Arg Arg
1               5                   10                  15

His His Arg His Glu Ile Arg Asp Asn Gln Cys Ser Ser Ser Leu Val
            20                  25                  30

Lys His Ile Lys Ala Pro Val His Leu Val Trp Ser Leu Val Arg Ser
        35                  40                  45

Phe Asp Gln Pro Gln Lys Tyr Lys Pro Phe Val Ser Arg Cys Ile Val
    50                  55                  60

Gln Gly Asp Leu Glu Ile Gly Ser Val Arg Glu Val Asn Val Lys Ser
```

```
                65                  70                  75                  80
Gly Leu Pro Ala Thr Thr Ser Thr Glu Arg Leu Glu Leu Leu Asp Asp
                    85                  90                  95

Glu Glu His Ile Phe Gly Met Arg Ile Val Gly Gly Asp His Arg Leu
                100                 105                 110

Lys Asn Tyr Ser Ser Ile Val Thr Val His Pro Glu Ile Ile Asp Gly
                115                 120                 125

Arg Pro Gly Thr Leu Val Ile Glu Ser Phe Val Val Asp Val Pro Asp
            130                 135                 140

Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Ile Gln
                165                 170                 175

Asp Arg Thr Glu Pro Ile Asp Arg Met
            180                 185

<210> SEQ ID NO 51
<211> LENGTH: 185
<212> TYPE: PRT
<213> ORGANISM: Vitis vinifera
<220> FEATURE:
<223> OTHER INFORMATION: wine grape cultivar PN40024 unnamed protein
      product, locus tag GSVIVT00006507001, GenBank Accession No.
      CAO69376.1

<400> SEQUENCE: 51

Met Asn Gly Asn Gly Leu Ser Ser Met Glu Ser Glu Tyr Ile Arg Arg
1               5                   10                  15

His His Arg His Glu Pro Ala Glu Asn Gln Cys Ser Ser Ala Leu Val
                20                  25                  30

Lys His Ile Lys Ala Pro Val Pro Leu Val Trp Ser Leu Val Arg Arg
            35                  40                  45

Phe Asp Gln Pro Gln Lys Tyr Lys Pro Phe Ile Ser Arg Cys Val Val
50                  55                  60

Gln Gly Asn Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                    85                  90                  95

Asp Glu His Ile Leu Ser Met Arg Ile Ile Gly Gly Asp His Arg Leu
                100                 105                 110

Arg Asn Tyr Ser Ser Ile Ile Ser Leu His Pro Glu Ile Ile Asp Gly
                115                 120                 125

Arg Pro Gly Thr Met Val Ile Glu Ser Tyr Val Val Asp Val Pro Glu
            130                 135                 140

Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Arg Met
            180                 185

<210> SEQ ID NO 52
<211> LENGTH: 208
<212> TYPE: PRT
<213> ORGANISM: Oryza sativa
<220> FEATURE:
<223> OTHER INFORMATION: rice Japonica Group, cultivar Nipponbare,
      hypothetical protein OsJ_21703, GenBank Accession No. EAZ37364.1
```

<400> SEQUENCE: 52

Met Glu Ala His Val Glu Arg Ala Leu Arg Glu Gly Leu Thr Glu Glu
1               5                   10                  15

Glu Arg Ala Ala Leu Glu Pro Ala Val Met Ala His His Thr Phe Pro
            20                  25                  30

Pro Ser Thr Thr Thr Ala Thr Thr Ala Ala Ala Thr Cys Thr Ser Leu
        35                  40                  45

Val Thr Gln Arg Val Ala Ala Pro Val Arg Ala Val Trp Pro Ile Val
    50                  55                  60

Arg Ser Phe Gly Asn Pro Gln Arg Tyr Lys His Phe Val Arg Thr Cys
65                  70                  75                  80

Ala Leu Ala Ala Gly Asn Gly Pro Ser Phe Gly Ser Val Arg Glu Val
                85                  90                  95

Thr Val Val Ser Gly Pro Ser Arg Leu Pro Pro Gly Thr Glu Arg Leu
            100                 105                 110

Glu Met Leu Asp Asp Asp Arg His Ile Ile Ser Phe Arg Val Val Gly
        115                 120                 125

Gly Gln His Arg Leu Arg Asn Tyr Arg Ser Val Thr Ser Val Thr Glu
130                 135                 140

Phe Gln Pro Pro Ala Ala Gly Pro Gly Pro Ala Pro Pro Tyr Cys Val
145                 150                 155                 160

Val Val Glu Ser Tyr Val Val Asp Val Pro Asp Gly Asn Thr Ala Glu
                165                 170                 175

Asp Thr Arg Met Phe Thr Asp Thr Val Val Lys Leu Asn Leu Gln Met
            180                 185                 190

Leu Ala Ala Val Ala Glu Asp Ser Ser Ser Ala Ser Arg Arg Arg Asp
        195                 200                 205

<210> SEQ ID NO 53
<211> LENGTH: 186
<212> TYPE: PRT
<213> ORGANISM: Capsicum annuum
<220> FEATURE:
<223> OTHER INFORMATION: pepper cultivar hanbyul, CAPIP1 protein,
      GenBank Accession No. AAT35532.1

<400> SEQUENCE: 53

Met Met Asn Ala Asn Gly Phe Ser Gly Val Glu Lys Glu Tyr Ile Arg
1               5                   10                  15

Lys His His Leu His Gln Pro Lys Glu Asn Gln Cys Ser Ser Phe Leu
            20                  25                  30

Val Lys His Ile Arg Ala Pro Val His Leu Val Trp Ser Leu Val Arg
        35                  40                  45

Arg Phe Asp Gln Pro Gln Lys Tyr Lys Pro Phe Val Ser Arg Cys Ile
    50                  55                  60

Ala Gln Gly Asp Leu Glu Ile Gly Ser Leu Arg Glu Val Asp Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Ser Phe Arg Ile Ile Gly Gly Asp His Arg
            100                 105                 110

Leu Arg Asn Tyr Ser Ser Ile Ile Ser Leu His Pro Glu Val Ile Asp
        115                 120                 125

Gly Arg Pro Gly Thr Leu Val Ile Glu Ser Phe Val Val Asp Val Pro
130                 135                 140

```
Gln Gly Asn Thr Lys Asp Glu Thr Cys Tyr Phe Val Glu Ala Leu Ile
145                 150                 155                 160

Asn Cys Asn Leu Lys Ser Leu Ala Asp Val Ser Glu Arg Leu Ala Val
                165                 170                 175

Gln Asp Arg Thr Glu Pro Ile Asp Gln Val
            180                 185

<210> SEQ ID NO 54
<211> LENGTH: 186
<212> TYPE: PRT
<213> ORGANISM: Populus trichocarpa
<220> FEATURE:
<223> OTHER INFORMATION: California poplar (Western balsam poplar, black
      cottonwood) cultivar 383-2499 (Nisqually-1), unknown protein,
      clone PX0011_1113, GenBank Accession No. ABK92491.1

<400> SEQUENCE: 54

Met Asn Gly Ser Asp Ala Tyr Ser Ala Thr Glu Ala Gln Tyr Val Arg
1               5                   10                  15

Arg His His Lys His Glu Pro Arg Glu Asn Gln Cys Thr Ser Ala Leu
                20                  25                  30

Val Lys His Ile Lys Ala Pro Ala His Leu Val Trp Ser Leu Val Arg
            35                  40                  45

Arg Phe Asp Gln Pro Gln Arg Tyr Lys Pro Phe Val Ser Arg Cys Val
    50                  55                  60

Met Asn Gly Glu Leu Gly Ile Gly Ser Val Arg Glu Val Asn Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Gly Val Gln Ile Val Gly Gly Asp His Arg
            100                 105                 110

Leu Lys Asn Tyr Ser Ser Ile Met Thr Val His Pro Glu Phe Ile Asp
        115                 120                 125

Gly Arg Pro Gly Thr Leu Val Ile Glu Ser Phe Ile Val Asp Val Pro
    130                 135                 140

Asp Gly Asn Thr Lys Asp Glu Thr Cys Tyr Phe Val Glu Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
            180                 185

<210> SEQ ID NO 55
<211> LENGTH: 185
<212> TYPE: PRT
<213> ORGANISM: Capsicum annuum
<220> FEATURE:
<223> OTHER INFORMATION: pepper cultivar hanbyul, PIP1 protein, GenBank
      Accession No. ABF72432.1

<400> SEQUENCE: 55

Met Asn Ala Asn Gly Phe Ser Gly Val Glu Lys Glu Tyr Ile Arg Lys
1               5                   10                  15

His His Leu His Gln Pro Lys Glu Asn Gln Cys Ser Ser Phe Leu Val
                20                  25                  30

Lys His Ile Arg Ala Pro Val His Leu Val Trp Ser Leu Val Arg Arg
            35                  40                  45

Phe Asp Gln Pro Gln Lys Tyr Lys Pro Phe Val Ser Arg Cys Ile Ala
```

```
                     50                  55                  60

Gln Gly Asp Leu Glu Ile Gly Ser Leu Arg Glu Val Asp Val Lys Ser
 65                  70                  75                  80

Gly Leu Pro Ala Thr Thr Ser Thr Glu Arg Leu Glu Leu Leu Asp Asp
                     85                  90                  95

Glu Glu His Ile Leu Ser Phe Arg Ile Gly Gly Asp His Arg Leu
                    100                 105                 110

Arg Asn Tyr Ser Ser Ile Ile Ser Leu His Pro Glu Val Ile Asp Gly
                115                 120                 125

Arg Pro Gly Thr Leu Val Ile Glu Ser Phe Val Val Asp Val Pro Gln
            130                 135                 140

Gly Asn Thr Lys Asp Glu Thr Cys Tyr Phe Val Glu Ala Leu Ile Asn
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Gln Val
            180                 185

<210> SEQ ID NO 56
<211> LENGTH: 186
<212> TYPE: PRT
<213> ORGANISM: Populus trichocarpa x Populus deltoides
<220> FEATURE:
<223> OTHER INFORMATION: California poplar (Western balsam poplar, black
      cottonwood) x Eastern cottonwood, cultivar H11-11, unknown
      protein, clone WS0133_I04, GenBank Accession No. ABK96505.1

<400> SEQUENCE: 56

Met Asn Gly Ser Asp Ala Tyr Ser Ala Thr Glu Ala Gln Tyr Val Arg
  1               5                  10                  15

Arg His His Lys His Glu Pro Arg Glu Asn Gln Cys Thr Ser Ala Leu
                 20                  25                  30

Val Lys His Ile Lys Ala Pro Ala His Leu Val Trp Ser Leu Val Arg
             35                  40                  45

Arg Phe Asp Gln Pro Gln Arg Tyr Lys Pro Phe Val Ser Arg Cys Val
         50                  55                  60

Met Asn Gly Glu Leu Gly Ile Gly Ser Val Arg Glu Val Asn Val Lys
 65                  70                  75                  80

Ser Gly Leu Pro Ala Thr Thr Ser Thr Glu Arg Leu Glu Leu Leu Asp
                 85                  90                  95

Asp Glu Glu His Ile Leu Gly Val Gln Ile Val Gly Gly Asp His Arg
            100                 105                 110

Leu Lys Asn Tyr Ser Ser Ile Met Thr Val His Pro Glu Phe Ile Asp
        115                 120                 125

Gly Arg Pro Gly Thr Leu Val Ile Glu Ser Phe Ile Val Asp Val Pro
    130                 135                 140

Asp Gly Asn Thr Lys Asp Glu Thr Cys Tyr Phe Val Lys Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
            180                 185

<210> SEQ ID NO 57
<211> LENGTH: 188
<212> TYPE: PRT
<213> ORGANISM: Pisum sativum
```

<220> FEATURE:
<223> OTHER INFORMATION: pea AT-rich element binding factor 3 (PsATF, ATF3), potential transcription factor, GenBank Accession No. AAV85853.1

<400> SEQUENCE: 57

```
Met Asn Asn Gly Gly Glu Gln Tyr Ser Ala Ile Glu Thr Gln Tyr Ile
1               5                  10                  15

Arg Arg Arg His Lys His Asp Leu Arg Asp Asn Gln Cys Ser Ser Ala
            20                  25                  30

Leu Val Lys His Ile Lys Ala Pro Val His Leu Val Trp Ser Leu Val
        35                  40                  45

Arg Arg Phe Asp Gln Pro Gln Lys Tyr Lys Pro Phe Val Ser Arg Cys
    50                  55                  60

Ile Met Gln Gly Asp Leu Gly Ile Gly Ser Val Arg Glu Val Asn Val
65                  70                  75                  80

Lys Ser Gly Leu Pro Ala Thr Thr Ser Thr Glu Arg Leu Glu Gln Leu
                85                  90                  95

Asp Asp Glu Glu His Ile Leu Gly Ile Arg Ile Val Gly Gly Asp His
            100                 105                 110

Arg Leu Arg Asn Tyr Ser Ser Val Ile Thr Val His Pro Glu Val Ile
        115                 120                 125

Asp Gly Arg Pro Gly Thr Met Val Ile Glu Ser Phe Val Val Asp Val
    130                 135                 140

Pro Glu Gly Asn Thr Arg Asp Glu Thr Cys Tyr Phe Val Glu Ala Leu
145                 150                 155                 160

Ile Arg Gly Asn Leu Ser Ser Leu Ala Asp Val Ser Glu Arg Met Ala
                165                 170                 175

Val Gln Gly Arg Thr Asp Pro Ile Asn Val Asn Pro
            180                 185
```

<210> SEQ ID NO 58
<211> LENGTH: 177
<212> TYPE: PRT
<213> ORGANISM: Vitis vinifera
<220> FEATURE:
<223> OTHER INFORMATION: wine grape cultivar PN40024 unnamed protein product, locus tag GSVIVT00027009001, GenBank Accession No. CAO39744.1

<400> SEQUENCE: 58

```
Met Glu Ala Gln Val Ile Cys Arg His His Ala His Glu Pro Arg Glu
1               5                  10                  15

Asn Gln Cys Ser Ser Val Leu Val Arg His Val Lys Ala Pro Ala Asn
            20                  25                  30

Leu Val Trp Ser Leu Val Arg Arg Phe Asp Gln Pro Gln Lys Tyr Lys
        35                  40                  45

Pro Phe Val Ser Arg Cys Val Val Gln Gly Asp Leu Arg Ile Gly Ser
    50                  55                  60

Val Arg Glu Val Asn Val Lys Thr Gly Leu Pro Ala Thr Thr Ser Thr
65                  70                  75                  80

Glu Arg Leu Glu Leu Phe Asp Asp Asp Glu His Val Leu Gly Ile Lys
                85                  90                  95

Ile Leu Asp Gly Asp His Arg Leu Arg Asn Tyr Ser Ser Val Ile Thr
            100                 105                 110

Val His Pro Glu Ile Ile Asp Gly Arg Pro Gly Thr Leu Val Ile Glu
        115                 120                 125
```

```
Ser Phe Val Val Asp Val Pro Glu Gly Asn Thr Lys Asp Asp Thr Cys
    130                 135                 140

Tyr Phe Val Arg Ala Leu Ile Asn Cys Asn Leu Lys Cys Leu Ala Glu
145                 150                 155                 160

Val Ser Glu Arg Met Ala Met Leu Gly Arg Val Glu Pro Ala Asn Ala
                165                 170                 175

Val

<210> SEQ ID NO 59
<211> LENGTH: 178
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_004915, GenBank
      Accession No. CAN82501.1

<400> SEQUENCE: 59

Met Met Glu Ala Gln Val Ile Cys Arg His His Ala His Glu Pro Arg
1               5                   10                  15

Glu Asn Gln Cys Ser Ser Val Leu Val Arg His Val Lys Ala Pro Ala
                20                  25                  30

Asn Leu Val Trp Ser Leu Val Arg Arg Phe Asp Gln Pro Gln Lys Tyr
            35                  40                  45

Lys Pro Phe Val Ser Arg Cys Val Val Gln Gly Asp Leu Arg Ile Gly
    50                  55                  60

Ser Val Arg Glu Val Asn Val Lys Thr Gly Leu Pro Ala Thr Thr Ser
65                  70                  75                  80

Thr Glu Arg Leu Glu Leu Phe Asp Asp Asp Glu His Val Leu Gly Ile
                85                  90                  95

Lys Ile Leu Asp Gly Asp His Arg Leu Arg Asn Tyr Ser Ser Val Ile
            100                 105                 110

Thr Val His Pro Glu Ile Ile Asp Gly Arg Pro Gly Thr Leu Val Ile
        115                 120                 125

Glu Ser Phe Val Val Asp Val Pro Glu Gly Asn Thr Lys Asp Asp Thr
    130                 135                 140

Cys Tyr Phe Val Arg Ala Leu Ile Asn Cys Asn Leu Lys Cys Leu Ala
145                 150                 155                 160

Glu Val Ser Glu Arg Met Ala Met Leu Gly Arg Val Glu Pro Ala Asn
                165                 170                 175

Ala Val

<210> SEQ ID NO 60
<211> LENGTH: 193
<212> TYPE: PRT
<213> ORGANISM: Arachis hypogaea
<220> FEATURE:
<223> OTHER INFORMATION: peanut pathogenesis-induced protein (PIP),
      GenBank Accession No. ACG76109.1
<220> FEATURE:
<221> NAME/KEY: VARIANT
<222> LOCATION: (162)...(162)
<223> OTHER INFORMATION: Xaa = any amino acid

<400> SEQUENCE: 60

Met Met Asn Gly Ser Cys Gly Gly Gly Gly Gly Glu Ala Tyr Gly
1               5                   10                  15

Ala Ile Glu Ala Gln Tyr Ile Arg Arg His His Arg His Glu Pro Arg
                20                  25                  30
```

-continued

```
Asp Asn Gln Cys Thr Ser Ala Leu Val Lys His Ile Arg Ala Pro Val
            35                  40                  45

His Leu Val Trp Ser Leu Val Arg Arg Phe Asp Gln Pro Gln Lys Tyr
 50                  55                  60

Lys Pro Phe Val Ser Arg Cys Ile Met Gln Gly Asp Leu Gly Ile Gly
 65                  70                  75                  80

Ser Val Arg Glu Val Asn Val Lys Ser Gly Leu Pro Ala Thr Thr Ser
                 85                  90                  95

Thr Glu Arg Leu Glu Gln Leu Asp Asp Glu His Ile Leu Gly Ile
            100                 105                 110

Arg Ile Val Gly Gly Asp His Arg Leu Arg Asn Tyr Ser Ser Ile Ile
        115                 120                 125

Thr Val His Pro Glu Val Ile Glu Gly Arg Pro Gly Thr Met Val Ile
    130                 135                 140

Glu Ser Phe Val Val Asp Val Pro Asp Gly Asn Thr Lys Asp Glu Thr
145                 150                 155                 160

Cys Xaa Phe Val Glu Ala Leu Ile Arg Cys Asn Leu Ser Ser Leu Ala
                165                 170                 175

Asp Val Ser Glu Arg Met Ala Val Gln Gly Arg Thr Asp Pro Ile Asn
            180                 185                 190

Gln

<210> SEQ ID NO 61
<211> LENGTH: 217
<212> TYPE: PRT
<213> ORGANISM: Zea mays
<220> FEATURE:
<223> OTHER INFORMATION: maize AT-rich element binding factor 3, clone
      300908, GenBank Accession No. ACG39386.1

<400> SEQUENCE: 61

Met Val Val Glu Met Asp Gly Gly Val Gly Val Ala Ala Gly Gly Gly
 1               5                  10                  15

Gly Gly Ala Gln Thr Pro Ala Pro Ala Pro Pro Arg Arg Trp Arg Leu
             20                  25                  30

Ala Asp Glu Arg Cys Asp Leu Arg Ala Met Glu Thr Asp Tyr Val Arg
         35                  40                  45

Arg Phe His Arg His Glu Pro Arg Asp His Gln Cys Ser Ser Ala Val
 50                  55                  60

Ala Lys His Ile Lys Ala Pro Val His Leu Val Trp Ser Leu Val Arg
 65                  70                  75                  80

Arg Phe Asp Gln Pro Gln Leu Phe Lys Pro Phe Val Ser Arg Cys Glu
                 85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
        115                 120                 125

Asp Asp Glu Arg Ile Leu Ser Val Arg Phe Val Gly Gly Asp His Arg
    130                 135                 140

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Val Asp Val Pro
                165                 170                 175

Asp Gly Asn Thr Lys Asp Glu Thr Cys Tyr Phe Val Glu Ala Leu Leu
            180                 185                 190
```

```
Lys Cys Asn Leu Arg Ser Leu Ala Glu Val Ser Glu Gly Gln Val Ile
            195                 200                 205

Met Asp Gln Thr Glu Pro Leu Asp Arg
    210                 215
```

<210> SEQ ID NO 62
<211> LENGTH: 217
<212> TYPE: PRT
<213> ORGANISM: Zea mays
<220> FEATURE:
<223> OTHER INFORMATION: maize strain B73, unknown protein, clone
      ZM_BFb0036A01, GenBank Accession No. ACF80077.1

<400> SEQUENCE: 62

```
Met Val Val Glu Met Asp Gly Gly Val Gly Val Ala Ala Ala Gly Gly
1               5                   10                  15

Gly Gly Ala Gln Thr Pro Ala Pro Pro Pro Arg Arg Trp Arg Leu
            20                  25                  30

Ala Asp Glu Arg Cys Asp Leu Arg Ala Met Glu Thr Asp Tyr Val Arg
        35                  40                  45

Arg Phe His Arg His Glu Pro Arg Asp His Gln Cys Ser Ser Ala Val
    50                  55                  60

Ala Lys His Ile Lys Ala Pro Val His Leu Val Trp Ser Leu Val Arg
65                  70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
        115                 120                 125

Asp Asp Glu Arg Ile Leu Ser Val Arg Phe Val Gly Asp His Arg
    130                 135                 140

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Val Asp Val Pro
                165                 170                 175

Asp Gly Asn Thr Lys Asp Glu Thr Cys Tyr Phe Val Glu Ala Leu Leu
            180                 185                 190

Lys Cys Asn Leu Arg Ser Leu Ala Glu Val Ser Glu Gly Gln Val Ile
        195                 200                 205

Met Asp Gln Thr Glu Pro Leu Asp Arg
    210                 215
```

<210> SEQ ID NO 63
<211> LENGTH: 206
<212> TYPE: PRT
<213> ORGANISM: Oryza sativa
<220> FEATURE:
<223> OTHER INFORMATION: rice Japonica Group, cultivar Nipponbare,
      hypothetical protein Os06g0528300, GenBank Accession No.
      NP_001057772.1

<400> SEQUENCE: 63

```
Met Asn Gly Val Gly Gly Ala Gly Gly Ala Ala Gly Lys Leu Pro
1               5                   10                  15

Met Val Ser His Arg Arg Val Gln Trp Arg Leu Ala Asp Glu Arg Cys
            20                  25                  30

Glu Leu Arg Glu Glu Glu Met Glu Tyr Ile Arg Arg Phe His Arg His
        35                  40                  45
```

```
Glu Pro Ser Ser Asn Gln Cys Thr Ser Phe Ala Ala Lys His Ile Lys
        50                  55                  60

Ala Pro Leu His Thr Val Trp Ser Leu Val Arg Arg Phe Asp Gln Pro
 65                  70                  75                  80

Gln Leu Phe Lys Pro Phe Val Arg Asn Cys Val Met Arg Glu Asn Ile
                 85                  90                  95

Ile Ala Thr Gly Cys Ile Arg Glu Val Asn Val Gln Ser Gly Leu Pro
               100                 105                 110

Ala Thr Arg Ser Thr Glu Arg Leu Glu Leu Leu Asp Asp Asn Glu His
           115                 120                 125

Ile Leu Lys Val Asn Phe Ile Gly Gly Asp His Met Leu Lys Asn Tyr
       130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Pro Glu Gly Asn Thr
                165                 170                 175

Lys Asp Asp Ile Ser Tyr Phe Ile Glu Asn Val Leu Arg Cys Asn Leu
            180                 185                 190

Arg Thr Leu Ala Asp Val Ser Glu Glu Arg Leu Ala Asn Pro
        195                 200                 205

<210> SEQ ID NO 64
<211> LENGTH: 206
<212> TYPE: PRT
<213> ORGANISM: Oryza sativa
<220> FEATURE:
<223> OTHER INFORMATION: rice Indica Group, cultivar 93-11, hypothetical
      protein OsI_23215, GenBank Accession No. EAZ01188.1

<400> SEQUENCE: 64

Met Asn Gly Ala Gly Gly Ala Gly Gly Ala Ala Ala Gly Lys Leu Pro
 1               5                  10                  15

Met Val Ser His Arg Gln Val Gln Trp Arg Leu Ala Asp Glu Arg Cys
            20                  25                  30

Glu Leu Arg Glu Glu Glu Met Glu Tyr Ile Arg Gln Phe His Arg His
         35                  40                  45

Glu Pro Ser Ser Asn Gln Cys Thr Ser Phe Val Ala Lys His Ile Lys
     50                  55                  60

Ala Pro Leu Gln Thr Val Trp Ser Leu Val Arg Arg Phe Asp Gln Pro
 65                  70                  75                  80

Gln Leu Phe Lys Pro Phe Val Arg Lys Cys Val Met Arg Glu Asn Ile
                 85                  90                  95

Ile Ala Thr Gly Cys Val Arg Glu Val Asn Val Gln Ser Gly Leu Pro
               100                 105                 110

Ala Thr Arg Ser Thr Glu Arg Leu Glu Leu Leu Asp Asp Asn Glu His
           115                 120                 125

Ile Leu Lys Val Lys Phe Ile Gly Gly Asp His Met Leu Lys Asn Tyr
       130                 135                 140

Ser Ser Ile Leu Thr Ile His Ser Glu Val Ile Asp Gly Gln Leu Gly
145                 150                 155                 160

Thr Leu Val Val Glu Ser Phe Val Val Asp Ile Pro Glu Gly Asn Thr
                165                 170                 175

Lys Asp Asp Ile Cys Tyr Phe Ile Glu Asn Ile Leu Arg Cys Asn Leu
            180                 185                 190

Met Thr Leu Ala Asp Val Ser Glu Glu Arg Leu Ala Asn Pro
        195                 200                 205
```

```
                   195                 200                 205

<210> SEQ ID NO 65
<211> LENGTH: 205
<212> TYPE: PRT
<213> ORGANISM: Oryza sativa
<220> FEATURE:
<223> OTHER INFORMATION: rice Japonica Group, cultivar Nipponbare,
      hypothetical protein OsJ_06125, GenBank Accession No. EAZ22456.1

<400> SEQUENCE: 65

Met Val Glu Val Gly Gly Gly Ala Ala Glu Ala Ala Ala Gly Arg Arg
1               5                   10                  15

Trp Arg Leu Ala Asp Glu Arg Cys Asp Leu Arg Ala Ala Glu Thr Glu
            20                  25                  30

Tyr Val Arg Arg Phe His Arg His Glu Pro Arg Asp His Gln Cys Ser
        35                  40                  45

Ser Ala Val Ala Lys His Ile Lys Ala Pro Val His Leu Val Trp Ser
    50                  55                  60

Leu Val Arg Arg Phe Asp Gln Pro Gln Leu Phe Lys Pro Phe Val Ser
65                  70                  75                  80

Arg Cys Glu Met Lys Gly Asn Ile Glu Ile Gly Ser Val Arg Glu Val
                85                  90                  95

Asn Val Lys Ser Gly Leu Pro Ala Thr Arg Ser Thr Glu Arg Leu Glu
            100                 105                 110

Leu Leu Asp Asp Asn Glu His Ile Leu Ser Val Arg Phe Val Gly Gly
        115                 120                 125

Asp His Arg Leu Lys Asn Tyr Ser Ser Ile Leu Thr Val His Pro Glu
    130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
            180                 185                 190

Leu Val Cys Gln Gly Pro Asn Arg Ala Pro Ser Thr Arg
        195                 200                 205

<210> SEQ ID NO 66
<211> LENGTH: 204
<212> TYPE: PRT
<213> ORGANISM: Oryza sativa
<220> FEATURE:
<223> OTHER INFORMATION: rice Japonica Group, cultivar Nipponbare,
      hypothetical protein Os02g0255500, similar to extensin (fragment),
      GenBank Accession No. NP_001046464.1

<400> SEQUENCE: 66

Met Val Glu Val Gly Gly Gly Ala Ala Glu Ala Ala Ala Gly Arg Arg
1               5                   10                  15

Trp Arg Leu Ala Asp Glu Arg Cys Asp Leu Arg Ala Ala Glu Thr Glu
            20                  25                  30

Tyr Val Arg Arg Phe His Arg His Glu Pro Arg Asp His Gln Cys Ser
        35                  40                  45

Ser Ala Val Ala Lys His Ile Lys Ala Pro Val His Leu Val Trp Ser
    50                  55                  60

Leu Val Arg Arg Phe Asp Gln Pro Gln Leu Phe Lys Pro Phe Val Ser
65                  70                  75                  80
```

```
Arg Cys Glu Met Lys Gly Asn Ile Glu Ile Gly Ser Val Arg Glu Val
                85                  90                  95

Asn Val Lys Ser Gly Leu Pro Ala Thr Arg Ser Thr Glu Arg Leu Glu
            100                 105                 110

Leu Leu Asp Asp Asn Glu His Ile Leu Ser Val Arg Phe Val Gly Gly
            115                 120                 125

Asp His Arg Leu Lys Asn Tyr Ser Ser Ile Leu Thr Val His Pro Glu
            130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
            180                 185                 190

Leu Val Val Lys Asp Gln Thr Glu Pro Leu Asp Arg
            195                 200

<210> SEQ ID NO 67
<211> LENGTH: 199
<212> TYPE: PRT
<213> ORGANISM: Medicago truncatula
<220> FEATURE:
<223> OTHER INFORMATION: barrel medic unknown protein, clone
      MTYFP_FQ_FR_FS1G-G-11, GenBank Accession No. ACJ86004.1

<400> SEQUENCE: 67

Met Glu Lys Met Asn Gly Thr Glu Asn Gly Val Phe Asn Ser Thr
1               5                   10                  15

Glu Met Glu Tyr Ile Arg Arg His His Asn Gln Gln Pro Gly Glu Asn
                20                  25                  30

Gln Cys Ser Ser Ala Leu Val Lys His Ile Arg Ala Pro Val Pro Leu
            35                  40                  45

Val Trp Ser Leu Val Arg Arg Phe Asp Gln Pro Gln Lys Tyr Lys Pro
50                  55                  60

Phe Val Ser Arg Cys Val Val Arg Gly Asn Leu Glu Ile Gly Ser Leu
65                  70                  75                  80

Arg Glu Val Asp Val Lys Ser Gly Leu Pro Ala Thr Thr Ser Thr Glu
                85                  90                  95

Arg Leu Glu Val Leu Asp Asp Asn Glu His Ile Leu Ser Ile Arg Ile
            100                 105                 110

Ile Gly Gly Asp His Arg Leu Arg Asn Tyr Ser Ser Ile Met Ser Leu
            115                 120                 125

His Pro Glu Ile Ile Asp Gly Arg Pro Gly Thr Leu Val Ile Glu Ser
            130                 135                 140

Phe Val Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
                165                 170                 175

Ser Glu Gly His Ala Val Gln Asp Leu Thr Glu Pro Leu Asp Arg Val
            180                 185                 190

His Glu Leu Leu Ile Ser Gly
            195

<210> SEQ ID NO 68
<211> LENGTH: 199
<212> TYPE: PRT
<213> ORGANISM: Medicago truncatula
```

-continued

<220> FEATURE:
<223> OTHER INFORMATION: barrel medic unknown protein, clone
     MTYF1_F2_F3_FY1G-K-4, GenBank Accession No. ACJ83958.1

<400> SEQUENCE: 68

Met Glu Lys Met Asn Gly Thr Glu Asn Asn Gly Val Phe Asn Ser Thr
1               5                   10                  15

Glu Met Glu Tyr Ile Arg Arg His His Asn Gln Gln Pro Gly Glu Asn
            20                  25                  30

Gln Cys Ser Ser Ala Leu Val Lys His Ile Arg Ala Pro Val Pro Leu
        35                  40                  45

Val Trp Ser Leu Val Arg Arg Phe Asp Gln Pro Gln Lys Tyr Lys Pro
    50                  55                  60

Phe Val Ser Arg Cys Val Val Arg Gly Asn Leu Glu Ile Gly Ser Leu
65                  70                  75                  80

Arg Glu Val Asp Val Lys Ser Gly Leu Pro Ala Thr Thr Ser Thr Glu
                85                  90                  95

Arg Leu Glu Val Leu Asp Asp Asn Glu His Ile Leu Ser Ile Arg Ile
            100                 105                 110

Ile Gly Gly Asp His Arg Leu Arg Asn Tyr Ser Ser Ile Met Ser Leu
        115                 120                 125

His Pro Glu Ile Ile Asp Gly Arg Pro Gly Thr Leu Val Ile Glu Ser
    130                 135                 140

Phe Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
                165                 170                 175

Ser Glu Gly His Ala Ala Gln Asp Leu Thr Glu Pro Leu Asp Arg Met
            180                 185                 190

His Glu Leu Leu Ile Ser Gly
        195

<210> SEQ ID NO 69
<211> LENGTH: 197
<212> TYPE: PRT
<213> ORGANISM: Zea mays
<220> FEATURE:
<223> OTHER INFORMATION: maize CAPIP1 protein, clone 244179, GenBank
     Accession No. ACG34726.1

<400> SEQUENCE: 69

Met Val Gly Leu Val Gly Gly Ser Thr Ala Arg Ala Glu His Val Val
1               5                   10                  15

Ala Asn Ala Gly Gly Glu Ala Glu Tyr Val Arg Arg Met His Arg His
            20                  25                  30

Ala Pro Thr Glu His Gln Cys Thr Ser Thr Leu Val Lys His Ile Lys
        35                  40                  45

Ala Pro Val His Leu Val Trp Gln Leu Val Arg Arg Phe Asp Gln Pro
    50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
        115                 120                 125

-continued

Ser Ser Ile Ile Thr Val His Pro Glu Ser Ile Asp Gly Arg Pro Gly
            130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
            165                 170                 175

Asn Ser Leu Ala Glu Val Ser Glu Gln Leu Ala Val Glu Ser Pro Thr
            180                 185                 190

Ser Leu Ile Asp Gln
        195

<210> SEQ ID NO 70
<211> LENGTH: 197
<212> TYPE: PRT
<213> ORGANISM: Zea mays
<220> FEATURE:
<223> OTHER INFORMATION: maize CAPIP1 protein, clone 1448906, GenBank
      Accession No. ACG26022.1

<400> SEQUENCE: 70

Met Val Gly Leu Val Gly Gly Ser Thr Ala Arg Ala Glu His Val Val
1               5                   10                  15

Ala Asn Ala Gly Gly Glu Ala Glu Tyr Val Arg Arg Met His Arg His
            20                  25                  30

Ala Pro Thr Glu His Gln Cys Thr Ser Thr Leu Val Lys His Ile Lys
            35                  40                  45

Ala Pro Val His Leu Val Trp Glu Leu Val Arg Arg Phe Asp Gln Pro
    50                  55                  60

Gln Arg Tyr Lys Pro Phe Val Arg Asn Cys Val Val Arg Gly Asp Gln
65              70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
            115                 120                 125

Ser Ser Ile Ile Thr Val His Pro Glu Ser Ile Asp Gly Arg Pro Gly
            130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
            165                 170                 175

Asn Ser Leu Ala Glu Val Ser Glu Gln Leu Ala Val Glu Ser Pro Thr
            180                 185                 190

Ser Leu Ile Asp Gln
        195

<210> SEQ ID NO 71
<211> LENGTH: 212
<212> TYPE: PRT
<213> ORGANISM: Zea mays
<220> FEATURE:
<223> OTHER INFORMATION: maize strain B73 unknown protein, clone
      ZM_BFc0183D21, GenBank Accession No. ACF86162.1

<400> SEQUENCE: 71

Met Val Met Val Glu Met Asp Gly Gly Val Gly Gly Gly Gly Gly Gly
1               5                   10                  15

Gly Gln Thr Pro Ala Pro Arg Arg Trp Arg Leu Ala Asp Glu Arg Cys
            20                  25                  30

Asp Leu Arg Ala Met Glu Thr Asp Tyr Val Arg Arg Phe His Arg His
        35                  40                  45

Glu Pro Arg Glu His Gln Cys Ser Ser Ala Val Ala Lys His Ile Lys
    50                  55                  60

Ala Pro Val His Leu Val Trp Ser Leu Val Arg Arg Phe Asp Gln Pro
65                  70                  75                  80

Gln Leu Phe Lys Pro Phe Val Ser Arg Cys Glu Met Lys Gly Asn Ile
                85                  90                  95

Glu Ile Gly Ser Val Arg Glu Val Asn Val Lys Ser Gly Leu Pro Ala
            100                 105                 110

Thr Arg Ser Thr Glu Arg Leu Glu Leu Leu Asp Asp Asn Glu His Ile
        115                 120                 125

Leu Ser Val Arg Phe Val Gly Gly Asp His Arg Leu Gln Asn Tyr Ser
130                 135                 140

Ser Ile Leu Thr Val His Pro Glu Val Ile Asp Gly Arg Pro Gly Thr
145                 150                 155                 160

Leu Val Ile Glu Ser Phe Val Val Asp Val Pro Asp Gly Asn Thr Lys
                165                 170                 175

Asp Glu Thr Cys Tyr Phe Val Gly Ala Leu Leu Lys Cys Asn Leu Lys
            180                 185                 190

Ser Leu Ala Glu Val Ser Glu Arg Gln Val Val Lys Asp Gln Thr Glu
        195                 200                 205

Pro Leu Asp Arg
    210

<210> SEQ ID NO 72
<211> LENGTH: 205
<212> TYPE: PRT
<213> ORGANISM: Oryza sativa
<220> FEATURE:
<223> OTHER INFORMATION: rice Japonica Group, cultivar Nipponbare,
      conserved hypothetical protein Os06g0527800, GenBank Accession No.
      NP_001057771.1

<400> SEQUENCE: 72

Met Asn Gly Ala Gly Gly Ala Gly Gly Ala Ala Gly Lys Leu Pro
1               5                   10                  15

Met Val Ser His Arg Arg Val Gln Cys Arg Leu Ala Asp Lys Arg Cys
            20                  25                  30

Glu Leu Arg Glu Glu Glu Met Glu Tyr Ile Arg Gln Phe His Arg His
        35                  40                  45

Glu Pro Ser Ser Asn Gln Cys Thr Ser Phe Val Ala Lys His Ile Lys
    50                  55                  60

Ala Pro Leu Gln Thr Val Trp Ser Leu Val Arg Arg Phe Asp Gln Pro
65                  70                  75                  80

Gln Leu Phe Lys Pro Phe Val Arg Lys Cys Val Met Arg Glu Asn Ile
                85                  90                  95

Ile Val Thr Gly Cys Val Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

Ile Leu Lys Val Lys Phe Ile Gly Gly Asp His Met Leu Lys Asn Tyr
130                 135                 140

```
Ser Ser Ile Leu Thr Ile His Ser Glu Val Ile Asp Gly Gln Leu Gly
145                 150                 155                 160

Thr Leu Val Val Glu Ser Phe Val Val Asp Ile Pro Asp Gly Asn Thr
                165                 170                 175

Lys Asp Asp Ile Cys Tyr Phe Ile Glu Asn Val Leu Arg Cys Asn Leu
            180                 185                 190

Met Thr Leu Ala Asp Val Ser Glu Glu Arg Leu Ala Asn
        195                 200                 205

<210> SEQ ID NO 73
<211> LENGTH: 197
<212> TYPE: PRT
<213> ORGANISM: Zea mays
<220> FEATURE:
<223> OTHER INFORMATION: maize strain B73 unknown protein, clone
      ZM_BFc0063E17, GenBank Accession No. ACF85073.1

<400> SEQUENCE: 73

Met Val Gly Leu Val Gly Gly Ser Thr Ala Arg Ala Glu His Val Val
1               5                   10                  15

Ala Asn Ala Gly Gly Glu Thr Glu Tyr Val Arg Arg Leu His Arg His
            20                  25                  30

Ala Pro Ala Glu His Gln Cys Thr Ser Thr Leu Val Lys His Ile Lys
        35                  40                  45

Ala Pro Val His Leu Val Trp Glu Leu Val Arg Ser Phe Asp Gln Pro
    50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
        115                 120                 125

Ser Ser Ile Ile Thr Val His Pro Glu Ser Ile Asp Gly Arg Pro Gly
    130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Lys Ser Leu Ala Glu Val Ser Glu Gln Leu Ala Val Glu Ser Pro Thr
            180                 185                 190

Ser Pro Ile Asp Gln
        195

<210> SEQ ID NO 74
<211> LENGTH: 206
<212> TYPE: PRT
<213> ORGANISM: Oryza sativa
<220> FEATURE:
<223> OTHER INFORMATION: rice Indica Group, cultivar 93-11, hypothetical
      protein OsI_23218, GenBank Accession No. EAZ01191.1

<400> SEQUENCE: 74

Met Asn Gly Val Gly Gly Ala Gly Gly Ala Ala Ala Gly Lys Leu Pro
1               5                   10                  15

Met Val Ser His Arg Arg Val Gln Trp Arg Leu Ala Asp Glu Arg Cys
            20                  25                  30
```

Glu Leu Arg Glu Glu Met Glu Tyr Ile Arg Arg Phe His Arg His
          35                  40                  45

Glu Pro Ser Ser Asn Gln Cys Thr Ser Phe Ala Ala Lys His Ile Lys
 50                  55                  60

Ala Pro Leu His Thr Val Trp Ser Leu Val Arg Arg Phe Asp Gln Pro
 65                  70                  75                  80

Gln Leu Phe Lys Pro Phe Val Arg Asn Cys Val Met Arg Glu Asn Ile
              85                  90                  95

Ile Ala Thr Gly Cys Ile Arg Glu Val Asn Val Gln Ser Gly Leu Pro
             100                 105                 110

Ala Thr Arg Ser Thr Glu Arg Leu Glu Leu Leu Asp Asp Asn Glu His
             115                 120                 125

Ile Leu Lys Val Lys Phe Ile Gly Gly Asp His Met Leu Lys Asn Tyr
130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Leu Glu Gly Asn Thr
                165                 170                 175

Lys Asp Asp Ile Ser Tyr Phe Ile Glu Asn Val Leu Arg Cys Asn Leu
            180                 185                 190

Arg Thr Leu Ala Asp Val Ser Glu Glu Arg Leu Ala Asn Pro
        195                 200                 205

<210> SEQ ID NO 75
<211> LENGTH: 209
<212> TYPE: PRT
<213> ORGANISM: Oryza sativa
<220> FEATURE:
<223> OTHER INFORMATION: rice Japonica Group, cultivar Nipponbare,
      conserved hypothetical protein Os05g0213500, GenBank Accession No.
      NP_001054923.1

<400> SEQUENCE: 75

Met Val Gly Leu Val Gly Gly Gly Gly Trp Arg Val Gly Asp Asp Ala
  1               5                  10                  15

Ala Gly Gly Gly Gly Gly Ala Val Ala Ala Gly Ala Ala Ala Ala
             20                  25                  30

Ala Glu Ala Glu His Met Arg Arg Leu His Ser His Ala Pro Gly Glu
         35                  40                  45

His Gln Cys Ser Ser Ala Leu Val Lys His Ile Lys Ala Pro Val His
 50                  55                  60

Leu Val Trp Ser Leu Val Arg Ser Phe Asp Gln Pro Gln Arg Tyr Lys
 65                  70                  75                  80

Pro Phe Val Ser Arg Cys Val Val Arg Gly Gly Asp Leu Glu Ile Gly
             85                  90                  95

Ser Val Arg Glu Val Asn Val Lys Thr Gly Leu Pro Ala Thr Thr Ser
            100                 105                 110

Thr Glu Arg Leu Glu Leu Leu Asp Asp Glu His Ile Leu Ser Val
            115                 120                 125

Lys Phe Val Gly Gly Asp His Arg Leu Arg Asn Tyr Ser Ser Ile Val
130                 135                 140

Thr Val His Pro Glu Ser Ile Asp Gly Arg Pro Gly Thr Leu Val Ile
145                 150                 155                 160

Glu Ser Phe Val Val Asp Val Pro Asp Gly Asn Thr Lys Asp Glu Thr
                165                 170                 175

Cys Tyr Phe Val Glu Ala Val Ile Lys Cys Asn Leu Thr Ser Leu Ala

```
                    180                 185                 190

Glu Val Ser Glu Arg Leu Ala Val Gln Ser Pro Thr Ser Pro Leu Glu
            195                 200                 205

Gln

<210> SEQ ID NO 76
<211> LENGTH: 180
<212> TYPE: PRT
<213> ORGANISM: Oryza sativa
<220> FEATURE:
<223> OTHER INFORMATION: rice Japonica Group, cultivar Nipponbare,
      Bet v I allergen-like protein, clone OSJNBa0052K15, gene
      OSJNBa0052K15.17, GenBank Accession No. BAD29692.1

<400> SEQUENCE: 76

Met Val Glu Met Asp Ala Gly Gly Arg Pro Glu Pro Ser Pro Pro Ser
1               5                   10                  15

Gly Gln Cys Ser Ser Ala Val Thr Met Arg Ile Asn Ala Pro Val His
            20                  25                  30

Leu Val Trp Ser Ile Val Arg Arg Phe Glu Glu Pro His Ile Phe Gln
        35                  40                  45

Pro Phe Val Arg Gly Cys Thr Met Arg Gly Ser Thr Ser Leu Ala Val
50                  55                  60

Gly Cys Val Arg Glu Val Asp Phe Lys Ser Gly Phe Pro Ala Lys Ser
65                  70                  75                  80

Ser Val Glu Arg Leu Glu Ile Leu Asp Asp Lys Glu His Val Phe Gly
                85                  90                  95

Val Arg Ile Ile Gly Gly Asp His Arg Leu Lys Asn Tyr Ser Ser Val
            100                 105                 110

Leu Thr Ala Lys Pro Glu Val Ile Asp Gly Glu Pro Ala Thr Leu Val
        115                 120                 125

Ser Glu Ser Phe Val Val Asp Val Pro Glu Gly Asn Thr Ala Asp Glu
    130                 135                 140

Thr Arg His Phe Val Glu Phe Leu Ile Arg Cys Asn Leu Arg Ser Leu
145                 150                 155                 160

Ala Met Val Ser Gln Arg Leu Leu Leu Ala Gln Gly Asp Leu Ala Glu
                165                 170                 175

Pro Pro Ala Gln
            180

<210> SEQ ID NO 77
<211> LENGTH: 176
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_029498, GenBank
      Accession No. CAN64668.1

<400> SEQUENCE: 77

Met Asn Gly Asn Gly Leu Ser Ser Met Glu Ser Glu Tyr Ile Arg Arg
1               5                   10                  15

His His Arg His Glu Pro Ala Glu Asn Gln Cys Ser Ser Ala Leu Val
            20                  25                  30

Lys His Ile Lys Ala Pro Val Pro Leu Val Trp Ser Leu Val Arg Arg
        35                  40                  45

Phe Asp Gln Pro Gln Lys Tyr Lys Pro Phe Ile Ser Arg Cys Val Val
50                  55                  60
```

```
Gln Gly Asn Leu Glu Ile Gly Ser Leu Arg Glu Val Asp Val Lys Ser
 65                  70                  75                  80

Gly Leu Pro Ala Thr Thr Ser Thr Glu Arg Leu Glu Leu Leu Asp Asp
                 85                  90                  95

Asp Glu His Ile Leu Ser Met Arg Ile Ile Gly Gly Asp His Arg Leu
            100                 105                 110

Arg Asn Tyr Ser Ser Ile Ile Ser Leu His Pro Glu Ile Ile Asp Gly
        115                 120                 125

Arg Pro Gly Thr Met Val Ile Glu Ser Tyr Val Val Asp Val Pro Glu
    130                 135                 140

Gly Asn Thr Lys Asp Glu Thr Cys Tyr Phe Ser Leu Ala Asp Val Ser
145                 150                 155                 160

Glu Arg Leu Ala Val Ala Gly Thr Val Thr Glu Pro Ile Asp Arg Met
                165                 170                 175

<210> SEQ ID NO 78
<211> LENGTH: 180
<212> TYPE: PRT
<213> ORGANISM: Oryza sativa
<220> FEATURE:
<223> OTHER INFORMATION: rice Indica Group, cultivar 93-11, hypothetical
      protein, locus tag OsI_06615, GenBank Accession No. EEC72859.1

<400> SEQUENCE: 78

Met Val Glu Met Asp Ala Gly Gly Arg Pro Glu Pro Ser Pro Pro Ser
 1               5                  10                  15

Gly Gln Cys Ser Ser Ala Val Thr Met Arg Ile Asn Ala Pro Val His
             20                  25                  30

Leu Val Trp Ser Ile Val Arg Arg Phe Glu Glu Pro His Ile Phe Gln
         35                  40                  45

Pro Phe Val Arg Gly Cys Thr Met Arg Gly Ser Thr Ser Leu Ala Val
     50                  55                  60

Gly Cys Val Arg Glu Val Asp Phe Lys Ser Gly Phe Ser Ala Lys Ser
 65                  70                  75                  80

Ser Val Glu Arg Leu Glu Ile Leu Asp Asp Lys Glu His Val Phe Gly
                 85                  90                  95

Val Arg Ile Ile Gly Gly Asp His Arg Leu Lys Asn Tyr Ser Ser Val
            100                 105                 110

Leu Thr Ala Lys Pro Glu Val Ile Asp Gly Pro Ala Thr Leu Val
        115                 120                 125

Ser Glu Ser Phe Val Ile Asp Val Pro Glu Gly Asn Thr Ala Asp Glu
    130                 135                 140

Thr Arg His Phe Val Glu Phe Leu Ile Arg Cys Asn Leu Arg Ser Leu
145                 150                 155                 160

Ala Met Val Ser Gln Arg Leu Leu Leu Ala Gln Gly Asp Leu Ala Glu
                165                 170                 175

Pro Pro Ala Gln
            180

<210> SEQ ID NO 79
<211> LENGTH: 215
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_10498, GenBank Accession No.
      EAZ26598.1

<400> SEQUENCE: 79
```

-continued

```
Met Pro Cys Ile Pro Ala Ser Ser Pro Gly Ile Pro His Gln His Gln
1               5                   10                  15

His Gln His His Arg Ala Leu Ala Gly Val Gly Met Ala Val Gly Cys
            20                  25                  30

Ala Ala Glu Ala Ala Val Ala Ala Gly Val Ala Gly Thr Arg Cys
        35                  40                  45

Gly Ala His Asp Gly Glu Val Pro Met Glu Val Ala Arg His His Glu
    50                  55                  60

His Ala Glu Pro Gly Ser Gly Arg Cys Cys Ser Ala Val Val Gln His
65                  70                  75                  80

Val Ala Ala Pro Ala Ala Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Leu Gly Lys Val Arg Glu Arg Leu Glu Ile Leu Asp
        115                 120                 125

Asp Glu Ser His Val Leu Ser Phe Arg Val Val Gly Gly Glu His Arg
    130                 135                 140

Leu Lys Asn Tyr Leu Ser Val Thr Thr Val His Pro Ser Pro Ser Ala
145                 150                 155                 160

Pro Thr Ala Ala Thr Val Val Glu Ser Tyr Val Val Asp Val Pro
                165                 170                 175

Pro Gly Asn Thr Pro Glu Asp Thr Arg Val Phe Val Asp Thr Ile Val
            180                 185                 190

Lys Cys Asn Leu Gln Ser Leu Ala Lys Thr Ala Glu Lys Leu Ala Ala
        195                 200                 205

Gly Ala Arg Ala Ala Gly Ser
    210                 215

<210> SEQ ID NO 80
<211> LENGTH: 186
<212> TYPE: PRT
<213> ORGANISM: Rheum australe
<220> FEATURE:
<223> OTHER INFORMATION: Himalayan rhubarb pathogen-induced protein-like
      protein, GenBank Accession No. ACH63237.1

<400> SEQUENCE: 80

Met Asn Gly Asp Gly Tyr Gly Gly Ser Glu Glu Phe Val Lys Arg
1               5                   10                  15

Tyr His Glu His Val Leu Ala Asp His Gln Cys Ser Ser Val Leu Val
            20                  25                  30

Glu His Ile Asn Ala Pro Leu His Leu Val Trp Ser Leu Val Arg Ser
        35                  40                  45

Phe Asp Gln Pro Gln Lys Tyr Lys Pro Phe Val Ser Arg Cys Val Val
    50                  55                  60

Gln Gly Gly Asp Leu Glu Ile Gly Ser Val Arg Glu Val Asp Val Lys
65                  70                  75                  80

Ser Gly Leu Pro Ala Thr Thr Ser Met Glu Glu Leu Glu Leu Leu Asp
                85                  90                  95

Asp Lys Glu His Val Leu Arg Val Lys Phe Val Gly Gly Asp His Arg
            100                 105                 110

Leu Lys Asn Tyr Ser Ser Ile Val Ser Leu His Pro Glu Ile Ile Gly
        115                 120                 125

Gly Arg Ser Gly Thr Met Val Ile Glu Ser Phe Ile Val Asp Ile Ala
```

```
                    130                 135                 140
Asp Gly Asn Thr Lys Glu Glu Thr Cys Tyr Phe Ile Glu Ser Leu Ile
145                 150                 155                 160

Asn Cys Asn Leu Lys Ser Leu Ser Cys Val Ser Glu Arg Leu Ala Val
                165                 170                 175

Glu Asp Ile Ala Glu Arg Ile Ala Gln Met
                180                 185

<210> SEQ ID NO 81
<211> LENGTH: 254
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_016770, GenBank Accession No.
      EAZ33287.1

<400> SEQUENCE: 81

Met Val Gly Leu Val Gly Gly Gly Gly Trp Arg Val Gly Asp Asp Ala
1               5                   10                  15

Ala Gly Gly Gly Gly Gly Ala Val Ala Ala Gly Ala Ala Ala Ala
                20                  25                  30

Ala Glu Ala Glu His Met Arg Arg Leu His Ser Gln Gly Pro Arg Arg
            35                  40                  45

Ala Pro Val Gln Leu Arg Ala Arg Gln Ala His Gln Gly Ser Cys Ser
50                  55                  60

Pro Pro Arg Ile Glu Cys Ala Asn Phe Ala Val Phe Leu Ala Ala Arg
65                  70                  75                  80

Asp Pro Lys Ile Val Trp Ser Leu Val Arg Ser Phe Asp Gln Pro Gln
                85                  90                  95

Arg Tyr Lys Pro Phe Val Ser Arg Cys Val Val Arg Gly Gly Asp Leu
            100                 105                 110

Glu Ile Gly Ser Val Arg Glu Val Asn Val Lys Thr Gly Leu Pro Ala
        115                 120                 125

Thr Thr Ser Thr Glu Arg Leu Glu Leu Leu Asp Asp Asp Glu His Ile
130                 135                 140

Leu Ser Val Lys Phe Val Gly Gly Asp His Arg Leu Arg Asn Tyr Ser
145                 150                 155                 160

Ser Ile Val Thr Val His Pro Glu Ser Ile Asp Gly Arg Pro Gly Thr
                165                 170                 175

Leu Val Ile Glu Ser Phe Val Val Asp Val Pro Asp Gly Asn Thr Lys
            180                 185                 190

Asp Glu Thr Cys Tyr Phe Val Glu Ala Val Ile Lys Cys Asn Leu Thr
        195                 200                 205

Ser Leu Ala Glu Met Val Arg Met Ile Ser Leu Val Leu Pro Phe Met
210                 215                 220

Leu Val Asp Arg Met Ser Gly Ile Thr Cys Glu Ser His Leu Glu Thr
225                 230                 235                 240

Thr Leu Val Arg Cys Gly Glu Tyr Ala Val Leu Ala His Val
                245                 250

<210> SEQ ID NO 82
<211> LENGTH: 186
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_005784, GenBank Accession No.
```

EAZ22301.1

<400> SEQUENCE: 82

| Met | Glu | Pro | His | Met | Glu | Arg | Ala | Leu | Arg | Glu | Ala | Val | Ala | Ser | Glu |
|---|---|---|---|---|---|---|---|---|---|---|---|---|---|---|---|
| 1 | | | | 5 | | | | | 10 | | | | | 15 | |

| Ala | Glu | Arg | Arg | Glu | Leu | Glu | Gly | Val | Val | Arg | Ala | His | His | Thr | Gly |
|---|---|---|---|---|---|---|---|---|---|---|---|---|---|---|---|
| | | | 20 | | | | | 25 | | | | | 30 | | |

| Trp | Asn | Ala | Pro | Leu | Ala | Ala | Val | Trp | Pro | His | Arg | Ala | Arg | Val | Arg |
|---|---|---|---|---|---|---|---|---|---|---|---|---|---|---|---|
| | | 35 | | | | | 40 | | | | | 45 | | | |

| Pro | Thr | Arg | Ser | Gly | Thr | Ser | Thr | Ser | Ser | Ser | Arg | Ala | Ser | Ser | Pro |
|---|---|---|---|---|---|---|---|---|---|---|---|---|---|---|---|
| | 50 | | | | | 55 | | | | | 60 | | | | |

| Pro | Gly | Asp | Gly | Ala | Thr | Val | Gly | Ser | Val | Arg | Glu | Val | Ala | Val | Val |
|---|---|---|---|---|---|---|---|---|---|---|---|---|---|---|---|
| 65 | | | | | 70 | | | | | 75 | | | | | 80 |

| Ser | Gly | Leu | Pro | Ala | Ser | Thr | Ser | Thr | Glu | Arg | Leu | Glu | Ile | Leu | Asp |
|---|---|---|---|---|---|---|---|---|---|---|---|---|---|---|---|
| | | | | 85 | | | | | 90 | | | | | 95 | |

| Asp | Asp | Arg | His | Val | Leu | Ser | Phe | Arg | Val | Val | Gly | Gly | Asp | His | Arg |
|---|---|---|---|---|---|---|---|---|---|---|---|---|---|---|---|
| | | | | 100 | | | | | 105 | | | | | 110 | |

| Leu | Arg | Asn | Tyr | Arg | Ser | Val | Thr | Ser | Val | Thr | Glu | Phe | Ser | Ser | Pro |
|---|---|---|---|---|---|---|---|---|---|---|---|---|---|---|---|
| | | | 115 | | | | | 120 | | | | | 125 | | |

| Ser | Ser | Pro | Pro | Arg | Pro | Tyr | Cys | Val | Val | Glu | Ser | Tyr | Val | Val |
|---|---|---|---|---|---|---|---|---|---|---|---|---|---|---|
| | 130 | | | | | 135 | | | | | 140 | | | |

| Asp | Val | Pro | Glu | Gly | Asn | Thr | Glu | Asp | Thr | Arg | Met | Phe | Thr | Asp |
|---|---|---|---|---|---|---|---|---|---|---|---|---|---|---|
| 145 | | | | | 150 | | | | | 155 | | | | | 160 |

| Thr | Val | Val | Lys | Leu | Asn | Leu | Gln | Lys | Leu | Ala | Ala | Val | Ala | Thr | Ser |
|---|---|---|---|---|---|---|---|---|---|---|---|---|---|---|---|
| | | | | 165 | | | | | 170 | | | | | 175 | |

| Ser | Ser | Pro | Pro | Ala | Ala | Gly | Asn | His | His |
|---|---|---|---|---|---|---|---|---|---|
| | | | 180 | | | | | 185 | |

<210> SEQ ID NO 83
<211> LENGTH: 150
<212> TYPE: PRT
<213> ORGANISM: Oryza sativa
<220> FEATURE:
<223> OTHER INFORMATION: rice Japonica Group, cultivar Nipponbare, hypothetical protein, locus tag OsJ_005938, GenBank Accession No. EAZ22455.1

<400> SEQUENCE: 83

| Met | Glu | Val | Val | Trp | Ser | Ile | Val | Arg | Arg | Phe | Glu | Glu | Pro | His | Ile |
|---|---|---|---|---|---|---|---|---|---|---|---|---|---|---|---|
| 1 | | | | 5 | | | | | 10 | | | | | 15 | |

| Phe | Gln | Pro | Phe | Val | Arg | Gly | Cys | Thr | Met | Arg | Gly | Ser | Thr | Ser | Leu |
|---|---|---|---|---|---|---|---|---|---|---|---|---|---|---|---|
| | | | 20 | | | | | 25 | | | | | 30 | | |

| Ala | Val | Gly | Cys | Val | Arg | Glu | Val | Asp | Phe | Lys | Ser | Gly | Phe | Pro | Ala |
|---|---|---|---|---|---|---|---|---|---|---|---|---|---|---|---|
| | | 35 | | | | | 40 | | | | | 45 | | | |

| Lys | Ser | Ser | Val | Glu | Arg | Leu | Glu | Ile | Leu | Asp | Asp | Lys | Glu | His | Val |
|---|---|---|---|---|---|---|---|---|---|---|---|---|---|---|---|
| | 50 | | | | | 55 | | | | | 60 | | | | |

| Phe | Gly | Val | Arg | Ile | Ile | Gly | Gly | Asp | His | Arg | Leu | Lys | Asn | Tyr | Ser |
|---|---|---|---|---|---|---|---|---|---|---|---|---|---|---|---|
| 65 | | | | | 70 | | | | | 75 | | | | | 80 |

| Ser | Val | Leu | Thr | Ala | Lys | Pro | Glu | Val | Ile | Asp | Gly | Glu | Pro | Ala | Thr |
|---|---|---|---|---|---|---|---|---|---|---|---|---|---|---|---|
| | | | | 85 | | | | | 90 | | | | | 95 | |

| Leu | Val | Ser | Glu | Ser | Phe | Val | Val | Asp | Val | Pro | Glu | Gly | Asn | Thr | Ala |
|---|---|---|---|---|---|---|---|---|---|---|---|---|---|---|---|
| | | | | 100 | | | | | 105 | | | | | 110 | |

| Asp | Glu | Thr | Arg | His | Phe | Val | Glu | Phe | Leu | Ile | Arg | Cys | Asn | Leu | Arg |
|---|---|---|---|---|---|---|---|---|---|---|---|---|---|---|---|
| | | | 115 | | | | | 120 | | | | | 125 | | |

| Ser | Leu | Ala | Met | Val | Ser | Gln | Arg | Leu | Leu | Ala | Gln | Gly | Asp | Leu |
|---|---|---|---|---|---|---|---|---|---|---|---|---|---|---|
| | 130 | | | | | 135 | | | | | 140 | | | |

Ala Glu Pro Pro Gly Gln
145                 150

<210> SEQ ID NO 84
<211> LENGTH: 206
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_018129, GenBank Accession No.
      EAZ34646.1

<400> SEQUENCE: 84

Met Pro Tyr Thr Ala Pro Arg Pro Ser Pro Pro Gln His Ser Arg Ile
1               5                   10                  15

Gly Gly Cys Gly Gly Gly Gly Val Leu Lys Ala Ala Gly Ala Ala Gly
                20                  25                  30

His Ala Ala Ser Cys Val Ala Val Pro Ala Glu Val Ala Arg His His
            35                  40                  45

Glu His Ala Ala Gly Val Gly Gln Cys Cys Ser Ala Val Val Gln Ala
        50                  55                  60

Ile Ala Ala Pro Val Asp Ala Val Trp Arg Thr Ser Thr Ser Ser Gly
65                  70                  75                  80

Ala Ala Ala Ser Trp Thr Ala Thr Ala Thr Ala Gly Pro Leu Pro Val
                85                  90                  95

Gly Ser Val Arg Glu Phe Arg Val Leu Ser Gly Leu Pro Gly Thr Ser
                100                 105                 110

Ser Arg Glu Arg Leu Glu Ile Leu Asp Asp Glu Arg Arg Val Leu Ser
            115                 120                 125

Phe Arg Val Val Gly Gly Glu His Arg Leu Ser Asn Tyr Arg Ser Val
130                 135                 140

Thr Thr Val His Glu Thr Ala Ala Gly Ala Ala Ala Val Val Val
145                 150                 155                 160

Glu Ser Tyr Val Val Asp Val Pro His Gly Asn Thr Ala Asp Glu Thr
                165                 170                 175

Arg Met Phe Val Asp Thr Ile Val Arg Cys Asn Leu Gln Ser Leu Ala
            180                 185                 190

Arg Thr Ala Glu Gln Leu Ala Leu Ala Ala Pro Arg Ala Ala
        195                 200                 205

<210> SEQ ID NO 85
<211> LENGTH: 396
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_001710, GenBank
      Accession No. CAN76441.1
<220> FEATURE:
<221> NAME/KEY: VARIANT
<222> LOCATION: (1)...(396)
<223> OTHER INFORMATION: Xaa = any amino acid

<400> SEQUENCE: 85

Met Pro Ile Ser Ser Leu Pro Phe Ser Leu Tyr Thr Val Thr Pro Asn
1               5                   10                  15

Pro Leu Lys Leu Ile Thr Thr His Ala His Ala Phe Thr Pro His Thr
                20                  25                  30

His Ile Phe Thr Leu Lys Phe Met Ser His Thr Tyr Cys Pro His Ile
            35                  40                  45

```
His His Ile Thr Ser Ile His Tyr Thr His Leu Leu Xaa Pro Ile Pro
    50                  55                  60

His Met Pro Leu Gln Pro Pro Leu Pro Pro His Pro Ile Leu Pro Ser
65                  70                  75                  80

Met Pro Ala Phe Gln His Leu Tyr Ser Thr Asn Gln His Leu Gln Val
                85                  90                  95

Ala Leu Phe Ser Ala Arg Gly Pro Asn Ile Arg Asp Phe Asn Phe Gln
            100                 105                 110

Asp Ala Asp Leu Leu Lys Leu Asp Ile Leu Ala Pro Gly Ser Leu Ile
        115                 120                 125

Trp Ala Ala Trp Ser Pro Asn Gly Thr Asp Glu Ala Asn Tyr Val Gly
130                 135                 140

Glu Gly Ser Pro Thr Val Ala Met Ile Ala Lys Arg Gly Pro Arg His
145                 150                 155                 160

Gly Lys Tyr Met Ala Phe Cys Xaa Met Tyr Arg Asp Asn Val Ala Pro
                165                 170                 175

Lys Gly Val Asn Xaa Ala Val Ala Thr Val Lys Thr Lys Arg Thr Ile
            180                 185                 190

Gln Leu Lys Thr Ser Leu Glu Ile Ala Cys His Tyr Ala Gly Ile Asn
        195                 200                 205

Ile Ser Gly Ile Asn Gly Glu Val Met Pro Gly Gln Trp Glu Tyr Gln
210                 215                 220

Val Gly Pro Gly Gln Cys Ser Ser Leu Leu Ala Gln Arg Val His Val
225                 230                 235                 240

Pro Leu Ser Ala Val Gly Ser Val Val His Arg Phe Asp Lys Pro Gln
                245                 250                 255

Arg Tyr Gln His Val Ile Lys Ser Cys Arg Ile Glu Asp Gly Phe Glu
            260                 265                 270

Met Arg Met Gly Xaa Leu Arg Asp Val Asn Ile Ile Ser Gly Leu Pro
        275                 280                 285

Thr Ala Thr Asn Thr Gly Arg Leu Asp Met Gln Asp Asp Glu Arg His
290                 295                 300

Val Thr Arg Cys Pro His Gln Arg Gln Ser Glu Ser Lys Tyr Thr Glu
305                 310                 315                 320

Asn Asn Asn Ser Asp Ala Ser Ser Ile Lys Ser Pro Ile Asn Gly Pro
                325                 330                 335

Ser Glu His Leu Lys Thr Ala Ala Ser Pro Lys Thr Glu Ser Ile Ile
            340                 345                 350

Val Ile Asp Thr Ser Lys Phe Leu Asn Glu Glu Asp Phe Glu Gly Lys
        355                 360                 365

Asp Glu Thr Ser Ser Ser Asn Gln Val Gln Ile Glu Asp Glu Asn Trp
370                 375                 380

Glu Thr Arg Phe Pro Asn Thr Asp Ala Gly Ile Trp
385                 390                 395

<210> SEQ ID NO 86
<211> LENGTH: 443
<212> TYPE: PRT
<213> ORGANISM: Vitis vinifera
<220> FEATURE:
<223> OTHER INFORMATION: wine grape cultivar Pinot Noir hypothetical
      protein, clone ENTAV 115, locus tag VITISV_014403, GenBank
      Accession No. CAN9881.1
<220> FEATURE:
<221> NAME/KEY: VARIANT
<222> LOCATION: (1)...(443)
<223> OTHER INFORMATION: Xaa = any amino acid
```

<400> SEQUENCE: 86

Met Pro Ser Ala Xaa Lys Ser Ser Thr Val Pro Leu Ser Leu Xaa Gln
1               5                   10                  15

Phe Lys Leu Gly Leu Arg His Gly His Arg Val Ile Pro Trp Gly Asp
            20                  25                  30

Leu Asp Ser Leu Ala Met Leu Gln Arg Gln Leu Asp Val Asp Ile Leu
        35                  40                  45

Val Thr Gly His Thr His Arg Phe Thr Ala Tyr Lys His Glu Gly Gly
    50                  55                  60

Val Val Ile Asn Pro Gly Ser Ala Thr Gly Ala Phe Gly Ser Ile Thr
65                  70                  75                  80

Tyr Asp Val Asn Pro Ser Phe Val Leu Met Asp Ile Asp Gly Leu Arg
                85                  90                  95

Val Val Val Cys Val Tyr Glu Leu Ile Asp Glu Thr Ala Asn Ile Ile
            100                 105                 110

Lys Glu Leu His Ala Arg Lys Ile Ser Phe Gly Thr Lys Ser Met Ile
        115                 120                 125

Xaa Cys Leu Leu Leu Lys Arg Arg Ser Thr Pro Lys Phe Arg Arg Lys
130                 135                 140

Lys Leu Phe Leu Phe Gln Cys Arg Val Gln Met Thr Leu Thr Leu Thr
145                 150                 155                 160

Asn Leu Ala Val Ser Gly Ile Ala Gln Thr Leu Gln Val Asp Gln Trp
                165                 170                 175

Thr Val Cys Ala Leu Ile Phe Met Thr Arg Arg Asp Ile His Leu Asp
            180                 185                 190

Lys Ala Arg Phe Leu Asp Phe Lys Asp Met Gly Lys Leu Leu Ala Asp
        195                 200                 205

Ala Ser Gly Leu Arg Lys Ala Leu Ser Gly Gly Xaa Val Thr Ala Gly
    210                 215                 220

Met Ala Ile Phe Asp Thr Met Arg His Ile Arg Pro Asp Val Pro Thr
225                 230                 235                 240

Val Cys Val Gly Leu Ala Ala Val Ala Met Ile Ala Lys Arg Gly Pro
                245                 250                 255

Arg His Gly Lys Tyr Met Ala Phe Cys Pro Met Tyr Arg Asp Asn Val
            260                 265                 270

Ala Pro Lys Gly Val Asn Val Ala Val Val Thr Val Lys Thr Lys Arg
        275                 280                 285

Thr Ile Gln Leu Lys Thr Ser Leu Glu Ile Ala Cys His Tyr Ala Gly
    290                 295                 300

Ile Asn Ile Ser Gly Ile Asn Gly Glu Val Met Pro Gly Gln Trp Glu
305                 310                 315                 320

Tyr Gln Val Gly Pro Gly Gln Cys Ser Ser Leu Leu Ala Gln Arg Val
                325                 330                 335

His Val Pro Leu Ser Ala Val Gly Ser Val Val His Arg Phe Asp Lys
            340                 345                 350

Pro Gln Arg Tyr Gln His Val Ile Lys Ser Cys Arg Ile Glu Asp Gly
        355                 360                 365

Phe Glu Met Arg Met Gly Arg Leu Arg Asp Val Asn Ile Ile Ser Gly
    370                 375                 380

Leu Pro Thr Ala Thr Asn Thr Gly Arg Leu Asp Met Gln Asp Asp Glu
385                 390                 395                 400

Xaa His Val Thr Arg Cys Pro His Gln Arg Gln Ser Glu Ser Lys Tyr

```
                    405                 410                 415
Thr Glu Asn Asn Asn Ser Asp Ala Ser Ser Val Lys Ser Pro Ile Asn
                420                 425                 430

Gly Pro Ser Glu His Leu Lys Thr Ala Ala Xaa
            435                 440

<210> SEQ ID NO 87
<211> LENGTH: 95
<212> TYPE: PRT
<213> ORGANISM: Oryza sativa
<220> FEATURE:
<223> OTHER INFORMATION: rice Indica Group, cultivar Pokkali, capip1
      protein, clone OSR-385-428-D5, GenBank Accession No. ABR25904.1

<400> SEQUENCE: 87

Glu Ile Gly Ser Val Arg Glu Val Asn Val Lys Thr Gly Leu Pro Ala
1               5                   10                  15

Thr Thr Ser Thr Glu Arg Leu Glu Leu Leu Asp Asp Asp Glu His Ile
            20                  25                  30

Leu Ser Val Lys Phe Val Gly Gly Asp His Arg Leu Arg Asn Tyr Ser
        35                  40                  45

Ser Ile Val Thr Val His Pro Glu Ser Ile Asp Gly Arg Pro Gly Thr
    50                  55                  60

Leu Val Ile Glu Ser Phe Val Val Asp Val Pro Asp Gly Asn Thr Lys
65                  70                  75                  80

Asp Glu Thr Cys Tyr Phe Val Glu Ala Val Ile Lys Cys Asn Leu
                85                  90                  95

<210> SEQ ID NO 88
<211> LENGTH: 191
<212> TYPE: PRT
<213> ORGANISM: Zea mays
<220> FEATURE:
<223> OTHER INFORMATION: maize strain B73 unknown protein, clone
      ZM_BFc0034007, GenBank Accession No. ACF84624.1

<400> SEQUENCE: 88

Met Val Val Glu Met Asp Gly Val Gly Val Ala Ala Ala Gly Gly
1               5                   10                  15

Gly Gly Ala Gln Thr Pro Ala Pro Pro Pro Arg Arg Trp Arg Leu
            20                  25                  30

Ala Asp Glu Arg Cys Asp Leu Arg Ala Met Glu Thr Asp Tyr Val Arg
        35                  40                  45

Arg Phe His Arg His Glu Pro Arg Asp His Gln Cys Ser Ser Ala Val
    50                  55                  60

Ala Lys His Ile Lys Ala Pro Val His Leu Val Trp Ser Leu Val Arg
65                  70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
        115                 120                 125

Asp Asp Glu Arg Ile Leu Ser Val Arg Phe Val Gly Gly Asp His Arg
    130                 135                 140

Leu Gln Val Cys Ser Val Leu His Leu Ser Ile Phe Cys Ala Ala His
145                 150                 155                 160

Ala Arg Tyr Phe Ala His His Leu Lys Cys Val Leu Glu Phe Leu Cys
```

```
                    165                 170                 175

Gln Met His Leu Asp Val Leu Pro Cys Asp Asp Ala Ile Leu Glu
            180                 185                 190

<210> SEQ ID NO 89
<211> LENGTH: 239
<212> TYPE: PRT
<213> ORGANISM: Oryza sativa
<220> FEATURE:
<223> OTHER INFORMATION: rice Japonica Group, cultivar Nipponbare,
      hypothetical protein, locus tag OsJ_020681, GenBank Accession No.
      EAZ37198.1

<400> SEQUENCE: 89

Met Asn Gly Cys Thr Gly Gly Ala Gly Gly Val Ala Ala Gly Arg Leu
1               5                   10                  15

Pro Ala Val Ser Leu Gln Gln Ala Gln Trp Lys Leu Val Asp Glu Arg
            20                  25                  30

Cys Glu Leu Arg Glu Glu Glu Met Glu Tyr Val Arg Arg Phe His Arg
        35                  40                  45

His Glu Ile Gly Ser Asn Gln Cys Asn Ser Phe Ile Ala Lys His Val
    50                  55                  60

Arg Ala Pro Leu Gln Asn Val Trp Ser Leu Val Arg Arg Phe Asp Gln
65                  70                  75                  80

Pro Gln Ile Tyr Lys Pro Phe Val Arg Lys Cys Val Met Arg Gly Asn
                85                  90                  95

Val Glu Thr Gly Ser Val Arg Glu Ile Ile Val Gln Ser Gly Leu Pro
            100                 105                 110

Ala Thr Arg Ser Ile Glu Arg Leu Glu Phe Leu Asp Asp Asn Glu Tyr
        115                 120                 125

Ile Leu Arg Val Lys Phe Ile Gly Gly Asp His Met Leu Lys Lys Arg
    130                 135                 140

Ile Pro Lys Lys Thr Tyr Ala Ile Ser Ser Arg Thr Cys Ser Asp Ser
145                 150                 155                 160

Ala Ile Ile Ala Val Gly Gln Ser Asn Cys Ala Pro Glu Ile Thr Ala
                165                 170                 175

Met Asn Gly Gly Val Ser Ile Gln Pro Trp Leu Ile Leu Leu Ala Phe
            180                 185                 190

Phe Ser Ser Pro Ser Asn Gln Thr Asn Pro Asp Ser Leu Arg Asp Met
        195                 200                 205

His Pro Gly Ser Trp Phe Gln Ile Leu Leu Val Leu Ala Met Phe Thr
    210                 215                 220

Cys Ser Lys Gly Ser Val Leu Pro Pro Ser Glu Lys Val Asn Val
225                 230                 235

<210> SEQ ID NO 90
<211> LENGTH: 188
<212> TYPE: PRT
<213> ORGANISM: Zea mays
<220> FEATURE:
<223> OTHER INFORMATION: maize GRMZM2G154987_P01 protein

<400> SEQUENCE: 90

Met Glu Pro His Met Glu Ser Ala Leu Arg Gln Gly Leu Ser Glu Ala
1               5                   10                  15

Glu Gln Arg Glu Leu Glu Gly Val Val Arg Ala His His Thr Phe Pro
            20                  25                  30

Gly Arg Ala Pro Gly Thr Cys Thr Ser Leu Val Thr Gln Arg Val Asp
```

```
                35                  40                  45
Ala Pro Leu Ala Ala Val Trp Pro Ile Val Arg Gly Phe Gly Ser Pro
            50                  55                  60
Gln Arg Tyr Lys His Phe Ile Lys Ser Cys Asp Leu Lys Ala Gly Asp
65                  70                  75                  80
Gly Ala Thr Val Gly Ser Val Arg Glu Val Thr Val Val Ser Gly Leu
                85                  90                  95
Pro Ala Ser Thr Ser Thr Glu Arg Leu Glu Ile Leu Asp Asp His Arg
            100                 105                 110
His Ile Leu Ser Phe Arg Val Val Gly Gly Asp His Arg Leu Arg Asn
        115                 120                 125
Tyr Arg Ser Val Thr Ser Val Thr Glu Phe Gln Pro Gly Pro Tyr Cys
    130                 135                 140
Val Val Leu Glu Ser Tyr Val Val Asp Val Pro Asp Gly Asn Thr Glu
145                 150                 155                 160
Glu Asp Thr Arg Met Phe Thr Asp Thr Val Val Lys Leu Asn Leu Gln
                165                 170                 175
Lys Leu Ala Ala Ile Ala Thr Ser Ser Ser Ala Asn
            180                 185

<210> SEQ ID NO 91
<211> LENGTH: 205
<212> TYPE: PRT
<213> ORGANISM: Zea mays
<220> FEATURE:
<223> OTHER INFORMATION: maize GRMZM2G134731_P01 protein

<400> SEQUENCE: 91

Met Asp Gln Gln Gly Ala Gly Gly Asp Val Glu Val Pro Ala Gly Leu
1               5                   10                  15
Gly Leu Thr Ala Ala Glu Tyr Glu Gln Leu Arg Pro Thr Val Asp Ala
            20                  25                  30
His His Arg Tyr Ala Val Gly Glu Gly Gln Cys Ser Ser Leu Leu Ala
        35                  40                  45
Gln Arg Ile His Ala Pro Pro Ala Ala Val Trp Ala Ile Val Arg Arg
    50                  55                  60
Phe Asp Cys Pro Gln Val Tyr Lys His Phe Ile Arg Ser Cys Ala Val
65                  70                  75                  80
Arg Pro Asp Pro Asp Ala Gly Asp Ala Leu Arg Pro Gly Arg Leu Arg
                85                  90                  95
Glu Val Cys Val Ile Ser Gly Leu Pro Ala Ser Thr Ser Thr Glu Arg
            100                 105                 110
Leu Asp His Leu Asp Asp Ala Ala Arg Val Phe Gly Phe Ser Ile Thr
        115                 120                 125
Gly Gly Glu His Arg Leu Arg Asn Tyr Arg Ser Val Thr Thr Val Ser
    130                 135                 140
Glu Leu Ala Gly Pro Gly Ile Cys Thr Val Val Leu Glu Ser Tyr Ala
145                 150                 155                 160
Val Asp Val Pro Asp Gly Asn Thr Glu Asp Thr Arg Leu Phe Ala
                165                 170                 175
Asp Thr Val Ile Arg Leu Asn Leu Gln Lys Leu Lys Ser Val Ala Glu
            180                 185                 190
Ala Ser Thr Ser Ser Ser Ala Pro Pro Pro Ser Glu
        195                 200                 205
```

```
<210> SEQ ID NO 92
<211> LENGTH: 220
<212> TYPE: PRT
<213> ORGANISM: Zea mays
<220> FEATURE:
<223> OTHER INFORMATION: maize GRMZM2G144224_P01 protein

<400> SEQUENCE: 92

Met Pro Cys Ile Gln Ala Ser Ser Pro Gly Gly Met Pro His Gln His
1               5                   10                  15

Gly Arg Gly Arg Val Leu Gly Gly Val Gly Cys Ala Ala Glu Val
            20                  25                  30

Ala Ala Ala Val Ala Ala Ser Ala Gly Gly Met Arg Cys Gly Ala His
        35                  40                  45

Asp Gly Glu Val Pro Ala Glu Ala Ala Arg His His Glu His Ala Ala
    50                  55                  60

Ala Gly Pro Gly Arg Cys Cys Ser Ala Val Val Gln His Val Ala Ala
65                  70                  75                  80

Pro Ala Ala Ala Val Trp Ser Val Val Arg Arg Phe Asp Gln Pro Gln
                85                  90                  95

Val Tyr Lys Arg Phe Val Arg Ser Cys Ala Leu Leu Ala Gly Asp Gly
            100                 105                 110

Gly Val Gly Thr Leu Arg Glu Val Arg Val Val Ser Gly Leu Pro Ala
        115                 120                 125

Ala Ser Ser Arg Glu Arg Leu Glu Val Leu Asp Asp Glu Ser His Val
    130                 135                 140

Leu Ser Phe Arg Val Val Gly Gly Glu His Arg Leu Arg Asn Tyr Leu
145                 150                 155                 160

Ser Val Thr Thr Val His Pro Ser Pro Ala Ala Pro Asp Ala Ala Thr
                165                 170                 175

Val Val Val Glu Ser Tyr Val Val Asp Val Pro Pro Gly Asn Thr Pro
            180                 185                 190

Glu Asp Thr Arg Val Phe Val Asp Thr Ile Val Lys Cys Asn Leu Gln
        195                 200                 205

Ser Leu Ala Thr Thr Ala Glu Lys Leu Ala Ala Val
    210                 215                 220

<210> SEQ ID NO 93
<211> LENGTH: 221
<212> TYPE: PRT
<213> ORGANISM: Glycine max
<220> FEATURE:
<223> OTHER INFORMATION: soybean Glyma01g02290.1 protein

<400> SEQUENCE: 93

Met Glu Lys Ala Glu Ser Ser Ala Ser Thr Ser Glu Pro Asp Ser Asp
1               5                   10                  15

Glu Asn His His Arg His Pro Thr Asn His His Ile Asn Pro Pro Ser
            20                  25                  30

Gly Leu Thr Pro Leu Glu Phe Ala Ser Leu Ile Pro Ser Val Ala Glu
        35                  40                  45

His His Ser Tyr Leu Val Gly Ser Gly Gln Cys Ser Ser Leu Leu Ala
    50                  55                  60

Gln Arg Val Gln Ala Pro Pro Asp Ala Val Trp Ser Val Val Arg Arg
65                  70                  75                  80

Phe Asp Lys Pro Gln Thr Tyr Lys His Phe Ile Lys Ser Cys Ala Val
                85                  90                  95
```

```
Lys Glu Pro Phe His Met Ala Val Gly Val Thr Arg Asp Val Asn Val
                100                 105                 110

Ile Ser Gly Leu Pro Ala Ala Thr Ser Thr Glu Arg Leu Asp Leu Leu
            115                 120                 125

Asp Asp Ile Arg Cys Val Thr Gly Phe Ser Ile Ile Gly Gly Glu His
        130                 135                 140

Arg Leu Arg Asn Tyr Arg Ser Val Thr Thr Val His Ser Phe Glu Asp
145                 150                 155                 160

Asp Ala Asp Asp Gly Lys Ile Tyr Thr Val Val Leu Glu Ser Tyr Val
                165                 170                 175

Val Asp Val Pro Asp Gly Asn Thr Glu Glu Asp Thr Arg Leu Phe Ala
            180                 185                 190

Asp Thr Val Val Lys Leu Asn Leu Gln Lys Leu Ala Ser Val Thr Glu
        195                 200                 205

Gly Thr Asn Arg Asp Gly Asp Gly Lys Ser His Ser Arg
            210                 215                 220

<210> SEQ ID NO 94
<211> LENGTH: 214
<212> TYPE: PRT
<213> ORGANISM: Glycine max
<220> FEATURE:
<223> OTHER INFORMATION: soybean Glyma01g12970.1 protein

<400> SEQUENCE: 94

Met Glu Lys Thr His Ser Ser Ala Glu Glu Gln Asp Pro Thr Arg
1               5                   10                  15

Arg His Leu Asp Pro Pro Gly Leu Thr Ala Glu Glu Phe Glu Asp
            20                  25                  30

Leu Lys Pro Ser Val Leu Glu His His Thr Tyr Ser Val Thr Pro Thr
        35                  40                  45

Arg Gln Ser Ser Ser Leu Leu Ala Gln Arg Ile His Ala Pro Pro His
    50                  55                  60

Ala Val Trp Ser Val Val Arg Cys Phe Asp Asn Pro Gln Ala Tyr Lys
65                  70                  75                  80

His Phe Ile Lys Ser Cys His Val Lys Glu Gly Phe Gln Leu Ala Val
                85                  90                  95

Gly Ser Thr Arg Asp Val His Val Ile Ser Gly Leu Pro Ala Ala Thr
            100                 105                 110

Ser Thr Glu Arg Leu Asp Leu Leu Asp Asp Arg His Val Ile Gly
        115                 120                 125

Phe Thr Ile Val Gly Gly Asp His Arg Leu Arg Asn Tyr Arg Ser Val
    130                 135                 140

Thr Ser Val His Gly Phe Glu Cys Asp Gly Lys Ile Trp Thr Val Val
145                 150                 155                 160

Leu Glu Ser Tyr Val Val Asp Val Pro Glu Gly Asn Thr Glu Glu Asp
                165                 170                 175

Thr Arg Leu Phe Ala Asp Thr Val Val Lys Leu Asn Leu Gln Lys Leu
            180                 185                 190

Ala Ser Val Ser Glu Gly Met Cys Gly Asp Gly Asp Gly Asp Gly Asp
        195                 200                 205

Gly Lys Gly Asn Lys Ser
    210

<210> SEQ ID NO 95
<211> LENGTH: 216
```

```
<212> TYPE: PRT
<213> ORGANISM: Glycine max
<220> FEATURE:
<223> OTHER INFORMATION: soybean Glyma01g31320.1 protein

<400> SEQUENCE: 95
```

| | | | | | | | | | | | | | | |
|---|---|---|---|---|---|---|---|---|---|---|---|---|---|---|
| Met | Leu | Gln | Asn | Ser | Ser | Met | Ser | Ser | Leu | Leu | His | Arg | Ile | Asn |
| 1 | | | | 5 | | | | | 10 | | | | | 15 |
| Gly | Gly | Gly | Gly | Ala | Thr | Thr | Ala | Thr | Asn | Cys | His | Asp | Thr | Val | Phe |
| | | | 20 | | | | | 25 | | | | | 30 | |
| Met | Thr | Val | Pro | Asp | Gly | Val | Ala | Arg | Tyr | His | Thr | His | Ala | Val | Ala |
| | | | 35 | | | | | 40 | | | | | 45 | |
| Pro | Asn | Gln | Cys | Cys | Ser | Ser | Val | Ala | Gln | Glu | Ile | Gly | Ala | Ser | Val |
| | 50 | | | | | 55 | | | | | 60 | | | | |
| Ala | Thr | Val | Trp | Ser | Val | Leu | Arg | Arg | Phe | Asp | Asn | Pro | Gln | Ala | Tyr |
| 65 | | | | | 70 | | | | | 75 | | | | | 80 |
| Lys | His | Phe | Val | Lys | Ser | Cys | His | Val | Ile | Gly | Gly | Asp | Gly | Asp | Val |
| | | | | 85 | | | | | 90 | | | | | 95 | |
| Gly | Thr | Leu | Arg | Glu | Val | His | Val | Ile | Ser | Gly | Leu | Pro | Ala | Ala | Arg |
| | | | 100 | | | | | 105 | | | | | 110 | | |
| Ser | Thr | Glu | Arg | Leu | Glu | Ile | Leu | Asp | Asp | Arg | His | Val | Ile | Ser |
| | | | 115 | | | | | 120 | | | | | 125 | |
| Phe | Ser | Val | Val | Gly | Gly | Asp | His | Arg | Leu | Ala | Asn | Tyr | Arg | Ser | Val |
| | 130 | | | | | 135 | | | | | 140 | | | | |
| Thr | Thr | Leu | His | Pro | Thr | Ala | Ser | Ser | Ala | Ser | Gly | Cys | Ser | Gly |
| 145 | | | | | 150 | | | | | 155 | | | | | 160 |
| Thr | Val | Val | Val | Glu | Ser | Tyr | Val | Val | Asp | Val | Pro | Pro | Gly | Asn | Thr |
| | | | | 165 | | | | | 170 | | | | | 175 | |
| Arg | Glu | Asp | Thr | Arg | Val | Phe | Val | Asp | Thr | Ile | Val | Lys | Cys | Asn | Leu |
| | | | 180 | | | | | 185 | | | | | 190 | | |
| Gln | Ser | Leu | Ala | Gln | Thr | Ala | Glu | Asn | Leu | Thr | Leu | Arg | Lys | Asn | Asn |
| | | | 195 | | | | | 200 | | | | | 205 | | |
| Asn | Asn | Asp | Tyr | Lys | Cys | Cys | Ser |
| | | 210 | | | | | 215 |

```
<210> SEQ ID NO 96
<211> LENGTH: 208
<212> TYPE: PRT
<213> ORGANISM: Glycine max
<220> FEATURE:
<223> OTHER INFORMATION: soybean Glyma02g42990.1 protein

<400> SEQUENCE: 96
```

| | | | | | | | | | | | | | | | |
|---|---|---|---|---|---|---|---|---|---|---|---|---|---|---|---|
| Met | Thr | Ser | Leu | Gln | Phe | His | Arg | Phe | Asn | Pro | Ala | Thr | Asp | Thr | Ser |
| 1 | | | | 5 | | | | | 10 | | | | | 15 | |
| Thr | Ala | Ile | Ala | Asn | Gly | Val | Asn | Cys | Pro | Lys | Pro | Ser | Thr | Leu |
| | | | 20 | | | | | 25 | | | | | 30 | |
| Arg | Leu | Leu | Ala | Lys | Val | Ser | Leu | Ser | Val | Pro | Glu | Thr | Val | Ala | Arg |
| | | | 35 | | | | | 40 | | | | | 45 | | |
| His | His | Ala | His | Pro | Val | Gly | Pro | Asn | Gln | Cys | Cys | Ser | Val | Val | Ile |
| | 50 | | | | | 55 | | | | | 60 | | | | |
| Gln | Ala | Ile | Asp | Ala | Pro | Val | Ser | Ala | Val | Trp | Pro | Val | Arg | Arg |
| 65 | | | | | 70 | | | | | 75 | | | | | 80 |
| Phe | Asp | Asn | Pro | Gln | Ala | Tyr | Lys | His | Phe | Val | Lys | Ser | Cys | His | Val |
| | | | | 85 | | | | | 90 | | | | | 95 | |
| Val | Ala | Ala | Ala | Gly | Gly | Gly | Glu | Asp | Gly | Ile | Arg | Val | Gly | Ala | Leu |
| | | | 100 | | | | | 105 | | | | | 110 | | |

Arg Glu Val Arg Val Val Ser Gly Leu Pro Ala Val Ser Ser Thr Glu
            115                 120                 125

Arg Leu Glu Ile Leu Asp Asp Glu Arg His Val Met Ser Phe Ser Val
    130                 135                 140

Val Gly Gly Asp His Arg Leu Arg Asn Tyr Arg Ser Val Thr Thr Leu
145                 150                 155                 160

His Gly Asp Gly Asn Gly Gly Thr Val Ile Glu Ser Tyr Val Val
                165                 170                 175

Asp Val Pro Pro Gly Asn Thr Lys Glu Glu Thr Cys Val Phe Val Asp
                180                 185                 190

Thr Ile Val Arg Cys Asn Leu Gln Ser Leu Ala Gln Ile Ala Glu Thr
            195                 200                 205

<210> SEQ ID NO 97
<211> LENGTH: 176
<212> TYPE: PRT
<213> ORGANISM: Glycine max
<220> FEATURE:
<223> OTHER INFORMATION: soybean Glyma04g05380.1 protein

<400> SEQUENCE: 97

Ala Tyr Pro Val Leu Gly Leu Thr Pro Glu Glu Phe Ser Glu Leu Glu
1               5                   10                  15

Ser Ile Ile Asn Thr His His Lys Phe Glu Pro Ser Pro Glu Ile Cys
            20                  25                  30

Ser Ser Ile Ile Ala Gln Arg Ile Asp Ala Pro Ala His Thr Val Trp
        35                  40                  45

Pro Leu Val Arg Ser Phe Glu Asn Pro Gln Lys Tyr Lys His Phe Val
    50                  55                  60

Lys Ser Cys Asn Met Arg Ser Gly Asp Gly Val Gly Ser Ile Arg
65                  70                  75                  80

Glu Val Thr Val Ser Gly Leu Pro Ala Ser Thr Ser Thr Glu Arg
                85                  90                  95

Leu Glu Ile Leu Asp Asp Lys His Leu Leu Ser Phe Arg Val Val
            100                 105                 110

Gly Gly Glu His Arg Leu His Asn Tyr Arg Ser Val Thr Ser Val Asn
        115                 120                 125

Glu Phe Lys Asn Pro Asp Asn Gly Lys Val Tyr Thr Ile Val Leu Glu
    130                 135                 140

Ser Tyr Val Val Asp Ile Pro Glu Gly Asn Thr Gly Val Asp Thr Lys
145                 150                 155                 160

Met Phe Val Asp Thr Val Val Lys Leu Asn Leu Gln Lys Leu Gly Glu
                165                 170                 175

<210> SEQ ID NO 98
<211> LENGTH: 172
<212> TYPE: PRT
<213> ORGANISM: Glycine max
<220> FEATURE:
<223> OTHER INFORMATION: soybean Glyma06g05440.1 protein

<400> SEQUENCE: 98

Glu Phe Thr Glu Leu Glu Ser Thr Ile Asn Thr His His Lys Phe Glu
1               5                   10                  15

Ala Ser Pro Glu Ile Cys Ser Ser Ile Ile Ala Gln Arg Ile Asp Ala
            20                  25                  30

Pro Ala His Thr Val Trp Pro Leu Val Arg Ser Phe Glu Asn Pro Gln

```
            35                  40                  45
Lys Tyr Lys His Phe Val Lys Ser Cys Asn Met Arg Ser Gly Asp Gly
     50                  55                  60

Gly Val Gly Ser Ile Arg Glu Val Thr Val Val Ser Gly Leu Pro Ala
 65                  70                  75                  80

Ser Thr Ser Thr Glu Arg Leu Glu Ile Leu Asp Asp Asp Asn His Leu
                 85                  90                  95

Leu Ser Phe Arg Val Val Gly Gly Glu His Arg Leu His Asn Tyr Arg
                100                 105                 110

Ser Val Thr Ser Val Asn Glu Phe Lys Arg Pro Asp Asn Gly Lys Val
                115                 120                 125

Tyr Thr Ile Val Leu Glu Ser Tyr Val Val Asp Ile Pro Glu Gly Asn
                130                 135                 140

Thr Gly Val Asp Thr Lys Met Phe Val Asp Thr Val Val Lys Leu Asn
145                 150                 155                 160

Leu Gln Lys Leu Gly Glu Val Ala Met Ala Thr Asn
                165                 170

<210> SEQ ID NO 99
<211> LENGTH: 191
<212> TYPE: PRT
<213> ORGANISM: Glycine max
<220> FEATURE:
<223> OTHER INFORMATION: soybean Glyma06g13150.1 protein

<400> SEQUENCE: 99

Met Thr Glu Leu Ser Ser Arg Glu Val Glu Tyr Ile Arg Arg His His
 1               5                  10                  15

Ser Lys Ala Ala Glu Asp Asn Gln Cys Ala Ser Ala Leu Val Lys His
                 20                  25                  30

Ile Arg Ala Pro Leu Pro Leu Val Trp Ser Leu Val Arg Arg Phe Asp
                 35                  40                  45

Glu Pro Gln Lys Tyr Lys Pro Phe Val Ser Arg Cys Val Val Arg Gly
     50                  55                  60

Asn Leu Glu Ile Gly Ser Leu Arg Glu Val Asp Val Lys Ser Gly Leu
 65                  70                  75                  80

Pro Ala Thr Thr Ser Thr Glu Arg Leu Glu Ile Leu Asp Asp Asn His
                 85                  90                  95

His Ile Leu Ser Val Arg Ile Ile Gly Gly Asp His Arg Leu Arg Asn
                100                 105                 110

Tyr Ser Ser Ile Met Ser Leu His Pro Glu Ile Val Asp Gly Arg Pro
                115                 120                 125

Gly Thr Leu Val Ile Glu Ser Phe Val Val Asp Ile Pro Glu Gly Asn
                130                 135                 140

Thr Lys Asp Glu Thr Cys Tyr Phe Val Glu Ala Leu Ile Lys Cys Asn
145                 150                 155                 160

Leu Lys Ser Leu Ala Asp Val Ser Glu Gly Leu Thr Leu Gln Asp His
                165                 170                 175

Thr Glu Pro Ile Asp Arg Lys Tyr Glu Leu Leu Ile Thr Arg Gly
                180                 185                 190

<210> SEQ ID NO 100
<211> LENGTH: 185
<212> TYPE: PRT
<213> ORGANISM: Glycine max
<220> FEATURE:
<223> OTHER INFORMATION: soybean Glyma07g06270.1 protein
```

<400> SEQUENCE: 100

Met Asn Gly Gly Glu Ser Tyr Gly Ala Ile Glu Thr Gln Tyr Ile Arg
1               5                   10                  15

Arg His His Lys His Glu Pro Arg Glu Asn Gln Cys Thr Ser Ala Leu
            20                  25                  30

Val Lys His Ile Arg Ala Pro Val His Leu Val Trp Ser Leu Val Arg
        35                  40                  45

Arg Phe Asp Gln Pro Gln Lys Tyr Lys Pro Phe Val Ser Arg Cys Ile
    50                  55                  60

Met Gln Gly Asp Leu Gly Ile Gly Ser Val Arg Glu Val Asn Val Lys
65                  70                  75                  80

Ser Gly Leu Pro Ala Thr Thr Ser Thr Glu Arg Leu Glu Gln Leu Asp
                85                  90                  95

Asp Glu Glu His Ile Leu Gly Ile Arg Ile Val Gly Gly Asp His Arg
            100                 105                 110

Leu Arg Asn Tyr Ser Ser Ile Ile Thr Val His Pro Glu Val Ile Asp
        115                 120                 125

Gly Arg Pro Gly Thr Met Val Ile Glu Ser Phe Val Val Asp Val Pro
    130                 135                 140

Asp Gly Asn Thr Arg Asp Glu Thr Cys Tyr Phe Val Glu Ala Leu Ile
145                 150                 155                 160

Arg Cys Asn Leu Ser Ser Leu Ala Asp Val Ser Glu Arg Met Ala Val
                165                 170                 175

Gln Gly Arg Thr Asn Pro Ile Asn His
            180                 185

<210> SEQ ID NO 101
<211> LENGTH: 178
<212> TYPE: PRT
<213> ORGANISM: Glycine max
<220> FEATURE:
<223> OTHER INFORMATION: soybean Glyma07g19120.1 protein

<400> SEQUENCE: 101

Met Ser Pro Asn Asn Pro Ser Thr Ile Val Ser Asp Ala Val Ala Arg
1               5                   10                  15

His His Thr His Val Val Ser Pro His Gln Cys Cys Ser Ala Val Val
            20                  25                  30

Gln Glu Ile Ala Ala Pro Val Ser Thr Val Trp Ser Val Val Arg Arg
        35                  40                  45

Phe Asp Asn Pro Gln Ala Tyr Lys His Phe Val Lys Ser Cys His Val
    50                  55                  60

Ile Leu Gly Asp Gly Asp Val Gly Thr Leu Arg Glu Val Arg Val Ile
65                  70                  75                  80

Ser Gly Leu Pro Ala Ala Val Ser Thr Glu Arg Leu Asp Val Leu Asp
                85                  90                  95

Asp Glu Arg His Val Ile Gly Phe Ser Met Val Gly Gly Asp His Arg
            100                 105                 110

Leu Ser Asn Tyr Arg Ser Val Thr Ile Leu His Pro Arg Ser Ala Thr
        115                 120                 125

Asp Thr Val Val Val Glu Ser Tyr Val Val Asp Val Pro Ala Gly Asn
    130                 135                 140

Thr Thr Glu Asp Thr Arg Val Phe Val Asp Thr Ile Leu Arg Cys Asn
145                 150                 155                 160

Leu Gln Ser Leu Ala Lys Phe Ala Glu Asn Leu Thr Asn Lys Leu His
                165                 170                 175

Gln Arg

<210> SEQ ID NO 102
<211> LENGTH: 246
<212> TYPE: PRT
<213> ORGANISM: Glycine max
<220> FEATURE:
<223> OTHER INFORMATION: soybean Glyma08g36770.1 protein

<400> SEQUENCE: 102

Met Ser Arg Ser His Asn Lys Arg Lys Pro Phe Ser Phe Ile Phe Lys
1               5                   10                  15

Ile Thr Leu Leu Glu Leu Leu Ser Ser Leu Leu Ser Ser Ser Leu Arg
            20                  25                  30

Phe Ala Met Asp Lys Thr His Ser Gly Glu Glu Gln Asp Pro Asn Pro
        35                  40                  45

Thr His Pro Thr Arg Asn His Leu Asp Pro Pro Gly Leu Thr Pro
    50                  55                  60

Glu Glu Phe Glu Asp Leu Lys Pro Ser Val Leu Glu His His Thr Tyr
65                  70                  75                  80

Ser Val Thr Pro Thr Arg Gln Cys Ser Ser Leu Leu Ala Gln Arg Ile
                85                  90                  95

His Ala Pro Pro His Thr Val Trp Thr Val Arg Cys Phe Asp Asn
            100                 105                 110

Pro Gln Ala Tyr Lys His Phe Ile Lys Ser Cys His Val Lys Glu Gly
        115                 120                 125

Phe Gln Leu Ala Val Gly Ser Thr Arg Asp Val His Val Ile Ser Gly
    130                 135                 140

Leu Pro Ala Ala Thr Ser Thr Glu Arg Leu Asp Leu Leu Asp Asp Asp
145                 150                 155                 160

Arg His Val Ile Gly Phe Thr Ile Val Gly Gly Asp His Arg Leu Arg
                165                 170                 175

Asn Tyr Arg Ser Val Thr Ser Val His Gly Phe Glu Arg Asp Gly Lys
            180                 185                 190

Ile Trp Thr Val Val Leu Glu Ser Tyr Val Val Asp Val Pro Glu Gly
        195                 200                 205

Asn Thr Glu Glu Asp Thr Arg Leu Phe Ala Asp Thr Val Val Lys Leu
    210                 215                 220

Asn Leu Gln Lys Leu Ala Ser Val Thr Glu Gly Met Cys Gly Asp Ser
225                 230                 235                 240

Asp Gly Lys Gly Asn Asn
                245

<210> SEQ ID NO 103
<211> LENGTH: 223
<212> TYPE: PRT
<213> ORGANISM: Glycine max
<220> FEATURE:
<223> OTHER INFORMATION: soybean Glyma09g33700.1 protein

<400> SEQUENCE: 103

Met Glu Lys Ala Glu Ser Ser Ala Ser Thr Ser Glu Pro Asp Ser Asp
1               5                   10                  15

Asp Asn His His Arg His Pro Thr Asn His His Leu Asn Pro Pro Ser
            20                  25                  30

Gly Leu Thr Pro Leu Glu Phe Ala Ser Leu Val Pro Ser Val Ala Glu
            35                  40                  45

His His Ser Tyr Leu Val Gly Pro Gly Gln Cys Ser Ser Leu Leu Ala
 50                  55                  60

Gln Arg Val His Ala Pro Pro Asp Ala Val Trp Ser Phe Val Arg Arg
 65                  70                  75                  80

Phe Asp Lys Pro Gln Thr Tyr Lys His Phe Ile Lys Ser Cys Ala Val
                 85                  90                  95

Lys Glu Pro Phe His Met Ala Val Gly Val Thr Arg Asp Val Asn Val
                100                 105                 110

Ile Ser Gly Leu Pro Ala Ala Thr Ser Thr Glu Arg Leu Asp Phe Leu
            115                 120                 125

Asp Asp Val Arg Arg Val Thr Gly Phe Ser Ile Ile Gly Gly Glu His
130                 135                 140

Arg Leu Arg Asn Tyr Arg Ser Val Thr Thr Val His Ser Phe Asp Asp
145                 150                 155                 160

Asp Asn Ala Ser Ala Asp Gly Lys Ile Tyr Thr Val Val Leu Glu Ser
                165                 170                 175

Tyr Val Val Asp Val Pro Asp Gly Asn Thr Glu Glu Asp Thr Arg Leu
            180                 185                 190

Phe Ala Asp Thr Val Val Lys Leu Asn Leu Gln Lys Leu Ala Ser Val
            195                 200                 205

Thr Glu Gly Thr Asn Gly Asp Gly Asp Gly Lys Pro His Ser Arg
        210                 215                 220

<210> SEQ ID NO 104
<211> LENGTH: 229
<212> TYPE: PRT
<213> ORGANISM: Glycine max
<220> FEATURE:
<223> OTHER INFORMATION: soybean Glyma11g35670.1 protein

<400> SEQUENCE: 104

Met Pro Ser Ser Leu His Phe Asp Arg Phe Asn Pro Ile Thr His Ala
1               5                   10                  15

Ala Thr Thr Val Ala Ile Ala Asn Gly Val Asn Cys Pro Lys Gln Pro
            20                  25                  30

Gln Ala Pro Pro Ser Ser Thr Ala Ala Arg Arg Leu Val Val Pro Ser
        35                  40                  45

Leu Ser Ser Gly Arg Gly Ile Ala Ala Pro Asp Thr Val Ala Leu His
 50                  55                  60

His Ala His Val Val Asp Pro Asn Gln Cys Cys Ser Ile Val Thr Gln
 65                  70                  75                  80

His Ile Asn Ala Pro Val Ser Ala Val Trp Ala Val Val Arg Arg Phe
                85                  90                  95

Asp Asn Pro Gln Gly Tyr Lys Asn Phe Val Arg Ser Cys His Val Ile
                100                 105                 110

Thr Gly Asp Gly Ile Arg Val Gly Ala Val Arg Glu Val Arg Val Val
            115                 120                 125

Ser Gly Leu Pro Ala Glu Thr Ser Thr Glu Arg Leu Glu Ile Leu Asp
130                 135                 140

Asp Glu Arg His Val Ile Ser Phe Ser Met Val Gly Asp His Arg
145                 150                 155                 160

Leu Arg Asn Tyr Gln Ser Val Thr Thr Leu His Ala Asn Gly Asn Gly
                165                 170                 175

```
Thr Leu Val Ile Glu Ser Tyr Val Val Asp Val Pro Gln Gly Asn Thr
                180                 185                 190

Lys Glu Glu Thr Cys Val Phe Val Asp Thr Ile Val Arg Cys Asn Leu
            195                 200                 205

Gln Ser Leu Ala Gln Ile Ala Glu Asn Arg Thr Asn Asn Cys Glu His
        210                 215                 220

Thr Ala Gln His Cys
225
```

<210> SEQ ID NO 105
<211> LENGTH: 191
<212> TYPE: PRT
<213> ORGANISM: Glycine max
<220> FEATURE:
<223> OTHER INFORMATION: soybean Glyma13g08120.1 protein

<400> SEQUENCE: 105

```
Met Asn Gly Ile Gly Asn Asp Gly Gly Gly Leu Ser Asn Val Glu
1               5                   10                  15

Met Glu Tyr Ile Arg Arg His His Arg His Glu Pro Gly Glu Asn Gln
                20                  25                  30

Cys Gly Ser Ala Leu Val Lys His Ile Arg Ala Pro Val Pro Gln Val
            35                  40                  45

Trp Ser Leu Val Arg Arg Phe Asp Gln Pro Gln Lys Tyr Lys Pro Phe
        50                  55                  60

Val Ser Arg Cys Val Val Arg Gly Asn Leu Glu Ile Gly Ser Leu Arg
65                  70                  75                  80

Glu Val Asp Val Lys Ser Gly Leu Pro Ala Thr Thr Ser Thr Glu Arg
                85                  90                  95

Leu Glu Leu Leu Asp Asp Asn Glu His Leu Leu Ser Ile Arg Ile Ile
            100                 105                 110

Gly Gly Asp His Arg Leu Arg Asn Tyr Ser Ser Ile Met Ser Leu His
        115                 120                 125

Pro Glu Ile Ile Asp Gly Arg Pro Gly Thr Leu Val Ile Glu Ser Phe
    130                 135                 140

Val Val Asp Val Pro Glu Gly Asn Thr Lys Asp Glu Thr Cys Tyr Phe
145                 150                 155                 160

Val Glu Ala Leu Ile Lys Cys Asn Leu Lys Ser Leu Ala Asp Val Ser
                165                 170                 175

Glu Gly Ile Ala Val Gln Asp Arg Thr Glu Pro Ile Asp Arg Ile
            180                 185                 190
```

<210> SEQ ID NO 106
<211> LENGTH: 169
<212> TYPE: PRT
<213> ORGANISM: Glycine max
<220> FEATURE:
<223> OTHER INFORMATION: soybean Glyma14g06100.1 protein

<400> SEQUENCE: 106

```
Met Val Ala Arg His His Ala His Ala Val Gly Pro Asn Gln Cys Cys
1               5                   10                  15

Ser Phe Val Ile Gln Ala Ile Asp Ala Pro Val Ser Ala Val Trp Pro
                20                  25                  30

Val Val Arg Arg Phe Asp Asn Pro Gln Ala Tyr Lys His Phe Val Lys
            35                  40                  45

Ser Cys His Val Val Ala Ala Gly Gly Ala Gly Gly Asp Gly Gly Ile
        50                  55                  60
```

His Val Gly Ala Leu Arg Glu Val Arg Val Val Ser Gly Leu Pro Ala
65                  70                  75                  80

Val Ser Ser Thr Glu Arg Leu Glu Ile Leu Asp Asp Glu Arg His Val
                85                  90                  95

Met Ser Phe Ser Val Val Gly Gly Asp His Arg Leu Arg Asn Tyr Arg
            100                 105                 110

Ser Val Thr Thr Leu His Gly Asp Gly Ser Asn Gly Gly Thr Val Val
        115                 120                 125

Ile Glu Ser Tyr Val Val Asp Ile Pro Ala Gly Asn Thr Lys Glu Glu
    130                 135                 140

Thr Cys Val Phe Val Asp Thr Ile Val Arg Cys Asn Leu Gln Ser Leu
145                 150                 155                 160

Ala Gln Met Ala Glu Asn Met Gly Ser
                165

<210> SEQ ID NO 107
<211> LENGTH: 210
<212> TYPE: PRT
<213> ORGANISM: Glycine max
<220> FEATURE:
<223> OTHER INFORMATION: soybean Glyma14g10730.1 protein

<400> SEQUENCE: 107

Met Thr Ile Leu Pro His Ser Asn Asn Lys Ser Ser Asn His Lys Phe
1               5                   10                  15

Ile Ala His Gln Asn Tyr Met Ala Ser Glu Thr His His Val Gln
                20                  25                  30

Gly Leu Thr Pro Glu Glu Leu Thr Lys Leu Glu Pro Ile Ile Lys Lys
            35                  40                  45

Tyr His Leu Phe Glu Gln Ser Pro Asn Thr Cys Phe Ser Ile Ile Thr
        50                  55                  60

Tyr Arg Ile Glu Ala Pro Ala Lys Ala Val Trp Pro Phe Val Arg Ser
65                  70                  75                  80

Phe Asp Asn Pro Gln Lys Tyr Lys His Phe Ile Lys Gly Cys Asn Met
                85                  90                  95

Arg Gly Asp Gly Gly Val Gly Ser Ile Arg Glu Val Thr Val Val Ser
            100                 105                 110

Gly Leu Pro Ala Ser Thr Ser Thr Glu Arg Leu Glu Ile Leu Asp Asp
        115                 120                 125

Asp Lys His Val Leu Ser Phe Arg Val Val Gly Gly Glu His Arg Leu
    130                 135                 140

Lys Asn Tyr Arg Ser Val Thr Ser Val Asn Glu Phe Asn Lys Glu Gly
145                 150                 155                 160

Lys Val Tyr Thr Ile Val Leu Glu Ser Tyr Ile Val Asp Ile Pro Glu
                165                 170                 175

Gly Asn Thr Glu Glu Asp Thr Lys Met Phe Val Asp Thr Val Val Lys
            180                 185                 190

Leu Asn Leu Gln Lys Leu Gly Val Val Ala Met Ala Ser Ser Met His
        195                 200                 205

Gly Gln
    210

<210> SEQ ID NO 108
<211> LENGTH: 193
<212> TYPE: PRT
<213> ORGANISM: Glycine max
<220> FEATURE:
<223> OTHER INFORMATION: soybean Glyma14g30260.1 protein

<400> SEQUENCE: 108

```
Met Asn Arg Ile Gly Asn Gly Gly Gly Gly Gly Gly Leu Ser Asn
1               5                  10                  15

Val Glu Met Glu Tyr Ile Arg Arg His Arg His Glu Pro Gly Glu
            20                  25                  30

Asn Gln Cys Gly Ser Ala Leu Val Lys His Ile Arg Ala Pro Val Pro
        35                  40                  45

Gln Val Trp Ser Leu Val Arg Arg Phe Asp Gln Pro Gln Lys Tyr Lys
    50                  55                  60

Pro Phe Ile Ser Arg Cys Val Val Arg Gly Asn Leu Glu Ile Gly Ser
65                  70                  75                  80

Leu Arg Glu Val Asp Val Lys Ser Gly Leu Pro Ala Thr Thr Ser Thr
                85                  90                  95

Glu Arg Leu Glu Leu Leu Asp Asp Asn Glu His Ile Leu Ser Ile Arg
            100                 105                 110

Ile Ile Gly Gly Asp His Arg Leu Arg Asn Tyr Ser Ser Ile Met Ser
        115                 120                 125

Leu His Pro Glu Ile Ile Asp Gly Arg Pro Gly Thr Leu Val Ile Glu
    130                 135                 140

Ser Phe Val Val Asp Val Pro Glu Gly Asn Thr Lys Asp Glu Thr Cys
145                 150                 155                 160

Tyr Phe Val Glu Ala Leu Ile Lys Cys Asn Leu Lys Ser Leu Ala Asp
                165                 170                 175

Val Ser Glu Gly Leu Ala Val Gln Asp Cys Thr Glu Pro Ile Asp Arg
            180                 185                 190

Ile
```

<210> SEQ ID NO 109
<211> LENGTH: 188
<212> TYPE: PRT
<213> ORGANISM: Glycine max
<220> FEATURE:
<223> OTHER INFORMATION: soybean Glyma17g34800.1 protein

<400> SEQUENCE: 109

```
Met Ala Ser Glu Thr His His His Val Gln Gly Leu Thr Pro Glu Glu
1               5                  10                  15

Leu Thr Gln Leu Glu Pro Ile Ile Lys Lys Tyr His Leu Phe Glu Ala
            20                  25                  30

Ser Ser Asn Lys Cys Phe Ser Ile Ile Thr His Arg Ile Glu Ala Pro
        35                  40                  45

Ala Ser Ser Val Trp Pro Leu Val Arg Asn Phe Asp Asn Pro Gln Lys
    50                  55                  60

Tyr Lys His Phe Ile Lys Gly Cys Asn Met Lys Gly Asp Gly Ser Val
65                  70                  75                  80

Gly Ser Ile Arg Glu Val Thr Val Val Ser Gly Leu Pro Ala Ser Thr
                85                  90                  95

Ser Thr Glu Arg Leu Glu Ile Leu Asp Asp Asp Lys His Val Leu Ser
            100                 105                 110

Phe Arg Val Val Gly Gly Glu His Arg Leu Gln Asn Tyr Arg Ser Val
        115                 120                 125

Thr Ser Val Asn Glu Phe His Lys Glu Gly Lys Val Tyr Thr Ile Val
    130                 135                 140
```

```
Leu Glu Ser Tyr Ile Val Asp Ile Pro Glu Gly Asn Thr Glu Glu Asp
145                 150                 155                 160

Thr Lys Met Phe Val Asp Thr Val Val Lys Leu Asn Leu Gln Lys Leu
                165                 170                 175

Gly Val Val Ala Met Ala Ser Ser Met Asn Gly Arg
            180                 185
```

<210> SEQ ID NO 110
<211> LENGTH: 177
<212> TYPE: PRT
<213> ORGANISM: Glycine max
<220> FEATURE:
<223> OTHER INFORMATION: soybean Glyma18g43680.1 protein

<400> SEQUENCE: 110

```
Met Leu Pro Asn Asn Pro Ser Thr Ile Val Pro Asp Ala Val Ala Arg
1               5                   10                  15

His His Thr His Val Val Ser Pro Gln Gln Cys Cys Ser Ala Val Val
            20                  25                  30

Gln Glu Ile Ala Ala Pro Val Ser Thr Val Trp Ser Val Val Arg Arg
        35                  40                  45

Phe Asp Asn Pro Gln Ala Tyr Lys His Phe Val Lys Ser Cys His Val
    50                  55                  60

Ile Leu Gly Asp Gly Asp Val Gly Thr Leu Arg Glu Val His Val Ile
65                  70                  75                  80

Ser Gly Leu Pro Ala Ala Val Ser Thr Glu Arg Leu Asp Val Leu Asp
                85                  90                  95

Asp Glu Arg His Val Ile Gly Phe Ser Met Val Gly Gly Asp His Arg
            100                 105                 110

Leu Phe Asn Tyr Arg Ser Val Thr Thr Leu His Pro Arg Ser Ala Ala
        115                 120                 125

Gly Thr Val Val Val Glu Ser Tyr Val Val Asp Val Pro Pro Gly Asn
    130                 135                 140

Thr Thr Glu Asp Thr Arg Val Phe Val Asp Thr Ile Leu Arg Cys Asn
145                 150                 155                 160

Leu Gln Ser Leu Ala Lys Phe Ala Glu Asn Leu Thr Lys Leu His Gln
                165                 170                 175

Arg
```

<210> SEQ ID NO 111
<211> LENGTH: 185
<212> TYPE: PRT
<213> ORGANISM: Glycine max
<220> FEATURE:
<223> OTHER INFORMATION: soybean Glyma07g06270.2 protein

<400> SEQUENCE: 111

```
Met Asn Gly Gly Glu Ser Tyr Gly Ala Ile Glu Thr Gln Tyr Ile Arg
1               5                   10                  15

Arg His His Lys His Glu Pro Arg Glu Asn Gln Cys Thr Ser Ala Leu
            20                  25                  30

Val Lys His Ile Arg Ala Pro Val His Leu Val Trp Ser Leu Val Arg
        35                  40                  45

Arg Phe Asp Gln Pro Gln Lys Tyr Lys Pro Phe Val Ser Arg Cys Ile
    50                  55                  60

Met Gln Gly Asp Leu Gly Ile Gly Ser Val Arg Glu Val Asn Val Lys
65                  70                  75                  80
```

Ser Gly Leu Pro Ala Thr Thr Ser Thr Glu Arg Leu Glu Gln Leu Asp
            85                  90                  95

Asp Glu Glu His Ile Leu Gly Ile Arg Ile Val Gly Gly Asp His Arg
           100                 105                 110

Leu Arg Asn Tyr Ser Ser Ile Ile Thr Val His Pro Glu Val Ile Asp
            115                 120                 125

Gly Arg Pro Gly Thr Met Val Ile Glu Ser Phe Val Val Asp Val Pro
130                 135                 140

Asp Gly Asn Thr Arg Asp Glu Thr Cys Tyr Phe Val Glu Ala Leu Ile
145                 150                 155                 160

Arg Cys Asn Leu Ser Ser Leu Ala Asp Val Ser Glu Arg Met Ala Val
            165                 170                 175

Gln Gly Arg Thr Asn Pro Ile Asn His
            180                 185

<210> SEQ ID NO 112
<211> LENGTH: 191
<212> TYPE: PRT
<213> ORGANISM: Glycine max
<220> FEATURE:
<223> OTHER INFORMATION: soybean Glyma16g02910.1 protein

<400> SEQUENCE: 112

Met Gly Ile Thr Ile Gly Ile Gln Cys Leu Glu Ile Glu Glu Ile Ser
1               5                   10                  15

Ile Cys Asp Gly Met Phe Cys Tyr Leu Val Asp Phe Val Asp Val Lys
            20                  25                  30

Glu Lys Met Asn Tyr Cys Leu Met Trp Phe Gly Tyr Phe Pro Ser Gln
        35                  40                  45

Val Trp Ser Leu Val Arg Arg Phe Asp Gln Pro Gln Lys Tyr Lys Pro
    50                  55                  60

Phe Val Ser Arg Cys Ile Met Gln Gly Asp Leu Gly Ile Gly Ser Val
65                  70                  75                  80

Arg Glu Val Asn Val Lys Ser Gly Leu Pro Ala Thr Thr Ser Thr Glu
            85                  90                  95

Arg Leu Glu Gln Leu Asp Asp Glu Glu His Ile Leu Gly Ile Arg Ile
           100                 105                 110

Val Gly Gly Asp His Arg Leu Arg Asn Tyr Ser Ser Ile Ile Thr Val
            115                 120                 125

His Pro Glu Val Ile Asp Gly Arg Pro Ser Thr Met Val Ile Glu Ser
130                 135                 140

Phe Val Val Asp Val Pro Asp Gly Asn Thr Arg Asp Glu Thr Cys Tyr
145                 150                 155                 160

Phe Val Glu Ala Leu Ile Arg Cys Asn Leu Ser Ser Leu Ala Asp Val
            165                 170                 175

Ser Glu Arg Met Ala Val Gln Gly Arg Thr Asp Pro Ile Asn His
            180                 185                 190

<210> SEQ ID NO 113
<211> LENGTH: 185
<212> TYPE: PRT
<213> ORGANISM: Artificial Sequence
<220> FEATURE:
<223> OTHER INFORMATION: synthetic PYR/PYL receptor protein

<400> SEQUENCE: 113

Met Asn Gly Gly Glu Ser Tyr Gly Ala Ile Glu Thr Gln Tyr Ile Arg

```
1               5                   10                  15
Arg His His Lys His Glu Pro Arg Glu Asn Gln Cys Thr Ser Ala Leu
            20                  25                  30
Val Lys His Ile Arg Ala Pro Val His Leu Val Trp Ser Leu Val Arg
            35                  40                  45
Arg Phe Asp Gln Pro Gln Lys Tyr Lys Pro Phe Val Ser Arg Cys Ile
        50                  55                  60
Met Gln Gly Asp Leu Gly Ile Gly Ser Val Arg Glu Val Asn Val Lys
65                  70                  75                  80
Ser Gly Leu Pro Ala Thr Thr Ser Thr Glu Arg Leu Glu Gln Leu Asp
                85                  90                  95
Asp Glu Glu His Ile Leu Gly Ile Arg Ile Val Gly Gly Asp His Arg
                100                 105                 110
Leu Arg Asn Tyr Ser Ser Ile Ile Thr Val His Pro Glu Val Ile Asp
                115                 120                 125
Gly Arg Pro Ser Thr Met Val Ile Glu Ser Phe Val Val Asp Val Pro
        130                 135                 140
Asp Gly Asn Thr Arg Asp Glu Thr Cys Tyr Phe Val Glu Ala Leu Ile
145                 150                 155                 160
Arg Cys Asn Leu Ser Ser Leu Ala Asp Val Ser Glu Arg Met Ala Val
                165                 170                 175
Gln Gly Arg Thr Asp Pro Ile Asn His
                180                 185
```

<210> SEQ ID NO 114
<211> LENGTH: 204
<212> TYPE: PRT
<213> ORGANISM: Sorghum bicolor
<220> FEATURE:
<223> OTHER INFORMATION: sorghum Sb10g022200 protein

<400> SEQUENCE: 114

```
Met Glu Thr His Val Glu Arg Ala Leu Arg Ala Thr Leu Thr Glu Ala
1               5                   10                  15
Glu Val Arg Ala Leu Glu Pro Ala Val Arg Glu His His Thr Phe Pro
            20                  25                  30
Ala Gly Arg Val Ala Ala Gly Thr Thr Thr Pro Thr Pro Thr Thr Cys
            35                  40                  45
Thr Ser Leu Val Ala Gln Arg Val Ser Ala Pro Val Arg Ala Val Trp
        50                  55                  60
Pro Ile Val Arg Ser Phe Gly Asn Pro Gln Arg Tyr Lys His Phe Val
65                  70                  75                  80
Arg Thr Cys Ala Leu Ala Ala Gly Asp Gly Ala Ser Val Gly Ser Val
                85                  90                  95
Arg Glu Val Thr Val Val Ser Gly Leu Pro Ala Ser Ser Ser Thr Glu
                100                 105                 110
Arg Leu Glu Val Leu Asp Asp Asp Arg His Ile Leu Ser Phe Arg Val
                115                 120                 125
Val Gly Gly Asp His Arg Leu Arg Asn Tyr Arg Ser Val Thr Ser Val
        130                 135                 140
Thr Glu Phe Gln Pro Gly Pro Tyr Cys Val Val Glu Ser Tyr Ala
145                 150                 155                 160
Val Asp Val Pro Glu Gly Asn Thr Ala Glu Asp Thr Arg Met Phe Thr
                165                 170                 175
Asp Thr Val Val Arg Leu Asn Leu Gln Lys Leu Ala Ala Val Ala Glu
```

180                 185                 190
Glu Ser Ala Ala Ala Ala Ala Gly Asn Arg Arg
        195                 200

<210> SEQ ID NO 115
<211> LENGTH: 204
<212> TYPE: PRT
<213> ORGANISM: Sorghum bicolor
<220> FEATURE:
<223> OTHER INFORMATION: sorghum Sb04g008040 protein

<400> SEQUENCE: 115

Met Glu Pro His Met Glu Thr Ala Leu Arg Gln Gly Gly Leu Ser Glu
1               5                   10                  15

Leu Glu Gln Arg Glu Leu Glu Pro Val Val Arg Ala His His Thr Phe
            20                  25                  30

Pro Gly Arg Ser Pro Gly Thr Thr Cys Thr Ser Leu Val Thr Gln Arg
        35                  40                  45

Val Asp Ala Pro Leu Ser Ala Val Trp Pro Ile Val Arg Gly Phe Ala
    50                  55                  60

Ala Pro Gln Arg Tyr Lys His Phe Ile Lys Ser Cys Asp Leu Arg Ser
65                  70                  75                  80

Gly Asp Gly Ala Thr Val Gly Ser Val Arg Glu Val Thr Val Val Ser
                85                  90                  95

Gly Leu Pro Ala Ser Thr Ser Thr Glu Arg Leu Glu Ile Leu Asp Asp
            100                 105                 110

Asp Arg His Ile Leu Ser Phe Arg Val Val Gly Asp His Arg Leu
        115                 120                 125

Arg Asn Tyr Arg Ser Val Thr Ser Val Thr Glu Phe His His His His
    130                 135                 140

Gln Ala Ala Ala Gly Arg Pro Tyr Cys Val Val Glu Ser Tyr Val
145                 150                 155                 160

Val Asp Val Pro Glu Gly Asn Thr Glu Glu Asp Thr Arg Met Phe Thr
                165                 170                 175

Asp Thr Val Val Lys Leu Asn Leu Gln Lys Leu Ala Ala Ile Ala Thr
            180                 185                 190

Ser Ser Ala Ala Ala Ala Ala Ser Asn Ser Ser Thr
        195                 200

<210> SEQ ID NO 116
<211> LENGTH: 258
<212> TYPE: PRT
<213> ORGANISM: Sorghum bicolor
<220> FEATURE:
<223> OTHER INFORMATION: sorghum Sb01g028330 protein

<400> SEQUENCE: 116

Met Val Glu Ser Pro Asn Pro Asn Ser Pro Ser Arg Pro Leu Cys Ile
1               5                   10                  15

Lys Tyr Thr Arg Ala Pro Ala Arg His Phe Ser Pro Leu Pro Phe
            20                  25                  30

Ser Ser Leu Ile Ile Ser Ala Asn Pro Ile Glu Pro Lys Ala Met Asp
        35                  40                  45

Lys Gln Gly Ala Gly Gly Asp Val Glu Val Pro Ala Gly Leu Gly Leu
    50                  55                  60

Thr Ala Ala Glu Tyr Glu Gln Leu Arg Ser Thr Val Asp Ala His His
65                  70                  75                  80

```
Arg Tyr Ala Val Gly Glu Gly Gln Cys Ser Ser Leu Leu Ala Gln Arg
                85                  90                  95

Ile Gln Ala Pro Pro Ala Ala Val Trp Ala Ile Val Arg Arg Phe Asp
            100                 105                 110

Cys Pro Gln Val Tyr Lys His Phe Ile Arg Ser Cys Ala Leu Arg Pro
            115                 120                 125

Asp Pro Glu Ala Gly Asp Ala Leu Arg Pro Gly Arg Leu Arg Glu Val
            130                 135                 140

Ser Val Ile Ser Gly Leu Pro Ala Ser Thr Ser Thr Glu Arg Leu Asp
145                 150                 155                 160

Leu Leu Asp Asp Ala Ala Arg Val Phe Gly Phe Ser Ile Thr Gly Gly
                165                 170                 175

Glu His Arg Leu Arg Asn Tyr Arg Ser Val Thr Thr Val Ser Glu Leu
            180                 185                 190

Ala Asp Pro Gly Ile Cys Thr Val Val Leu Glu Ser Tyr Val Val Asp
            195                 200                 205

Val Pro Asp Gly Asn Thr Glu Asp Asp Thr Arg Leu Phe Ala Asp Thr
            210                 215                 220

Val Ile Arg Leu Asn Leu Gln Lys Leu Lys Ser Val Ala Glu Ala Asn
225                 230                 235                 240

Ala Ala Ala Ala Ala Ser Phe Val Ser Val Val Pro Pro Glu Pro
                245                 250                 255

Glu Glu

<210> SEQ ID NO 117
<211> LENGTH: 222
<212> TYPE: PRT
<213> ORGANISM: Sorghum bicolor
<220> FEATURE:
<223> OTHER INFORMATION: sorghum Sb01g038150 protein

<400> SEQUENCE: 117

Met Pro Cys Leu Gln Ala Ser Ser Pro Gly Ser Met Pro His Gln
1               5                   10                  15

His His Gly Arg Val Leu Ala Gly Val Gly Cys Ala Ala Glu Val Ala
                20                  25                  30

Ala Ala Val Ala Ala Thr Ser Pro Ala Ala Gly Met Arg Cys Gly
            35                  40                  45

Ala His Asp Gly Glu Val Pro Ala Glu Ala Ala Arg His His Glu His
        50                  55                  60

Ala Ala Pro Gly Pro Gly Arg Cys Cys Ser Ala Val Val Gln His Val
65                  70                  75                  80

Ala Ala Pro Ala Ser Ala Val Trp Ser Val Val Arg Arg Phe Asp Gln
                85                  90                  95

Pro Gln Ala Tyr Lys Arg Phe Val Arg Ser Cys Ala Leu Leu Ala Gly
            100                 105                 110

Asp Gly Gly Val Gly Thr Leu Arg Glu Val Arg Val Val Ser Gly Leu
            115                 120                 125

Pro Ala Ala Ser Ser Arg Glu Arg Leu Glu Val Leu Asp Asp Glu Ser
            130                 135                 140

His Val Leu Ser Phe Arg Val Val Gly Gly Glu His Arg Leu Gln Asn
145                 150                 155                 160

Tyr Leu Ser Val Thr Thr Val His Pro Ser Pro Ala Ala Pro Asp Ala
                165                 170                 175

Ala Thr Val Val Val Glu Ser Tyr Val Val Asp Val Pro Pro Gly Asn
```

```
                     180                 185                 190

Thr Pro Glu Asp Thr Arg Val Phe Val Asp Thr Ile Val Lys Cys Asn
            195                 200                 205

Leu Gln Ser Leu Ala Thr Thr Ala Glu Lys Leu Ala Ala Val
    210                 215                 220

<210> SEQ ID NO 118
<211> LENGTH: 211
<212> TYPE: PRT
<213> ORGANISM: Sorghum bicolor
<220> FEATURE:
<223> OTHER INFORMATION: sorghum Sb04g009280 protein

<400> SEQUENCE: 118

Met Val Glu Met Asp Gly Gly Val Gly Val Val Gly Gly Gly Gln Gln
1               5                   10                  15

Thr Pro Ala Pro Arg Arg Trp Arg Leu Ala Asp Glu Leu Arg Cys Asp
            20                  25                  30

Leu Arg Ala Met Glu Thr Asp Tyr Val Arg Arg Phe His Arg His Glu
        35                  40                  45

Pro Arg Asp His Gln Cys Ser Ser Ala Val Ala Lys His Ile Lys Ala
    50                  55                  60

Pro Val His Leu Val Trp Ser Leu Val Arg Arg Phe Asp Gln Pro Gln
65                  70                  75                  80

Leu Phe Lys Pro Phe Val Ser Arg Cys Glu Met Lys Gly Asn Ile Glu
                85                  90                  95

Ile Gly Ser Val Arg Glu Val Asn Val Lys Ser Gly Leu Pro Ala Thr
            100                 105                 110

Arg Ser Thr Glu Arg Leu Glu Leu Leu Asp Asp Asn Glu His Ile Leu
        115                 120                 125

Ser Val Lys Phe Val Gly Gly Asp His Arg Leu Gln Asn Tyr Ser Ser
    130                 135                 140

Ile Leu Thr Val His Pro Glu Val Ile Asp Gly Arg Pro Gly Thr Leu
145                 150                 155                 160

Val Ile Glu Ser Phe Val Val Asp Val Pro Asp Gly Asn Thr Lys Asp
                165                 170                 175

Glu Thr Cys Tyr Phe Val Glu Ala Leu Leu Lys Cys Asn Leu Lys Ser
            180                 185                 190

Leu Ala Glu Val Ser Glu Arg Gln Val Ile Lys Asp Gln Thr Glu Pro
        195                 200                 205

Leu Asp Arg
    210

<210> SEQ ID NO 119
<211> LENGTH: 216
<212> TYPE: PRT
<213> ORGANISM: Sorghum bicolor
<220> FEATURE:
<223> OTHER INFORMATION: sorghum Sb09g023180 protein

<400> SEQUENCE: 119

Met Pro Tyr Thr Ala Pro Arg Pro Ser Pro Gln Gln His Ser Arg Val
1               5                   10                  15

Thr Gly Gly Gly Ala Lys Ala Ala Ile Val Ala Ala Ser His Gly Ala
            20                  25                  30

Ser Cys Ala Ala Val Pro Ala Glu Val Ala Arg His His Glu His Ala
        35                  40                  45
```

```
Ala Arg Ala Gly Gln Cys Cys Ser Ala Val Val Gln Ala Ile Ala Ala
     50                  55                  60

Pro Val Gly Ala Val Trp Ser Val Val Arg Arg Phe Asp Arg Pro Gln
 65                  70                  75                  80

Ala Tyr Lys His Phe Ile Arg Ser Cys Arg Leu Val Asp Asp Gly Gly
                 85                  90                  95

Gly Gly Ala Gly Ala Gly Ala Gly Ala Thr Val Ala Val Gly Ser Val
            100                 105                 110

Arg Glu Val Arg Val Val Ser Gly Leu Pro Ala Thr Ser Ser Arg Glu
            115                 120                 125

Arg Leu Glu Ile Leu Asp Asp Glu Arg Arg Val Leu Ser Phe Arg Val
130                 135                 140

Val Gly Gly Glu His Arg Leu Ala Asn Tyr Arg Ser Val Thr Thr Val
145                 150                 155                 160

His Glu Ala Glu Ala Gly Ala Gly Gly Thr Val Val Glu Ser Tyr
                165                 170                 175

Val Val Asp Val Pro Pro Gly Asn Thr Ala Asp Glu Thr Arg Val Phe
            180                 185                 190

Val Asp Thr Ile Val Arg Cys Asn Leu Gln Ser Leu Ala Arg Thr Ala
            195                 200                 205

Glu Arg Leu Ala Leu Ala Leu Ala
210                 215

<210> SEQ ID NO 120
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 H60P

<400> SEQUENCE: 120

Met Pro Ser Glu Leu Thr Pro Glu Glu Arg Ser Glu Leu Lys Asn Ser
  1               5                  10                  15

Ile Ala Glu Phe His Thr Tyr Gln Leu Asp Pro Gly Ser Cys Ser Ser
                 20                  25                  30

Leu His Ala Gln Arg Ile His Ala Pro Pro Glu Leu Val Trp Ser Ile
             35                  40                  45

Val Arg Arg Phe Asp Lys Pro Gln Thr Tyr Lys Pro Phe Ile Lys Ser
 50                  55                  60

Cys Ser Val Glu Gln Asn Phe Glu Met Arg Val Gly Cys Thr Arg Asp
 65                  70                  75                  80

Val Ile Phe Ile Ser Gly Leu Pro Ala Asn Thr Ser Thr Glu Arg Leu
                 85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
            115                 120                 125

Phe Glu Lys Glu Asn Arg Ile Trp Thr Val Val Leu Glu Ser Tyr Val
130                 135                 140

Val Asp Met Pro Glu Gly Asn Ser Glu Asp Asp Thr Arg Met Val Ala
145                 150                 155                 160

Asp Thr Val Val Lys Leu Asn Leu Gln Lys Leu Ala Thr Val Ala Glu
            165                 170                 175

Ala Met Ala Arg Asn Ser Gly Asp Gly Ser Gly Ser Gln Val Thr
            180                 185                 190
```

<210> SEQ ID NO 121
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 H60W

<400> SEQUENCE: 121

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys Trp Phe Ile Lys Ser
50                  55                  60

Cys Ser Val Glu Gln Asn Phe Glu Met Arg Val Gly Cys Thr Arg Asp
65                  70                  75                  80

Val Ile Phe Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
130                 135                 140

Val Asp Met Pro Glu Gly Asn Ser Glu Asp Thr Arg Met Val Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 122
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 H60R

<400> SEQUENCE: 122

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys Arg Phe Ile Lys Ser
50                  55                  60

Cys Ser Val Glu Gln Asn Phe Glu Met Arg Val Gly Cys Thr Arg Asp
65                  70                  75                  80

Val Ile Phe Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Val His Arg
            115                 120                 125

Phe Glu Lys Glu Asn Arg Ile Trp Thr Val Val Leu Glu Ser Tyr Val
        130                 135                 140

Val Asp Met Pro Glu Gly Asn Ser Glu Asp Thr Arg Met Val Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 123
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 H60I

<400> SEQUENCE: 123

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys Ile Phe Ile Lys Ser
50                  55                  60

Cys Ser Val Glu Gln Asn Phe Glu Met Arg Val Gly Cys Thr Arg Asp
65                  70                  75                  80

Val Ile Phe Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
            115                 120                 125

Phe Glu Lys Glu Asn Arg Ile Trp Thr Val Val Leu Glu Ser Tyr Val
        130                 135                 140

Val Asp Met Pro Glu Gly Asn Ser Glu Asp Thr Arg Met Val Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 124
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 H60K

<400> SEQUENCE: 124

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys Lys Phe Ile Lys Ser
    50                  55                  60

Cys Ser Val Glu Gln Asn Phe Glu Met Arg Val Gly Cys Thr Arg Asp
65                  70                  75                  80

Val Ile Phe Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
                100                 105                 110

Gly Glu His Arg Leu Thr Asn Tyr Lys Ser Val Thr Thr Val His Arg
            115                 120                 125

Phe Glu Lys Glu Asn Arg Ile Trp Thr Val Val Leu Glu Ser Tyr Val
        130                 135                 140

Val Asp Met Pro Glu Gly Asn Ser Glu Asp Thr Arg Met Val Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 125
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 H60V

<400> SEQUENCE: 125

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys Val Phe Ile Lys Ser
    50                  55                  60

Cys Ser Val Glu Gln Asn Phe Glu Met Arg Val Gly Cys Thr Arg Asp
65                  70                  75                  80

Val Ile Phe Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
                100                 105                 110

Gly Glu His Arg Leu Thr Asn Tyr Lys Ser Val Thr Thr Val His Arg
            115                 120                 125

Phe Glu Lys Glu Asn Arg Ile Trp Thr Val Val Leu Glu Ser Tyr Val
        130                 135                 140

Val Asp Met Pro Glu Gly Asn Ser Glu Asp Thr Arg Met Val Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

```
<210> SEQ ID NO 126
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 H60A

<400> SEQUENCE: 126

Met Pro Ser Glu Leu Thr Pro Glu Arg Ser Glu Leu Lys Asn Ser
1               5                   10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys Ala Phe Ile Lys Ser
        50                  55                  60

Cys Ser Val Glu Gln Asn Phe Glu Met Arg Val Gly Cys Thr Arg Asp
65                  70                  75                  80

Val Ile Phe Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Met Val Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 127
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 H60G

<400> SEQUENCE: 127

Met Pro Ser Glu Leu Thr Pro Glu Arg Ser Glu Leu Lys Asn Ser
1               5                   10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys Gly Phe Ile Lys Ser
        50                  55                  60

Cys Ser Val Glu Gln Asn Phe Glu Met Arg Val Gly Cys Thr Arg Asp
65                  70                  75                  80

Val Ile Phe Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
```

115                 120                 125

Phe Glu Lys Glu Asn Arg Ile Trp Thr Val Val Leu Glu Ser Tyr Val
        130                 135                 140

Val Asp Met Pro Glu Gly Asn Ser Glu Asp Asp Thr Arg Met Val Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
        180                 185                 190

<210> SEQ ID NO 128
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 H60M

<400> SEQUENCE: 128

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys Met Phe Ile Lys Ser
    50                  55                  60

Cys Ser Val Glu Gln Asn Phe Glu Met Arg Val Gly Cys Thr Arg Asp
65                  70                  75                  80

Val Ile Phe Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Met Val Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
        180                 185                 190

<210> SEQ ID NO 129
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 V83L

<400> SEQUENCE: 129

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile

```
            35                  40                  45
Val Arg Arg Phe Asp Lys Pro Gln Thr Tyr Lys His Phe Ile Lys Ser
 50                  55                  60

Cys Ser Val Glu Gln Asn Phe Glu Met Arg Val Gly Cys Thr Arg Asp
 65                  70                  75                  80

Val Ile Leu Ile Ser Gly Leu Pro Ala Asn Thr Ser Thr Glu Arg Leu
                 85                  90                  95

Asp Ile Leu Asp Asp Glu Arg Arg Val Thr Gly Phe Ser Ile Ile Gly
                100                 105                 110

Gly Glu His Arg Leu Thr Asn Tyr Lys Ser Val Thr Thr Val His Arg
                115                 120                 125

Phe Glu Lys Glu Asn Arg Ile Trp Thr Val Val Leu Glu Ser Tyr Val
130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
                180                 185                 190
```

<210> SEQ ID NO 130
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 V83P

<400> SEQUENCE: 130

```
Met Pro Ser Glu Leu Thr Pro Glu Glu Arg Ser Glu Leu Lys Asn Ser
 1               5                  10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
                35                  40                  45

Val Arg Arg Phe Asp Lys Pro Gln Thr Tyr Lys His Phe Ile Lys Ser
 50                  55                  60

Cys Ser Val Glu Gln Asn Phe Glu Met Arg Val Gly Cys Thr Arg Asp
 65                  70                  75                  80

Val Ile Pro Ile Ser Gly Leu Pro Ala Asn Thr Ser Thr Glu Arg Leu
                 85                  90                  95

Asp Ile Leu Asp Asp Glu Arg Arg Val Thr Gly Phe Ser Ile Ile Gly
                100                 105                 110

Gly Glu His Arg Leu Thr Asn Tyr Lys Ser Val Thr Thr Val His Arg
                115                 120                 125

Phe Glu Lys Glu Asn Arg Ile Trp Thr Val Val Leu Glu Ser Tyr Val
130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
                180                 185                 190
```

<210> SEQ ID NO 131
<211> LENGTH: 191

<212> TYPE: PRT
<213> ORGANISM: Artificial Sequence
<220> FEATURE:
<223> OTHER INFORMATION: synthetic mutated PYR/PYL receptor polypeptide
      PYR1 V83F

<400> SEQUENCE: 131

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys His Phe Ile Lys Ser
50                  55                  60

Cys Ser Val Glu Gln Asn Phe Glu Met Arg Val Gly Cys Thr Arg Asp
65                  70                  75                  80

Val Ile Phe Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 132
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 I84E

<400> SEQUENCE: 132

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys His Phe Ile Lys Ser
50                  55                  60

Cys Ser Val Glu Gln Asn Phe Glu Met Arg Val Gly Cys Thr Arg Asp
65                  70                  75                  80

Val Ile Val Glu Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
                180                 185                 190

<210> SEQ ID NO 133
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 I84P

<400> SEQUENCE: 133

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys His Phe Ile Lys Ser
50                  55                  60

Cys Ser Val Glu Gln Asn Phe Glu Met Arg Val Gly Cys Thr Arg Asp
65                  70                  75                  80

Val Ile Val Pro Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
                100                 105                 110

Gly Glu His Arg Leu Thr Asn Tyr Lys Ser Val Thr Thr Val His Arg
            115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
                180                 185                 190

<210> SEQ ID NO 134
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 I84H

<400> SEQUENCE: 134

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys His Phe Ile Lys Ser
 50                  55                  60

Cys Ser Val Glu Gln Asn Phe Glu Met Arg Val Gly Cys Thr Arg Asp
 65                  70                  75                  80

Val Ile Val His Ser Gly Leu Pro Ala Asn Thr Ser Thr Glu Arg Leu
                 85                  90                  95

Asp Ile Leu Asp Asp Glu Arg Arg Val Thr Gly Phe Ser Ile Ile Gly
                100                 105                 110

Gly Glu His Arg Leu Thr Asn Tyr Lys Ser Val Thr Thr Val His Arg
                115                 120                 125

Phe Glu Lys Glu Asn Arg Ile Trp Thr Val Val Leu Glu Ser Tyr Val
130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
                180                 185                 190

<210> SEQ ID NO 135
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 I84Q

<400> SEQUENCE: 135

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys His Phe Ile Lys Ser
 50                  55                  60

Cys Ser Val Glu Gln Asn Phe Glu Met Arg Val Gly Cys Thr Arg Asp
 65                  70                  75                  80

Val Ile Val Gln Ser Gly Leu Pro Ala Asn Thr Ser Thr Glu Arg Leu
                 85                  90                  95

Asp Ile Leu Asp Asp Glu Arg Arg Val Thr Gly Phe Ser Ile Ile Gly
                100                 105                 110

Gly Glu His Arg Leu Thr Asn Tyr Lys Ser Val Thr Thr Val His Arg
                115                 120                 125

Phe Glu Lys Glu Asn Arg Ile Trp Thr Val Val Leu Glu Ser Tyr Val
130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
                180                 185                 190

<210> SEQ ID NO 136
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide PYR1 I84K

<400> SEQUENCE: 136

```
Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
    50                  55                  60

Cys Ser Val Glu Gln Asn Phe Glu Met Arg Val Gly Cys Thr Arg Asp
65                  70                  75                  80

Val Ile Val Lys Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190
```

<210> SEQ ID NO 137
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide PYR1 L87F

<400> SEQUENCE: 137

```
Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
    50                  55                  60

Cys Ser Val Glu Gln Asn Phe Glu Met Arg Val Gly Cys Thr Arg Asp
65                  70                  75                  80

Val Ile Val Ile Ser Gly Phe Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140
```

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 138
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 A89W

<400> SEQUENCE: 138

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
50                  55                  60

Cys Ser Val Glu Gln Asn Phe Glu Met Arg Val Gly Cys Thr Arg Asp
65                  70                  75                  80

Val Ile Val Ile Ser Gly Leu Pro Trp Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 139
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 M158C

<400> SEQUENCE: 139

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
50                  55                  60

-continued

Cys Ser Val Glu Gln Asn Phe Glu Met Arg Val Gly Cys Thr Arg Asp
 65                  70                  75                  80

Val Ile Val Ile Ser Gly Leu Pro Ala Asn Thr Ser Thr Glu Arg Leu
                 85                  90                  95

Asp Ile Leu Asp Asp Glu Arg Arg Val Thr Gly Phe Ser Ile Ile Gly
             100                 105                 110

Gly Glu His Arg Leu Thr Asn Tyr Lys Ser Val Thr Thr Val His Arg
         115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Thr Arg Cys Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 140
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 M158I

<400> SEQUENCE: 140

Met Pro Ser Glu Leu Thr Pro Glu Glu Arg Ser Glu Leu Lys Asn Ser
  1               5                  10                  15

Ile Ala Glu Phe His Thr Tyr Gln Leu Asp Pro Gly Ser Cys Ser Ser
                 20                  25                  30

Leu His Ala Gln Arg Ile His Ala Pro Pro Glu Leu Val Trp Ser Ile
             35                  40                  45

Val Arg Arg Phe Asp Lys Pro Gln Thr Tyr Lys His Phe Ile Lys Ser
 50                  55                  60

Cys Ser Val Glu Gln Asn Phe Glu Met Arg Val Gly Cys Thr Arg Asp
 65                  70                  75                  80

Val Ile Val Ile Ser Gly Leu Pro Ala Asn Thr Ser Thr Glu Arg Leu
                 85                  90                  95

Asp Ile Leu Asp Asp Glu Arg Arg Val Thr Gly Phe Ser Ile Ile Gly
             100                 105                 110

Gly Glu His Arg Leu Thr Asn Tyr Lys Ser Val Thr Thr Val His Arg
         115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Thr Arg Ile Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 141
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide

PYR1 M158T

<400> SEQUENCE: 141

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Thr Arg Thr Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 142
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 M158V

<400> SEQUENCE: 142

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Thr Arg Val Phe Ala

```
                    145                 150                 155                 160
Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 143
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 F159V

<400> SEQUENCE: 143

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys His Phe Ile Lys Ser
        50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
                100                 105                 110

Gly Glu His Arg Leu Thr Asn Tyr Lys Ser Val Thr Thr Val His Arg
            115                 120                 125

Phe Glu Lys Glu Asn Arg Ile Trp Thr Val Val Leu Glu Ser Tyr Val
        130                 135                 140

Val Asp Met Pro Glu Gly Asn Ser Glu Asp Asp Thr Arg Met Val Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 144
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 F159A

<400> SEQUENCE: 144

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys His Phe Ile Lys Ser
        50                  55                  60

Cys Ser Val Glu Gln Asn Phe Glu Met Arg Val Gly Cys Thr Arg Asp
```

```
                65                  70                  75                  80
Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Thr Arg Met Ala Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190
```

<210> SEQ ID NO 145
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide PYR1 T162F

<400> SEQUENCE: 145

```
Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys His Phe Ile Lys Ser
        50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Thr Arg Met Phe Ala
145                 150                 155                 160

Asp Phe Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190
```

<210> SEQ ID NO 146
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide PYR1 L166F

```
<400> SEQUENCE: 146

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys His Phe Ile Lys Ser
    50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
                100                 105                 110

Gly Glu His Arg Leu Thr Asn Tyr Lys Ser Val Thr Thr Val His Arg
            115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Phe Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 147
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 L166Y

<400> SEQUENCE: 147

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
                20                  25                  30

Leu His Ala Gln Arg Ile His Ala Pro Pro Glu Leu Val Trp Ser Ile
            35                  40                  45

Val Arg Arg Phe Asp Lys Pro Gln Thr Tyr Lys His Phe Ile Lys Ser
    50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
                100                 105                 110

Gly Glu His Arg Leu Thr Asn Tyr Lys Ser Val Thr Thr Val His Arg
            115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160
```

```
Asp Thr Val Val Lys Tyr Asn Leu Gln Lys Leu Ala Thr Val Ala Glu
            165                 170                 175

Ala Met Ala Arg Asn Ser Gly Asp Gly Ser Gly Ser Gln Val Thr
            180                 185                 190

<210> SEQ ID NO 148
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 K170W

<400> SEQUENCE: 148

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
    50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Trp Leu Ala Thr Val Ala Glu
            165                 170                 175

Ala Met Ala Arg Asn Ser Gly Asp Gly Ser Gly Ser Gln Val Thr
            180                 185                 190

<210> SEQ ID NO 149
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 H60P/V83F/F159V (CA3)

<400> SEQUENCE: 149

Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys Pro Phe Ile Lys Ser
    50                  55                  60

Cys Ser Val Glu Gln Asn Phe Glu Met Arg Val Gly Cys Thr Arg Asp
65                  70                  75                  80
```

```
Val Ile Phe Ile Ser Gly Leu Pro Ala Asn Thr Ser Thr Glu Arg Leu
            85                  90                  95

Asp Ile Leu Asp Asp Glu Arg Arg Val Thr Gly Phe Ser Ile Ile Gly
        100                 105                 110

Gly Glu His Arg Leu Thr Asn Tyr Lys Ser Val Thr Thr Val His Arg
            115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Thr Arg Met Val Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
                180                 185                 190
```

<210> SEQ ID NO 150
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 H60P/V83FM158I/F159V (CA4)

<400> SEQUENCE: 150

```
Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys Pro Phe Ile Lys Ser
    50                  55                  60

Cys Ser Val Glu Gln Asn Phe Glu Met Arg Val Gly Cys Thr Arg Asp
65                  70                  75                  80

Val Ile Phe Ile Ser Gly Leu Pro Ala Asn Thr Ser Thr Glu Arg Leu
            85                  90                  95

Asp Ile Leu Asp Asp Glu Arg Arg Val Thr Gly Phe Ser Ile Ile Gly
        100                 105                 110

Gly Glu His Arg Leu Thr Asn Tyr Lys Ser Val Thr Thr Val His Arg
            115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Thr Arg Ile Val Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
                180                 185                 190
```

<210> SEQ ID NO 151
<211> LENGTH: 191
<212> TYPE: PRT
<213> ORGANISM: Artificial Sequence
<220> FEATURE:
<223> OTHER INFORMATION: synthetic mutated PYR/PYL receptor polypeptide
      PYR1 H60P/A89W/F159V

<400> SEQUENCE: 151

```
Met Pro Ser Glu Leu Thr Pro Glu Glu Arg Ser Glu Leu Lys Asn Ser
1               5                   10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys Pro Phe Ile Lys Ser
    50                  55                  60

Cys Ser Val Glu Gln Asn Phe Glu Met Arg Val Gly Cys Thr Arg Asp
65                  70                  75                  80

Val Ile Val Ile Ser Gly Leu Pro Trp Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Thr Arg Met Val Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190

<210> SEQ ID NO 152
<211> LENGTH: 190
<212> TYPE: PRT
<213> ORGANISM: Artificial Sequence
<220> FEATURE:
<223> OTHER INFORMATION: synthetic mutated PYR/PYL receptor polypeptide
      PYL2 H65P/V87F/F165V (CA3)

<400> SEQUENCE: 152

Met Ser Ser Ser Pro Ala Val Lys Gly Leu Thr Asp Glu Glu Gln Lys
1               5                   10                  15

Thr Leu Glu Pro Val Ile Lys Thr Tyr His Gln Phe Glu Pro Asp Pro
            20                  25                  30

Thr Thr Cys Thr Ser Leu Ile Thr Gln Arg Ile His Ala Pro Ala Ser
        35                  40                  45

Val Val Trp Pro Leu Ile Arg Arg Phe Asp Asn Pro Glu Arg Tyr Lys
    50                  55                  60

Pro Phe Val Lys Arg Cys Arg Leu Ile Ser Gly Asp Gly Asp Val Gly
65                  70                  75                  80

Ser Val Arg Glu Val Thr Phe Ile Ser Gly Leu Pro Ala Ser Thr Ser
                85                  90                  95

Thr Glu Arg Leu Glu Phe Val Asp Asp His Arg Val Leu Ser Phe
            100                 105                 110

Arg Val Val Gly Gly Glu His Arg Leu Lys Asn Tyr Lys Ser Val Thr
        115                 120                 125

Ser Val Asn Glu Phe Leu Asn Gln Asp Ser Gly Lys Val Tyr Thr Val
    130                 135                 140

Val Leu Glu Ser Tyr Thr Val Asp Ile Pro Glu Gly Asn Thr Glu Glu
145                 150                 155                 160

Asp Thr Lys Met Val Val Asp Thr Val Val Lys Leu Asn Leu Gln Lys
                165                 170                 175
```

Leu Gly Val Ala Ala Thr Ser Ala Pro Met His Asp Asp Glu
            180                 185                 190

<210> SEQ ID NO 153
<211> LENGTH: 190
<212> TYPE: PRT
<213> ORGANISM: Artificial Sequence
<220> FEATURE:
<223> OTHER INFORMATION: synthetic mutated PYR/PYL receptor polypeptide
      PYL2 H65P/V87F/M164I/F165V (CA4)

<400> SEQUENCE: 153

Met Ser Ser Ser Pro Ala Val Lys Gly Leu Thr Asp Glu Glu Gln Lys
1               5                   10                  15

Thr Leu Glu Pro Val Ile Lys Thr Tyr His Gln Phe Glu Pro Asp Pro
            20                  25                  30

Thr Thr Cys Thr Ser Leu Ile Thr Gln Arg Ile His Ala Pro Ala Ser
        35                  40                  45

Val Val Trp Pro Leu Ile Arg Arg Phe Asp Asn Pro Glu Arg Tyr Lys
    50                  55                  60

Pro Phe Val Lys Arg Cys Arg Leu Ile Ser Gly Asp Gly Asp Val Gly
65                  70                  75                  80

Ser Val Arg Glu Val Thr Phe Ile Ser Gly Leu Pro Ala Ser Thr Ser
                85                  90                  95

Thr Glu Arg Leu Glu Phe Val Asp Asp Asp His Arg Val Leu Ser Phe
            100                 105                 110

Arg Val Val Gly Gly Glu His Arg Leu Lys Asn Tyr Lys Ser Val Thr
        115                 120                 125

Ser Val Asn Glu Phe Leu Asn Gln Asp Ser Gly Lys Val Tyr Thr Val
    130                 135                 140

Val Leu Glu Ser Tyr Thr Val Asp Ile Pro Glu Gly Asn Thr Glu Glu
145                 150                 155                 160

Asp Thr Lys Ile Val Val Asp Thr Val Val Lys Leu Asn Leu Gln Lys
                165                 170                 175

Leu Gly Val Ala Ala Thr Ser Ala Pro Met His Asp Asp Glu
            180                 185                 190

<210> SEQ ID NO 154
<211> LENGTH: 190
<212> TYPE: PRT
<213> ORGANISM: Artificial Sequence
<220> FEATURE:
<223> OTHER INFORMATION: synthetic mutated PYR/PYL receptor polypeptide
      PYL2 H65P/A93W/F165V

<400> SEQUENCE: 154

Met Ser Ser Ser Pro Ala Val Lys Gly Leu Thr Asp Glu Glu Gln Lys
1               5                   10                  15

Thr Leu Glu Pro Val Ile Lys Thr Tyr His Gln Phe Glu Pro Asp Pro
            20                  25                  30

Thr Thr Cys Thr Ser Leu Ile Thr Gln Arg Ile His Ala Pro Ala Ser
        35                  40                  45

Val Val Trp Pro Leu Ile Arg Arg Phe Asp Asn Pro Glu Arg Tyr Lys
    50                  55                  60

Pro Phe Val Lys Arg Cys Arg Leu Ile Ser Gly Asp Gly Asp Val Gly
65                  70                  75                  80

Ser Val Arg Glu Val Thr Val Ile Ser Gly Leu Pro Trp Ser Thr Ser
                85                  90                  95

```
Thr Glu Arg Leu Glu Phe Val Asp Asp His Arg Val Leu Ser Phe
            100                 105                 110

Arg Val Val Gly Gly Glu His Arg Leu Lys Asn Tyr Lys Ser Val Thr
            115                 120                 125

Ser Val Asn Glu Phe Leu Asn Gln Asp Ser Gly Lys Val Tyr Thr Val
            130                 135                 140

Val Leu Glu Ser Tyr Thr Val Asp Ile Pro Glu Gly Asn Thr Glu Glu
145                 150                 155                 160

Asp Thr Lys Met Val Val Asp Thr Val Val Lys Leu Asn Leu Gln Lys
                165                 170                 175

Leu Gly Val Ala Ala Thr Ser Ala Pro Met His Asp Asp Glu
            180                 185                 190

<210> SEQ ID NO 155
<211> LENGTH: 187
<212> TYPE: PRT
<213> ORGANISM: Artificial Sequence
<220> FEATURE:
<223> OTHER INFORMATION: synthetic mutated PYR/PYL receptor polypeptide
      PYL9 V85F/Y160I/F161V

<400> SEQUENCE: 155

Met Met Asp Gly Val Glu Gly Gly Thr Ala Met Tyr Gly Gly Leu Glu
1               5                   10                  15

Thr Val Gln Tyr Val Arg Thr His His Gln His Leu Cys Arg Glu Asn
            20                  25                  30

Gln Cys Thr Ser Ala Leu Val Lys His Ile Lys Ala Pro Leu His Leu
            35                  40                  45

Val Trp Ser Leu Val Arg Arg Phe Asp Gln Pro Gln Lys Tyr Lys Pro
50                  55                  60

Phe Val Ser Arg Cys Thr Val Ile Gly Asp Pro Glu Ile Gly Ser Leu
65                  70                  75                  80

Arg Glu Val Asn Phe Lys Ser Gly Leu Pro Ala Thr Thr Ser Thr Glu
            85                  90                  95

Arg Leu Glu Leu Leu Asp Asp Glu Glu His Ile Leu Gly Ile Lys Ile
            100                 105                 110

Ile Gly Gly Asp His Arg Leu Lys Asn Tyr Ser Ser Ile Leu Thr Val
            115                 120                 125

His Pro Glu Ile Ile Glu Gly Arg Ala Gly Thr Met Val Ile Glu Ser
            130                 135                 140

Phe Val Val Asp Val Pro Gln Gly Asn Thr Lys Asp Glu Thr Cys Ile
145                 150                 155                 160

Val Val Glu Ala Leu Ile Arg Cys Asn Leu Lys Ser Leu Ala Asp Val
                165                 170                 175

Ser Glu Arg Leu Ala Ser Gln Asp Ile Thr Gln
            180                 185

<210> SEQ ID NO 156
<211> LENGTH: 5
<212> TYPE: PRT
<213> ORGANISM: Artificial Sequence
<220> FEATURE:
<223> OTHER INFORMATION: synthetic PYR1 positions 59-63, PYL1 positions
      86-90, PYL3 positions 79-83

<400> SEQUENCE: 156

Lys His Phe Ile Lys
1               5
```

<210> SEQ ID NO 157
<211> LENGTH: 7
<212> TYPE: PRT
<213> ORGANISM: Artificial Sequence
<220> FEATURE:
<223> OTHER INFORMATION: synthetic PYR1 positions 83-89, PYL1 positions
      110-116, PYL2 positions 87-93, Zea mays PYR1 homolog positions
      100-106

<400> SEQUENCE: 157

Val Ile Ser Gly Leu Pro Ala
1               5

<210> SEQ ID NO 158
<211> LENGTH: 5
<212> TYPE: PRT
<213> ORGANISM: Artificial Sequence
<220> FEATURE:
<223> OTHER INFORMATION: synthetic PYL2 positions 64-68, PYL6 90-94,
      PYL12 positions 39-43

<400> SEQUENCE: 158

Lys His Phe Val Lys
1               5

<210> SEQ ID NO 159
<211> LENGTH: 7
<212> TYPE: PRT
<213> ORGANISM: Artificial Sequence
<220> FEATURE:
<223> OTHER INFORMATION: synthetic PYL3 positions 107-113, PYL4
      positions 105-111, PYL5 positions 111-117, PYL6 positions 114-120,
      PYL11 positions 62-68

<400> SEQUENCE: 159

Val Val Ser Gly Leu Pro Ala
1               5

<210> SEQ ID NO 160
<211> LENGTH: 5
<212> TYPE: PRT
<213> ORGANISM: Artificial Sequence
<220> FEATURE:
<223> OTHER INFORMATION: synthetic PYL4 positions 81-85

<400> SEQUENCE: 160

Lys His Phe Leu Lys
1               5

<210> SEQ ID NO 161
<211> LENGTH: 5
<212> TYPE: PRT
<213> ORGANISM: Artificial Sequence
<220> FEATURE:
<223> OTHER INFORMATION: synthetic PYL5 positions 87-91

<400> SEQUENCE: 161

Lys Asn Phe Ile Arg
1               5

<210> SEQ ID NO 162
<211> LENGTH: 5
<212> TYPE: PRT
<213> ORGANISM: Artificial Sequence
<220> FEATURE:
<223> OTHER INFORMATION: synthetic PYL7 positions 65-69, PYL8 positions
      61-65, PYL10 positions 56-60

```
<400> SEQUENCE: 162

Lys Pro Phe Ile Ser
1               5

<210> SEQ ID NO 163
<211> LENGTH: 7
<212> TYPE: PRT
<213> ORGANISM: Artificial Sequence
<220> FEATURE:
<223> OTHER INFORMATION: synthetic PYL7 positions 87-93, PYL8 positions
      83-89, PYL9 positions 85-91

<400> SEQUENCE: 163

Val Lys Ser Gly Leu Pro Ala
1               5

<210> SEQ ID NO 164
<211> LENGTH: 5
<212> TYPE: PRT
<213> ORGANISM: Artificial Sequence
<220> FEATURE:
<223> OTHER INFORMATION: synthetic PYL9 positions 63-67

<400> SEQUENCE: 164

Lys Pro Phe Val Ser
1               5

<210> SEQ ID NO 165
<211> LENGTH: 7
<212> TYPE: PRT
<213> ORGANISM: Artificial Sequence
<220> FEATURE:
<223> OTHER INFORMATION: synthetic PYL10 positions 79-85

<400> SEQUENCE: 165

Leu Lys Ser Gly Leu Pro Ala
1               5

<210> SEQ ID NO 166
<211> LENGTH: 5
<212> TYPE: PRT
<213> ORGANISM: Artificial Sequence
<220> FEATURE:
<223> OTHER INFORMATION: synthetic PYL11 positions 39-43

<400> SEQUENCE: 166

Lys Gln Phe Val Lys
1               5

<210> SEQ ID NO 167
<211> LENGTH: 7
<212> TYPE: PRT
<213> ORGANISM: Artificial Sequence
<220> FEATURE:
<223> OTHER INFORMATION: synthetic PYL12 positions 62-68

<400> SEQUENCE: 167

Val Val Ser Asp Leu Pro Ala
1               5

<210> SEQ ID NO 168
<211> LENGTH: 5
<212> TYPE: PRT
<213> ORGANISM: Artificial Sequence
<220> FEATURE:
<223> OTHER INFORMATION: synthetic PYL13 positions 38-42
```

```
<400> SEQUENCE: 168

Gln Arg Phe Val Lys
1               5

<210> SEQ ID NO 169
<211> LENGTH: 7
<212> TYPE: PRT
<213> ORGANISM: Artificial Sequence
<220> FEATURE:
<223> OTHER INFORMATION: synthetic PYL13 positions 67-73

<400> SEQUENCE: 169

Leu Val Ser Gly Phe Pro Ala
1               5

<210> SEQ ID NO 170
<211> LENGTH: 5
<212> TYPE: PRT
<213> ORGANISM: Artificial Sequence
<220> FEATURE:
<223> OTHER INFORMATION: synthetic Physcomitrella patens PYR1 homolog
      positions 63-67

<400> SEQUENCE: 170

Lys Arg Phe Ile Gln
1               5

<210> SEQ ID NO 171
<211> LENGTH: 7
<212> TYPE: PRT
<213> ORGANISM: Artificial Sequence
<220> FEATURE:
<223> OTHER INFORMATION: synthetic Physcomitrella patens PYR1 homolog
      positions 86-92

<400> SEQUENCE: 171

Leu Val Ser Ser Ile Pro Ala
1               5

<210> SEQ ID NO 172
<211> LENGTH: 5
<212> TYPE: PRT
<213> ORGANISM: Artificial Sequence
<220> FEATURE:
<223> OTHER INFORMATION: synthetic Zea mays PYR1 homolog positions 72-76

<400> SEQUENCE: 172

Lys His Phe Ile Arg
1               5

<210> SEQ ID NO 173
<211> LENGTH: 6
<212> TYPE: PRT
<213> ORGANISM: Artificial Sequence
<220> FEATURE:
<223> OTHER INFORMATION: synthetic 6xHis

<400> SEQUENCE: 173

His His His His His His
1               5

<210> SEQ ID NO 174
<211> LENGTH: 20
<212> TYPE: DNA
<213> ORGANISM: Artificial Sequence
<220> FEATURE:
```

```
<223> OTHER INFORMATION: synthetic quantitative real-time PCR (qRT-PCR)
      oligo-dT-20

<400> SEQUENCE: 174
tttttttttt tttttttttt                                              20

<210> SEQ ID NO 175
<211> LENGTH: 21
<212> TYPE: DNA
<213> ORGANISM: Artificial Sequence
<220> FEATURE:
<223> OTHER INFORMATION: synthetic quantitative real-time PCR (qRT-PCR)
      ribosomal RNA primer

<400> SEQUENCE: 175
acatctaagg gcatcacaga c                                            21

<210> SEQ ID NO 176
<211> LENGTH: 20
<212> TYPE: DNA
<213> ORGANISM: Artificial Sequence
<220> FEATURE:
<223> OTHER INFORMATION: synthetic gene specific primer for detecting
      Em6 (At2g40170)

<400> SEQUENCE: 176
tcgaagctca acagcatctc                                              20

<210> SEQ ID NO 177
<211> LENGTH: 20
<212> TYPE: DNA
<213> ORGANISM: Artificial Sequence
<220> FEATURE:
<223> OTHER INFORMATION: synthetic gene specific primer for detecting
      Em6 (At2g40170)

<400> SEQUENCE: 177
actgctcctt tcgagtttgc                                              20

<210> SEQ ID NO 178
<211> LENGTH: 20
<212> TYPE: DNA
<213> ORGANISM: Artificial Sequence
<220> FEATURE:
<223> OTHER INFORMATION: synthetic gene specific primer for detecting
      LEA (At2g21490)

<400> SEQUENCE: 178
cgtcggtctg gaagttcatc                                              20

<210> SEQ ID NO 179
<211> LENGTH: 20
<212> TYPE: DNA
<213> ORGANISM: Artificial Sequence
<220> FEATURE:
<223> OTHER INFORMATION: synthetic gene specific primer for detecting
      LEA (At2g21490)

<400> SEQUENCE: 179
tcttcttcct cctccctcct                                              20

<210> SEQ ID NO 180
<211> LENGTH: 19
<212> TYPE: DNA
<213> ORGANISM: Artificial Sequence
<220> FEATURE:
<223> OTHER INFORMATION: synthetic gene specific primer for detecting
```

```
                                Rd29b (At5g52300)

<400> SEQUENCE: 180
atccgaaaac ccatagtcc                                                    19

<210> SEQ ID NO 181
<211> LENGTH: 20
<212> TYPE: DNA
<213> ORGANISM: Artificial Sequence
<220> FEATURE:
<223> OTHER INFORMATION: synthetic gene specific primer for detecting
      Rd29b (At5g52300)

<400> SEQUENCE: 181
tggtggggaa agttaaagga                                                   20

<210> SEQ ID NO 182
<211> LENGTH: 20
<212> TYPE: DNA
<213> ORGANISM: Artificial Sequence
<220> FEATURE:
<223> OTHER INFORMATION: synthetic gene specific primer for detecting
      rRNA

<400> SEQUENCE: 182
aaacggctac cacatccaag                                                   20

<210> SEQ ID NO 183
<211> LENGTH: 20
<212> TYPE: DNA
<213> ORGANISM: Artificial Sequence
<220> FEATURE:
<223> OTHER INFORMATION: synthetic gene specific primer for detecting
      rRNA

<400> SEQUENCE: 183
gactcgaaag agcccggtat                                                   20

<210> SEQ ID NO 184
<211> LENGTH: 32
<212> TYPE: DNA
<213> ORGANISM: Artificial Sequence
<220> FEATURE:
<223> OTHER INFORMATION: synthetic mutagenesis primer ply2A93W
      (ply2A93W+)

<400> SEQUENCE: 184
ctccggcctc ccatggtcaa ccagtaccga gc                                     32

<210> SEQ ID NO 185
<211> LENGTH: 30
<212> TYPE: DNA
<213> ORGANISM: Artificial Sequence
<220> FEATURE:
<223> OTHER INFORMATION: synthetic mutagenesis primer ply2V87F
      (ply2V87F+)

<400> SEQUENCE: 185
cagagaagtg acctttatct ccggcctccc                                        30

<210> SEQ ID NO 186
<211> LENGTH: 38
<212> TYPE: DNA
<213> ORGANISM: Artificial Sequence
<220> FEATURE:
<223> OTHER INFORMATION: synthetic mutagenesis primer PRY1R116#
<220> FEATURE:
```

<221> NAME/KEY: modified_base
<222> LOCATION: (17)...(18)
<223> OTHER INFORMATION: n = g, a, c or t

<400> SEQUENCE: 186
catcggaggc gaacatnnkc tgacgaatta caaatccg        38

<210> SEQ ID NO 187
<211> LENGTH: 38
<212> TYPE: DNA
<213> ORGANISM: Artificial Sequence
<220> FEATURE:
<223> OTHER INFORMATION: synthetic mutagenesis primer PYR1R116E

<400> SEQUENCE: 187
catcggaggc gaacatgagc tgacgaatta caaatccg        38

<210> SEQ ID NO 188
<211> LENGTH: 38
<212> TYPE: DNA
<213> ORGANISM: Artificial Sequence
<220> FEATURE:
<223> OTHER INFORMATION: synthetic mutagenesis primer PYR1R116H

<400> SEQUENCE: 188
catcggaggc gaacatcatc tgacgaatta caaatccg        38

<210> SEQ ID NO 189
<211> LENGTH: 38
<212> TYPE: DNA
<213> ORGANISM: Artificial Sequence
<220> FEATURE:
<223> OTHER INFORMATION: synthetic mutagenesis primer PYR1R116I

<400> SEQUENCE: 189
catcggaggc gaacatattc tgacgaatta caaatccg        38

<210> SEQ ID NO 190
<211> LENGTH: 38
<212> TYPE: DNA
<213> ORGANISM: Artificial Sequence
<220> FEATURE:
<223> OTHER INFORMATION: synthetic mutagenesis primer PYR1R116T

<400> SEQUENCE: 190
catcggaggc gaacataccc tgacgaatta caaatccg        38

<210> SEQ ID NO 191
<211> LENGTH: 38
<212> TYPE: DNA
<213> ORGANISM: Artificial Sequence
<220> FEATURE:
<223> OTHER INFORMATION: synthetic mutagenesis primer PYR1R116Y

<400> SEQUENCE: 191
catcggaggc gaacattatc tgacgaatta caaatccg        38

<210> SEQ ID NO 192
<211> LENGTH: 36
<212> TYPE: DNA
<213> ORGANISM: Artificial Sequence
<220> FEATURE:
<223> OTHER INFORMATION: synthetic mutagenesis primer PYL2E147K

<400> SEQUENCE: 192
cacggtggtt cttaaatctt acaccgttga tattcc        36

<210> SEQ ID NO 193
<211> LENGTH: 36
<212> TYPE: DNA
<213> ORGANISM: Artificial Sequence
<220> FEATURE:
<223> OTHER INFORMATION: synthetic mutagenesis primer PYL2E147L

<400> SEQUENCE: 193
cacggtggtt cttttatctt acaccgttga tattcc                                36

<210> SEQ ID NO 194
<211> LENGTH: 32
<212> TYPE: DNA
<213> ORGANISM: Artificial Sequence
<220> FEATURE:
<223> OTHER INFORMATION: synthetic mutagenesis primer PYL2E98D

<400> SEQUENCE: 194
cctcaaccag taccgatcgg cttgagttcg tc                                    32

<210> SEQ ID NO 195
<211> LENGTH: 36
<212> TYPE: DNA
<213> ORGANISM: Artificial Sequence
<220> FEATURE:
<223> OTHER INFORMATION: synthetic mutagenesis primer pyl2F165V+

<400> SEQUENCE: 195
gaggaagaca ctaaaatggt tgtggacact gtcgtc                                36

<210> SEQ ID NO 196
<211> LENGTH: 33
<212> TYPE: DNA
<213> ORGANISM: Artificial Sequence
<220> FEATURE:
<223> OTHER INFORMATION: synthetic mutagenesis primer pyl2H60P+
      (PYL2H65P+)

<400> SEQUENCE: 196
ccgaacgcta caaacccttt gtaaaaaggt gcc                                   33

<210> SEQ ID NO 197
<211> LENGTH: 37
<212> TYPE: DNA
<213> ORGANISM: Artificial Sequence
<220> FEATURE:
<223> OTHER INFORMATION: synthetic mutagenesis primer PYL2K64L

<400> SEQUENCE: 197
caaccccgaa cgctacttac actttgtaaa aaggtgc                               37

<210> SEQ ID NO 198
<211> LENGTH: 36
<212> TYPE: DNA
<213> ORGANISM: Artificial Sequence
<220> FEATURE:
<223> OTHER INFORMATION: synthetic mutagenesis primer pyl2m158I,f159v+

<400> SEQUENCE: 198
cagaggaaga cactaaaatc gttgtggaca ctgtcg                                36

<210> SEQ ID NO 199
<211> LENGTH: 34
<212> TYPE: DNA
<213> ORGANISM: Artificial Sequence

```
<220> FEATURE:
<223> OTHER INFORMATION: synthetic mutagenesis primer PYL2V85I

<400> SEQUENCE: 199
ggaagcgtca gagaaatcac cgtaatctcc ggcc                              34

<210> SEQ ID NO 200
<211> LENGTH: 39
<212> TYPE: DNA
<213> ORGANISM: Artificial Sequence
<220> FEATURE:
<223> OTHER INFORMATION: synthetic mutagenesis primer PYL9A91W+

<400> SEQUENCE: 200
tgttaaatct ggtcttcctt ggacaacatc tactgagag                          39

<210> SEQ ID NO 201
<211> LENGTH: 58
<212> TYPE: DNA
<213> ORGANISM: Artificial Sequence
<220> FEATURE:
<223> OTHER INFORMATION: synthetic mutagenesis primer PYL9 A91WV85F+

<400> SEQUENCE: 201
gcagtcttag agaagtcaat tttaaatctg gtcttccttg gacaacatct actgagag    58

<210> SEQ ID NO 202
<211> LENGTH: 35
<212> TYPE: DNA
<213> ORGANISM: Artificial Sequence
<220> FEATURE:
<223> OTHER INFORMATION: synthetic mutagenesis primer PYL9F161V+

<400> SEQUENCE: 202
gatgagactt gctacgttgt tgaagcactt atcag                             35

<210> SEQ ID NO 203
<211> LENGTH: 36
<212> TYPE: DNA
<213> ORGANISM: Artificial Sequence
<220> FEATURE:
<223> OTHER INFORMATION: synthetic mutagenesis primer PYL9V85F+

<400> SEQUENCE: 203
gtcttagaga agtcaatttt aaatctggtc ttcctg                            36

<210> SEQ ID NO 204
<211> LENGTH: 38
<212> TYPE: DNA
<213> ORGANISM: Artificial Sequence
<220> FEATURE:
<223> OTHER INFORMATION: synthetic mutagenesis primer PYR1A160#
<220> FEATURE:
<221> NAME/KEY: modified_base
<222> LOCATION: (20)...(21)
<223> OTHER INFORMATION: n = g, a, c or t

<400> SEQUENCE: 204
ggatgatact cgtatgtttn nkgatacggt tgtgaagc                          38

<210> SEQ ID NO 205
<211> LENGTH: 38
<212> TYPE: DNA
<213> ORGANISM: Artificial Sequence
<220> FEATURE:
<223> OTHER INFORMATION: synthetic mutagenesis primer PYR1A160E
```

<400> SEQUENCE: 205
ggatgatact cgtatgtttg aggatacggt tgtgaagc          38

<210> SEQ ID NO 206
<211> LENGTH: 38
<212> TYPE: DNA
<213> ORGANISM: Artificial Sequence
<220> FEATURE:
<223> OTHER INFORMATION: synthetic mutagenesis primer PYR1A160H

<400> SEQUENCE: 206
ggatgatact cgtatgtttc atgatacggt tgtgaagc          38

<210> SEQ ID NO 207
<211> LENGTH: 38
<212> TYPE: DNA
<213> ORGANISM: Artificial Sequence
<220> FEATURE:
<223> OTHER INFORMATION: synthetic mutagenesis primer PYR1A160K

<400> SEQUENCE: 207
ggatgatact cgtatgttta aagatacggt tgtgaagc          38

<210> SEQ ID NO 208
<211> LENGTH: 38
<212> TYPE: DNA
<213> ORGANISM: Artificial Sequence
<220> FEATURE:
<223> OTHER INFORMATION: synthetic mutagenesis primer PYR1A160N

<400> SEQUENCE: 208
ggatgatact cgtatgttta atgatacggt tgtgaagc          38

<210> SEQ ID NO 209
<211> LENGTH: 38
<212> TYPE: DNA
<213> ORGANISM: Artificial Sequence
<220> FEATURE:
<223> OTHER INFORMATION: synthetic mutagenesis primer PYR1A160Q

<400> SEQUENCE: 209
ggatgatact cgtatgtttc aagatacggt tgtgaagc          38

<210> SEQ ID NO 210
<211> LENGTH: 38
<212> TYPE: DNA
<213> ORGANISM: Artificial Sequence
<220> FEATURE:
<223> OTHER INFORMATION: synthetic mutagenesis primer PYR1A160T

<400> SEQUENCE: 210
ggatgatact cgtatgttta ctgatacggt tgtgaagc          38

<210> SEQ ID NO 211
<211> LENGTH: 36
<212> TYPE: DNA
<213> ORGANISM: Artificial Sequence
<220> FEATURE:
<223> OTHER INFORMATION: synthetic mutagenesis primer PYR1A89M+

<400> SEQUENCE: 211
catcagtgga ttaccgatga acacatcaac ggaaag          36

<210> SEQ ID NO 212
<211> LENGTH: 36

<212> TYPE: DNA
<213> ORGANISM: Artificial Sequence
<220> FEATURE:
<223> OTHER INFORMATION: synthetic mutagenesis primer pyr1a89N+

<400> SEQUENCE: 212
catcagtgga ttaccgaaca acacatcaac ggaaag        36

<210> SEQ ID NO 213
<211> LENGTH: 36
<212> TYPE: DNA
<213> ORGANISM: Artificial Sequence
<220> FEATURE:
<223> OTHER INFORMATION: synthetic mutagenesis primer PYR1A89NNN-
<220> FEATURE:
<221> NAME/KEY: modified_base
<222> LOCATION: (18)...(20)
<223> OTHER INFORMATION: n = g, a, c or t

<400> SEQUENCE: 213
ctttccgttg atgtgttnnn cggtaatcca ctgatg        36

<210> SEQ ID NO 214
<211> LENGTH: 36
<212> TYPE: DNA
<213> ORGANISM: Artificial Sequence
<220> FEATURE:
<223> OTHER INFORMATION: synthetic mutagenesis primer PYR1A89NNN+
<220> FEATURE:
<221> NAME/KEY: modified_base
<222> LOCATION: (17)...(19)
<223> OTHER INFORMATION: n = g, a, c or t

<400> SEQUENCE: 214
catcagtgga ttaccgnnna acacatcaac ggaaag        36

<210> SEQ ID NO 215
<211> LENGTH: 36
<212> TYPE: DNA
<213> ORGANISM: Artificial Sequence
<220> FEATURE:
<223> OTHER INFORMATION: synthetic mutagenesis primer PYR1A89W+

<400> SEQUENCE: 215
catcagtgga ttaccgtgga acacatcaac ggaaag        36

<210> SEQ ID NO 216
<211> LENGTH: 36
<212> TYPE: DNA
<213> ORGANISM: Artificial Sequence
<220> FEATURE:
<223> OTHER INFORMATION: synthetic mutagenesis primer pyr1a89Y+

<400> SEQUENCE: 216
catcagtgga ttaccgtaca acacatcaac ggaaag        36

<210> SEQ ID NO 217
<211> LENGTH: 40
<212> TYPE: DNA
<213> ORGANISM: Artificial Sequence
<220> FEATURE:
<223> OTHER INFORMATION: synthetic mutagenesis primer PYR1D154F

<400> SEQUENCE: 217
ccggaaggta actcggagtt tgatactcgt atgtttgctg        40

<210> SEQ ID NO 218

```
<211> LENGTH: 40
<212> TYPE: DNA
<213> ORGANISM: Artificial Sequence
<220> FEATURE:
<223> OTHER INFORMATION: synthetic mutagenesis primer PYR1D154I

<400> SEQUENCE: 218
ccggaaggta actcggagat tgatactcgt atgtttgctg                              40

<210> SEQ ID NO 219
<211> LENGTH: 40
<212> TYPE: DNA
<213> ORGANISM: Artificial Sequence
<220> FEATURE:
<223> OTHER INFORMATION: synthetic mutagenesis primer PYR1D154M

<400> SEQUENCE: 219
ccggaaggta actcggagat ggatactcgt atgtttgctg                              40

<210> SEQ ID NO 220
<211> LENGTH: 40
<212> TYPE: DNA
<213> ORGANISM: Artificial Sequence
<220> FEATURE:
<223> OTHER INFORMATION: synthetic mutagenesis primer PYR1D154Y

<400> SEQUENCE: 220
ccggaaggta actcggagta tgatactcgt atgtttgctg                              40

<210> SEQ ID NO 221
<211> LENGTH: 42
<212> TYPE: DNA
<213> ORGANISM: Artificial Sequence
<220> FEATURE:
<223> OTHER INFORMATION: synthetic mutagenesis primer PYR1D155#
<220> FEATURE:
<221> NAME/KEY: modified_base
<222> LOCATION: (20)...(21)
<223> OTHER INFORMATION: n = g, a, c or t

<400> SEQUENCE: 221
ggaaggtaac tcggaggatn nkactcgtat gtttgctgat ac                           42

<210> SEQ ID NO 222
<211> LENGTH: 42
<212> TYPE: DNA
<213> ORGANISM: Artificial Sequence
<220> FEATURE:
<223> OTHER INFORMATION: synthetic mutagenesis primer PYR1D155E

<400> SEQUENCE: 222
ggaaggtaac tcggaggatg aaactcgtat gtttgctgat ac                           42

<210> SEQ ID NO 223
<211> LENGTH: 42
<212> TYPE: DNA
<213> ORGANISM: Artificial Sequence
<220> FEATURE:
<223> OTHER INFORMATION: synthetic mutagenesis primer PYR1D155H

<400> SEQUENCE: 223
ggaaggtaac tcggaggatc atactcgtat gtttgctgat ac                           42

<210> SEQ ID NO 224
<211> LENGTH: 42
<212> TYPE: DNA
<213> ORGANISM: Artificial Sequence
```

```
<220> FEATURE:
<223> OTHER INFORMATION: synthetic mutagenesis primer PYR1D155P

<400> SEQUENCE: 224
ggaaggtaac tcggaggatc ctactcgtat gtttgctgat ac                              42

<210> SEQ ID NO 225
<211> LENGTH: 42
<212> TYPE: DNA
<213> ORGANISM: Artificial Sequence
<220> FEATURE:
<223> OTHER INFORMATION: synthetic mutagenesis primer PYR1D155T

<400> SEQUENCE: 225
ggaaggtaac tcggaggata ctactcgtat gtttgctgat ac                              42

<210> SEQ ID NO 226
<211> LENGTH: 36
<212> TYPE: DNA
<213> ORGANISM: Artificial Sequence
<220> FEATURE:
<223> OTHER INFORMATION: synthetic mutagenesis primer pyr1e141f+

<400> SEQUENCE: 226
ggacggtggt tttgttttct tacgtcgttg atatgc                                     36

<210> SEQ ID NO 227
<211> LENGTH: 36
<212> TYPE: DNA
<213> ORGANISM: Artificial Sequence
<220> FEATURE:
<223> OTHER INFORMATION: synthetic mutagenesis primer pyr1e141g+

<400> SEQUENCE: 227
ggacggtggt tttgggatct tacgtcgttg atatgc                                     36

<210> SEQ ID NO 228
<211> LENGTH: 36
<212> TYPE: DNA
<213> ORGANISM: Artificial Sequence
<220> FEATURE:
<223> OTHER INFORMATION: synthetic mutagenesis primer pyr1e141k+

<400> SEQUENCE: 228
ggacggtggt tttgaaatct tacgtcgttg atatgc                                     36

<210> SEQ ID NO 229
<211> LENGTH: 36
<212> TYPE: DNA
<213> ORGANISM: Artificial Sequence
<220> FEATURE:
<223> OTHER INFORMATION: synthetic mutagenesis primer pyr1e141L+

<400> SEQUENCE: 229
ggacggtggt tttgttgtct tacgtcgttg atatgc                                     36

<210> SEQ ID NO 230
<211> LENGTH: 36
<212> TYPE: DNA
<213> ORGANISM: Artificial Sequence
<220> FEATURE:
<223> OTHER INFORMATION: synthetic mutagenesis primer PYR1E141M+

<400> SEQUENCE: 230
ggacggtggt tttgatgtct tacgtcgttg atatgc                                     36
```

<210> SEQ ID NO 231
<211> LENGTH: 36
<212> TYPE: DNA
<213> ORGANISM: Artificial Sequence
<220> FEATURE:
<223> OTHER INFORMATION: synthetic mutagenesis primer PYR1E141NNN-
<220> FEATURE:
<221> NAME/KEY: modified_base
<222> LOCATION: (20)...(22)
<223> OTHER INFORMATION: n = g, a, c or t

<400> SEQUENCE: 231
gcatatcaac gacgtaagan nncaaaacca ccgtcc                       36

<210> SEQ ID NO 232
<211> LENGTH: 36
<212> TYPE: DNA
<213> ORGANISM: Artificial Sequence
<220> FEATURE:
<223> OTHER INFORMATION: synthetic mutagenesis primer PYR1E141NNN+
<220> FEATURE:
<221> NAME/KEY: modified_base
<222> LOCATION: (15)...(17)
<223> OTHER INFORMATION: n = g, a, c or t

<400> SEQUENCE: 232
ggacggtggt tttgnnntct tacgtcgttg atatgc                       36

<210> SEQ ID NO 233
<211> LENGTH: 36
<212> TYPE: DNA
<213> ORGANISM: Artificial Sequence
<220> FEATURE:
<223> OTHER INFORMATION: synthetic mutagenesis primer pyr1e141s+

<400> SEQUENCE: 233
ggacggtggt tttgtcatct tacgtcgttg atatgc                       36

<210> SEQ ID NO 234
<211> LENGTH: 36
<212> TYPE: DNA
<213> ORGANISM: Artificial Sequence
<220> FEATURE:
<223> OTHER INFORMATION: synthetic mutagenesis primer PYR1E141W+

<400> SEQUENCE: 234
ggacggtggt tttgtggtct tacgtcgttg atatgc                       36

<210> SEQ ID NO 235
<211> LENGTH: 34
<212> TYPE: DNA
<213> ORGANISM: Artificial Sequence
<220> FEATURE:
<223> OTHER INFORMATION: synthetic mutagenesis primer pyr1e94C+

<400> SEQUENCE: 235
gcgaacacat caacgtgtag actcgatata ctcg                         34

<210> SEQ ID NO 236
<211> LENGTH: 34
<212> TYPE: DNA
<213> ORGANISM: Artificial Sequence
<220> FEATURE:
<223> OTHER INFORMATION: synthetic mutagenesis primer pyr1e94D+

<400> SEQUENCE: 236
gcgaacacat caacggatag actcgatata ctcg                         34

<210> SEQ ID NO 237
<211> LENGTH: 34
<212> TYPE: DNA
<213> ORGANISM: Artificial Sequence
<220> FEATURE:
<223> OTHER INFORMATION: synthetic mutagenesis primer pyr1e94F+

<400> SEQUENCE: 237
gcgaacacat caacgttcag actcgatata ctcg                                34

<210> SEQ ID NO 238
<211> LENGTH: 34
<212> TYPE: DNA
<213> ORGANISM: Artificial Sequence
<220> FEATURE:
<223> OTHER INFORMATION: synthetic mutagenesis primer pyr1e94I+

<400> SEQUENCE: 238
gcgaacacat caacgataag actcgatata ctcg                                34

<210> SEQ ID NO 239
<211> LENGTH: 34
<212> TYPE: DNA
<213> ORGANISM: Artificial Sequence
<220> FEATURE:
<223> OTHER INFORMATION: synthetic mutagenesis primer PYR1E94M+

<400> SEQUENCE: 239
gcgaacacat caacgatgag actcgatata ctcg                                34

<210> SEQ ID NO 240
<211> LENGTH: 34
<212> TYPE: DNA
<213> ORGANISM: Artificial Sequence
<220> FEATURE:
<223> OTHER INFORMATION: synthetic mutagenesis primer PYR1E94NNN-
<220> FEATURE:
<221> NAME/KEY: modified_base
<222> LOCATION: (17)...(19)
<223> OTHER INFORMATION: n = g, a, c or t

<400> SEQUENCE: 240
cgagtatatc gagtctnnnc gttgatgtgt tcgc                                34

<210> SEQ ID NO 241
<211> LENGTH: 34
<212> TYPE: DNA
<213> ORGANISM: Artificial Sequence
<220> FEATURE:
<223> OTHER INFORMATION: synthetic mutagenesis primer PYR1E94NNN+
<220> FEATURE:
<221> NAME/KEY: modified_base
<222> LOCATION: (16)...(18)
<223> OTHER INFORMATION: n = g, a, c or t

<400> SEQUENCE: 241
gcgaacacat caacgnnnag actcgatata ctcg                                34

<210> SEQ ID NO 242
<211> LENGTH: 34
<212> TYPE: DNA
<213> ORGANISM: Artificial Sequence
<220> FEATURE:
<223> OTHER INFORMATION: synthetic mutagenesis primer pyr1e94R+

<400> SEQUENCE: 242

```
gcgaacacat caacgcgaag actcgatata ctcg                                    34
```

<210> SEQ ID NO 243
<211> LENGTH: 34
<212> TYPE: DNA
<213> ORGANISM: Artificial Sequence
<220> FEATURE:
<223> OTHER INFORMATION: synthetic mutagenesis primer PYR1E94W+

<400> SEQUENCE: 243

```
gcgaacacat caacgtggag actcgatata ctcg                                    34
```

<210> SEQ ID NO 244
<211> LENGTH: 34
<212> TYPE: DNA
<213> ORGANISM: Artificial Sequence
<220> FEATURE:
<223> OTHER INFORMATION: synthetic mutagenesis primer pyr1e94Y+

<400> SEQUENCE: 244

```
gcgaacacat caacgtatag actcgatata ctcg                                    34
```

<210> SEQ ID NO 245
<211> LENGTH: 31
<212> TYPE: DNA
<213> ORGANISM: Artificial Sequence
<220> FEATURE:
<223> OTHER INFORMATION: synthetic mutagenesis primer pyr1f108c+

<400> SEQUENCE: 245

```
ggagagttac cggatgcagt atcatcggag g                                       31
```

<210> SEQ ID NO 246
<211> LENGTH: 31
<212> TYPE: DNA
<213> ORGANISM: Artificial Sequence
<220> FEATURE:
<223> OTHER INFORMATION: synthetic mutagenesis primer pyr1f108d+

<400> SEQUENCE: 246

```
ggagagttac cggagacagt atcatcggag g                                       31
```

<210> SEQ ID NO 247
<211> LENGTH: 31
<212> TYPE: DNA
<213> ORGANISM: Artificial Sequence
<220> FEATURE:
<223> OTHER INFORMATION: synthetic mutagenesis primer pyr1f108e+

<400> SEQUENCE: 247

```
ggagagttac cggagagagt atcatcggag g                                       31
```

<210> SEQ ID NO 248
<211> LENGTH: 31
<212> TYPE: DNA
<213> ORGANISM: Artificial Sequence
<220> FEATURE:
<223> OTHER INFORMATION: synthetic mutagenesis primer pyr1f108k+

<400> SEQUENCE: 248

```
ggagagttac cggaaagagt atcatcggag g                                       31
```

<210> SEQ ID NO 249
<211> LENGTH: 31
<212> TYPE: DNA
<213> ORGANISM: Artificial Sequence
<220> FEATURE:
<223> OTHER INFORMATION: synthetic mutagenesis primer PYR1F108M+

<400> SEQUENCE: 249
ggagagttac cggaatgagt atcatcggag g                              31

<210> SEQ ID NO 250
<211> LENGTH: 31
<212> TYPE: DNA
<213> ORGANISM: Artificial Sequence
<220> FEATURE:
<223> OTHER INFORMATION: synthetic mutagenesis primer PYR1F108NNN-
<220> FEATURE:
<221> NAME/KEY: modified_base
<222> LOCATION: (15)...(17)
<223> OTHER INFORMATION: n = g, a, c or t

<400> SEQUENCE: 250
cctccgatga tactnnntcc ggtaactctc c                              31

<210> SEQ ID NO 251
<211> LENGTH: 31
<212> TYPE: DNA
<213> ORGANISM: Artificial Sequence
<220> FEATURE:
<223> OTHER INFORMATION: synthetic mutagenesis primer PYR1F108NNN+
<220> FEATURE:
<221> NAME/KEY: modified_base
<222> LOCATION: (15)...(17)
<223> OTHER INFORMATION: n = g, a, c or t

<400> SEQUENCE: 251
ggagagttac cggannnagt atcatcggag g                              31

<210> SEQ ID NO 252
<211> LENGTH: 31
<212> TYPE: DNA
<213> ORGANISM: Artificial Sequence
<220> FEATURE:
<223> OTHER INFORMATION: synthetic mutagenesis primer pyr1f108t+

<400> SEQUENCE: 252
ggagagttac cggaaccagt atcatcggag g                              31

<210> SEQ ID NO 253
<211> LENGTH: 31
<212> TYPE: DNA
<213> ORGANISM: Artificial Sequence
<220> FEATURE:
<223> OTHER INFORMATION: synthetic mutagenesis primer PYR1F108W+

<400> SEQUENCE: 253
ggagagttac cggatggagt atcatcggag g                              31

<210> SEQ ID NO 254
<211> LENGTH: 32
<212> TYPE: DNA
<213> ORGANISM: Artificial Sequence
<220> FEATURE:
<223> OTHER INFORMATION: synthetic mutagenesis primer pyr1f159a+

<400> SEQUENCE: 254
ggatgatact cgtatggctg ctgatacggt tg                             32

<210> SEQ ID NO 255
<211> LENGTH: 32
<212> TYPE: DNA

```
<213> ORGANISM: Artificial Sequence
<220> FEATURE:
<223> OTHER INFORMATION: synthetic mutagenesis primer pyr1f159d+

<400> SEQUENCE: 255
ggatgatact cgtatggatg ctgatacggt tg                                    32

<210> SEQ ID NO 256
<211> LENGTH: 32
<212> TYPE: DNA
<213> ORGANISM: Artificial Sequence
<220> FEATURE:
<223> OTHER INFORMATION: synthetic mutagenesis primer pyr1f159e+

<400> SEQUENCE: 256
ggatgatact cgtatggaag ctgatacggt tg                                    32

<210> SEQ ID NO 257
<211> LENGTH: 32
<212> TYPE: DNA
<213> ORGANISM: Artificial Sequence
<220> FEATURE:
<223> OTHER INFORMATION: synthetic mutagenesis primer pyr1f159h+

<400> SEQUENCE: 257
ggatgatact cgtatgcatg ctgatacggt tg                                    32

<210> SEQ ID NO 258
<211> LENGTH: 32
<212> TYPE: DNA
<213> ORGANISM: Artificial Sequence
<220> FEATURE:
<223> OTHER INFORMATION: synthetic mutagenesis primer pyr1f159L+

<400> SEQUENCE: 258
ggatgatact cgtatgttag ctgatacggt tg                                    32

<210> SEQ ID NO 259
<211> LENGTH: 32
<212> TYPE: DNA
<213> ORGANISM: Artificial Sequence
<220> FEATURE:
<223> OTHER INFORMATION: synthetic mutagenesis primer PYR1F159M+

<400> SEQUENCE: 259
ggatgatact cgtatgatgg ctgatacggt tg                                    32

<210> SEQ ID NO 260
<211> LENGTH: 32
<212> TYPE: DNA
<213> ORGANISM: Artificial Sequence
<220> FEATURE:
<223> OTHER INFORMATION: synthetic mutagenesis primer PYR1F159NNN-
<220> FEATURE:
<221> NAME/KEY: modified_base
<222> LOCATION: (14)...(16)
<223> OTHER INFORMATION: n = g, a, c or t

<400> SEQUENCE: 260
caaccgtatc agcnnncata cgagtatcat cc                                    32

<210> SEQ ID NO 261
<211> LENGTH: 32
<212> TYPE: DNA
<213> ORGANISM: Artificial Sequence
<220> FEATURE:
<223> OTHER INFORMATION: synthetic mutagenesis primer PYR1F159NNN+
```

-continued

<220> FEATURE:
<221> NAME/KEY: modified_base
<222> LOCATION: (17)...(19)
<223> OTHER INFORMATION: n = g, a, c or t

<400> SEQUENCE: 261
ggatgatact cgtatgnnng ctgatacggt tg    32

<210> SEQ ID NO 262
<211> LENGTH: 32
<212> TYPE: DNA
<213> ORGANISM: Artificial Sequence
<220> FEATURE:
<223> OTHER INFORMATION: synthetic mutagenesis primer pyr1f159t+

<400> SEQUENCE: 262
ggatgatact cgtatgactg ctgatacggt tg    32

<210> SEQ ID NO 263
<211> LENGTH: 32
<212> TYPE: DNA
<213> ORGANISM: Artificial Sequence
<220> FEATURE:
<223> OTHER INFORMATION: synthetic mutagenesis primer pyr1f159V+

<400> SEQUENCE: 263
ggatgatact cgtatggttg ctgatacggt tg    32

<210> SEQ ID NO 264
<211> LENGTH: 32
<212> TYPE: DNA
<213> ORGANISM: Artificial Sequence
<220> FEATURE:
<223> OTHER INFORMATION: synthetic mutagenesis primer PYR1F159W+

<400> SEQUENCE: 264
ggatgatact cgtatgtggg ctgatacggt tg    32

<210> SEQ ID NO 265
<211> LENGTH: 46
<212> TYPE: DNA
<213> ORGANISM: Artificial Sequence
<220> FEATURE:
<223> OTHER INFORMATION: synthetic mutagenesis primer pyr1f61d+

<400> SEQUENCE: 265
gacaaaccac aaacatacaa acacgacatc aaatcctgct ccgtcg    46

<210> SEQ ID NO 266
<211> LENGTH: 46
<212> TYPE: DNA
<213> ORGANISM: Artificial Sequence
<220> FEATURE:
<223> OTHER INFORMATION: synthetic mutagenesis primer pyr1f61e+

<400> SEQUENCE: 266
gacaaaccac aaacatacaa acacgagatc aaatcctgct ccgtcg    46

<210> SEQ ID NO 267
<211> LENGTH: 46
<212> TYPE: DNA
<213> ORGANISM: Artificial Sequence
<220> FEATURE:
<223> OTHER INFORMATION: synthetic mutagenesis primer pyr1f61h+

<400> SEQUENCE: 267
gacaaaccac aaacatacaa acaccacatc aaatcctgct ccgtcg        46

<210> SEQ ID NO 268
<211> LENGTH: 46
<212> TYPE: DNA
<213> ORGANISM: Artificial Sequence
<220> FEATURE:
<223> OTHER INFORMATION: synthetic mutagenesis primer PYR1F61M+

<400> SEQUENCE: 268
gacaaaccac aaacatacaa acacatgatc aaatcctgct ccgtcg        46

<210> SEQ ID NO 269
<211> LENGTH: 46
<212> TYPE: DNA
<213> ORGANISM: Artificial Sequence
<220> FEATURE:
<223> OTHER INFORMATION: synthetic mutagenesis primer PYR1F61NNN-
<220> FEATURE:
<221> NAME/KEY: modified_base
<222> LOCATION: (20)...(22)
<223> OTHER INFORMATION: n = g, a, c or t

<400> SEQUENCE: 269
cgacggagca ggatttgatn nngtgtttgt atgtttgtgg tttgtc        46

<210> SEQ ID NO 270
<211> LENGTH: 46
<212> TYPE: DNA
<213> ORGANISM: Artificial Sequence
<220> FEATURE:
<223> OTHER INFORMATION: synthetic mutagenesis primer PYR1F61NNN+
<220> FEATURE:
<221> NAME/KEY: modified_base
<222> LOCATION: (25)...(27)
<223> OTHER INFORMATION: n = g, a, c or t

<400> SEQUENCE: 270
gacaaaccac aaacatacaa acacnnnatc aaatcctgct ccgtcg        46

<210> SEQ ID NO 271
<211> LENGTH: 46
<212> TYPE: DNA
<213> ORGANISM: Artificial Sequence
<220> FEATURE:
<223> OTHER INFORMATION: synthetic mutagenesis primer pyr1f61q+

<400> SEQUENCE: 271
gacaaaccac aaacatacaa acaccaaatc aaatcctgct ccgtcg        46

<210> SEQ ID NO 272
<211> LENGTH: 46
<212> TYPE: DNA
<213> ORGANISM: Artificial Sequence
<220> FEATURE:
<223> OTHER INFORMATION: synthetic mutagenesis primer pyr1f61s+

<400> SEQUENCE: 272
gacaaaccac aaacatacaa acactccatc aaatcctgct ccgtcg        46

<210> SEQ ID NO 273
<211> LENGTH: 46
<212> TYPE: DNA
<213> ORGANISM: Artificial Sequence
<220> FEATURE:
<223> OTHER INFORMATION: synthetic mutagenesis primer PYR1F61W+

<400> SEQUENCE: 273

```
gacaaaccac aaacatacaa acactggatc aaatcctgct ccgtcg            46
```

<210> SEQ ID NO 274
<211> LENGTH: 41
<212> TYPE: DNA
<213> ORGANISM: Artificial Sequence
<220> FEATURE:
<223> OTHER INFORMATION: synthetic mutagenesis primer PYR1G150E

<400> SEQUENCE: 274

```
cgtcgttgat atgccggaag agaactcgga ggatgatact c                 41
```

<210> SEQ ID NO 275
<211> LENGTH: 41
<212> TYPE: DNA
<213> ORGANISM: Artificial Sequence
<220> FEATURE:
<223> OTHER INFORMATION: synthetic mutagenesis primer PYR1G150F

<400> SEQUENCE: 275

```
cgtcgttgat atgccggaat taactcgga ggatgatact c                  41
```

<210> SEQ ID NO 276
<211> LENGTH: 41
<212> TYPE: DNA
<213> ORGANISM: Artificial Sequence
<220> FEATURE:
<223> OTHER INFORMATION: synthetic mutagenesis primer PYR1G150I

<400> SEQUENCE: 276

```
cgtcgttgat atgccggaaa ttaactcgga ggatgatact c                 41
```

<210> SEQ ID NO 277
<211> LENGTH: 41
<212> TYPE: DNA
<213> ORGANISM: Artificial Sequence
<220> FEATURE:
<223> OTHER INFORMATION: synthetic mutagenesis primer PYR1G150N

<400> SEQUENCE: 277

```
cgtcgttgat atgccggaaa ataactcgga ggatgatact c                 41
```

<210> SEQ ID NO 278
<211> LENGTH: 41
<212> TYPE: DNA
<213> ORGANISM: Artificial Sequence
<220> FEATURE:
<223> OTHER INFORMATION: synthetic mutagenesis primer PYR1G150T

<400> SEQUENCE: 278

```
cgtcgttgat atgccggaaa ctaactcgga ggatgatact c                 41
```

<210> SEQ ID NO 279
<211> LENGTH: 41
<212> TYPE: DNA
<213> ORGANISM: Artificial Sequence
<220> FEATURE:
<223> OTHER INFORMATION: synthetic mutagenesis primer PYR1G150Y

<400> SEQUENCE: 279

```
cgtcgttgat atgccggaat ataactcgga ggatgatact c                 41
```

<210> SEQ ID NO 280
<211> LENGTH: 38
<212> TYPE: DNA

```
<213> ORGANISM: Artificial Sequence
<220> FEATURE:
<223> OTHER INFORMATION: synthetic mutagenesis primer PYR1G86#
<220> FEATURE:
<221> NAME/KEY: modified_base
<222> LOCATION: (19)...(20)
<223> OTHER INFORMATION: n = g, a, c or t

<400> SEQUENCE: 280
gacgtgatcg tcatcagtnn kttaccggcg aacacatc                              38

<210> SEQ ID NO 281
<211> LENGTH: 31
<212> TYPE: DNA
<213> ORGANISM: Artificial Sequence
<220> FEATURE:
<223> OTHER INFORMATION: synthetic mutagenesis primer pyr1H115D+

<400> SEQUENCE: 281
catcggaggc gaagataggc tgacgaatta c                                     31

<210> SEQ ID NO 282
<211> LENGTH: 31
<212> TYPE: DNA
<213> ORGANISM: Artificial Sequence
<220> FEATURE:
<223> OTHER INFORMATION: synthetic mutagenesis primer pyr1H115e+

<400> SEQUENCE: 282
catcggaggc gaagagaggc tgacgaatta c                                     31

<210> SEQ ID NO 283
<211> LENGTH: 31
<212> TYPE: DNA
<213> ORGANISM: Artificial Sequence
<220> FEATURE:
<223> OTHER INFORMATION: synthetic mutagenesis primer pyr1H115i+

<400> SEQUENCE: 283
catcggaggc gaaattaggc tgacgaatta c                                     31

<210> SEQ ID NO 284
<211> LENGTH: 31
<212> TYPE: DNA
<213> ORGANISM: Artificial Sequence
<220> FEATURE:
<223> OTHER INFORMATION: synthetic mutagenesis primer PYR1H115M+

<400> SEQUENCE: 284
catcggaggc gaaatgaggc tgacgaatta c                                     31

<210> SEQ ID NO 285
<211> LENGTH: 31
<212> TYPE: DNA
<213> ORGANISM: Artificial Sequence
<220> FEATURE:
<223> OTHER INFORMATION: synthetic mutagenesis primer pyr1H115n+

<400> SEQUENCE: 285
catcggaggc gaaaataggc tgacgaatta c                                     31

<210> SEQ ID NO 286
<211> LENGTH: 31
<212> TYPE: DNA
<213> ORGANISM: Artificial Sequence
<220> FEATURE:
<223> OTHER INFORMATION: synthetic mutagenesis primer PYR1H115NNN-
```

```
<220> FEATURE:
<221> NAME/KEY: modified_base
<222> LOCATION: (16)...(18)
<223> OTHER INFORMATION: n = g, a, c or t

<400> SEQUENCE: 286
gtaattcgtc agcctnnntt cgcctccgat g                               31

<210> SEQ ID NO 287
<211> LENGTH: 31
<212> TYPE: DNA
<213> ORGANISM: Artificial Sequence
<220> FEATURE:
<223> OTHER INFORMATION: synthetic mutagenesis primer PYR1H115NNN+
<220> FEATURE:
<221> NAME/KEY: modified_base
<222> LOCATION: (14)...(16)
<223> OTHER INFORMATION: n = g, a, c or t

<400> SEQUENCE: 287
catcggaggc gaannnaggc tgacgaatta c                               31

<210> SEQ ID NO 288
<211> LENGTH: 31
<212> TYPE: DNA
<213> ORGANISM: Artificial Sequence
<220> FEATURE:
<223> OTHER INFORMATION: synthetic mutagenesis primer PYR1H115W+

<400> SEQUENCE: 288
catcggaggc gaatggaggc tgacgaatta c                               31

<210> SEQ ID NO 289
<211> LENGTH: 46
<212> TYPE: DNA
<213> ORGANISM: Artificial Sequence
<220> FEATURE:
<223> OTHER INFORMATION: synthetic mutagenesis primer pyr1h60N+

<400> SEQUENCE: 289
gacaaaccac aaacatacaa aaacttcatc aaatcctgct ccgtcg               46

<210> SEQ ID NO 290
<211> LENGTH: 46
<212> TYPE: DNA
<213> ORGANISM: Artificial Sequence
<220> FEATURE:
<223> OTHER INFORMATION: synthetic mutagenesis primer pyr1h60S+

<400> SEQUENCE: 290
gacaaaccac aaacatacaa atccttcatc aaatcctgct ccgtcg               46

<210> SEQ ID NO 291
<211> LENGTH: 31
<212> TYPE: DNA
<213> ORGANISM: Artificial Sequence
<220> FEATURE:
<223> OTHER INFORMATION: synthetic mutagenesis primer pyr1I110E+

<400> SEQUENCE: 291
gttaccggat tcagtgagat cggaggcgaa c                               31

<210> SEQ ID NO 292
<211> LENGTH: 31
<212> TYPE: DNA
<213> ORGANISM: Artificial Sequence
<220> FEATURE:
```

<223> OTHER INFORMATION: synthetic mutagenesis primer PYR1I110M+

<400> SEQUENCE: 292
gttaccggat tcagtatgat cggaggcgaa c 31

<210> SEQ ID NO 293
<211> LENGTH: 31
<212> TYPE: DNA
<213> ORGANISM: Artificial Sequence
<220> FEATURE:
<223> OTHER INFORMATION: synthetic mutagenesis primer PYR1I110NNN-
<220> FEATURE:
<221> NAME/KEY: modified_base
<222> LOCATION: (14)...(16)
<223> OTHER INFORMATION: n = g, a, c or t

<400> SEQUENCE: 293
gttcgcctcc gatnnnactg aatccggtaa c 31

<210> SEQ ID NO 294
<211> LENGTH: 31
<212> TYPE: DNA
<213> ORGANISM: Artificial Sequence
<220> FEATURE:
<223> OTHER INFORMATION: synthetic mutagenesis primer PYR1I110NNN+
<220> FEATURE:
<221> NAME/KEY: modified_base
<222> LOCATION: (16)...(18)
<223> OTHER INFORMATION: n = g, a, c or t

<400> SEQUENCE: 294
gttaccggat tcagtnnnat cggaggcgaa c 31

<210> SEQ ID NO 295
<211> LENGTH: 31
<212> TYPE: DNA
<213> ORGANISM: Artificial Sequence
<220> FEATURE:
<223> OTHER INFORMATION: synthetic mutagenesis primer PYR1I110W+

<400> SEQUENCE: 295
gttaccggat tcagttggat cggaggcgaa c 31

<210> SEQ ID NO 296
<211> LENGTH: 43
<212> TYPE: DNA
<213> ORGANISM: Artificial Sequence
<220> FEATURE:
<223> OTHER INFORMATION: synthetic mutagenesis primer PYR1I62c+

<400> SEQUENCE: 296
ccacaaacat acaaacactt ctgcaaatcc tgctccgtcg aac 43

<210> SEQ ID NO 297
<211> LENGTH: 43
<212> TYPE: DNA
<213> ORGANISM: Artificial Sequence
<220> FEATURE:
<223> OTHER INFORMATION: synthetic mutagenesis primer PYR1I62H+

<400> SEQUENCE: 297
ccacaaacat acaaacactt ccataaatcc tgctccgtcg aac 43

<210> SEQ ID NO 298
<211> LENGTH: 43
<212> TYPE: DNA
<213> ORGANISM: Artificial Sequence

```
<220> FEATURE:
<223> OTHER INFORMATION: synthetic mutagenesis primer PYR1I62M+

<400> SEQUENCE: 298
ccacaaacat acaaacactt catgaaatcc tgctccgtcg aac          43

<210> SEQ ID NO 299
<211> LENGTH: 43
<212> TYPE: DNA
<213> ORGANISM: Artificial Sequence
<220> FEATURE:
<223> OTHER INFORMATION: synthetic mutagenesis primer PYR1I62n+

<400> SEQUENCE: 299
ccacaaacat acaaacactt caacaaatcc tgctccgtcg aac          43

<210> SEQ ID NO 300
<211> LENGTH: 43
<212> TYPE: DNA
<213> ORGANISM: Artificial Sequence
<220> FEATURE:
<223> OTHER INFORMATION: synthetic mutagenesis primer PYR1I62NNN-
<220> FEATURE:
<221> NAME/KEY: modified_base
<222> LOCATION: (20)...(22)
<223> OTHER INFORMATION: n = g, a, c or t

<400> SEQUENCE: 300
gttcgacgga gcaggatttn nngaagtgtt tgtatgtttg tgg          43

<210> SEQ ID NO 301
<211> LENGTH: 43
<212> TYPE: DNA
<213> ORGANISM: Artificial Sequence
<220> FEATURE:
<223> OTHER INFORMATION: synthetic mutagenesis primer PYR1I62NNN+
<220> FEATURE:
<221> NAME/KEY: modified_base
<222> LOCATION: (22)...(24)
<223> OTHER INFORMATION: n = g, a, c or t

<400> SEQUENCE: 301
ccacaaacat acaaacactt cnnnaaatcc tgctccgtcg aac          43

<210> SEQ ID NO 302
<211> LENGTH: 43
<212> TYPE: DNA
<213> ORGANISM: Artificial Sequence
<220> FEATURE:
<223> OTHER INFORMATION: synthetic mutagenesis primer PYR1I62W+

<400> SEQUENCE: 302
ccacaaacat acaaacactt ctggaaatcc tgctccgtcg aac          43

<210> SEQ ID NO 303
<211> LENGTH: 43
<212> TYPE: DNA
<213> ORGANISM: Artificial Sequence
<220> FEATURE:
<223> OTHER INFORMATION: synthetic mutagenesis primer PYR1I62Y+

<400> SEQUENCE: 303
ccacaaacat acaaacactt ctataaatcc tgctccgtcg aac          43

<210> SEQ ID NO 304
<211> LENGTH: 34
<212> TYPE: DNA
```

<213> ORGANISM: Artificial Sequence
<220> FEATURE:
<223> OTHER INFORMATION: synthetic mutagenesis primer pyr1I82#
<220> FEATURE:
<221> NAME/KEY: modified_base
<222> LOCATION: (13)...(14)
<223> OTHER INFORMATION: n = g, a, c or t

<400> SEQUENCE: 304
acgcgcgacg tgnnkgtcat cagtggatta ccgg        34

<210> SEQ ID NO 305
<211> LENGTH: 32
<212> TYPE: DNA
<213> ORGANISM: Artificial Sequence
<220> FEATURE:
<223> OTHER INFORMATION: synthetic mutagenesis primer PYR1I84#
<220> FEATURE:
<221> NAME/KEY: modified_base
<222> LOCATION: (15)...(15)
<223> OTHER INFORMATION: n = g, a, c or t

<400> SEQUENCE: 305
gcgacgtgat cgtcnkkagt ggattaccgg cg        32

<210> SEQ ID NO 306
<211> LENGTH: 38
<212> TYPE: DNA
<213> ORGANISM: Artificial Sequence
<220> FEATURE:
<223> OTHER INFORMATION: synthetic mutagenesis primer PYR1K170#
<220> FEATURE:
<221> NAME/KEY: modified_base
<222> LOCATION: (22)...(23)
<223> OTHER INFORMATION: n = g, a, c or t

<400> SEQUENCE: 306
gttgtgaagc ttaatttgca gnnkctcgcg acggttgc        38

<210> SEQ ID NO 307
<211> LENGTH: 38
<212> TYPE: DNA
<213> ORGANISM: Artificial Sequence
<220> FEATURE:
<223> OTHER INFORMATION: synthetic mutagenesis primer PYR1K170C

<400> SEQUENCE: 307
gttgtgaagc ttaatttgca gtgtctcgcg acggttgc        38

<210> SEQ ID NO 308
<211> LENGTH: 38
<212> TYPE: DNA
<213> ORGANISM: Artificial Sequence
<220> FEATURE:
<223> OTHER INFORMATION: synthetic mutagenesis primer PYR1K170F

<400> SEQUENCE: 308
gttgtgaagc ttaatttgca gtttctcgcg acggttgc        38

<210> SEQ ID NO 309
<211> LENGTH: 38
<212> TYPE: DNA
<213> ORGANISM: Artificial Sequence
<220> FEATURE:
<223> OTHER INFORMATION: synthetic mutagenesis primer PYR1K170H

<400> SEQUENCE: 309
gttgtgaagc ttaatttgca gcatctcgcg acggttgc        38

<210> SEQ ID NO 310
<211> LENGTH: 38
<212> TYPE: DNA
<213> ORGANISM: Artificial Sequence
<220> FEATURE:
<223> OTHER INFORMATION: synthetic mutagenesis primer PYR1K170I

<400> SEQUENCE: 310
gttgtgaagc ttaatttgca gatactcgcg acggttgc                        38

<210> SEQ ID NO 311
<211> LENGTH: 35
<212> TYPE: DNA
<213> ORGANISM: Artificial Sequence
<220> FEATURE:
<223> OTHER INFORMATION: synthetic mutagenesis primer pyr1k170w+

<400> SEQUENCE: 311
gaagcttaat ttgcagtggc tcgcgacggt tgctg                           35

<210> SEQ ID NO 312
<211> LENGTH: 37
<212> TYPE: DNA
<213> ORGANISM: Artificial Sequence
<220> FEATURE:
<223> OTHER INFORMATION: synthetic mutagenesis primer PYR1K59D+

<400> SEQUENCE: 312
caaaccacaa acatacgatc acttcatcaa atcctgc                         37

<210> SEQ ID NO 313
<211> LENGTH: 37
<212> TYPE: DNA
<213> ORGANISM: Artificial Sequence
<220> FEATURE:
<223> OTHER INFORMATION: synthetic mutagenesis primer PYR1K59E+

<400> SEQUENCE: 313
caaaccacaa acatacgaac acttcatcaa atcctgc                         37

<210> SEQ ID NO 314
<211> LENGTH: 37
<212> TYPE: DNA
<213> ORGANISM: Artificial Sequence
<220> FEATURE:
<223> OTHER INFORMATION: synthetic mutagenesis primer PYR1K59L+

<400> SEQUENCE: 314
caaaccacaa acataccttc acttcatcaa atcctgc                         37

<210> SEQ ID NO 315
<211> LENGTH: 37
<212> TYPE: DNA
<213> ORGANISM: Artificial Sequence
<220> FEATURE:
<223> OTHER INFORMATION: synthetic mutagenesis primer PYR1K59M+

<400> SEQUENCE: 315
caaaccacaa acatacatgc acttcatcaa atcctgc                         37

<210> SEQ ID NO 316
<211> LENGTH: 37
<212> TYPE: DNA
<213> ORGANISM: Artificial Sequence
<220> FEATURE:

<223> OTHER INFORMATION: synthetic mutagenesis primer PYR1K59N+

<400> SEQUENCE: 316
caaaccacaa acatacaatc acttcatcaa atcctgc             37

<210> SEQ ID NO 317
<211> LENGTH: 37
<212> TYPE: DNA
<213> ORGANISM: Artificial Sequence
<220> FEATURE:
<223> OTHER INFORMATION: synthetic mutagenesis primer PYR1K59NNN+
<220> FEATURE:
<221> NAME/KEY: modified_base
<222> LOCATION: (17)...(19)
<223> OTHER INFORMATION: n = g, a, c or t

<400> SEQUENCE: 317
caaaccacaa acatcnnnc acttcatcaa atcctgc             37

<210> SEQ ID NO 318
<211> LENGTH: 37
<212> TYPE: DNA
<213> ORGANISM: Artificial Sequence
<220> FEATURE:
<223> OTHER INFORMATION: synthetic mutagenesis primer PYR1K59Q+

<400> SEQUENCE: 318
caaaccacaa acataccaac acttcatcaa atcctgc             37

<210> SEQ ID NO 319
<211> LENGTH: 37
<212> TYPE: DNA
<213> ORGANISM: Artificial Sequence
<220> FEATURE:
<223> OTHER INFORMATION: synthetic mutagenesis primer PYR1K59W+

<400> SEQUENCE: 319
caaaccacaa acatactggc acttcatcaa atcctgc             37

<210> SEQ ID NO 320
<211> LENGTH: 33
<212> TYPE: DNA
<213> ORGANISM: Artificial Sequence
<220> FEATURE:
<223> OTHER INFORMATION: synthetic mutagenesis primer pyr1K63#
<220> FEATURE:
<221> NAME/KEY: modified_base
<222> LOCATION: (18)...(19)
<223> OTHER INFORMATION: n = g, a, c or t

<400> SEQUENCE: 320
catacaaaca cttcatcnnk tcctgctccg tcg             33

<210> SEQ ID NO 321
<211> LENGTH: 33
<212> TYPE: DNA
<213> ORGANISM: Artificial Sequence
<220> FEATURE:
<223> OTHER INFORMATION: synthetic mutagenesis primer pyr1K63A

<400> SEQUENCE: 321
catacaaaca cttcatcgca tcctgctccg tcg             33

<210> SEQ ID NO 322
<211> LENGTH: 33
<212> TYPE: DNA
<213> ORGANISM: Artificial Sequence

```
<220> FEATURE:
<223> OTHER INFORMATION: synthetic mutagenesis primer pyr1K63D

<400> SEQUENCE: 322
catacaaaca cttcatcgac tcctgctccg tcg                              33

<210> SEQ ID NO 323
<211> LENGTH: 33
<212> TYPE: DNA
<213> ORGANISM: Artificial Sequence
<220> FEATURE:
<223> OTHER INFORMATION: synthetic mutagenesis primer pyr1K63F

<400> SEQUENCE: 323
catacaaaca cttcatcttt tcctgctccg tcg                              33

<210> SEQ ID NO 324
<211> LENGTH: 33
<212> TYPE: DNA
<213> ORGANISM: Artificial Sequence
<220> FEATURE:
<223> OTHER INFORMATION: synthetic mutagenesis primer pyr1K63H

<400> SEQUENCE: 324
catacaaaca cttcatccac tcctgctccg tcg                              33

<210> SEQ ID NO 325
<211> LENGTH: 33
<212> TYPE: DNA
<213> ORGANISM: Artificial Sequence
<220> FEATURE:
<223> OTHER INFORMATION: synthetic mutagenesis primer pyr1K63R

<400> SEQUENCE: 325
catacaaaca cttcatcaga tcctgctccg tcg                              33

<210> SEQ ID NO 326
<211> LENGTH: 33
<212> TYPE: DNA
<213> ORGANISM: Artificial Sequence
<220> FEATURE:
<223> OTHER INFORMATION: synthetic mutagenesis primer pyr1K63T

<400> SEQUENCE: 326
catacaaaca cttcatcaca tcctgctccg tcg                              33

<210> SEQ ID NO 327
<211> LENGTH: 34
<212> TYPE: DNA
<213> ORGANISM: Artificial Sequence
<220> FEATURE:
<223> OTHER INFORMATION: synthetic mutagenesis primer pyr1L117A+

<400> SEQUENCE: 327
ggaggcgaac atagggcgac gaattacaaa tccg                             34

<210> SEQ ID NO 328
<211> LENGTH: 34
<212> TYPE: DNA
<213> ORGANISM: Artificial Sequence
<220> FEATURE:
<223> OTHER INFORMATION: synthetic mutagenesis primer pyr1L117D+

<400> SEQUENCE: 328
ggaggcgaac atagggatac gaattacaaa tccg                             34
```

<210> SEQ ID NO 329
<211> LENGTH: 34
<212> TYPE: DNA
<213> ORGANISM: Artificial Sequence
<220> FEATURE:
<223> OTHER INFORMATION: synthetic mutagenesis primer pyr1L117E+

<400> SEQUENCE: 329
ggaggcgaac atagggagac gaattacaaa tccg        34

<210> SEQ ID NO 330
<211> LENGTH: 34
<212> TYPE: DNA
<213> ORGANISM: Artificial Sequence
<220> FEATURE:
<223> OTHER INFORMATION: synthetic mutagenesis primer PYR1L117M+

<400> SEQUENCE: 330
ggaggcgaac ataggatgac gaattacaaa tccg        34

<210> SEQ ID NO 331
<211> LENGTH: 34
<212> TYPE: DNA
<213> ORGANISM: Artificial Sequence
<220> FEATURE:
<223> OTHER INFORMATION: synthetic mutagenesis primer pyr1L117N+

<400> SEQUENCE: 331
ggaggcgaac ataggaacac gaattacaaa tccg        34

<210> SEQ ID NO 332
<211> LENGTH: 34
<212> TYPE: DNA
<213> ORGANISM: Artificial Sequence
<220> FEATURE:
<223> OTHER INFORMATION: synthetic mutagenesis primer PYR1L117NNN-
<220> FEATURE:
<221> NAME/KEY: modified_base
<222> LOCATION: (17)...(19)
<223> OTHER INFORMATION: n = g, a, c or t

<400> SEQUENCE: 332
cggatttgta attcgtnnnc ctatgttcgc ctcc        34

<210> SEQ ID NO 333
<211> LENGTH: 34
<212> TYPE: DNA
<213> ORGANISM: Artificial Sequence
<220> FEATURE:
<223> OTHER INFORMATION: synthetic mutagenesis primer PYR1L117NNN+
<220> FEATURE:
<221> NAME/KEY: modified_base
<222> LOCATION: (16)...(18)
<223> OTHER INFORMATION: n = g, a, c or t

<400> SEQUENCE: 333
ggaggcgaac ataggnnnac gaattacaaa tccg        34

<210> SEQ ID NO 334
<211> LENGTH: 34
<212> TYPE: DNA
<213> ORGANISM: Artificial Sequence
<220> FEATURE:
<223> OTHER INFORMATION: synthetic mutagenesis primer PYR1L117W+

<400> SEQUENCE: 334
ggaggcgaac ataggtggac gaattacaaa tccg        34

<210> SEQ ID NO 335
<211> LENGTH: 41
<212> TYPE: DNA
<213> ORGANISM: Artificial Sequence
<220> FEATURE:
<223> OTHER INFORMATION: synthetic mutagenesis primer PYR1L166#
<220> FEATURE:
<221> NAME/KEY: modified_base
<222> LOCATION: (18)...(19)
<223> OTHER INFORMATION: n = g, a, c or t

<400> SEQUENCE: 335
ctgatacggt tgtgaagnnk aatttgcaga aactcgcgac g                          41

<210> SEQ ID NO 336
<211> LENGTH: 41
<212> TYPE: DNA
<213> ORGANISM: Artificial Sequence
<220> FEATURE:
<223> OTHER INFORMATION: synthetic mutagenesis primer PYR1L166E

<400> SEQUENCE: 336
ctgatacggt tgtgaaggaa aatttgcaga aactcgcgac g                          41

<210> SEQ ID NO 337
<211> LENGTH: 41
<212> TYPE: DNA
<213> ORGANISM: Artificial Sequence
<220> FEATURE:
<223> OTHER INFORMATION: synthetic mutagenesis primer PYR1L166H

<400> SEQUENCE: 337
ctgatacggt tgtgaagcat aatttgcaga aactcgcgac g                          41

<210> SEQ ID NO 338
<211> LENGTH: 41
<212> TYPE: DNA
<213> ORGANISM: Artificial Sequence
<220> FEATURE:
<223> OTHER INFORMATION: synthetic mutagenesis primer PYR1L166P

<400> SEQUENCE: 338
ctgatacggt tgtgaagcct aatttgcaga aactcgcgac g                          41

<210> SEQ ID NO 339
<211> LENGTH: 41
<212> TYPE: DNA
<213> ORGANISM: Artificial Sequence
<220> FEATURE:
<223> OTHER INFORMATION: synthetic mutagenesis primer PYR1L166Q

<400> SEQUENCE: 339
ctgatacggt tgtgaagcaa aatttgcaga aactcgcgac g                          41

<210> SEQ ID NO 340
<211> LENGTH: 41
<212> TYPE: DNA
<213> ORGANISM: Artificial Sequence
<220> FEATURE:
<223> OTHER INFORMATION: synthetic mutagenesis primer PYR1L166Y

<400> SEQUENCE: 340
ctgatacggt tgtgaagtat aatttgcaga aactcgcgac g                          41

<210> SEQ ID NO 341

-continued

```
<211> LENGTH: 38
<212> TYPE: DNA
<213> ORGANISM: Artificial Sequence
<220> FEATURE:
<223> OTHER INFORMATION: synthetic mutagenesis primer PYR1L87#
<220> FEATURE:
<221> NAME/KEY: modified_base
<222> LOCATION: (19)...(20)
<223> OTHER INFORMATION: n = g, a, c or t

<400> SEQUENCE: 341
gtgatcgtca tcagtggann kccggcgaac acatcaac                             38

<210> SEQ ID NO 342
<211> LENGTH: 42
<212> TYPE: DNA
<213> ORGANISM: Artificial Sequence
<220> FEATURE:
<223> OTHER INFORMATION: synthetic mutagenesis primer PYR1M158D

<400> SEQUENCE: 342
cggaggatga tactcgtgac tttgctgata cggttgtgaa gc                        42

<210> SEQ ID NO 343
<211> LENGTH: 42
<212> TYPE: DNA
<213> ORGANISM: Artificial Sequence
<220> FEATURE:
<223> OTHER INFORMATION: synthetic mutagenesis primer PYR1M158F

<400> SEQUENCE: 343
cggaggatga tactcgtttc tttgctgata cggttgtgaa gc                        42

<210> SEQ ID NO 344
<211> LENGTH: 42
<212> TYPE: DNA
<213> ORGANISM: Artificial Sequence
<220> FEATURE:
<223> OTHER INFORMATION: synthetic mutagenesis primer PYR1M158H

<400> SEQUENCE: 344
cggaggatga tactcgtcac tttgctgata cggttgtgaa gc                        42

<210> SEQ ID NO 345
<211> LENGTH: 36
<212> TYPE: DNA
<213> ORGANISM: Artificial Sequence
<220> FEATURE:
<223> OTHER INFORMATION: synthetic mutagenesis primer pyr1m158I+

<400> SEQUENCE: 345
cggaggatga tactcgtatt tttgctgata cggttg                               36

<210> SEQ ID NO 346
<211> LENGTH: 42
<212> TYPE: DNA
<213> ORGANISM: Artificial Sequence
<220> FEATURE:
<223> OTHER INFORMATION: synthetic mutagenesis primer PYR1M158N

<400> SEQUENCE: 346
cggaggatga tactcgtaac tttgctgata cggttgtgaa gc                        42

<210> SEQ ID NO 347
<211> LENGTH: 42
<212> TYPE: DNA
<213> ORGANISM: Artificial Sequence
```

<220> FEATURE:
<223> OTHER INFORMATION: synthetic mutagenesis primer PYR1M158Q

<400> SEQUENCE: 347
cggaggatga tactcgtcag tttgctgata cggttgtgaa gc                42

<210> SEQ ID NO 348
<211> LENGTH: 42
<212> TYPE: DNA
<213> ORGANISM: Artificial Sequence
<220> FEATURE:
<223> OTHER INFORMATION: synthetic mutagenesis primer PYR1M158Y

<400> SEQUENCE: 348
cggaggatga tactcgttat tttgctgata cggttgtgaa gc                42

<210> SEQ ID NO 349
<211> LENGTH: 39
<212> TYPE: DNA
<213> ORGANISM: Artificial Sequence
<220> FEATURE:
<223> OTHER INFORMATION: synthetic mutagenesis primer PYR1N151F

<400> SEQUENCE: 349
cgttgatatg ccggaaggtt tctcggagga tgatactcg                   39

<210> SEQ ID NO 350
<211> LENGTH: 39
<212> TYPE: DNA
<213> ORGANISM: Artificial Sequence
<220> FEATURE:
<223> OTHER INFORMATION: synthetic mutagenesis primer PYR1N151H

<400> SEQUENCE: 350
cgttgatatg ccggaaggtc actcggagga tgatactcg                   39

<210> SEQ ID NO 351
<211> LENGTH: 39
<212> TYPE: DNA
<213> ORGANISM: Artificial Sequence
<220> FEATURE:
<223> OTHER INFORMATION: synthetic mutagenesis primer PYR1N151I

<400> SEQUENCE: 351
cgttgatatg ccggaaggta tctcggagga tgatactcg                   39

<210> SEQ ID NO 352
<211> LENGTH: 39
<212> TYPE: DNA
<213> ORGANISM: Artificial Sequence
<220> FEATURE:
<223> OTHER INFORMATION: synthetic mutagenesis primer PYR1N151M

<400> SEQUENCE: 352
cgttgatatg ccggaaggta tgtcggagga tgatactcg                   39

<210> SEQ ID NO 353
<211> LENGTH: 39
<212> TYPE: DNA
<213> ORGANISM: Artificial Sequence
<220> FEATURE:
<223> OTHER INFORMATION: synthetic mutagenesis primer PYR1N151V

<400> SEQUENCE: 353
cgttgatatg ccggaaggtg tctcggagga tgatactcg                   39

<210> SEQ ID NO 354
<211> LENGTH: 39
<212> TYPE: DNA
<213> ORGANISM: Artificial Sequence
<220> FEATURE:
<223> OTHER INFORMATION: synthetic mutagenesis primer PYR1N151Y

<400> SEQUENCE: 354
cgttgatatg ccggaaggtt actcggagga tgatactcg                                      39

<210> SEQ ID NO 355
<211> LENGTH: 36
<212> TYPE: DNA
<213> ORGANISM: Artificial Sequence
<220> FEATURE:
<223> OTHER INFORMATION: synthetic mutagenesis primer pyr1N167a+

<400> SEQUENCE: 355
gatacggttg tgaagcttgc tttgcagaaa ctcgcg                                         36

<210> SEQ ID NO 356
<211> LENGTH: 36
<212> TYPE: DNA
<213> ORGANISM: Artificial Sequence
<220> FEATURE:
<223> OTHER INFORMATION: synthetic mutagenesis primer pyr1N167c+

<400> SEQUENCE: 356
gatacggttg tgaagctttg tttgcagaaa ctcgcg                                         36

<210> SEQ ID NO 357
<211> LENGTH: 36
<212> TYPE: DNA
<213> ORGANISM: Artificial Sequence
<220> FEATURE:
<223> OTHER INFORMATION: synthetic mutagenesis primer pyr1N167d+

<400> SEQUENCE: 357
gatacggttg tgaagcttga tttgcagaaa ctcgcg                                         36

<210> SEQ ID NO 358
<211> LENGTH: 36
<212> TYPE: DNA
<213> ORGANISM: Artificial Sequence
<220> FEATURE:
<223> OTHER INFORMATION: synthetic mutagenesis primer pyr1N167e+

<400> SEQUENCE: 358
gatacggttg tgaagcttga attgcagaaa ctcgcg                                         36

<210> SEQ ID NO 359
<211> LENGTH: 36
<212> TYPE: DNA
<213> ORGANISM: Artificial Sequence
<220> FEATURE:
<223> OTHER INFORMATION: synthetic mutagenesis primer pyr1N167g+

<400> SEQUENCE: 359
gatacggttg tgaagcttgg tttgcagaaa ctcgcg                                         36

<210> SEQ ID NO 360
<211> LENGTH: 36
<212> TYPE: DNA
<213> ORGANISM: Artificial Sequence
<220> FEATURE:
<223> OTHER INFORMATION: synthetic mutagenesis primer PYR1N167M+

```
<400> SEQUENCE: 360
gatacggttg tgaagcttat gttgcagaaa ctcgcg                                        36

<210> SEQ ID NO 361
<211> LENGTH: 36
<212> TYPE: DNA
<213> ORGANISM: Artificial Sequence
<220> FEATURE:
<223> OTHER INFORMATION: synthetic mutagenesis primer PYR1N167NNN-
<220> FEATURE:
<221> NAME/KEY: modified_base
<222> LOCATION: (16)...(18)
<223> OTHER INFORMATION: n = g, a, c or t

<400> SEQUENCE: 361
cgcgagtttc tgcaannnaa gcttcacaac cgtatc                                        36

<210> SEQ ID NO 362
<211> LENGTH: 36
<212> TYPE: DNA
<213> ORGANISM: Artificial Sequence
<220> FEATURE:
<223> OTHER INFORMATION: synthetic mutagenesis primer PYR1N167NNN+
<220> FEATURE:
<221> NAME/KEY: modified_base
<222> LOCATION: (19)...(21)
<223> OTHER INFORMATION: n = g, a, c or t

<400> SEQUENCE: 362
gatacggttg tgaagcttnn nttgcagaaa ctcgcg                                        36

<210> SEQ ID NO 363
<211> LENGTH: 36
<212> TYPE: DNA
<213> ORGANISM: Artificial Sequence
<220> FEATURE:
<223> OTHER INFORMATION: synthetic mutagenesis primer pyr1N167p+

<400> SEQUENCE: 363
gatacggttg tgaagcttcc tttgcagaaa ctcgcg                                        36

<210> SEQ ID NO 364
<211> LENGTH: 36
<212> TYPE: DNA
<213> ORGANISM: Artificial Sequence
<220> FEATURE:
<223> OTHER INFORMATION: synthetic mutagenesis primer pyr1N167s

<400> SEQUENCE: 364
gatacggttg tgaagctttc tttgcagaaa ctcgcg                                        36

<210> SEQ ID NO 365
<211> LENGTH: 36
<212> TYPE: DNA
<213> ORGANISM: Artificial Sequence
<220> FEATURE:
<223> OTHER INFORMATION: synthetic mutagenesis primer pyr1N167t+

<400> SEQUENCE: 365
gatacggttg tgaagcttac tttgcagaaa ctcgcg                                        36

<210> SEQ ID NO 366
<211> LENGTH: 36
<212> TYPE: DNA
<213> ORGANISM: Artificial Sequence
<220> FEATURE:
```

<223> OTHER INFORMATION: synthetic mutagenesis primer PYR1N167W+

<400> SEQUENCE: 366
gatacggttg tgaagctttg gttgcagaaa ctcgcg                     36

<210> SEQ ID NO 367
<211> LENGTH: 39
<212> TYPE: DNA
<213> ORGANISM: Artificial Sequence
<220> FEATURE:
<223> OTHER INFORMATION: synthetic mutagenesis primer PYR1P148#
<220> FEATURE:
<221> NAME/KEY: modified_base
<222> LOCATION: (18)...(19)
<223> OTHER INFORMATION: n = g, a, c or t

<400> SEQUENCE: 367
cttacgtcgt tgatatgnnk gaaggtaact cggaggatg                  39

<210> SEQ ID NO 368
<211> LENGTH: 43
<212> TYPE: DNA
<213> ORGANISM: Artificial Sequence
<220> FEATURE:
<223> OTHER INFORMATION: synthetic mutagenesis primer PYR1P55c+

<400> SEQUENCE: 368
cgtacgacga ttcgacaaat gtcaaacata caaacacttc atc             43

<210> SEQ ID NO 369
<211> LENGTH: 43
<212> TYPE: DNA
<213> ORGANISM: Artificial Sequence
<220> FEATURE:
<223> OTHER INFORMATION: synthetic mutagenesis primer PYR1P55h+

<400> SEQUENCE: 369
cgtacgacga ttcgacaaac cacaaacata caaacacttc atc             43

<210> SEQ ID NO 370
<211> LENGTH: 43
<212> TYPE: DNA
<213> ORGANISM: Artificial Sequence
<220> FEATURE:
<223> OTHER INFORMATION: synthetic mutagenesis primer PYR1P55i+

<400> SEQUENCE: 370
cgtacgacga ttcgacaaaa tacaaacata caaacacttc atc             43

<210> SEQ ID NO 371
<211> LENGTH: 43
<212> TYPE: DNA
<213> ORGANISM: Artificial Sequence
<220> FEATURE:
<223> OTHER INFORMATION: synthetic mutagenesis primer PYR1P55k+

<400> SEQUENCE: 371
cgtacgacga ttcgacaaaa agcaaacata caaacacttc atc             43

<210> SEQ ID NO 372
<211> LENGTH: 43
<212> TYPE: DNA
<213> ORGANISM: Artificial Sequence
<220> FEATURE:
<223> OTHER INFORMATION: synthetic mutagenesis primer PYR1P55M+

<400> SEQUENCE: 372
cgtacgacga ttcgacaaaa tgcaaacata caaacacttc atc            43

<210> SEQ ID NO 373
<211> LENGTH: 43
<212> TYPE: DNA
<213> ORGANISM: Artificial Sequence
<220> FEATURE:
<223> OTHER INFORMATION: synthetic mutagenesis primer PYR1P55NNN-
<220> FEATURE:
<221> NAME/KEY: modified_base
<222> LOCATION: (22)...(24)
<223> OTHER INFORMATION: n = g, a, c or t

<400> SEQUENCE: 373
gatgaagtgt ttgtatgttt gnnntttgtc gaatcgtcgt acg            43

<210> SEQ ID NO 374
<211> LENGTH: 43
<212> TYPE: DNA
<213> ORGANISM: Artificial Sequence
<220> FEATURE:
<223> OTHER INFORMATION: synthetic mutagenesis primer PYR1P55NNN+
<220> FEATURE:
<221> NAME/KEY: modified_base
<222> LOCATION: (20)...(22)
<223> OTHER INFORMATION: n = g, a, c or t

<400> SEQUENCE: 374
cgtacgacga ttcgacaaan nncaaacata caaacacttc atc            43

<210> SEQ ID NO 375
<211> LENGTH: 43
<212> TYPE: DNA
<213> ORGANISM: Artificial Sequence
<220> FEATURE:
<223> OTHER INFORMATION: synthetic mutagenesis primer PYR1P55v+

<400> SEQUENCE: 375
cgtacgacga ttcgacaaag tacaaacata caaacacttc atc            43

<210> SEQ ID NO 376
<211> LENGTH: 43
<212> TYPE: DNA
<213> ORGANISM: Artificial Sequence
<220> FEATURE:
<223> OTHER INFORMATION: synthetic mutagenesis primer PYR1P55W+

<400> SEQUENCE: 376
cgtacgacga ttcgacaaat ggcaaacata caaacacttc atc            43

<210> SEQ ID NO 377
<211> LENGTH: 43
<212> TYPE: DNA
<213> ORGANISM: Artificial Sequence
<220> FEATURE:
<223> OTHER INFORMATION: synthetic mutagenesis primer PYR1P55y+

<400> SEQUENCE: 377
cgtacgacga ttcgacaaat atcaaacata caaacacttc atc            43

<210> SEQ ID NO 378
<211> LENGTH: 33
<212> TYPE: DNA
<213> ORGANISM: Artificial Sequence
<220> FEATURE:
<223> OTHER INFORMATION: synthetic mutagenesis primer Pyr1p88a+

<400> SEQUENCE: 378
gtcatcagtg gattagcggc gaacacatca acg                33

<210> SEQ ID NO 379
<211> LENGTH: 33
<212> TYPE: DNA
<213> ORGANISM: Artificial Sequence
<220> FEATURE:
<223> OTHER INFORMATION: synthetic mutagenesis primer Pyr1p88D+

<400> SEQUENCE: 379
gtcatcagtg gattagatgc gaacacatca acg                33

<210> SEQ ID NO 380
<211> LENGTH: 33
<212> TYPE: DNA
<213> ORGANISM: Artificial Sequence
<220> FEATURE:
<223> OTHER INFORMATION: synthetic mutagenesis primer Pyr1p88g+

<400> SEQUENCE: 380
gtcatcagtg gattaggggc gaacacatca acg                33

<210> SEQ ID NO 381
<211> LENGTH: 33
<212> TYPE: DNA
<213> ORGANISM: Artificial Sequence
<220> FEATURE:
<223> OTHER INFORMATION: synthetic mutagenesis primer Pyr1p88K+

<400> SEQUENCE: 381
gtcatcagtg gattaaaggc gaacacatca acg                33

<210> SEQ ID NO 382
<211> LENGTH: 33
<212> TYPE: DNA
<213> ORGANISM: Artificial Sequence
<220> FEATURE:
<223> OTHER INFORMATION: synthetic mutagenesis primer PYR1P88M+

<400> SEQUENCE: 382
gtcatcagtg gattaatggc gaacacatca acg                33

<210> SEQ ID NO 383
<211> LENGTH: 33
<212> TYPE: DNA
<213> ORGANISM: Artificial Sequence
<220> FEATURE:
<223> OTHER INFORMATION: synthetic mutagenesis primer PYR1P88NNN-
<220> FEATURE:
<221> NAME/KEY: modified_base
<222> LOCATION: (16)...(18)
<223> OTHER INFORMATION: n = g, a, c or t

<400> SEQUENCE: 383
cgttgatgtg ttcgcnnnta atccactgat gac                33

<210> SEQ ID NO 384
<211> LENGTH: 33
<212> TYPE: DNA
<213> ORGANISM: Artificial Sequence
<220> FEATURE:
<223> OTHER INFORMATION: synthetic mutagenesis primer PYR1P88NNN+
<220> FEATURE:
<221> NAME/KEY: modified_base
<222> LOCATION: (16)...(18)
<223> OTHER INFORMATION: n = g, a, c or t

<400> SEQUENCE: 384
gtcatcagtg gattanngc gaacacatca acg                                    33

<210> SEQ ID NO 385
<211> LENGTH: 33
<212> TYPE: DNA
<213> ORGANISM: Artificial Sequence
<220> FEATURE:
<223> OTHER INFORMATION: synthetic mutagenesis primer PYR1P88W+

<400> SEQUENCE: 385
gtcatcagtg gattatgggc gaacacatca acg                                   33

<210> SEQ ID NO 386
<211> LENGTH: 33
<212> TYPE: DNA
<213> ORGANISM: Artificial Sequence
<220> FEATURE:
<223> OTHER INFORMATION: synthetic mutagenesis primer Pyr1p88y+

<400> SEQUENCE: 386
gtcatcagtg gattatatgc gaacacatca acg                                   33

<210> SEQ ID NO 387
<211> LENGTH: 37
<212> TYPE: DNA
<213> ORGANISM: Artificial Sequence
<220> FEATURE:
<223> OTHER INFORMATION: synthetic mutagenesis primer PYR1S122#
<220> FEATURE:
<221> NAME/KEY: modified_base
<222> LOCATION: (18)...(19)
<223> OTHER INFORMATION: n = g, a, c or t

<400> SEQUENCE: 387
ggctgacgaa ttacaaannk gttacgacgg tgcatcg                               37

<210> SEQ ID NO 388
<211> LENGTH: 37
<212> TYPE: DNA
<213> ORGANISM: Artificial Sequence
<220> FEATURE:
<223> OTHER INFORMATION: synthetic mutagenesis primer PYR1S122E

<400> SEQUENCE: 388
ggctgacgaa ttacaaagaa gttacgacgg tgcatcg                               37

<210> SEQ ID NO 389
<211> LENGTH: 37
<212> TYPE: DNA
<213> ORGANISM: Artificial Sequence
<220> FEATURE:
<223> OTHER INFORMATION: synthetic mutagenesis primer PYR1S122I

<400> SEQUENCE: 389
ggctgacgaa ttacaaaatc gttacgacgg tgcatcg                               37

<210> SEQ ID NO 390
<211> LENGTH: 37
<212> TYPE: DNA
<213> ORGANISM: Artificial Sequence
<220> FEATURE:
<223> OTHER INFORMATION: synthetic mutagenesis primer PYR1S122K

<400> SEQUENCE: 390

```
ggctgacgaa ttacaaaaaa gttacgacgg tgcatcg                               37
```

<210> SEQ ID NO 391
<211> LENGTH: 37
<212> TYPE: DNA
<213> ORGANISM: Artificial Sequence
<220> FEATURE:
<223> OTHER INFORMATION: synthetic mutagenesis primer PYR1S122W

<400> SEQUENCE: 391

```
ggctgacgaa ttacaaatgg gttacgacgg tgcatcg                               37
```

<210> SEQ ID NO 392
<211> LENGTH: 36
<212> TYPE: DNA
<213> ORGANISM: Artificial Sequence
<220> FEATURE:
<223> OTHER INFORMATION: synthetic mutagenesis primer PYR1S85#
<220> FEATURE:
<221> NAME/KEY: modified_base
<222> LOCATION: (17)...(18)
<223> OTHER INFORMATION: n = g, a, c or t

<400> SEQUENCE: 392

```
cgacgtgatc gtcatcnnkg gattaccggc gaacac                                36
```

<210> SEQ ID NO 393
<211> LENGTH: 28
<212> TYPE: DNA
<213> ORGANISM: Artificial Sequence
<220> FEATURE:
<223> OTHER INFORMATION: synthetic mutagenesis primer pyr1s92D+

<400> SEQUENCE: 393

```
ccggcgaaca cagatacgga aagactcg                                         28
```

<210> SEQ ID NO 394
<211> LENGTH: 28
<212> TYPE: DNA
<213> ORGANISM: Artificial Sequence
<220> FEATURE:
<223> OTHER INFORMATION: synthetic mutagenesis primer pyr1s92G+

<400> SEQUENCE: 394

```
ccggcgaaca caggaacgga aagactcg                                         28
```

<210> SEQ ID NO 395
<211> LENGTH: 28
<212> TYPE: DNA
<213> ORGANISM: Artificial Sequence
<220> FEATURE:
<223> OTHER INFORMATION: synthetic mutagenesis primer pyr1s92K+

<400> SEQUENCE: 395

```
ccggcgaaca caaagacgga aagactcg                                         28
```

<210> SEQ ID NO 396
<211> LENGTH: 28
<212> TYPE: DNA
<213> ORGANISM: Artificial Sequence
<220> FEATURE:
<223> OTHER INFORMATION: synthetic mutagenesis primer PYR1S92M+

<400> SEQUENCE: 396

```
ccggcgaaca caatgacgga aagactcg                                         28
```

<210> SEQ ID NO 397
<211> LENGTH: 28
<212> TYPE: DNA
<213> ORGANISM: Artificial Sequence
<220> FEATURE:
<223> OTHER INFORMATION: synthetic mutagenesis primer PYR1S92NNN-
<220> FEATURE:
<221> NAME/KEY: modified_base
<222> LOCATION: (14)...(16)
<223> OTHER INFORMATION: n = g, a, c or t

<400> SEQUENCE: 397
cgagtctttc cgtnnntgtg ttcgccgg                                          28

<210> SEQ ID NO 398
<211> LENGTH: 28
<212> TYPE: DNA
<213> ORGANISM: Artificial Sequence
<220> FEATURE:
<223> OTHER INFORMATION: synthetic mutagenesis primer PYR1S92NNN+
<220> FEATURE:
<221> NAME/KEY: modified_base
<222> LOCATION: (13)...(15)
<223> OTHER INFORMATION: n = g, a, c or t

<400> SEQUENCE: 398
ccggcgaaca cannnacgga aagactcg                                          28

<210> SEQ ID NO 399
<211> LENGTH: 28
<212> TYPE: DNA
<213> ORGANISM: Artificial Sequence
<220> FEATURE:
<223> OTHER INFORMATION: synthetic mutagenesis primer PYR1S92W+

<400> SEQUENCE: 399
ccggcgaaca catggacgga aagactcg                                          28

<210> SEQ ID NO 400
<211> LENGTH: 28
<212> TYPE: DNA
<213> ORGANISM: Artificial Sequence
<220> FEATURE:
<223> OTHER INFORMATION: synthetic mutagenesis primer pyr1s92y+

<400> SEQUENCE: 400
ccggcgaaca catatacgga aagactcg                                          28

<210> SEQ ID NO 401
<211> LENGTH: 42
<212> TYPE: DNA
<213> ORGANISM: Artificial Sequence
<220> FEATURE:
<223> OTHER INFORMATION: synthetic mutagenesis primer PYR1T156#
<220> FEATURE:
<221> NAME/KEY: modified_base
<222> LOCATION: (22)...(23)
<223> OTHER INFORMATION: n = g, a, c or t

<400> SEQUENCE: 401
gaaggtaact cggaggatga tnnkcgtatg tttgctgata cg                          42

<210> SEQ ID NO 402
<211> LENGTH: 42
<212> TYPE: DNA
<213> ORGANISM: Artificial Sequence
<220> FEATURE:
<223> OTHER INFORMATION: synthetic mutagenesis primer PYR1T156A

<400> SEQUENCE: 402
gaaggtaact cggaggatga tgctcgtatg tttgctgata cg    42

<210> SEQ ID NO 403
<211> LENGTH: 42
<212> TYPE: DNA
<213> ORGANISM: Artificial Sequence
<220> FEATURE:
<223> OTHER INFORMATION: synthetic mutagenesis primer PYR1T156H

<400> SEQUENCE: 403
gaaggtaact cggaggatga tcatcgtatg tttgctgata cg    42

<210> SEQ ID NO 404
<211> LENGTH: 42
<212> TYPE: DNA
<213> ORGANISM: Artificial Sequence
<220> FEATURE:
<223> OTHER INFORMATION: synthetic mutagenesis primer PYR1T156K

<400> SEQUENCE: 404
gaaggtaact cggaggatga taaacgtatg tttgctgata cg    42

<210> SEQ ID NO 405
<211> LENGTH: 42
<212> TYPE: DNA
<213> ORGANISM: Artificial Sequence
<220> FEATURE:
<223> OTHER INFORMATION: synthetic mutagenesis primer PYR1T156N

<400> SEQUENCE: 405
gaaggtaact cggaggatga taatcgtatg tttgctgata cg    42

<210> SEQ ID NO 406
<211> LENGTH: 42
<212> TYPE: DNA
<213> ORGANISM: Artificial Sequence
<220> FEATURE:
<223> OTHER INFORMATION: synthetic mutagenesis primer PYR1T156Q

<400> SEQUENCE: 406
gaaggtaact cggaggatga tcaacgtatg tttgctgata cg    42

<210> SEQ ID NO 407
<211> LENGTH: 42
<212> TYPE: DNA
<213> ORGANISM: Artificial Sequence
<220> FEATURE:
<223> OTHER INFORMATION: synthetic mutagenesis primer PYR1T156Y

<400> SEQUENCE: 407
gaaggtaact cggaggatga ttatcgtatg tttgctgata cg    42

<210> SEQ ID NO 408
<211> LENGTH: 42
<212> TYPE: DNA
<213> ORGANISM: Artificial Sequence
<220> FEATURE:
<223> OTHER INFORMATION: synthetic mutagenesis primer PYR1T162#
<220> FEATURE:
<221> NAME/KEY: modified_base
<222> LOCATION: (18)...(19)
<223> OTHER INFORMATION: n = g, a, c or t

<400> SEQUENCE: 408
ctcgtatgtt tgctgatnnk gttgtgaagc ttaatttgca ga    42

<210> SEQ ID NO 409
<211> LENGTH: 42
<212> TYPE: DNA
<213> ORGANISM: Artificial Sequence
<220> FEATURE:
<223> OTHER INFORMATION: synthetic mutagenesis primer PYR1T162F

<400> SEQUENCE: 409
ctcgtatgtt tgctgattttt gttgtgaagc ttaatttgca ga        42

<210> SEQ ID NO 410
<211> LENGTH: 42
<212> TYPE: DNA
<213> ORGANISM: Artificial Sequence
<220> FEATURE:
<223> OTHER INFORMATION: synthetic mutagenesis primer PYR1T162I

<400> SEQUENCE: 410
ctcgtatgtt tgctgatatt gttgtgaagc ttaatttgca ga        42

<210> SEQ ID NO 411
<211> LENGTH: 42
<212> TYPE: DNA
<213> ORGANISM: Artificial Sequence
<220> FEATURE:
<223> OTHER INFORMATION: synthetic mutagenesis primer PYR1T162Y

<400> SEQUENCE: 411
ctcgtatgtt tgctgattat gttgtgaagc ttaatttgca ga        42

<210> SEQ ID NO 412
<211> LENGTH: 47
<212> TYPE: DNA
<213> ORGANISM: Artificial Sequence
<220> FEATURE:
<223> OTHER INFORMATION: synthetic mutagenesis primer PYR1V163M+

<400> SEQUENCE: 412
cgtatgtttg ctgatacgat ggtgaagctt aatttgcaga aactcgc        47

<210> SEQ ID NO 413
<211> LENGTH: 47
<212> TYPE: DNA
<213> ORGANISM: Artificial Sequence
<220> FEATURE:
<223> OTHER INFORMATION: synthetic mutagenesis primer PYR1V163NNN-
<220> FEATURE:
<221> NAME/KEY: modified_base
<222> LOCATION: (27)...(29)
<223> OTHER INFORMATION: n = g, a, c or t

<400> SEQUENCE: 413
gcgagtttct gcaaattaag cttcacnnnc gtatcagcaa acatacg        47

<210> SEQ ID NO 414
<211> LENGTH: 47
<212> TYPE: DNA
<213> ORGANISM: Artificial Sequence
<220> FEATURE:
<223> OTHER INFORMATION: synthetic mutagenesis primer PYR1V163NNN+
<220> FEATURE:
<221> NAME/KEY: modified_base
<222> LOCATION: (19)...(21)
<223> OTHER INFORMATION: n = g, a, c or t

<400> SEQUENCE: 414
cgtatgtttg ctgatacgnn ngtgaagctt aatttgcaga aactcgc         47

<210> SEQ ID NO 415
<211> LENGTH: 47
<212> TYPE: DNA
<213> ORGANISM: Artificial Sequence
<220> FEATURE:
<223> OTHER INFORMATION: synthetic mutagenesis primer PYR1V163W+

<400> SEQUENCE: 415
cgtatgtttg ctgatacgtg ggtgaagctt aatttgcaga aactcgc         47

<210> SEQ ID NO 416
<211> LENGTH: 39
<212> TYPE: DNA
<213> ORGANISM: Artificial Sequence
<220> FEATURE:
<223> OTHER INFORMATION: synthetic mutagenesis primer PYR1V164#
<220> FEATURE:
<221> NAME/KEY: modified_base
<222> LOCATION: (22)...(23)
<223> OTHER INFORMATION: n = g, a, c or t

<400> SEQUENCE: 416
cgtatgtttg ctgatacggt tnnkaagctt aatttgcag               39

<210> SEQ ID NO 417
<211> LENGTH: 39
<212> TYPE: DNA
<213> ORGANISM: Artificial Sequence
<220> FEATURE:
<223> OTHER INFORMATION: synthetic mutagenesis primer PYR1V164A

<400> SEQUENCE: 417
cgtatgtttg ctgatacggt tgcgaagctt aatttgcag               39

<210> SEQ ID NO 418
<211> LENGTH: 39
<212> TYPE: DNA
<213> ORGANISM: Artificial Sequence
<220> FEATURE:
<223> OTHER INFORMATION: synthetic mutagenesis primer PYR1V164D

<400> SEQUENCE: 418
cgtatgtttg ctgatacggt tgacaagctt aatttgcag               39

<210> SEQ ID NO 419
<211> LENGTH: 39
<212> TYPE: DNA
<213> ORGANISM: Artificial Sequence
<220> FEATURE:
<223> OTHER INFORMATION: synthetic mutagenesis primer PYR1V164K

<400> SEQUENCE: 419
cgtatgtttg ctgatacggt taagaagctt aatttgcag               39

<210> SEQ ID NO 420
<211> LENGTH: 39
<212> TYPE: DNA
<213> ORGANISM: Artificial Sequence
<220> FEATURE:
<223> OTHER INFORMATION: synthetic mutagenesis primer PYR1V164N

<400> SEQUENCE: 420
cgtatgtttg ctgatacggt taataagctt aatttgcag               39

```
<210> SEQ ID NO 421
<211> LENGTH: 39
<212> TYPE: DNA
<213> ORGANISM: Artificial Sequence
<220> FEATURE:
<223> OTHER INFORMATION: synthetic mutagenesis primer PYR1V164W

<400> SEQUENCE: 421
cgtatgtttg ctgatacggt ttggaagctt aatttgcag                              39

<210> SEQ ID NO 422
<211> LENGTH: 39
<212> TYPE: DNA
<213> ORGANISM: Artificial Sequence
<220> FEATURE:
<223> OTHER INFORMATION: synthetic mutagenesis primer PYR1V164Y

<400> SEQUENCE: 422
cgtatgtttg ctgatacggt ttataagctt aatttgcag                              39

<210> SEQ ID NO 423
<211> LENGTH: 30
<212> TYPE: DNA
<213> ORGANISM: Artificial Sequence
<220> FEATURE:
<223> OTHER INFORMATION: synthetic mutagenesis primer PYR1V81c+

<400> SEQUENCE: 423
gatgcacgcg cgactgtatc gtcatcagtg                                        30

<210> SEQ ID NO 424
<211> LENGTH: 30
<212> TYPE: DNA
<213> ORGANISM: Artificial Sequence
<220> FEATURE:
<223> OTHER INFORMATION: synthetic mutagenesis primer PYR1V81e+

<400> SEQUENCE: 424
gatgcacgcg cgacgagatc gtcatcagtg                                        30

<210> SEQ ID NO 425
<211> LENGTH: 30
<212> TYPE: DNA
<213> ORGANISM: Artificial Sequence
<220> FEATURE:
<223> OTHER INFORMATION: synthetic mutagenesis primer PYR1V81I+

<400> SEQUENCE: 425
gatgcacgcg cgacatcatc gtcatcagtg                                        30

<210> SEQ ID NO 426
<211> LENGTH: 30
<212> TYPE: DNA
<213> ORGANISM: Artificial Sequence
<220> FEATURE:
<223> OTHER INFORMATION: synthetic mutagenesis primer PYR1V81M+

<400> SEQUENCE: 426
gatgcacgcg cgacatgatc gtcatcagtg                                        30

<210> SEQ ID NO 427
<211> LENGTH: 30
<212> TYPE: DNA
<213> ORGANISM: Artificial Sequence
<220> FEATURE:
<223> OTHER INFORMATION: synthetic mutagenesis primer PYR1V81NNN-
<220> FEATURE:
```

```
<221> NAME/KEY: modified_base
<222> LOCATION: (14)...(16)
<223> OTHER INFORMATION: n = g, a, c or t

<400> SEQUENCE: 427
cactgatgac gatnnngtcg cgcgtgcatc                                30

<210> SEQ ID NO 428
<211> LENGTH: 30
<212> TYPE: DNA
<213> ORGANISM: Artificial Sequence
<220> FEATURE:
<223> OTHER INFORMATION: synthetic mutagenesis primer PYR1V81NNN+
<220> FEATURE:
<221> NAME/KEY: modified_base
<222> LOCATION: (15)...(17)
<223> OTHER INFORMATION: n = g, a, c or t

<400> SEQUENCE: 428
gatgcacgcg cgacnnnatc gtcatcagtg                                30

<210> SEQ ID NO 429
<211> LENGTH: 30
<212> TYPE: DNA
<213> ORGANISM: Artificial Sequence
<220> FEATURE:
<223> OTHER INFORMATION: synthetic mutagenesis primer PYR1V81W+

<400> SEQUENCE: 429
gatgcacgcg cgactggatc gtcatcagtg                                30

<210> SEQ ID NO 430
<211> LENGTH: 30
<212> TYPE: DNA
<213> ORGANISM: Artificial Sequence
<220> FEATURE:
<223> OTHER INFORMATION: synthetic mutagenesis primer PYR1V81y+

<400> SEQUENCE: 430
gatgcacgcg cgactatatc gtcatcagtg                                30

<210> SEQ ID NO 431
<211> LENGTH: 31
<212> TYPE: DNA
<213> ORGANISM: Artificial Sequence
<220> FEATURE:
<223> OTHER INFORMATION: synthetic mutagenesis primer PYR1V83c+

<400> SEQUENCE: 431
cgcgcgacgt gatctgcatc agtggattac c                              31

<210> SEQ ID NO 432
<211> LENGTH: 31
<212> TYPE: DNA
<213> ORGANISM: Artificial Sequence
<220> FEATURE:
<223> OTHER INFORMATION: synthetic mutagenesis primer PYR1V83d+

<400> SEQUENCE: 432
cgcgcgacgt gatcgacatc agtggattac c                              31

<210> SEQ ID NO 433
<211> LENGTH: 31
<212> TYPE: DNA
<213> ORGANISM: Artificial Sequence
<220> FEATURE:
<223> OTHER INFORMATION: synthetic mutagenesis primer PYR1V83e+
```

<400> SEQUENCE: 433
cgcgcgacgt gatcgagatc agtggattac c                               31

<210> SEQ ID NO 434
<211> LENGTH: 31
<212> TYPE: DNA
<213> ORGANISM: Artificial Sequence
<220> FEATURE:
<223> OTHER INFORMATION: synthetic mutagenesis primer PYR1V83F+

<400> SEQUENCE: 434
cgcgcgacgt gatctttatc agtggattac c                               31

<210> SEQ ID NO 435
<211> LENGTH: 31
<212> TYPE: DNA
<213> ORGANISM: Artificial Sequence
<220> FEATURE:
<223> OTHER INFORMATION: synthetic mutagenesis primer PYR1V83k+

<400> SEQUENCE: 435
cgcgcgacgt gatcaagatc agtggattac c                               31

<210> SEQ ID NO 436
<211> LENGTH: 31
<212> TYPE: DNA
<213> ORGANISM: Artificial Sequence
<220> FEATURE:
<223> OTHER INFORMATION: synthetic mutagenesis primer PYR1V83M+

<400> SEQUENCE: 436
cgcgcgacgt gatcatgatc agtggattac c                               31

<210> SEQ ID NO 437
<211> LENGTH: 31
<212> TYPE: DNA
<213> ORGANISM: Artificial Sequence
<220> FEATURE:
<223> OTHER INFORMATION: synthetic mutagenesis primer PYR1V83NNN-
<220> FEATURE:
<221> NAME/KEY: modified_base
<222> LOCATION: (15)...(17)
<223> OTHER INFORMATION: n = g, a, c or t

<400> SEQUENCE: 437
ggtaatccac tgatnnngat cacgtcgcgc g                               31

<210> SEQ ID NO 438
<211> LENGTH: 31
<212> TYPE: DNA
<213> ORGANISM: Artificial Sequence
<220> FEATURE:
<223> OTHER INFORMATION: synthetic mutagenesis primer PYR1V83NNN+
<220> FEATURE:
<221> NAME/KEY: modified_base
<222> LOCATION: (15)...(17)
<223> OTHER INFORMATION: n = g, a, c or t

<400> SEQUENCE: 438
cgcgcgacgt gatcnnnatc agtggattac c                               31

<210> SEQ ID NO 439
<211> LENGTH: 31
<212> TYPE: DNA
<213> ORGANISM: Artificial Sequence
<220> FEATURE:

```
<223> OTHER INFORMATION: synthetic mutagenesis primer PYR1V83q+

<400> SEQUENCE: 439
cgcgcgacgt gatccaaatc agtggattac c                                31

<210> SEQ ID NO 440
<211> LENGTH: 31
<212> TYPE: DNA
<213> ORGANISM: Artificial Sequence
<220> FEATURE:
<223> OTHER INFORMATION: synthetic mutagenesis primer PYR1V83W+

<400> SEQUENCE: 440
cgcgcgacgt gatctggatc agtggattac c                                31

<210> SEQ ID NO 441
<211> LENGTH: 31
<212> TYPE: DNA
<213> ORGANISM: Artificial Sequence
<220> FEATURE:
<223> OTHER INFORMATION: synthetic mutagenesis primer PYR1V83y+

<400> SEQUENCE: 441
cgcgcgacgt gatctacatc agtggattac c                                31

<210> SEQ ID NO 442
<211> LENGTH: 33
<212> TYPE: DNA
<213> ORGANISM: Artificial Sequence
<220> FEATURE:
<223> OTHER INFORMATION: synthetic mutagenesis primer pyr1y120A+

<400> SEQUENCE: 442
cataggctga cgaatgccaa atccgttacg acg                              33

<210> SEQ ID NO 443
<211> LENGTH: 33
<212> TYPE: DNA
<213> ORGANISM: Artificial Sequence
<220> FEATURE:
<223> OTHER INFORMATION: synthetic mutagenesis primer pyr1y120C+

<400> SEQUENCE: 443
cataggctga cgaattgtaa atccgttacg acg                              33

<210> SEQ ID NO 444
<211> LENGTH: 33
<212> TYPE: DNA
<213> ORGANISM: Artificial Sequence
<220> FEATURE:
<223> OTHER INFORMATION: synthetic mutagenesis primer pyr1y120E+

<400> SEQUENCE: 444
cataggctga cgaatgagaa atccgttacg acg                              33

<210> SEQ ID NO 445
<211> LENGTH: 33
<212> TYPE: DNA
<213> ORGANISM: Artificial Sequence
<220> FEATURE:
<223> OTHER INFORMATION: synthetic mutagenesis primer pyr1y120G+

<400> SEQUENCE: 445
cataggctga cgaatggcaa atccgttacg acg                              33
```

<210> SEQ ID NO 446
<211> LENGTH: 33
<212> TYPE: DNA
<213> ORGANISM: Artificial Sequence
<220> FEATURE:
<223> OTHER INFORMATION: synthetic mutagenesis primer pyr1y120H+

<400> SEQUENCE: 446
cataggctga cgaatcacaa atccgttacg acg          33

<210> SEQ ID NO 447
<211> LENGTH: 33
<212> TYPE: DNA
<213> ORGANISM: Artificial Sequence
<220> FEATURE:
<223> OTHER INFORMATION: synthetic mutagenesis primer PYR1Y120M+

<400> SEQUENCE: 447
cataggctga cgaatatgaa atccgttacg acg          33

<210> SEQ ID NO 448
<211> LENGTH: 33
<212> TYPE: DNA
<213> ORGANISM: Artificial Sequence
<220> FEATURE:
<223> OTHER INFORMATION: synthetic mutagenesis primer PYR1Y120NNN-
<220> FEATURE:
<221> NAME/KEY: modified_base
<222> LOCATION: (16)...(18)
<223> OTHER INFORMATION: n = g, a, c or t

<400> SEQUENCE: 448
cgtcgtaacg gatttnnnat tcgtcagcct atg          33

<210> SEQ ID NO 449
<211> LENGTH: 33
<212> TYPE: DNA
<213> ORGANISM: Artificial Sequence
<220> FEATURE:
<223> OTHER INFORMATION: synthetic mutagenesis primer PYR1Y120NNN+
<220> FEATURE:
<221> NAME/KEY: modified_base
<222> LOCATION: (16)...(18)
<223> OTHER INFORMATION: n = g, a, c or t

<400> SEQUENCE: 449
cataggctga cgaatnnnaa atccgttacg acg          33

<210> SEQ ID NO 450
<211> LENGTH: 33
<212> TYPE: DNA
<213> ORGANISM: Artificial Sequence
<220> FEATURE:
<223> OTHER INFORMATION: synthetic mutagenesis primer pyr1y120P+

<400> SEQUENCE: 450
cataggctga cgaatcccaa atccgttacg acg          33

<210> SEQ ID NO 451
<211> LENGTH: 33
<212> TYPE: DNA
<213> ORGANISM: Artificial Sequence
<220> FEATURE:
<223> OTHER INFORMATION: synthetic mutagenesis primer pyr1y120Q+

<400> SEQUENCE: 451
cataggctga cgaatcagaa atccgttacg acg          33

```
<210> SEQ ID NO 452
<211> LENGTH: 33
<212> TYPE: DNA
<213> ORGANISM: Artificial Sequence
<220> FEATURE:
<223> OTHER INFORMATION: synthetic mutagenesis primer PYR1Y120W+

<400> SEQUENCE: 452
cataggctga cgaattggaa atccgttacg acg                                33

<210> SEQ ID NO 453
<211> LENGTH: 29
<212> TYPE: DNA
<213> ORGANISM: Artificial Sequence
<220> FEATURE:
<223> OTHER INFORMATION: synthetic amplification primer for Arabidopsis
      RD29A promoter

<400> SEQUENCE: 453
gagctcccat agatgcaatt caatcaaac                                     29

<210> SEQ ID NO 454
<211> LENGTH: 30
<212> TYPE: DNA
<213> ORGANISM: Artificial Sequence
<220> FEATURE:
<223> OTHER INFORMATION: synthetic amplification primer for Arabidopsis
      RD29A promoter

<400> SEQUENCE: 454
accggtcaaa gatttttttc tttccaatag                                    30
```

CONSTITUTIVELY ACTIVE ABA RECEPTOR MUTANTS

CROSS-REFERENCE TO RELATED APPLICATIONS

The present patent application is a national stage application under 35 U.S.C. 371 of International Application No. PCT/US2012/043121, filed Jun. 19, 2012, which claims benefit of U.S. Provisional Patent Application No. 61/503,816, filed Jul. 1, 2011, and of U.S. Provisional Patent Application No. 61/512,280, filed Jul. 27, 2011, the contents of each of which is incorporated by reference herein for all purposes.

STATEMENT AS TO RIGHTS TO INVENTIONS MADE UNDER FEDERALLY SPONSORED RESEARCH AND DEVELOPMENT

This invention was made with government support under Grant Number 10S0820508, awarded by the National Science Foundation. The Government has certain rights in this invention.

BACKGROUND OF THE INVENTION

Abscisic acid (ABA) is a plant hormone that regulates signal transduction associated with abiotic stress responses (Cutler et al., 2010). The ABA signaling pathway has been exploited to improve plant stress response and associated yield traits via numerous approaches (Yang et al., 2010). The direct application of ABA to plants improves their water use efficiency (Raedmacher et al., 1987); for this reason, the discovery of ABA agonists (Park et al., 2009; Melcher et al., 2010) has received increasing attention, as such molecules may be beneficial for improving crop yield (Notman et al., 2009). A complementary approach to activating the ABA pathway involves increasing a plant's sensitivity to ABA via genetic methods. For example, conditional antisense of farnesyl transferase beta subunit gene, which increases a plant's ABA sensitivity, improves yield under moderate drought in both canola and *Arabidopsis* (Wang et al., 2005). Thus, the manipulation of ABA signaling to improve traits contributing to yield is now well established.

It has recently been discovered that ABA elicits many of its cellular responses by binding to a soluble family of receptors called PYR/PYL proteins. PYR/PYL proteins belong to a large family of ligand-binding proteins named the START superfamily (Iyer et al., 2001; Ponting et al., 1999). These proteins contain a conserved three-dimensional architecture consisting of seven anti-parallel beta sheets, which surround a central alpha helix to form a "helix-grip" motif; together, these structural elements form a ligand-binding pocket for binding ABA or other agonists.

Structural and functional studies have uncovered a series of conformational changes and critical contacts between PYR/PYL receptors and type II C protein phosphatases (PP2Cs) that are necessary for ABA-mediated PP2C inhibition by receptors. For example, when ABA or another agonist binds within the ligand-binding pockets of PYR/PYL proteins, it stabilizes a conformational change that allows the receptors to bind and inhibit a family of PP2Cs that normally repress ABA signaling (Weiner et al., 2010). In particular, ABA binding leads to a large rearrangement in a flexible "gate" loop that flanks the ligand-binding pocket. Upon ABA binding, the gate loop adopts a closed conformation that is stabilized by several direct contacts between the loop and ABA. This agonist-bound, closed form of the gate allows PYR/PYL proteins to dock into, and inhibit, the active site of PP2Cs. The resulting inhibition in turn allows activation of downstream kinases in the SnRK2 class, which are responsible for the regulation of the activity of transcription factors, ion channels and other proteins involved in ABA responses (Weiner et al., 2010). Thus, the stabilization of a closed gate conformation of the receptors is critical to their activation and PYR/PYL receptors are molecular switches at the apex of a signaling cascade that regulates diverse ABA responses.

In addition to the important role that gate closure plays in receptor activation, other structural rearrangements are critical as well. For example, PYR1, PYL1, and PYL2 are homodimers in solution, but bind to PP2Cs as monomers. The homodimer interface overlaps with the PP2C binding interface and therefore an intact receptor homodimer cannot bind to and inhibit the PP2C. Thus, dimer formation is antagonistic to ABA signaling and receptor dimer-breaking is a necessary step in receptor activation. Additionally, a recognition module containing a central conserved tryptophan "lock" residue located on the PP2C inserts into a small pore formed in the ABA-bound receptors. Mutation of the tryptophan lock residue abolishes receptor-mediated inactivation of PP2C activity, demonstrating the importance of the lock residue's insertion into the receptor's pore.

BRIEF SUMMARY OF THE INVENTION

In one aspect, the present invention provides for isolated nucleic acids comprising a polynucleotide encoding a mutated PYR/PYL receptor polypeptide. In some embodiments, the polynucleotide encodes a mutated PYR/PYL receptor polypeptide comprising one or more amino acid substitutions in a ligand-binding pocket and/or a type 2 protein phosphatase (PP2C) binding interface as compared to a wild-type PYR/PYL receptor polypeptide, wherein the mutated PYR/PYL receptor binds to PP2C in the absence of abscisic acid.

In some embodiments, the mutated PYR/PYL receptor polypeptide comprises one or more amino acid substitutions in the ligand-binding pocket. In some embodiments, the mutated PYR/PYL receptor polypeptide comprises one or more amino acid substitutions corresponding to the amino acid substitutions H60P/G/R/A/W/I/K/V/M, V83F/L/P, L87F, A89W or F159V/A in PYR1 as set forth in SEQ ID NO:1. In some embodiments, the mutated PYR/PYL receptor polypeptide comprises one or more amino acid substitutions corresponding to the amino acid substitutions H60P/G, V83F, A89W or F159V in PYR1 as set forth in SEQ ID NO:1.

In some embodiments, the mutated PYR/PYL receptor polypeptide comprises one or more amino acid substitutions in the PP2C binding interface. In some embodiments, the mutated PYR/PYL receptor polypeptide comprises one or more amino acid substitutions corresponding to the amino acid substitutions H60P/G/R/A/W/I/K/V/M, I84Q/E/P/H/K, L87F, A89W, M158T/C/V/I, F159V/A, T162F, L166Y/F, or K170W in PYR1 as set forth in SEQ ID NO:1. In some embodiments, the mutated PYR/PYL receptor polypeptide comprises one or more amino acid substitutions corresponding to the amino acid substitutions H60P/G, I84Q, A89W, M158T/C, F159V, or K170W in PYR1 as set forth in SEQ ID NO:1.

In some embodiments, the mutated PYR/PYL receptor polypeptide comprises one or more amino acid substitutions in the ligand-binding pocket and one or more amino acid substitutions in the PP2C binding interface.

In some embodiments, the mutated PYR/PYL receptor polypeptide comprises amino acid substitutions corresponding to the amino acid substitutions H60P, V83F, and F159V in PYR1 as set forth in SEQ ID NO:1. In some embodiments, the mutated PYR/PYL receptor polypeptide comprises amino acid substitutions corresponding to the amino acid substitutions H60P, V83F, M158I, and F159V in PYR1 as set forth in SEQ ID NO:1. In some embodiments, the mutated PYR/PYL receptor polypeptide comprises amino acid substitutions corresponding to the amino acid substitutions H60P, A89W, M158I, and F159V in PYR1 as set forth in SEQ ID NO:1. In some embodiments, the mutated PYR/PYL receptor polypeptide comprises amino acid substitutions corresponding to the amino acid substitutions V83F, M158I, F159V, and K170W in PYR1 as set forth in SEQ ID NO:1.

In some embodiments, the mutated PYR/PYL receptor polypeptide significantly inhibits the activity of the PP2C in a phosphatase assay in the absence of abscisic acid. In some embodiments, the mutated PYR/PYL receptor polypeptide inhibits the activity of the PP2C by at least 50% in the absence of abscisic acid as compared to the level of PP2C activity of a PP2C that is contacted with a wild-type PYR/PYL receptor polypeptide in the absence of abscisic acid.

In some embodiments, the mutated PYR/PYL receptor polypeptide is substantially identical (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% amino acid sequence identity) to any of SEQ ID NOs:1-155. In some embodiments, the mutated PYR/PYL receptor polypeptide is any of SEQ ID NOs:120-155.

In some embodiments, the PP2C is HAB1 (Homology to ABI1), ABI1 (Abscisic acid insensitive 1), or ABI2 (Abscisic acid insensitive 2). In some embodiments, the PP2C is HAB1.

In another aspect, the present invention provides for expression cassettes comprising a promoter operably linked to a polynucleotide encoding a mutated PYR/PYL receptor polypeptide of the invention (e.g., as described herein), wherein introduction of the expression cassette into a plant results in the plant having a PYR/PYL receptor that binds to a type 2 protein phosphatase (PP2C) in the absence of abscisic acid. In some embodiments, the promoter is heterologous to the polynucleotide. In some embodiments, the promoter is inducible. In some embodiments, the promoter is a stress-inducible promoter, e.g., a drought-inducible promoter and/or a salinity-inducible promoter. In some embodiments, the promoter is tissue-specific.

In some embodiments, introduction of the expression cassette into a plant results in the plant having significantly inhibited PP2C activity in the absence of abscisic acid as compared to a plant lacking the expression cassette. In some embodiments, introduction of the expression cassette into the plant results in the plant having PP2C activity that is inhibited by at least about 10%, at least about 20%, at least about 30%, at least about 40%, at least about 50%, at least about 60%, at least about 70%, at least about 80% or more in the absence of ABA as compared to a plant lacking the expression cassette.

In another aspect, the present invention provides for expression vectors comprising an expression cassette of the invention (e.g., as described herein).

In yet another aspect, the present invention provides for plants (or a plant cell, seed, flower, leaf, fruit, or other plant part from such plants or processed food or food ingredient from such plants) comprising an expression cassette comprising a promoter operably linked to a polynucleotide encoding a mutated PYR/PYL receptor polypeptide of the invention (e.g., as described herein). In some embodiments, the plant has significantly inhibited PP2C activity in the absence of abscisic acid.

In still another aspect, the present invention provides for methods of producing a plant having significantly inhibited activity of a type 2 protein phosphatase (PP2C) in the absence of abscisic acid. In some embodiments, the method comprises:

introducing an expression cassette comprising a promoter operably linked to a polynucleotide encoding a mutated PYR/PYL receptor polypeptide of the invention (e.g., as described herein) into a plurality of plants; and
   selecting a plant that expresses the polynucleotide from the plurality of plants.

In yet another aspect, the present invention provides for methods of producing a plant having enhanced stress tolerance. In some embodiments, the method comprises:

introducing into a plurality of plants an expression cassette comprising a promoter operably linked to a polynucleotide encoding a mutated PYR/PYL receptor polypeptide of the invention comprising one or more amino acid substitutions in a ligand-binding pocket and/or a type 2 protein phosphatase (PP2C) binding interface as compared to a wild-type PYR/PYL receptor polypeptide, wherein the mutated PYR/PYL receptor binds to PP2C in the absence of abscisic acid; and
   selecting a plant that expresses the polynucleotide from the plurality of plants.

The mutated PYR/PYL receptor polypeptide to be introduced into the plurality of plants can be any PYR/PYL polypeptide as described herein. In some embodiments, the mutated PYR/PYL receptor polypeptide comprises one or more amino acid substitutions corresponding to the amino acid substitutions H60P/G/R/A/W/I/K/V/M, V83F/L/P, I84Q/E/P/H/K, L87F, A89W, M158T/C/V/I, F159V/A, T162F, L166Y/F, or K170W in PYR1 as set forth in SEQ ID NO:1. In some embodiments, the mutated PYR/PYL receptor polypeptide comprises amino acid substitutions corresponding to the amino acid substitutions H60P, V83F, and F159V in PYR1 as set forth in SEQ ID NO:1. In some embodiments, the mutated PYR/PYL receptor polypeptide comprises amino acid substitutions corresponding to the amino acid substitutions H60P, V83F, M158I, and F159V in PYR1 as set forth in SEQ ID NO:1. In some embodiments, the mutated PYR/PYL receptor polypeptide comprises amino acid substitutions corresponding to the amino acid substitutions H60P, A89W, M158I, and F159V in PYR1 as set forth in SEQ ID NO:1. In some embodiments, the mutated PYR/PYL receptor polypeptide comprises amino acid substitutions corresponding to the amino acid substitutions V83F, M158I, F159V, and K170W in PYR1 as set forth in SEQ ID NO:1.

For expressing the mutated PYR/PYL receptor polypeptide in a plant according to the methods of the present invention, in some embodiments, the polynucleotide encoding the mutated PYR/PYL receptor polypeptide is operably linked to a heterologous promoter. In some embodiments, the promoter is an inducible promoter. In some embodiments, the promoter is a stress-inducible promoter, e.g, a drought-inducible promoter and/or a salinity-inducible promoter. In some embodiments, the promoter is RD29A. In some embodiments, the promoter is tissue-specific.

BRIEF DESCRIPTION OF THE DRAWINGS

FIG. 1. PYR1 Ligand Binding and PP2C-Interaction Residues are Highly Conserved within the PYR/PYL Receptor Family.

Shown are the residues selected for mutagenesis in PYR1 and the corresponding amino acid position and residue for each selected residue in other members of the Arabidopsis PYR/PYL receptor family, as well as two PYR1 homologs from the moss Physcomitrella patens (GenBank Accession No. XP_001778048) and the monocot Zea mays (GenBank Accession No. ACR34816). Columns with an "@" indicate those residues where constitutive mutations were identified from saturation mutagenesis studies. Contiguous peptides=SEQ ID NOs:156-172.

Figure 2:
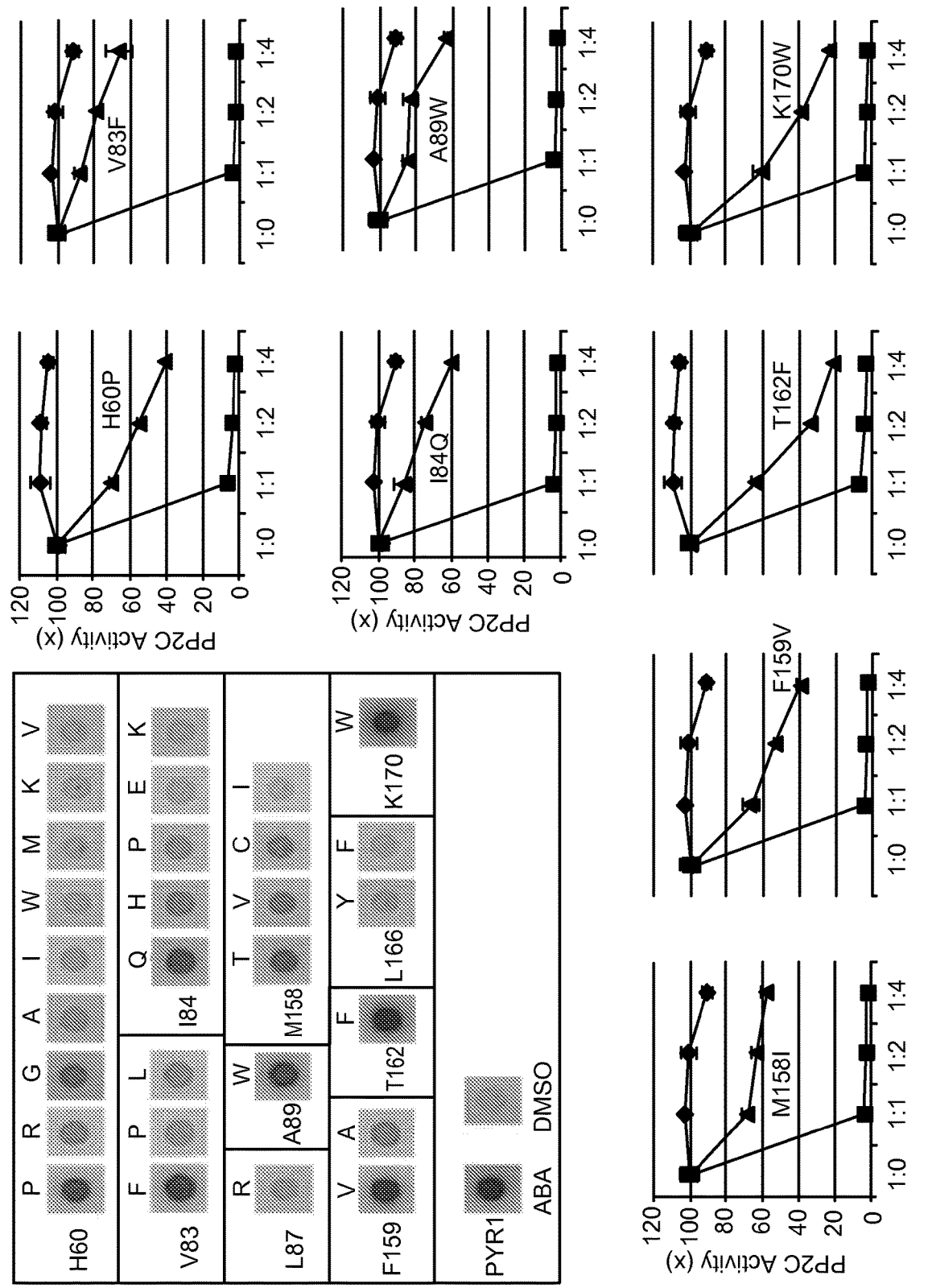

FIG. 2. Characterization of Constitutively Active Mutants.

In the absence of ABA, PYR1 does not bind HAB1 in the yeast two-hybrid assay, but addition of 10 μM ABA promotes a strong interaction between them (bottom of upper left panel). 29 of 741 PYR1 mutants constructed, located in 10 different residues, increase the interaction between PYR1 and HAB1 in the absence of ABA, as measured using the yeast two hybrid assay (upper left panel). Expression of a subset of mutant proteins at 8 of the 10 sites identified (H60P, V83F, I84Q, A89W, M158I, F159V, T162F, and K170W) demonstrated that the mutants all increase basal activity of receptors, as measured by the ability of receptor to inhibit HAB1 phosphatase activity in the absence of ABA. Each graph includes control wild-type PYR1 protein tested in the absence (diamonds) and presence (squares) of 10 μM ABA. Specific mutant proteins (triangles) were tested in the absence of ABA. All displayed partial constitutive receptor activation, as measured by inhibition of PP2C activity in the absence of activating ligand. Plotted in each graph is PP2C activity, expressed as % of control, which is the PP2C activity measured in the absence of ABA or receptor protein.

Figure 3:
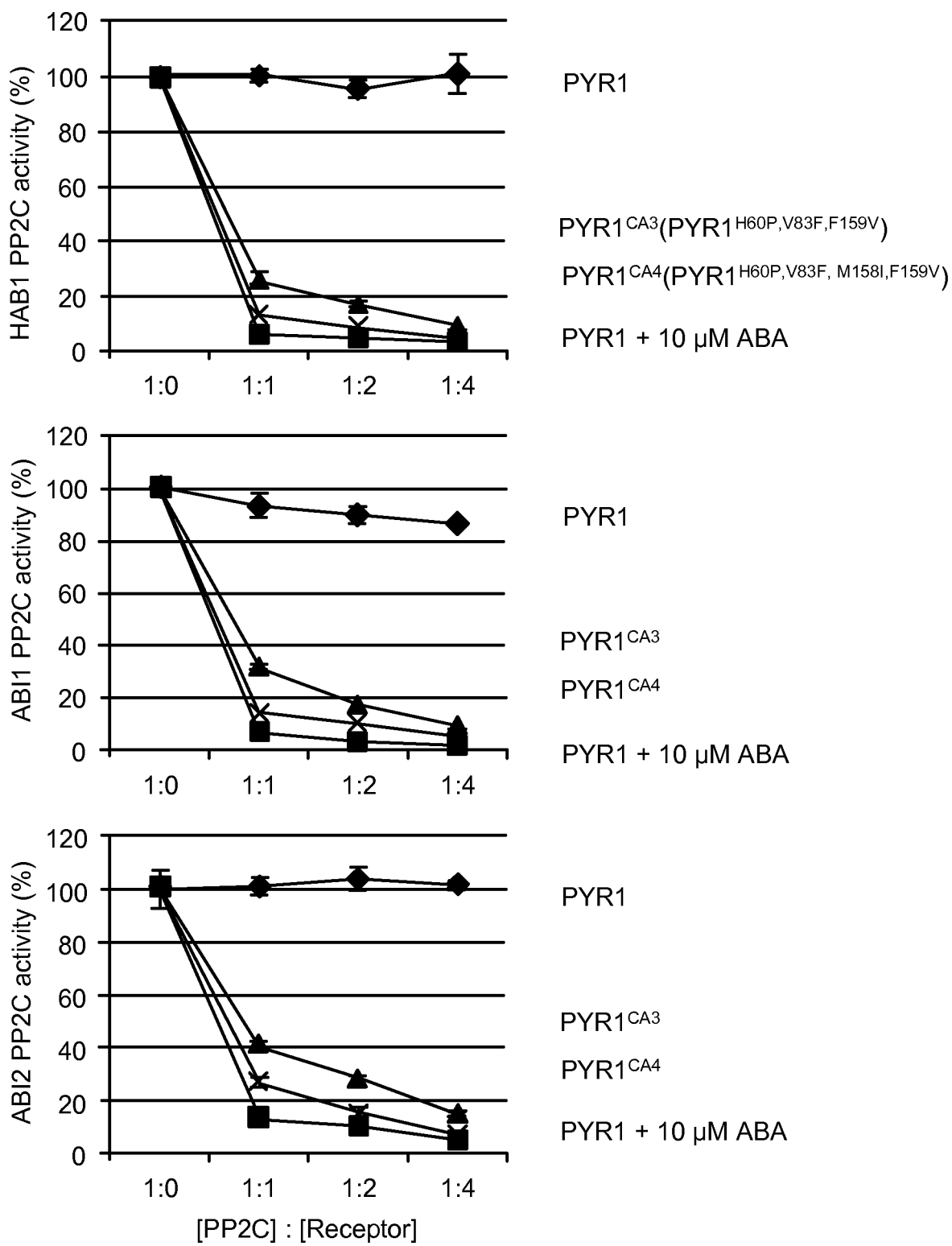

FIG. 3. Engineering Strong PYR1 CA Alleles by Combining Partial CA Mutations.

Combinations of partial constitutively active ("CA") alleles identified by saturation mutagenesis were made as described in the text and tested for their ability to inhibit PP2C activity in the absence of ABA, utilizing the PP2Cs HAB1 (top panel), ABI1 (middle panel), and ABI2 (bottom panel). Each graph includes control wild-type PYR1 protein tested in the absence (diamonds) and presence (squares) of 10 μM ABA with the particular PP2C (identified at left). CA mutants (PYR1$^{CA3}$ represented by triangles and PYR1$^{CA4}$ represented by crosses(x)) were tested in the absence of ABA. Plotted in each graph is PP2C activity, expressed as % of control, which is the PP2C activity measured in the absence of ABA or receptor protein.

Figure 4A:
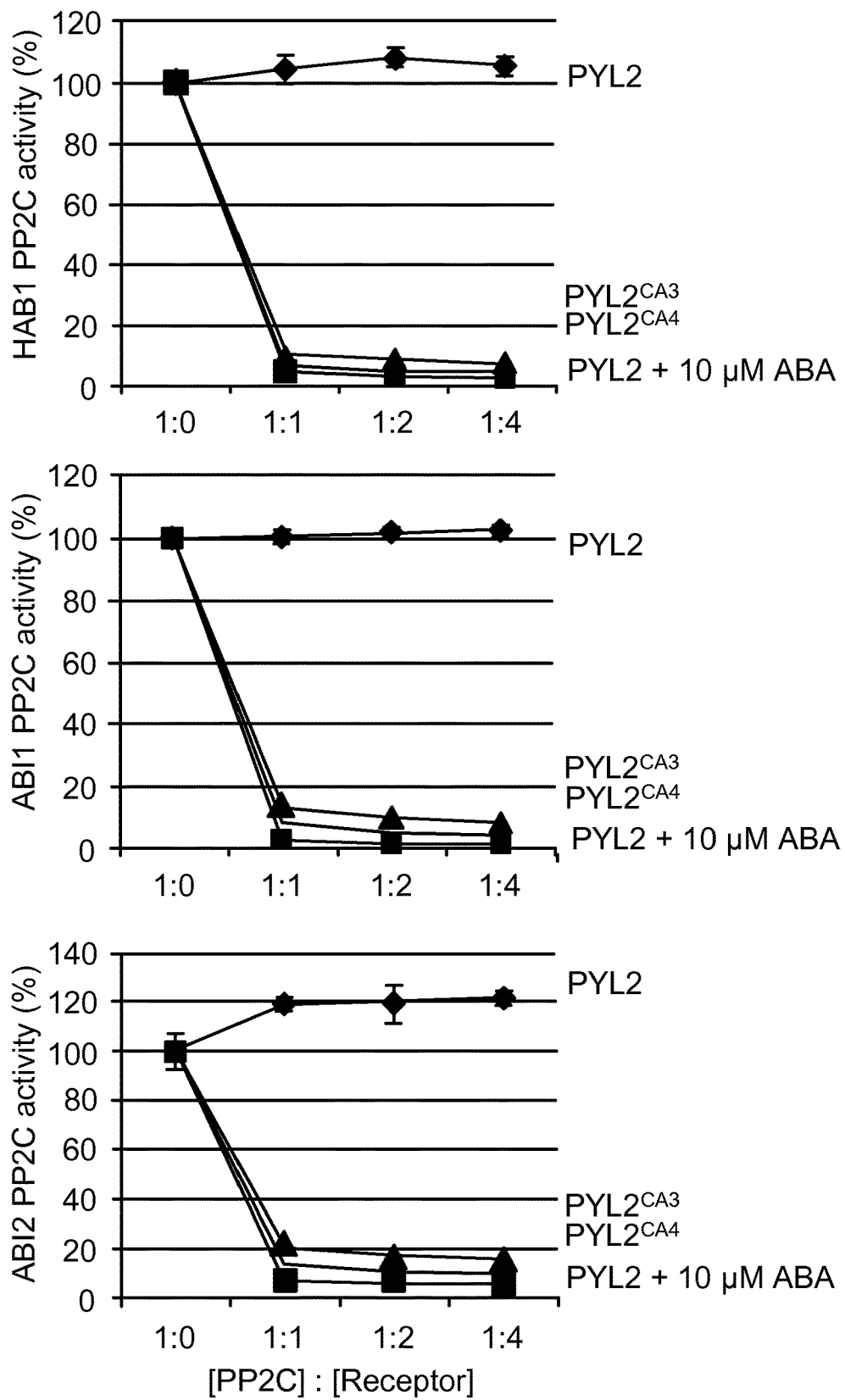
Figure 4B:
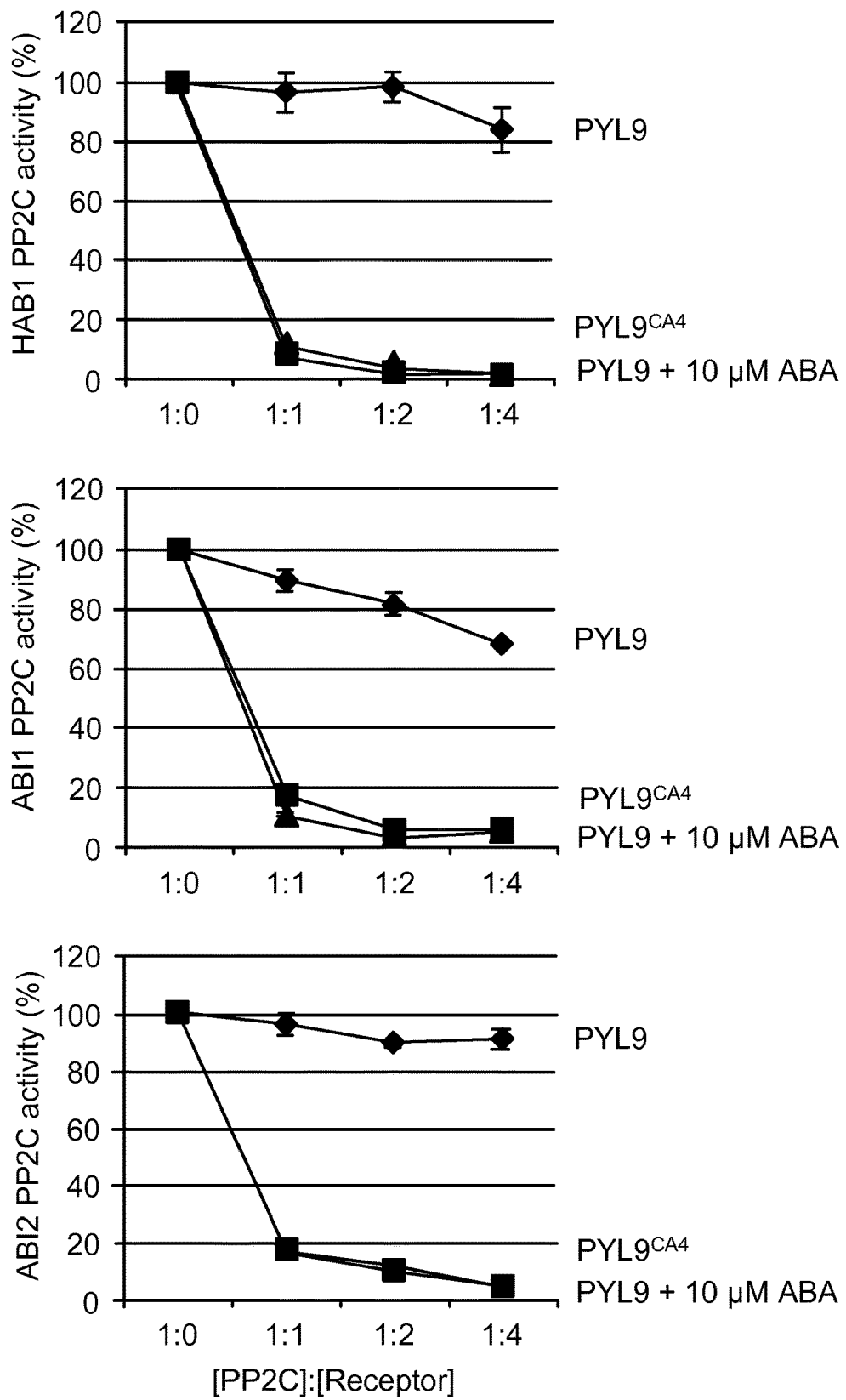

FIG. 4. Engineering Strong PYL2 and PYL9 CA Alleles.

The CA mutations of PYR1 were introduced into PYL2 (A) and PYL9 (B) to generate the mutants PYL2$^{CA3}$ (H65P, V87F, F169V), PYL2$^{CA4}$ (H65P, V87F, F169V, M164I) and PYL9$^{CA4}$ (V85F, Y160I, F161V). Recombinant proteins were used in in vitro PP2C assays at the stoichiometry shown ([PP2C]=600 nM) using recombinant proteins for HAB1, ABI1, and ABI2 (HAB1, top panel; ABI1, middle panel; ABI2, bottom panel). As observed with PYR1 CA alleles, the PYL2 and PYL9 CA alleles are show a high level of ligand-independent inhibition of PP2Cs and are active on multiple PP2Cs.

Figure 5:
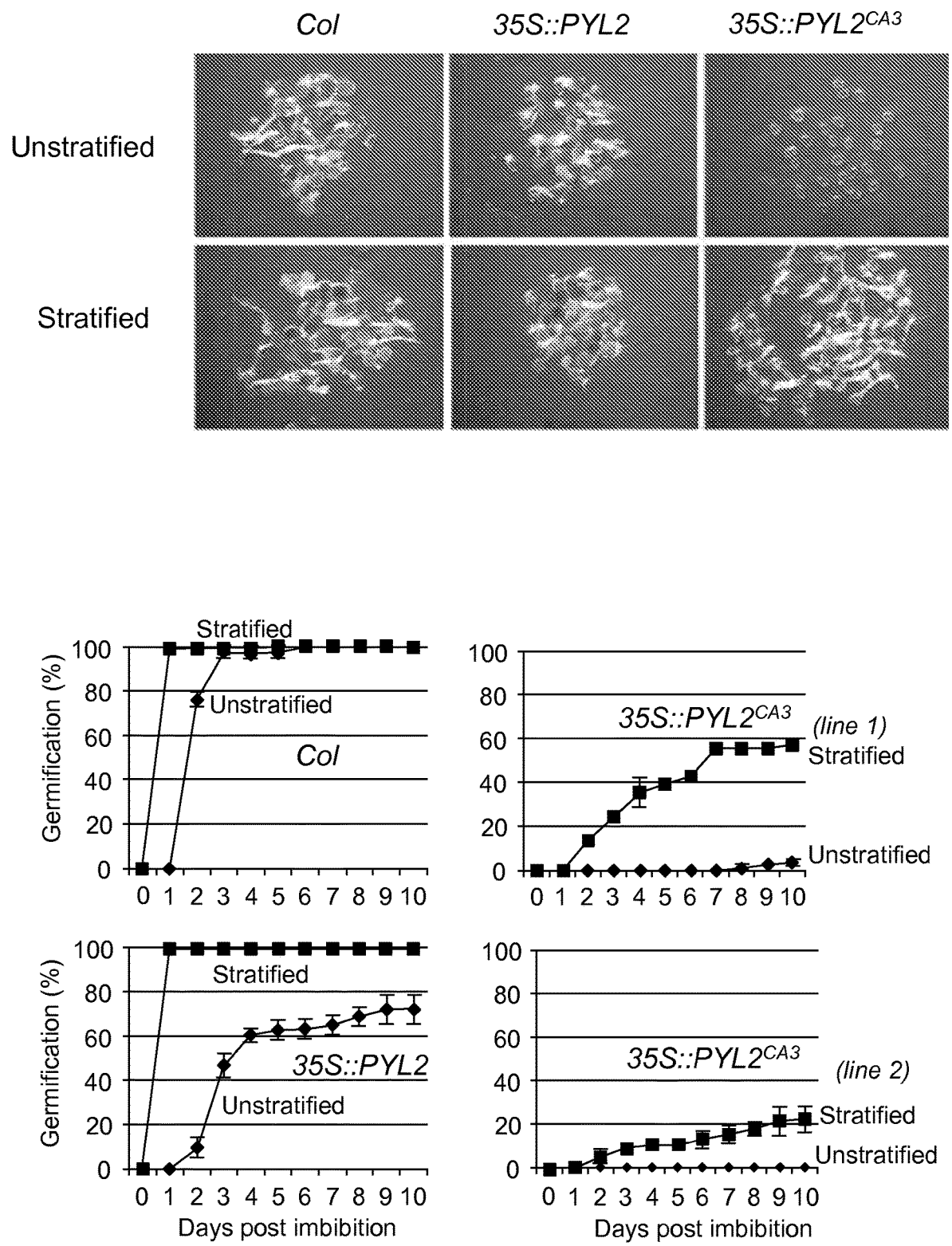

FIG. 5. PYL2$^{CA3}$ Overexpression Induces Hyperdormancy in Seeds.

Columbia (Col), 35S::PYL2 and two independent 35S::PYL2$^{CA3}$ seed samples were divided into two portions; one portion was stratified on ⅓ MS plates for 6 days at 4° C. and the second portion was plated six days later on ⅓ MS plates. Both samples were then transferred to room temperature (23° C.) and incubated in darkness, then germination was scored at 24 hour intervals after imbibition. The top panel shows a photograph taken 6 days after imbibition (line 1 of 35S::PYL2$^{CA3}$ is shown). The bottom graphs show germination data over a 10 day period.

Figure 6:
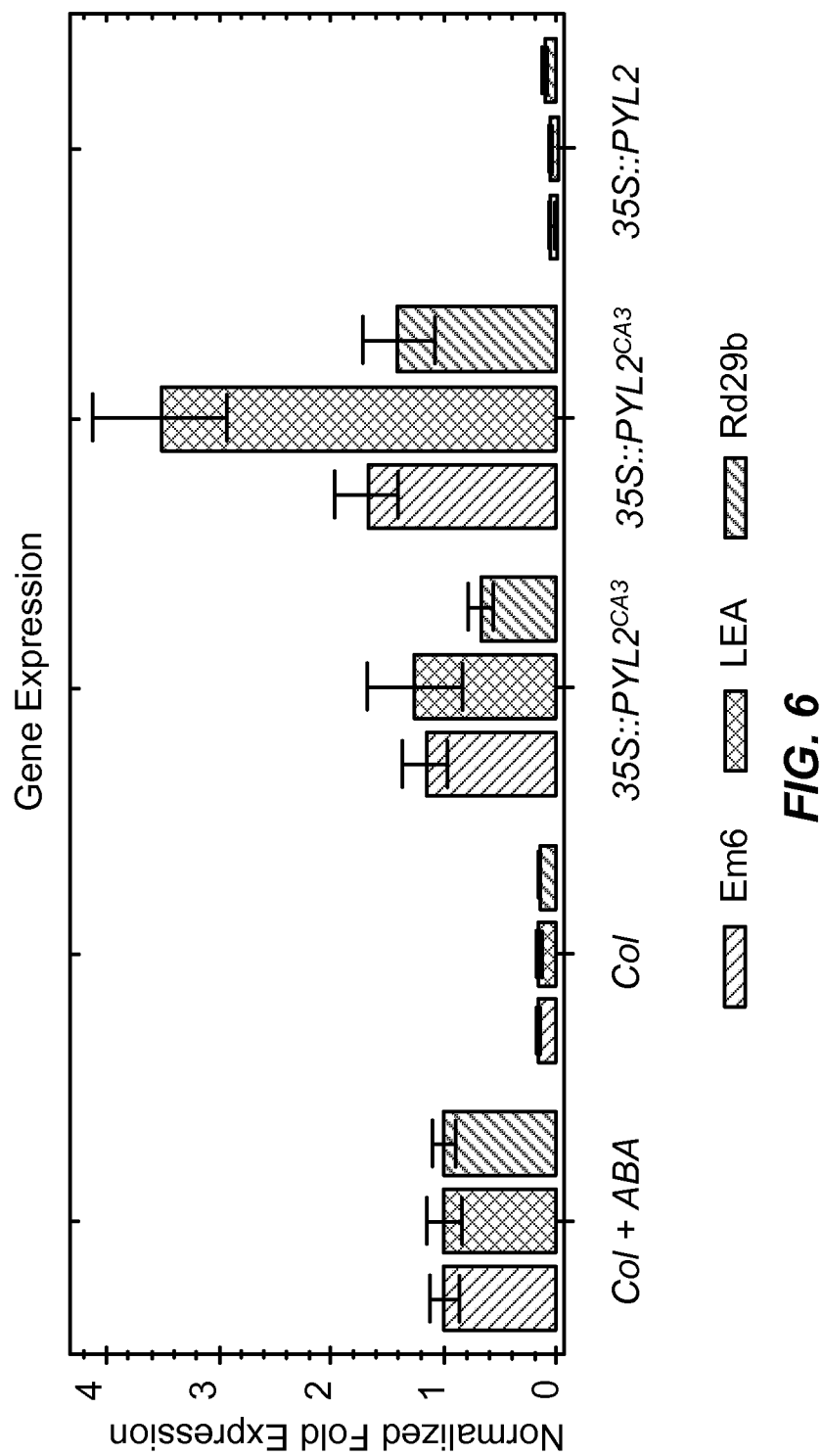

FIG. 6. PYL2$^{CA3}$ Overexpression Affects ABA-Regulated Gene Expression in Seeds.

Seeds of Col, 35S::PYL2 and two independent 35S::PYL2$^{CA3}$ transgenic lines were imbibed for 32 hours in either water or 5 μM ABA at room temperature under continuous illumination, after which total RNA was used in qRT-PCR reactions using primers for Em6, LEA and Rd29b. Biological duplicates with triple technical replicate measurements were conducted and gene expression levels were determined. Data are normalized to the levels observed in wild type seeds treated with 5 uM ABA.

Figure 7:
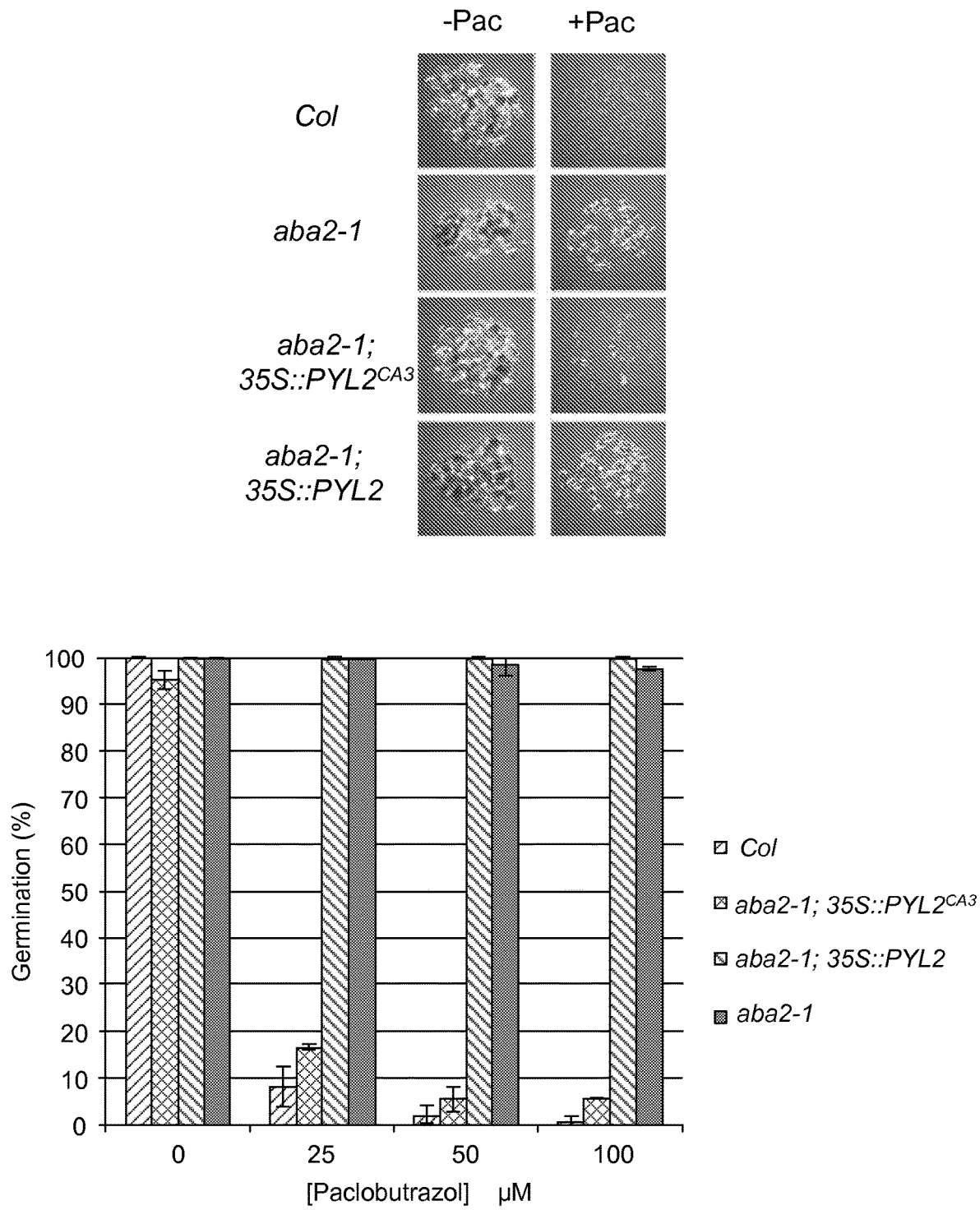

FIG. 7. PYL2$^{CA3}$ Overexpression Suppresses an aba2 Phenotype.

To test the ability of PYL2$^{CA3}$ to activate ABA signaling in vivo, we examined this allele's ability to suppress an aba2 phenotype. Wild-type Col, aba2-1, aba2-1; 35S::PYL2 and two independent aba2-1; 35S::PYL2$^{CA3}$ transgenic lines were germinated on different concentration of placlobutrazole, which aba2 mutants are resistant to due to defects in ABA-induced seed dormancy. PYL2$^{CA3}$ overexpression restores paclobutrazole sensitivity to aba2-1 mutant seeds.

Figure 8A:
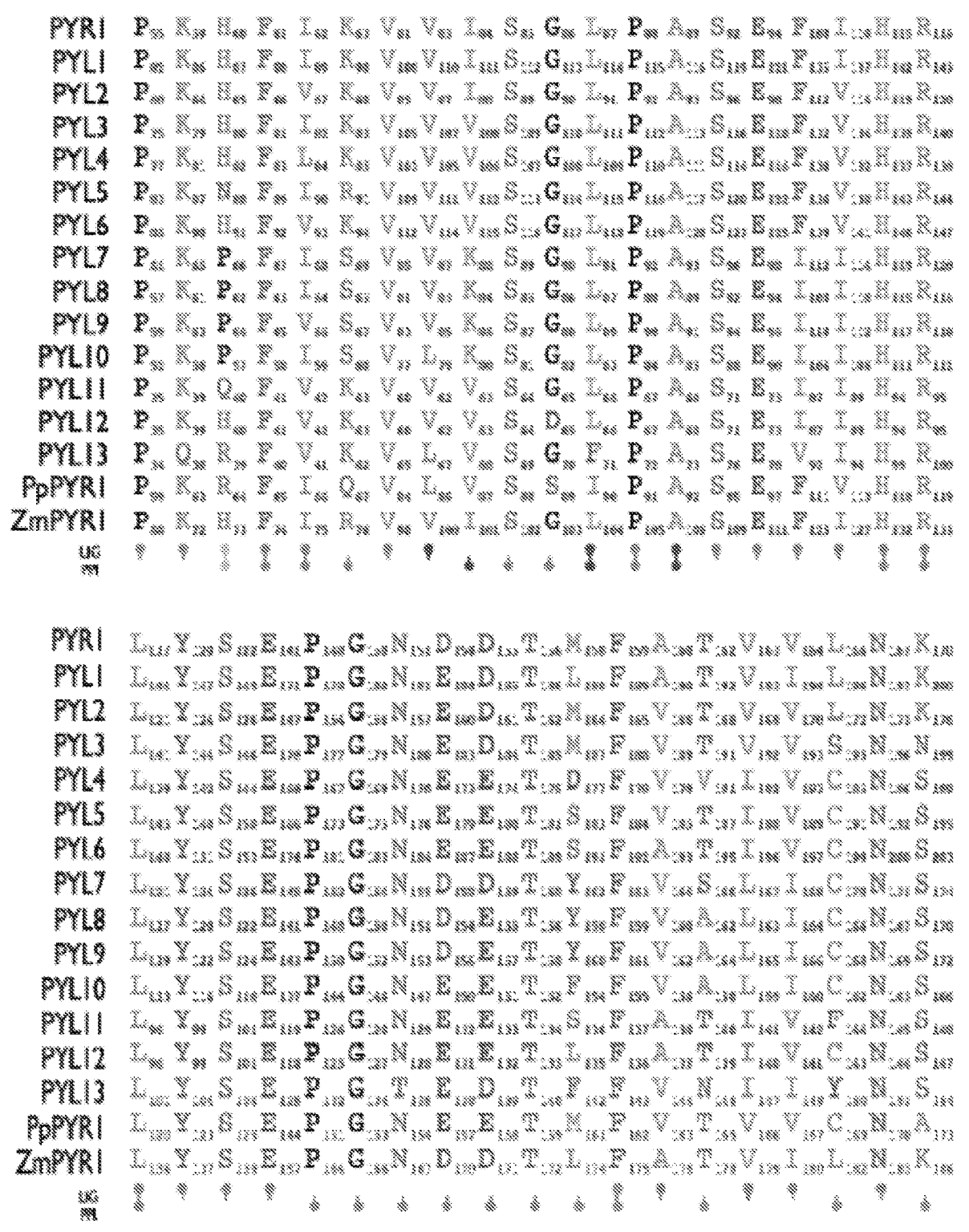
Figure 8B:
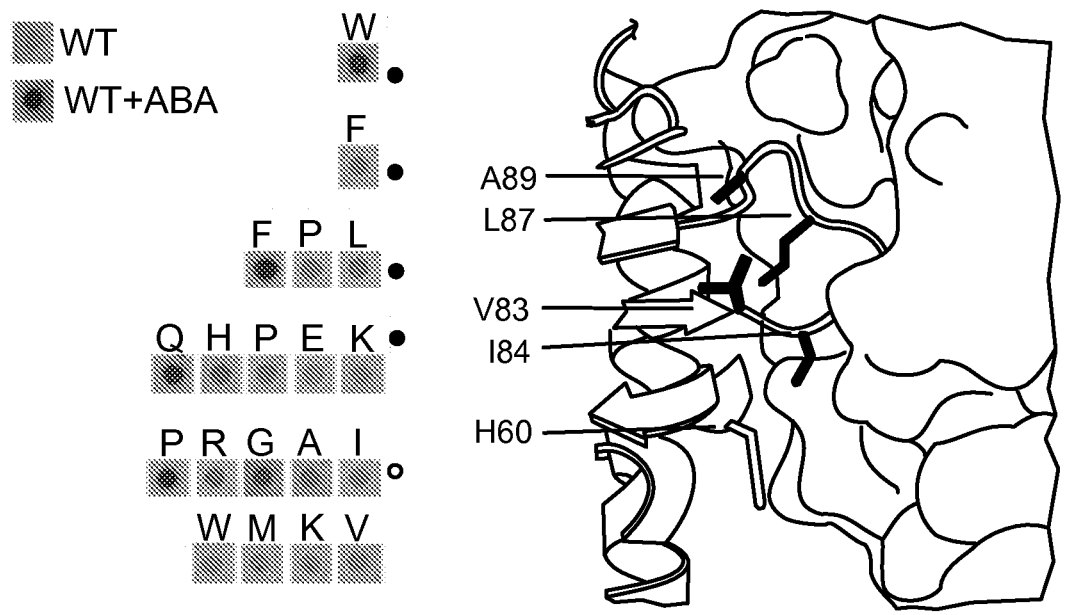
Figure 8B:
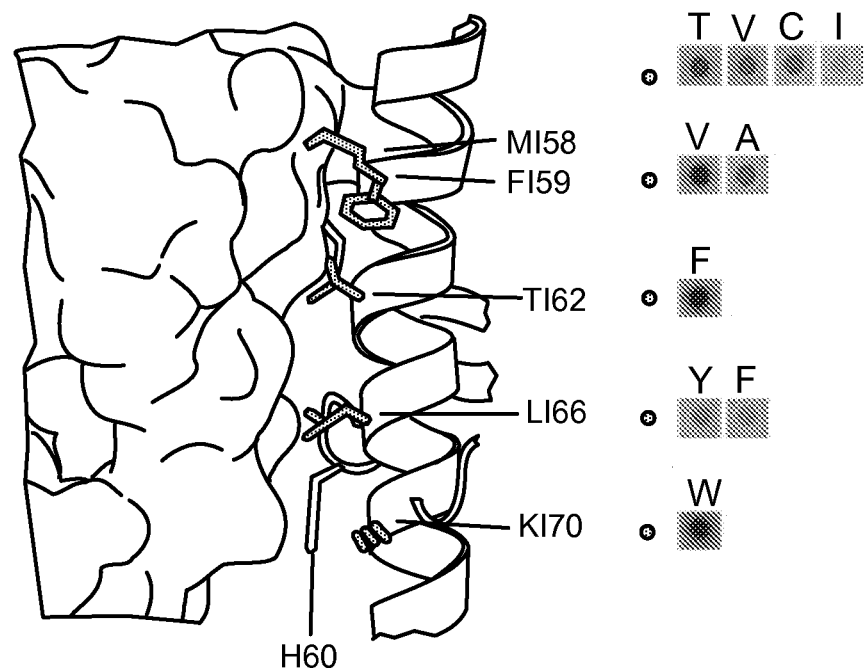

FIG. 8. Site-Saturation Mutagenesis of PYR1 Identifies Partial Activation Mutants.

(A) Sites selected for saturation mutagenesis. 39 residues involved in agonist (LIG) or PP2C (PPI) contacts were selected based on structure coordinates and subjected to site-saturation mutagenesis creating 741 PYR1 mutants; the alignment shows the identity and amino acid numbering of homologous residues in all Arabidopsis PYLs as well as maize and physcomitrella PYR1 orthologs. Contiguous peptides=SEQ ID NOs:156-172. (B) Activating mutations identified by site saturation mutagenesis. Of the 741 mutants constructed, 29 promoted interactions with HAB1 in the absence of ABA as measured using an established yeast two hybrid assay; the locations of activating mutations are mapped onto the PYR1-ABA-HAB1 structure. The top panel shows the gate residues (red), while the bottom panel shows the C-terminal helix residues (green); H60 is shown in cyan. Inset are images of X-gal stained yeast colonies for the subset of PYR1 mutants that bind HAB1 in the absence of ABA. For reference, the wild type PYR1-HAB1 interaction in the yeast two hybrid is shown in the presence and absence of 10 μM ABA.

Figure 9:
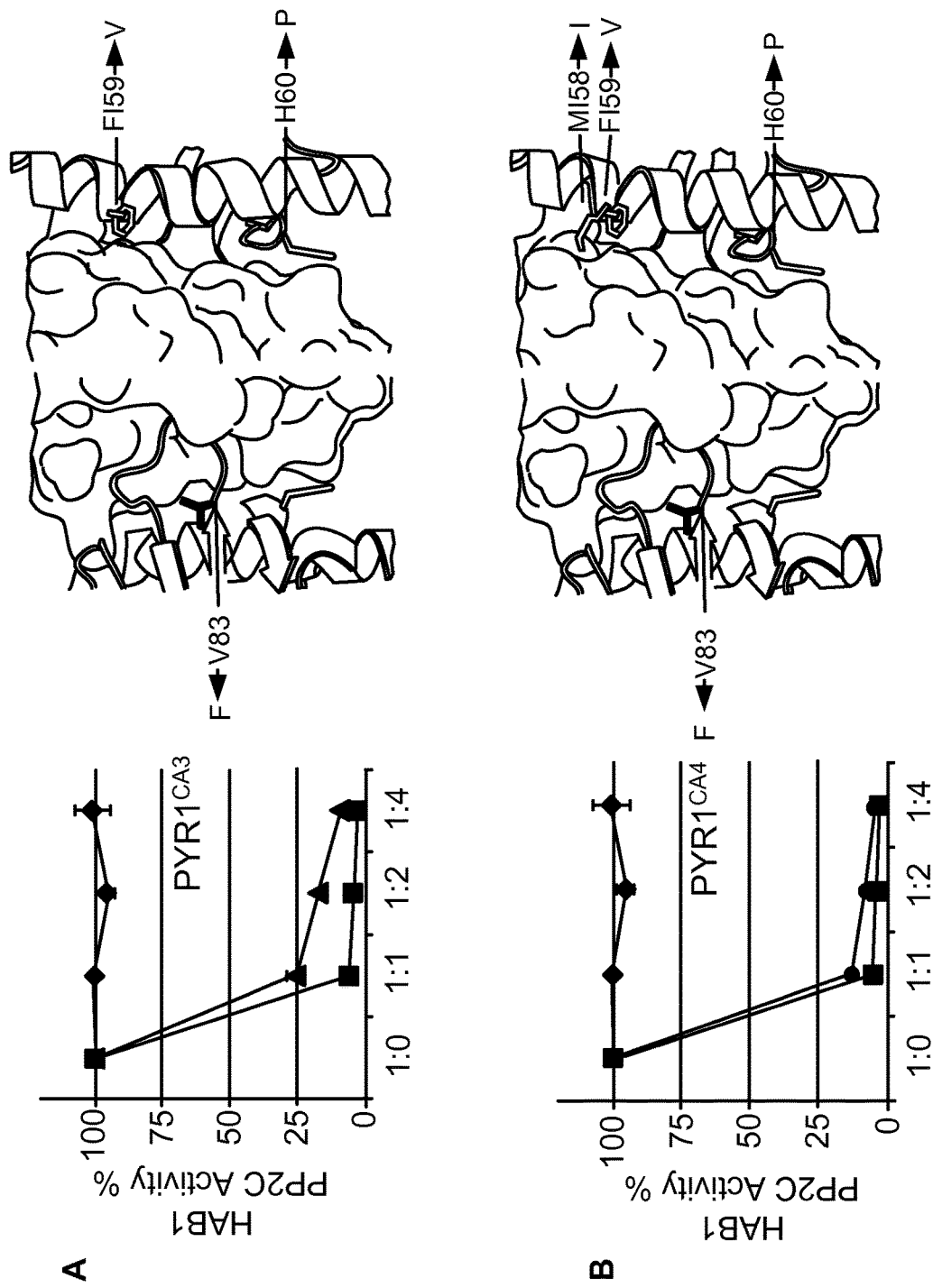
Figure 9C:
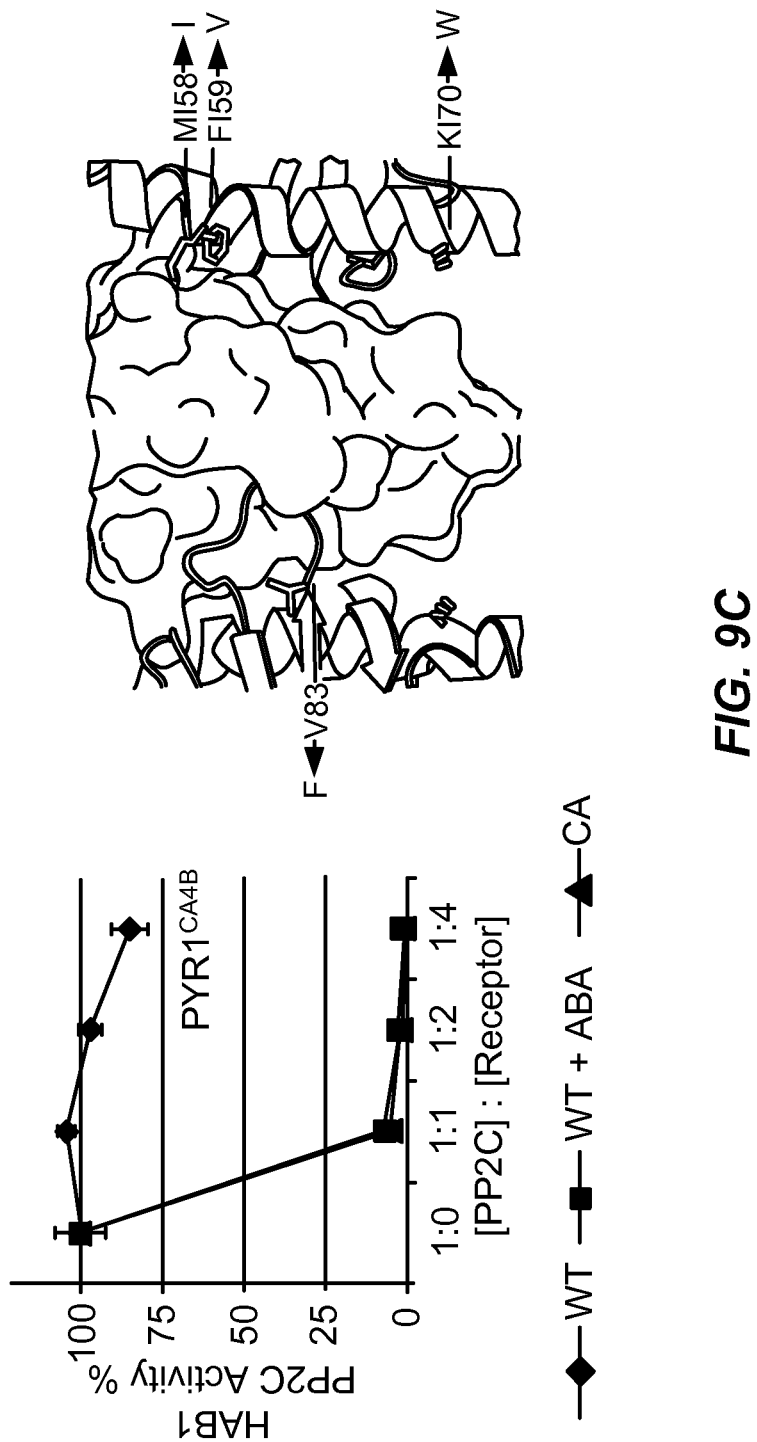

FIG. 9. Combining Partial Activation Mutants Leads to Constitutively Active PYR1.

Triple and quadruple mutant combinations of partial activation mutants were made as described in the text (see FIG. 17 for a complete list of all mutants characterized). Recombinant 6×His-PYR1 ("wt"), PYR1$^{CA3}$ (A), PYR1$^{CA4}$ (B), and PYR1$^{CA4B}$ (C) were expressed in E. coli, purified and utilized in PP2C assays with GST-HAB1. Reactions contain 600 nM GST-HAB1 and varying concentrations of receptor (0, 600, 1200, 2400 or 4800 nM receptor). PP2C activity is expressed as %-control, i.e. activity of PP2C in the absence of receptor and ABA, but otherwise identical reaction conditions. For comparison to the degree activation elicited by ABA on wild type receptor, each graph shows wild type PYR1 reactions run with either 0 (diamonds) or 10 μM ABA (squares); mutant proteins are represented by triangles and were assayed in the absence of ABA. The image at right shows the locations of the mutations mapped onto the crystal structure of PYR1-ABA-HAB1; the side chains for residues mutated are shown in stick form; red corresponds to gate mutation, green to C-terminal helix mutations and cyan to H60 mutations.

Figure 10A:
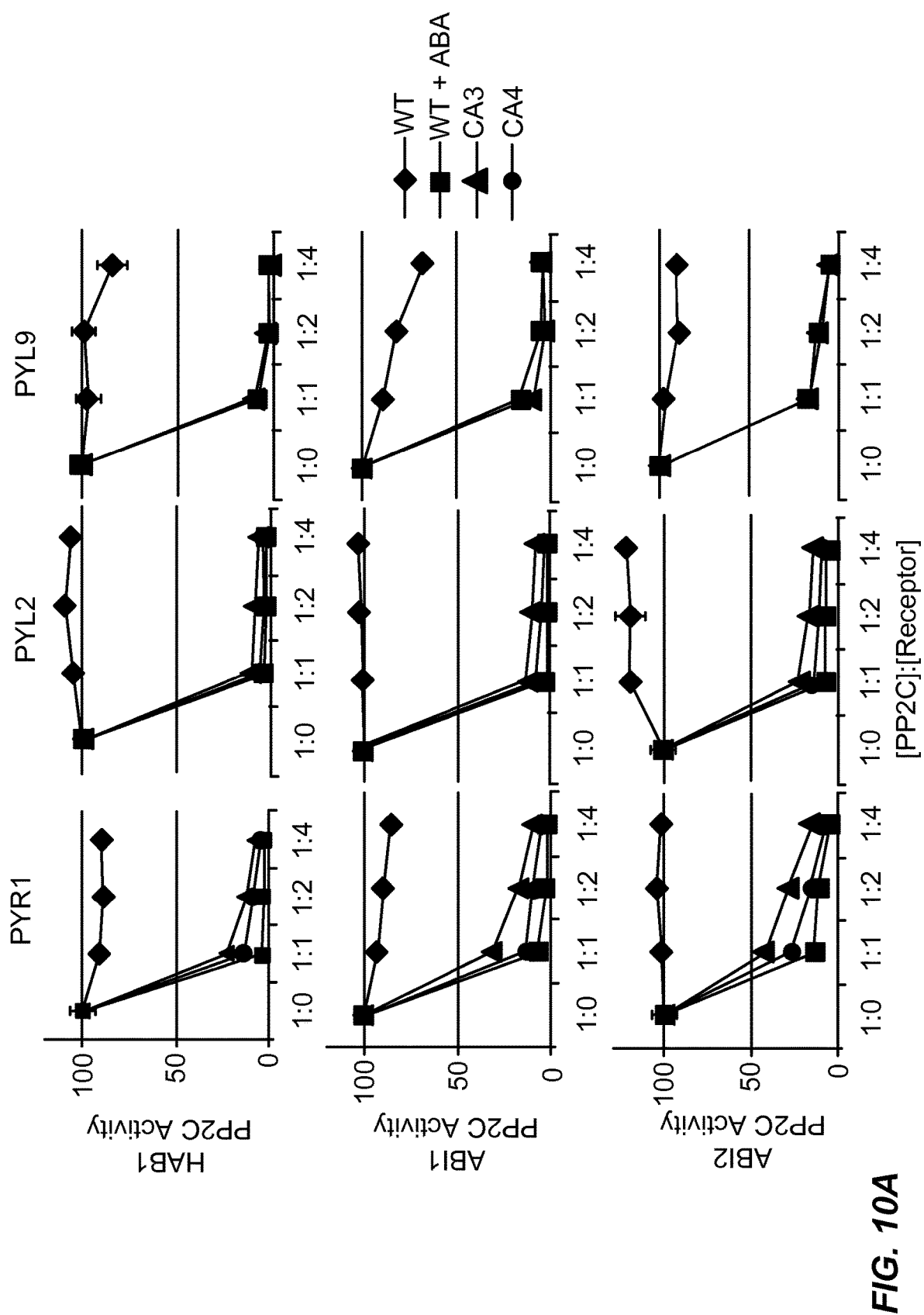

FIG. 10A. The CA3 and CA4 Mutations Function in the Context of Other Receptor Backbones.

The CA3 mutations from PYR1 were introduced into homologous positions in PYL2 and PYL9 (triangles), and the CA4 mutations from PYR1 were introduced into homologous positions in PYL2 (filled circles). Recombinant receptors were assayed for activity on GST-HAB1, 6×-His-Sumo-ABI1 and 6×-His-Sumo-ABI2. Reactions contain 600 nM PP2C and varying concentrations of receptor (0, 600, 1200, 2400 or 4800 nM receptor). PP2C activity is expressed as %-control, i.e., activity of PP2C in the absence of receptor and ABA; each graph shows wild type receptors in reactions run with either 0 (diamonds) or 10 μM ABA (squares).

Figure 11:
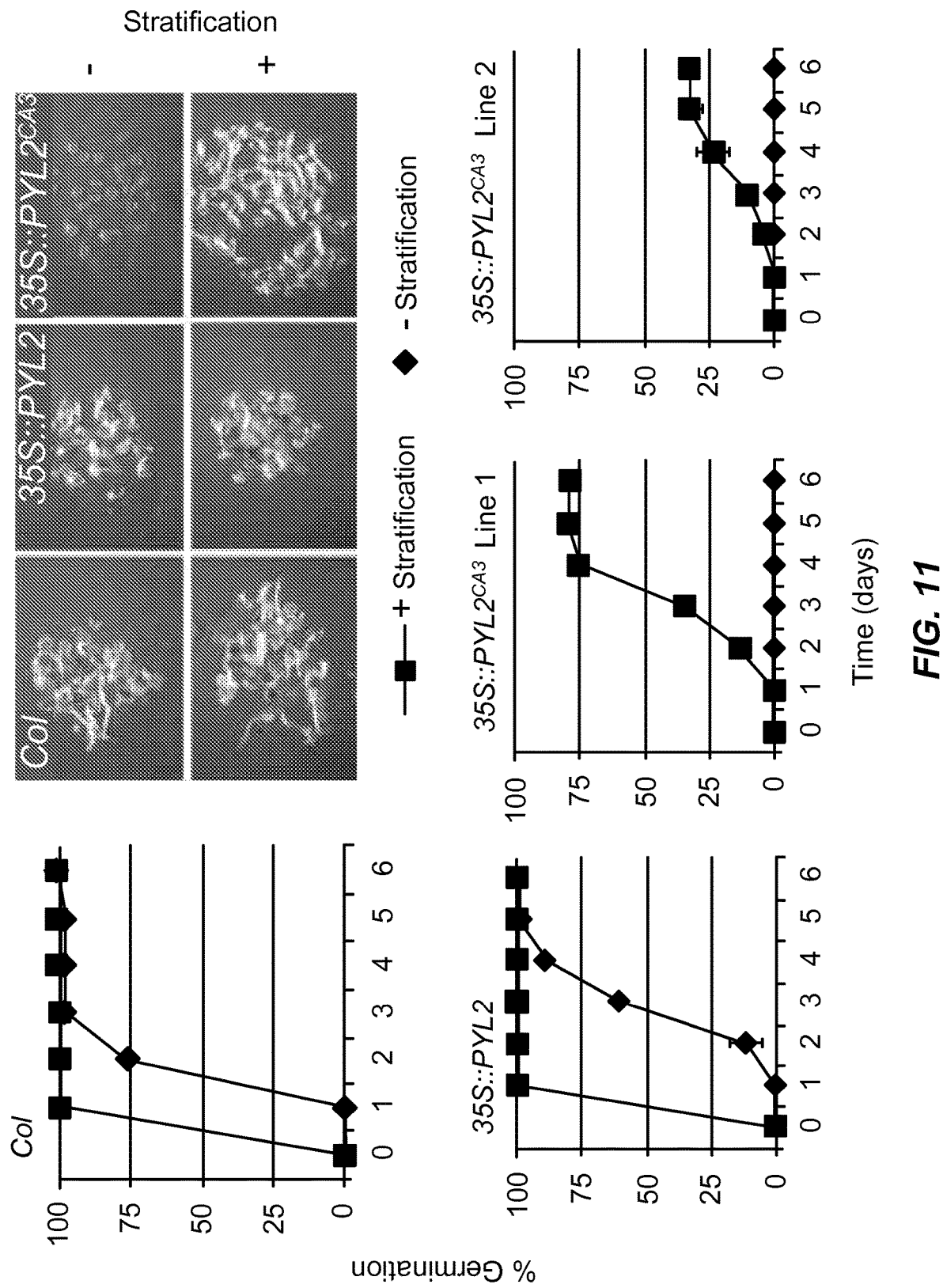

FIG. 11. Overexpression of PYL2$^{CA3}$ Induces Seed Hyper-Dormancy.

Seeds of the wild type Columbia (Col), 35S::GFP-PYL2 or two independent 35S::GFP-PYL2$^{CA3}$ lines were either stratified (squares) for 6 days at 4° C. or unstratified (diamonds) and then their germination monitored at 24 hour intervals post-imbibition. The image at right shows representative images at 48 hours post imbibition for Columbia, 35S::GFP-PYL2 or two independent 35S::GFP-PYL2$^{CA3}$ (line 1).

Figure 12:
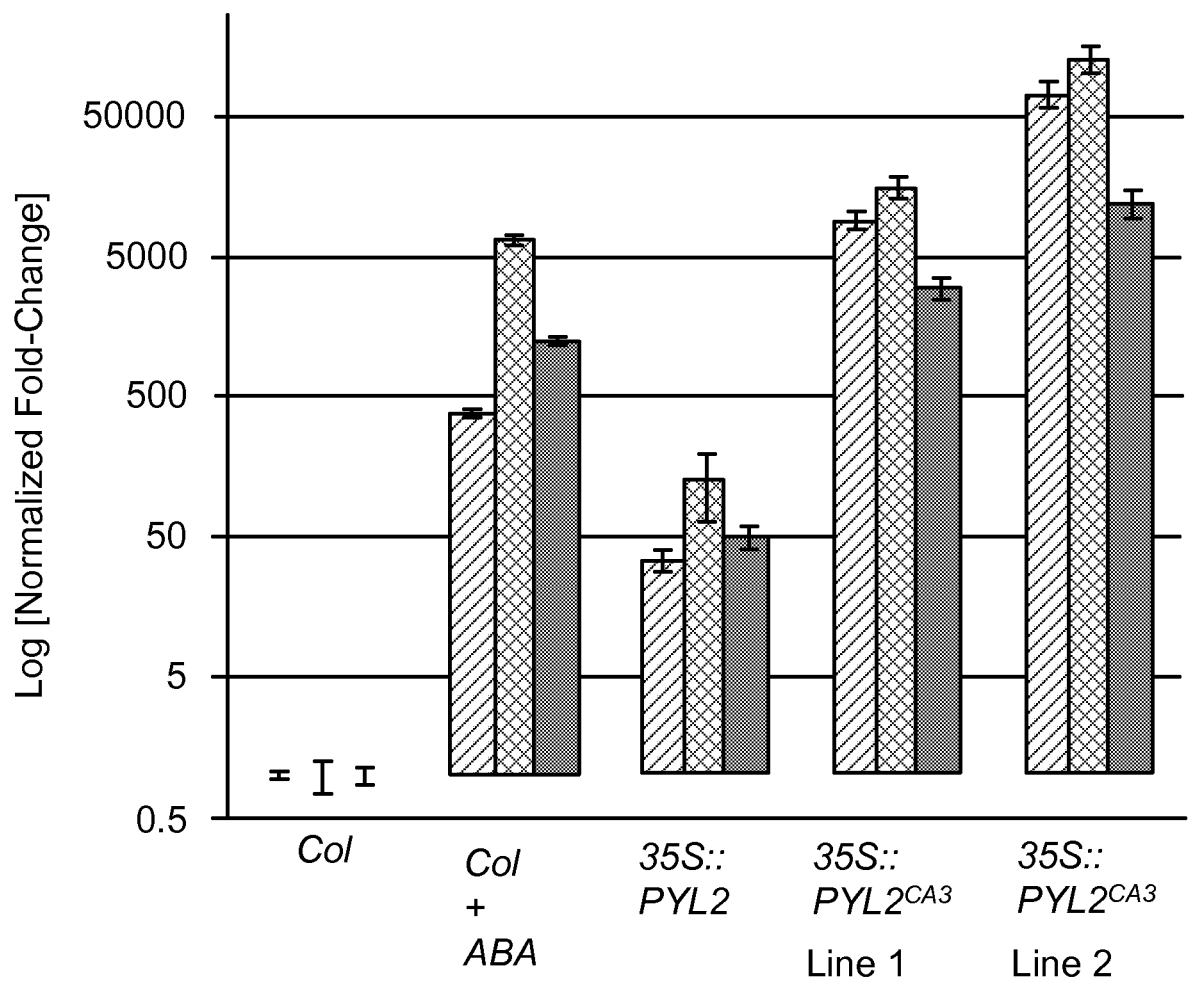

FIG. 12. Expression of PYL2$^{CA3}$ Elevates Levels of ABA-Regulated mRNAs.

Seeds of the wild type Columbia (Col), 35S::GFP-PYL2 or two independent 35S::GFP-PYL2$^{CA3}$ were imbibed for 32 hours at room temperature, RNA prepared and qRT-PCR reactions performed using primers for the Em6 (left), LEA (middle) or Rd29b (right) as described in the methods; wild type Columbia seeds were treated with either 0 or 5 μM ABA. The fold-induction with respect to wild type expression (arbitrarily set to a value of 1 using is shown BioRad's CFX Manager software); note that the Y-axis is displayed in log-scale.

Figure 13:
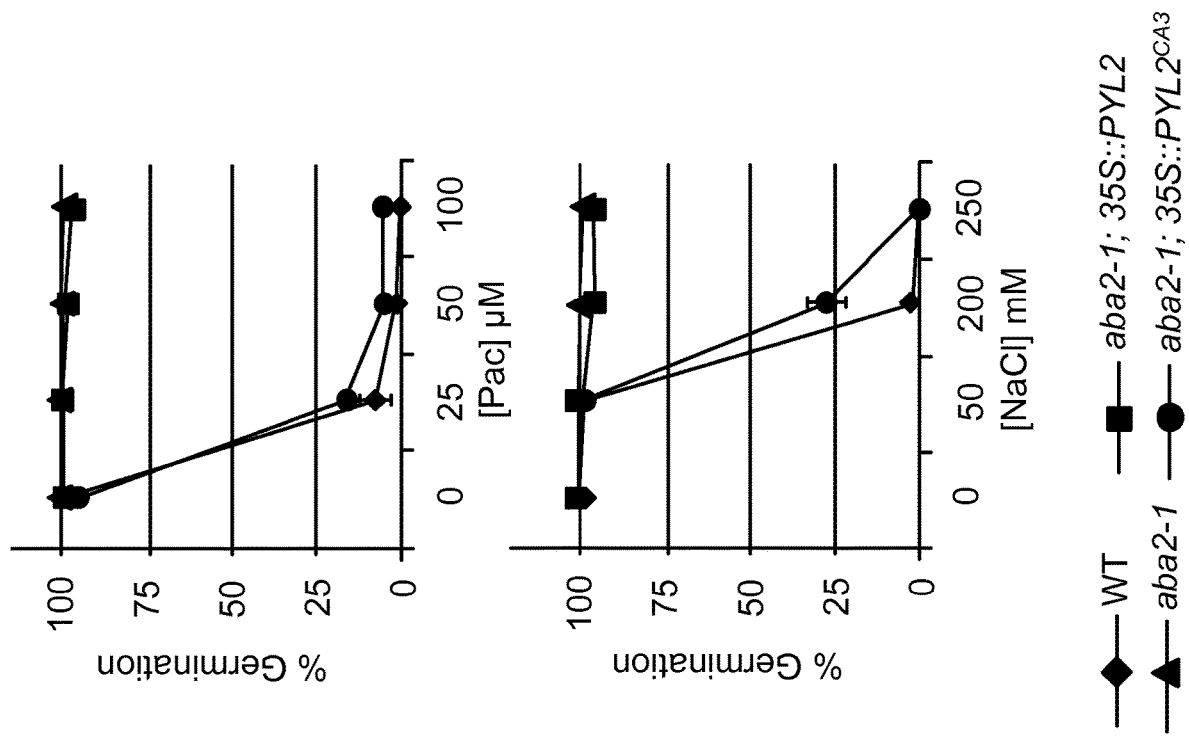
Figure 13:
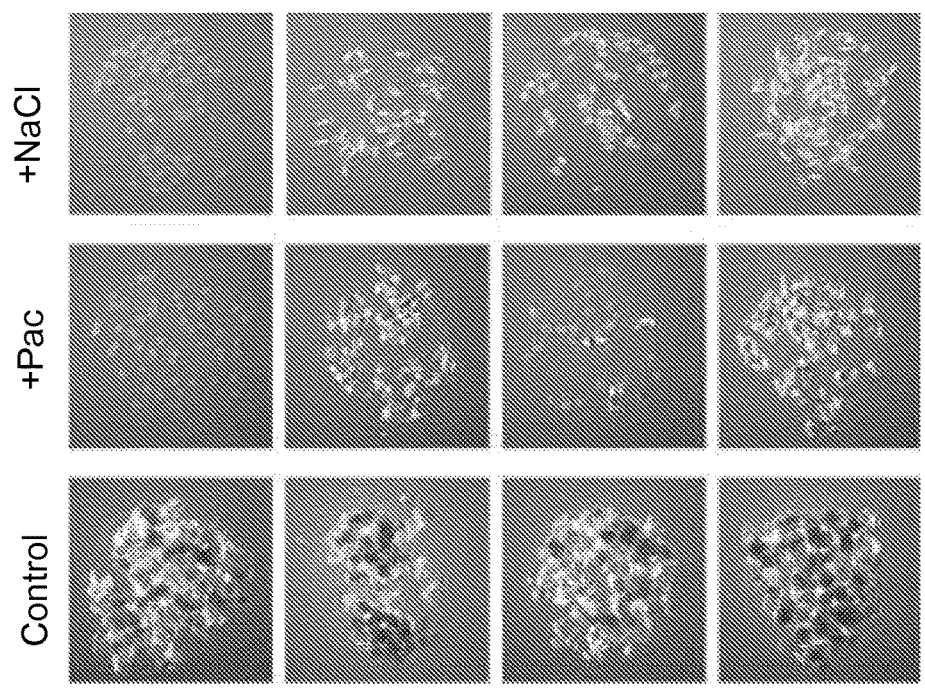

FIG. 13. PYL2$^{CA3}$ Suppresses Phenotypes Caused by ABA Deficiency.

Seeds of the wild type Columbia (Col), aba2-1, aba2-1; 35S::GFP-PYL2 or aba2-1; 35S::GFP-PYL2$^{CA3}$ genotypes were stratified for 4 days at 4° C. on agar media containing different concentrations of paclobutrazol or sodium chloride and germination scored after 72 hours post-imbibition. The experiment was conducted in triplicate and standard deviation is shown on graph points. The image at left shows representative images at 72 hours post imbibition for control, 50 μM paclobutrazol or 250 mM NaCl. Values plotted in graphs are the average of three independent measurements and error bars show standard deviation. WT (diamonds), aba2-1 (triangles), aba2-1; 35S::GFP-PYL2 (squares), aba2-1; 35S::GFP-PYL2$^{CA3}$ (filled circles).

Figure 14:
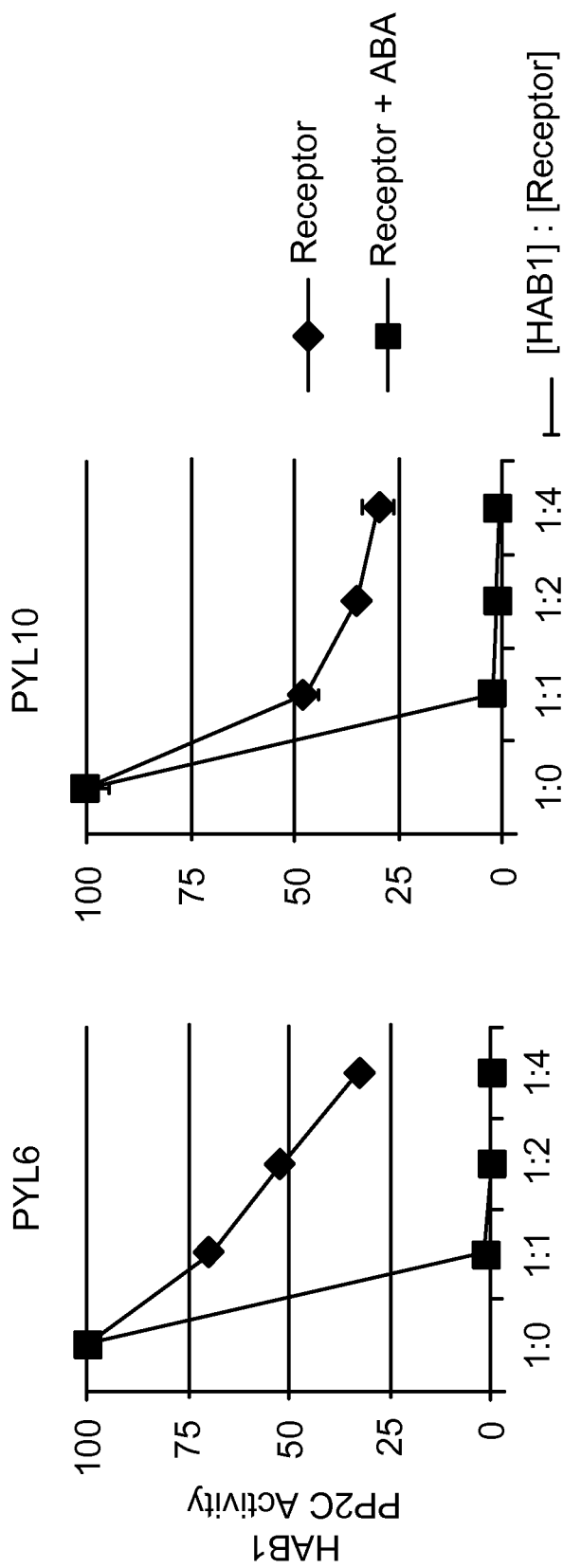

FIG. 14. PYL6 and PYL10 do not Possess Full Constitutive Activity.

Recombinant wild type 6×-His-PYL6 or 6×-His-PYL10 were prepared as described in the methods and assessed in in vitro PP2C assays using 600 nM GST-HAB1 and varying concentrations of receptor (0, 600, 1200, 2400 or 4800 nM receptor). PP2C activity is expressed as %-control, i.e., activity of PP2C in the absence of receptor and ABA, but otherwise identical reaction conditions. Graphs show reactions run with either 0 (diamonds) or 10 μM ABA (squares).

Figure 15:
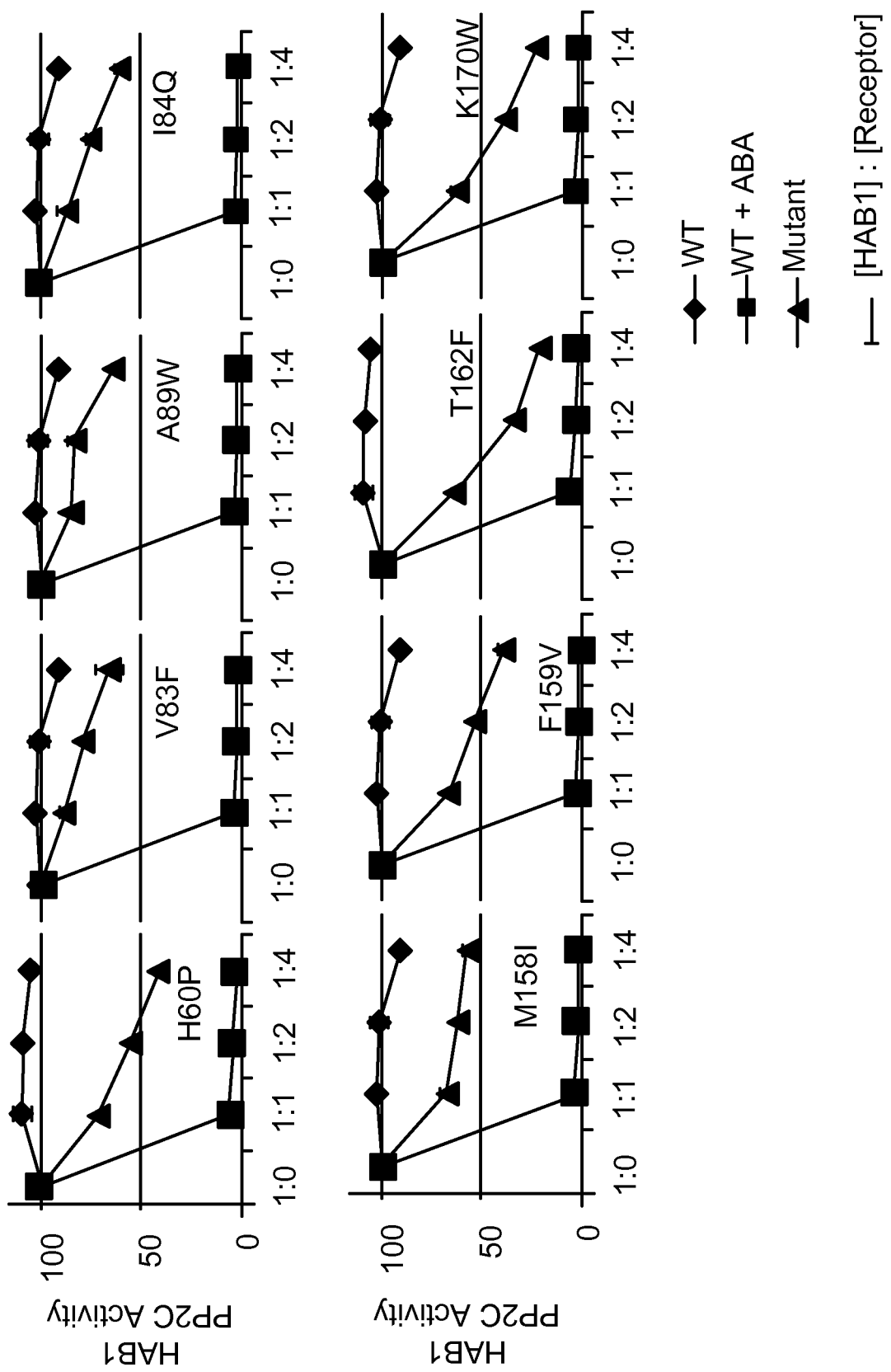

FIG. 15. Mutations Identified by Site-Saturation Mutagenesis Increase PYR1's Basal Activity.

Recombinant wild type 6×-His-PYR1 or mutants were prepared as described in the methods and assessed in in vitro PP2C assays using 600 nM GST-HAB1 and varying concentrations of receptor (0, 600, 1200, 2400 or 4800 nM receptor). PP2C activity is expressed as % of control, i.e., activity of PP2C in the absence of receptor and ABA, but otherwise identical reaction conditions. For comparison to the degree activation elicited by ABA on wild type receptor, each graph shows wild type PYR1 reactions run with either 0 (diamonds) or 10 μM ABA (squares); mutant proteins are represented by triangles and were assayed in the absence of ABA.

Figure 16:
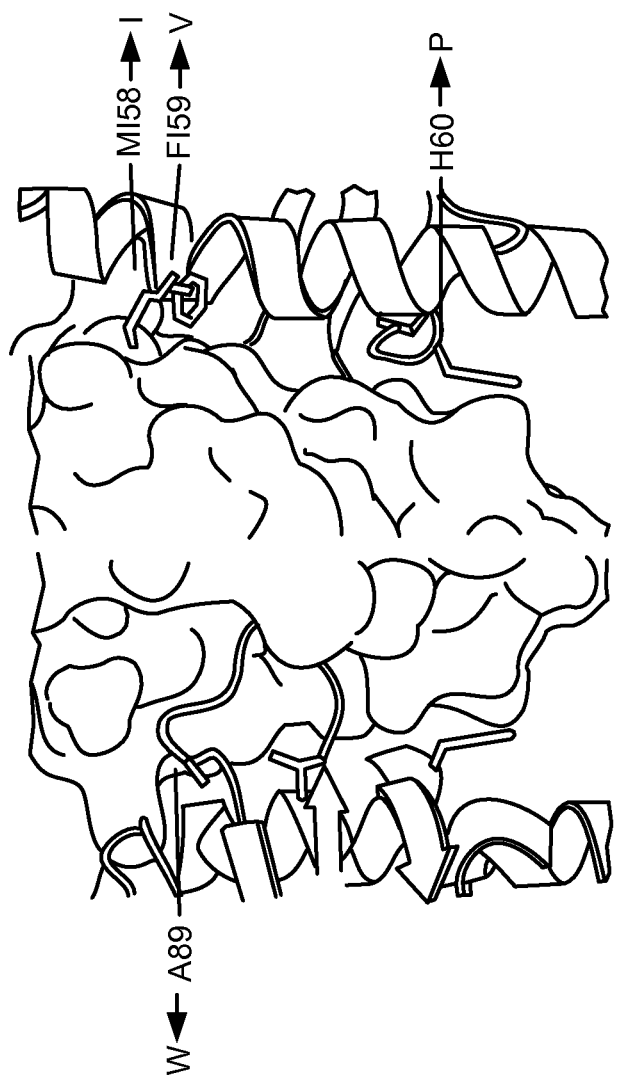
Figure 16:
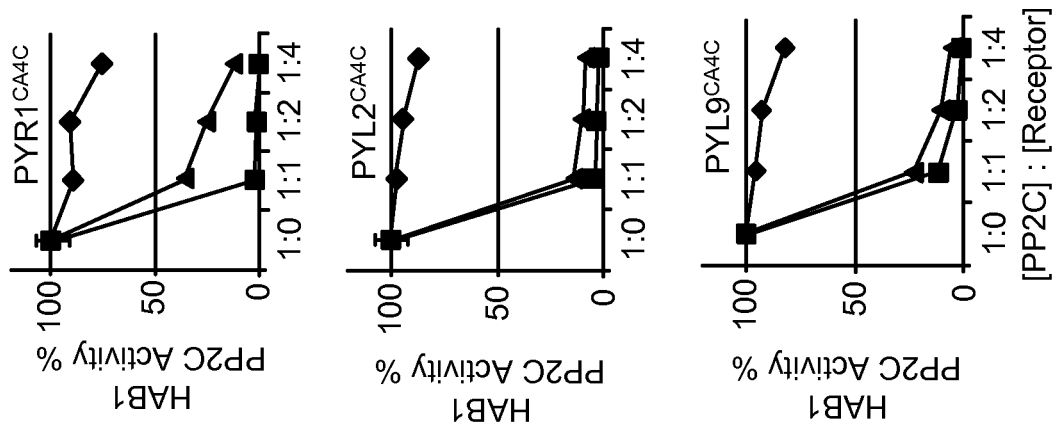

FIG. 16. The CA4C Allele Activates Multiple Receptors.

Recombinant wild type or mutant 6×-His-receptors were prepared as described in the methods and assessed in in vitro PP2C assays using 600 nM GST-HAB1 and varying concentrations of receptor (0, 600, 1200, 2400 or 4800 nM receptor). PP2C activity is expressed as %-control, i.e., activity of PP2C in the absence of receptor and ABA, but otherwise identical reaction conditions. For comparison to the degree activation elicited by ABA on wild type receptor, each graph shows wild type PYR1 reactions run with either 0 (diamonds) or 10 μM ABA (squares); mutant proteins are represented by triangles and were assayed in the absence of ABA. Values plotted in graphs are the average of three independent measurements and error bars show standard deviation.

FIG. 17. Summary of PP2C Activity for Single and Multiple Receptor Mutations.

Summary of experimental data showing the effects of wild-type control PYR/PYL proteins (in the absence or presence of ABA) and various PYR1, PYL2, and PYL9 single-mutation or multiple-mutation proteins (in the absence of added ABA) on HAB1, ABI1, and/or ABI2 activity.

Figure 18:
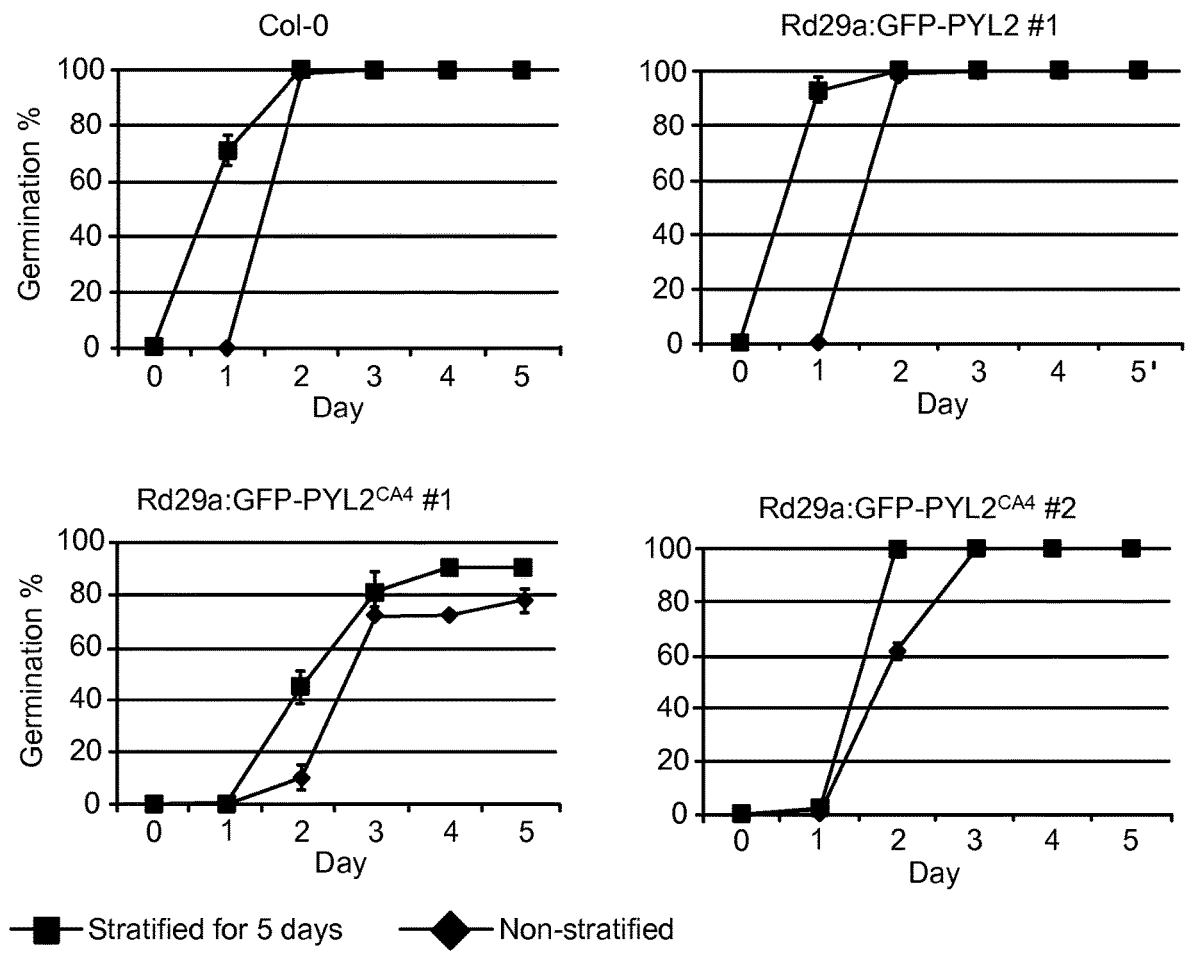

FIG. 18. The Rd29A::GFP-PYL2$^{CA4}$ Transgene Causes a Modest Germination Delay.

Seeds of the wild type Columbia (Col-0), Rd29A::GFP-PYL2 or two independent Rd29A::GFP-PYL2$^{CA4}$ lines were either stratified (red square) for 5 days at 4° C. or unstratified (blue diamond) and then their germination, indicated by radical emergence, monitored at 24 hour intervals post-imbibition. Graphs plot the averages of values from three biological replicates and error bars show one standard deviation.

Figure 19:
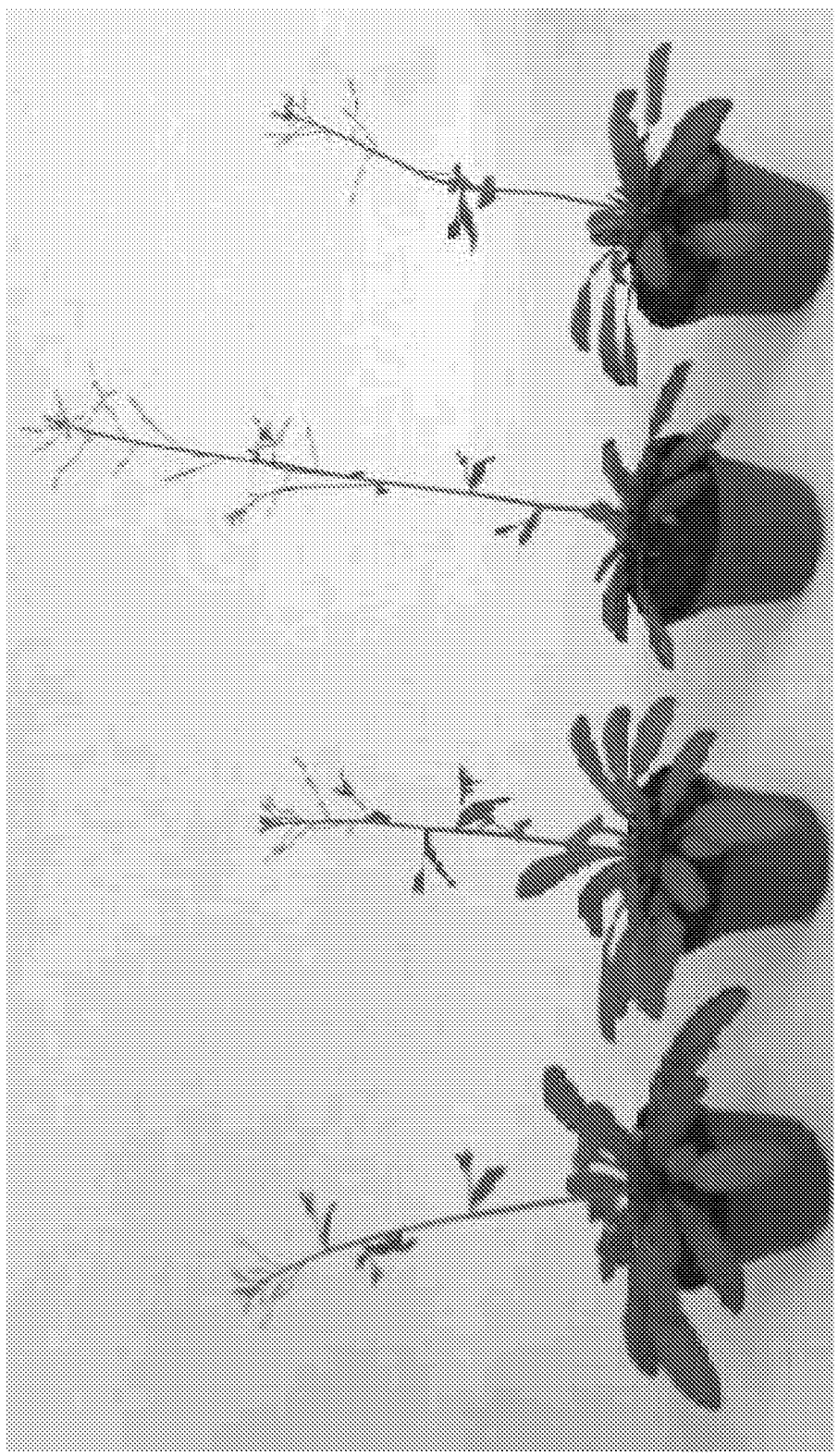

FIG. 19. Plants Containing an RD29A-Driven PYL2$^{CA4}$ Transgene are Phenotypically Similar to Wild Type.

From left to right, wild type, RD29A::GFP-PYL2, and two independent RD29A::GFP-PYL2$^{CA4}$ transgenic lines. Plants shown are four-week-old plants grown in jiffy pots under long day light conditions (16 light/8 dark).

Figure 20:
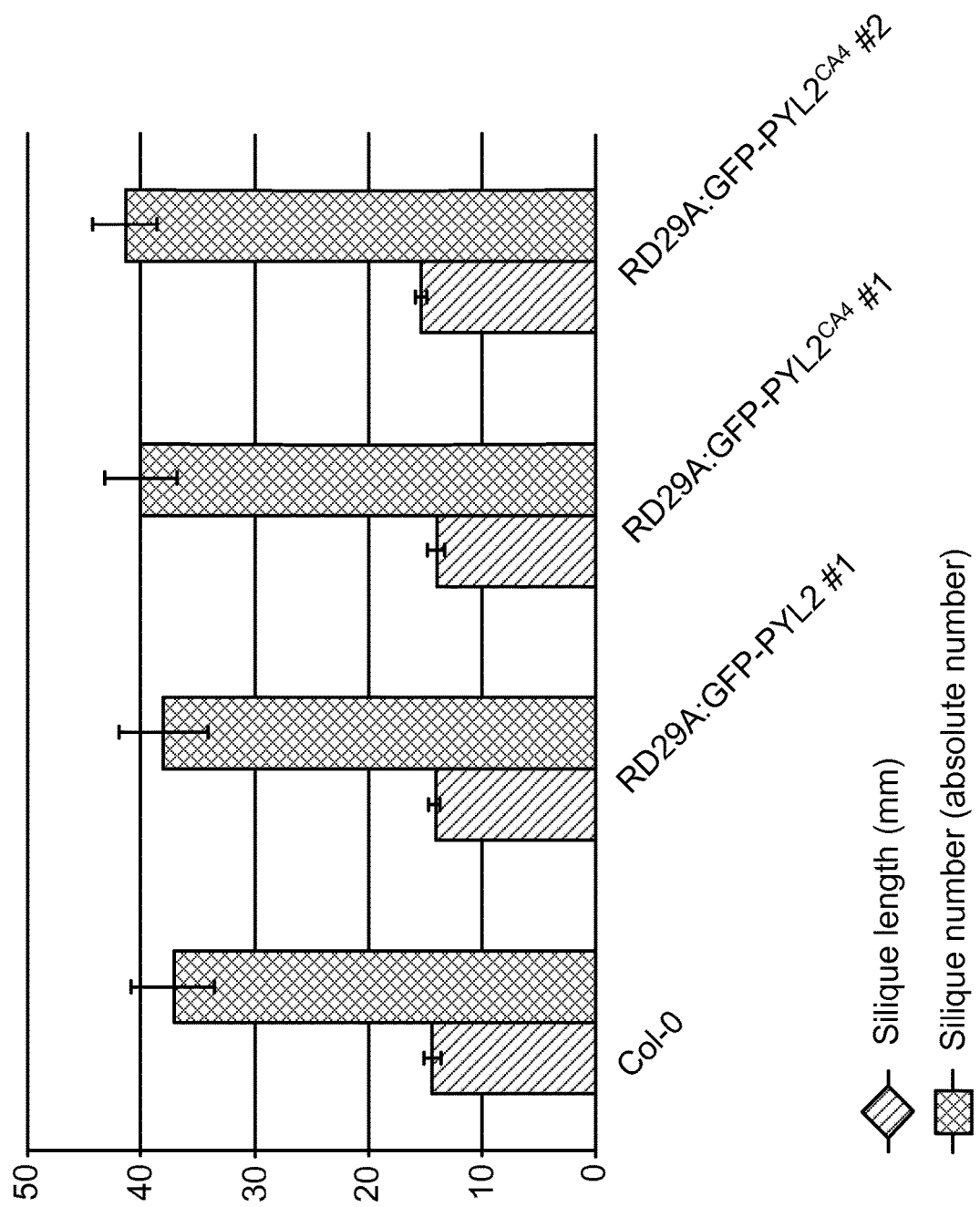

FIG. 20. The RD29A::GFP-PYL2CA4 Transgene does not Substantially Reduce Arabidopsis Fertility.

Siliques of wild type Columbia (Col-0), RD29A::GFP-PYL2 or two independent RD29A::GFP-PYL2$^{CA4}$ transgenic lines were characterized by two parameters: silique length (blue diamond) and number of siliques (red square). For silique length, five dry mature siliques located were measured. Total silique number on the main stem were counted from seven individual plants. Graphs plot the averages of values and error bars show one standard deviation.

Figure 21:
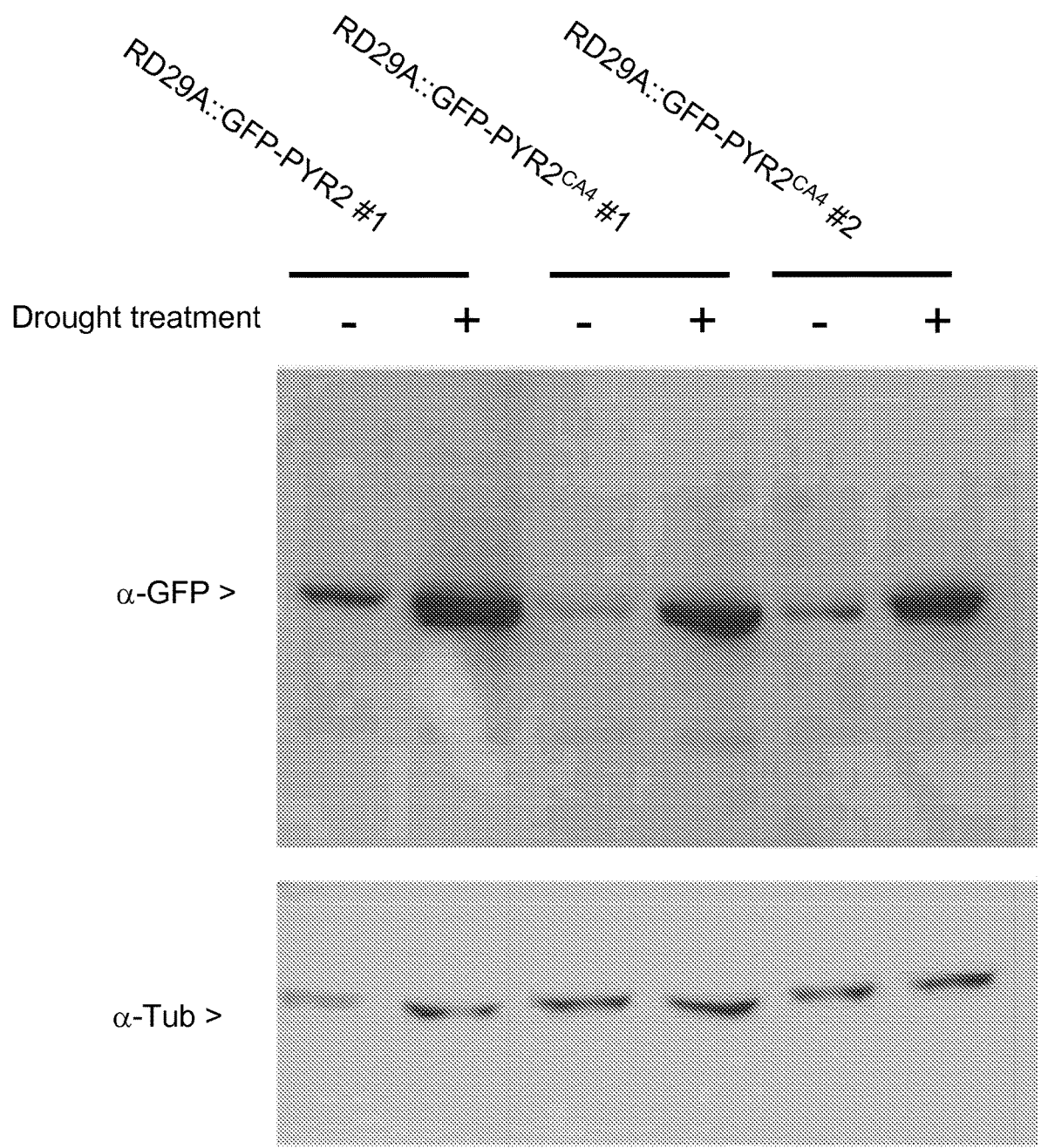

FIG. 21. The RD29A::GFP-PYL2CA4 Transgene Drives PYL2 Expression in Response to Drought.

Protein was isolated from RD29A::GFP-PYL2 and from two independent RD29A::GFP-PYL2$^{CA4}$ transgenic lines, from leaves of three-week-old plants (−) or leaves that were detached and dried for four hours (+). Western blot analyses were performed on 20 μg SDS-PAGE separated total proteins probed with either a 1/10,000 dilution of a GFP monoclonal antibody (Clontech, USA) or a 1/10,000 dilution of an α-Tubulin antibody (Sigma, USA), followed by 1/10,000 secondary HRP-conjugated anti-mouse IgG antibody (Sigma, USA) and detected by enhanced chemiluminescence (GE Healthcare, USA).

Figure 22:
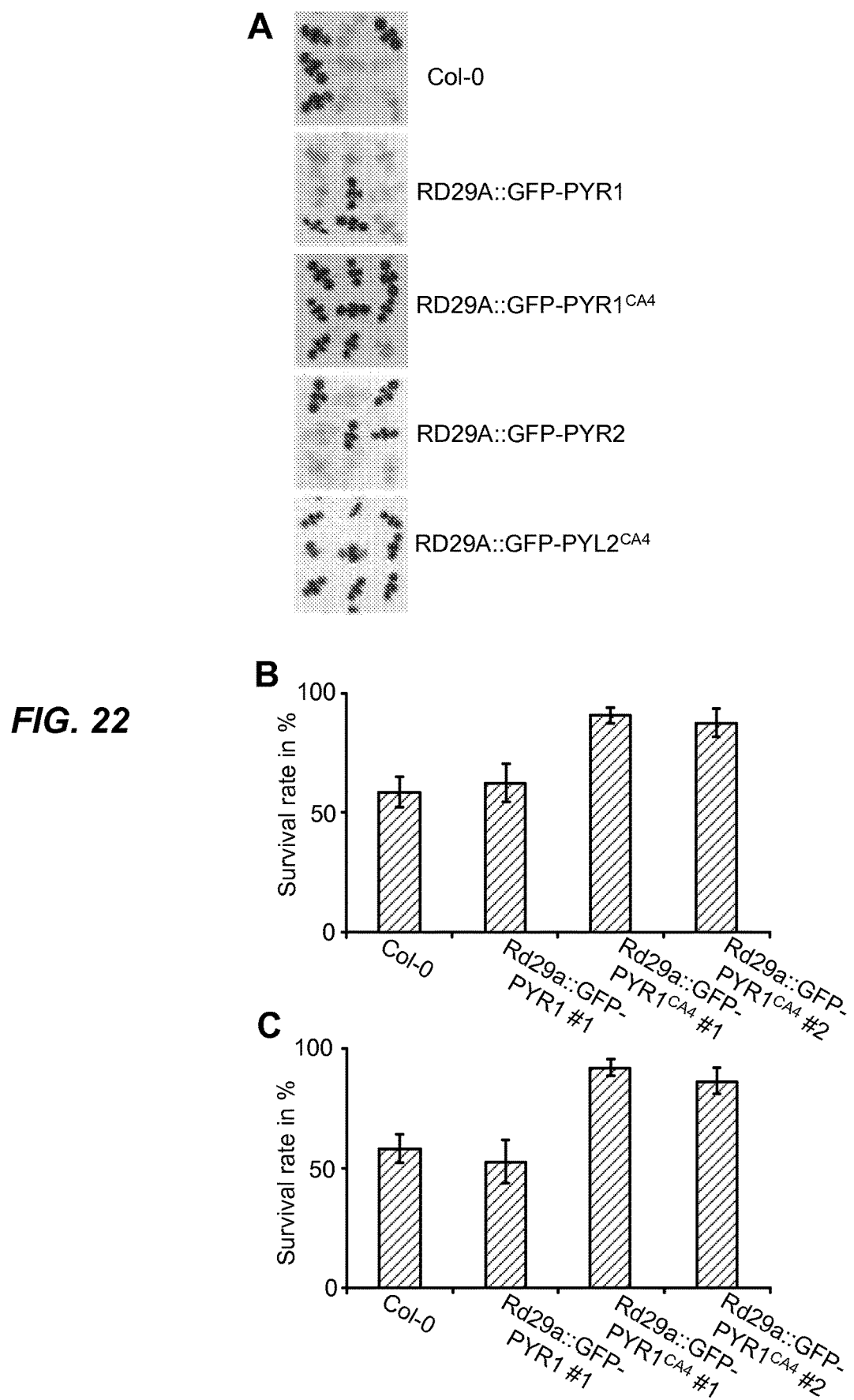

FIG. 22. Plants Containing the RD29A::GFP-PYL2CA4 Transgene Possess Increased Salinity Resistance.

Week-old seedlings of the wild-type Columbia (Col-0), RD29A::GFP-PYR1, RD29A:GFP-PYL2, or two independent RD29A::GFP-PYR1$^{CA4}$ or RD29A::GFP-PYL2$^{CA4}$ transgenic lines were subjected to 100 mM NaCl for 16 hours, then the seedlings were transferred to 250 mM NaCl for additional two weeks, after which survival rate was scored as follows: completely white seedlings were scored dead and seedlings retaining pigment were scored as alive. Then survival rates was calculated as a % of total seedling (N=99). (A) Representative image of seedlings after two weeks in 250 mM NaCl, (B) Quantification of PYR1 transgenic lines' survival rates, (C) Quantification of PYL2 transgenic lines' survival rates. Error bars show one standard deviation.

Figure 23:
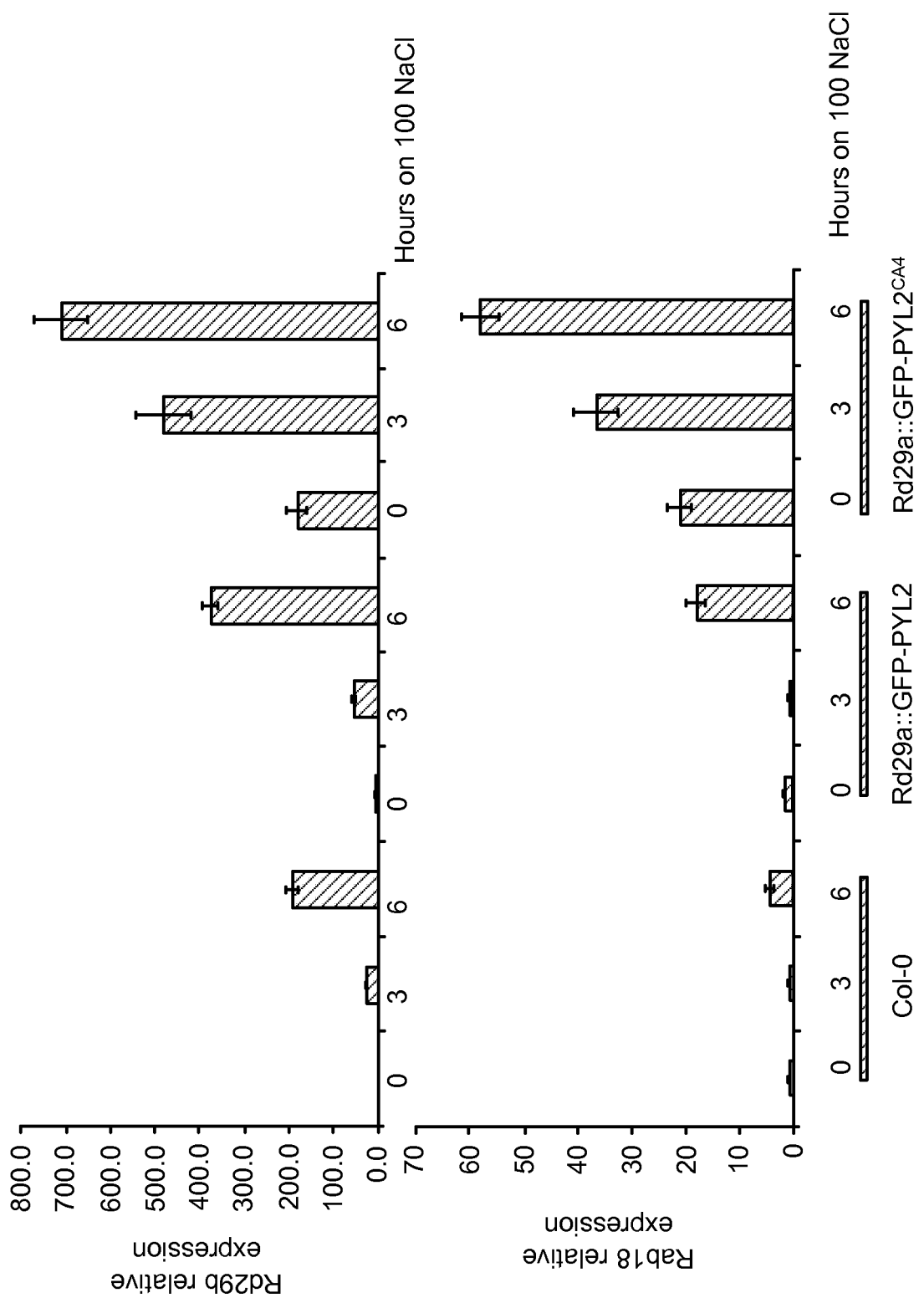

FIG. 23. The RD29A::GFP-PYL2CA4 Transgene Elevates Levels of ABA-Regulated mRNAs in Response to 100 mM NaCl.

Seedlings of the wild-type Columbia (Col), RD29A:: GFP-PYL2, or two independent RD29A::GFP-PYL2$^{CA4}$ lines were subjected to 100 mM NaCl for 0, 3 or 6 hours. RNA was prepared and qRT-PCR reactions were performed using primers for the RD29B (upper) or RAB18 (lower) gene as described in the Examples section. The fold induction plotted was calculated with respect to wild-type expression (arbitrarily set to a value of 1 using BioRad CFX Manager software). Graphs plot average values from three technical replicates, and error bars show 1 SD; the same trends in gene expression were seen in three separate biological replicates.

Figure 24:
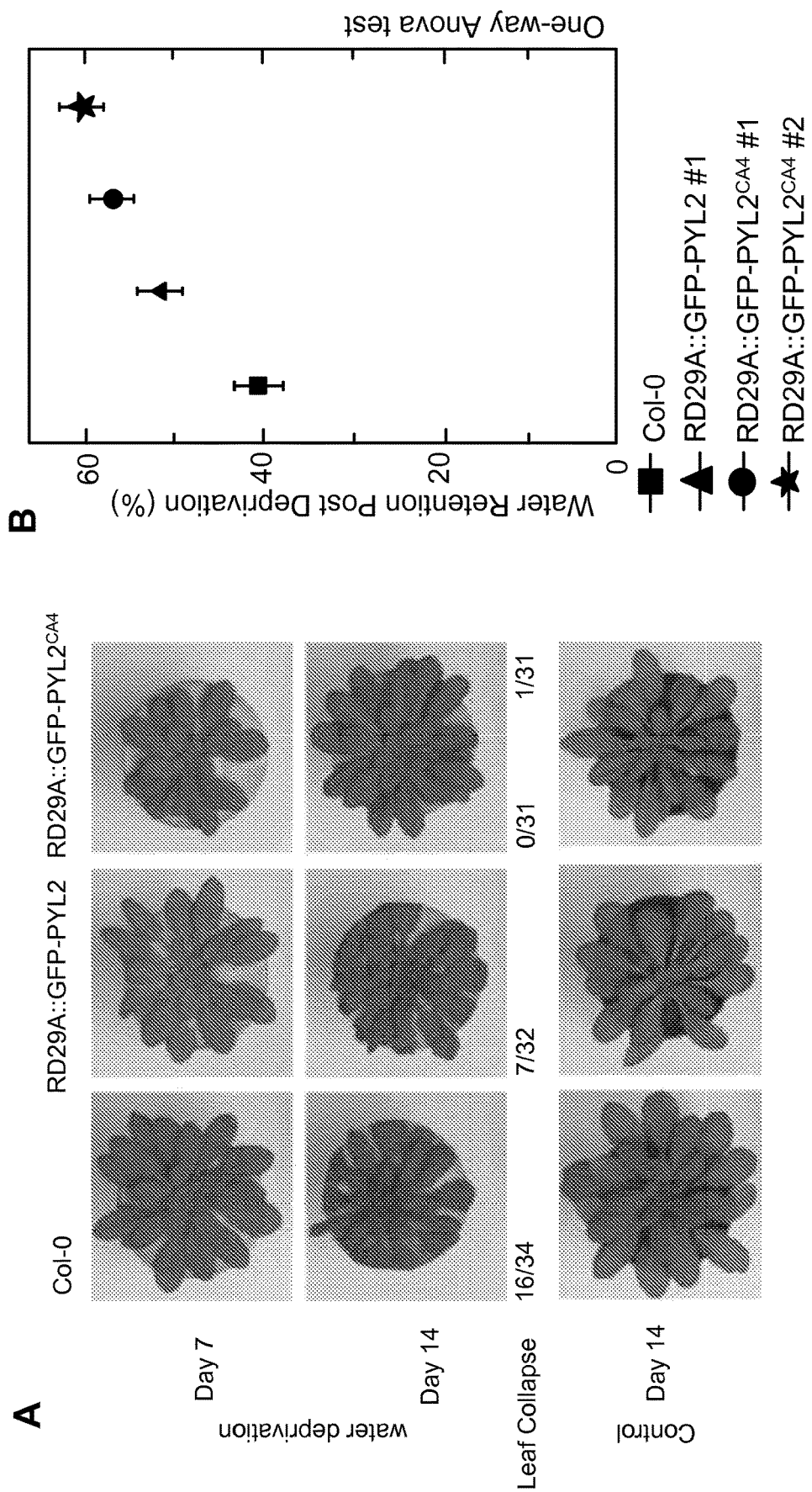

FIG. 24. The RD29A::GFP-PYL2CA4 Transgene Improves Water Use Efficacy.

Six-week-old plants from the wild-type Columbia (Col), RD29A:GFP-PYL2, or two independent RD29A::GFP-PYL2$^{CA4}$ lines were prepared for drought conditions by covering the pot to prevent water loss not attributed to transpiration. Water was then deprived for two weeks, during which time plants were photographed and weighed. Water retention was calculated as percent of initial water content. (A) Representative images of water-deprived plants after one or two weeks (upper panel) and controls which had continuous water supply. The numbers underneath the photos represent the fraction of plants where at least one leaf collapsed due to lack of water. (B) Statistical One-way Anova test of Water Retention. Plot indicate the Means with 95% Confidence Intervals.

Figure 25:
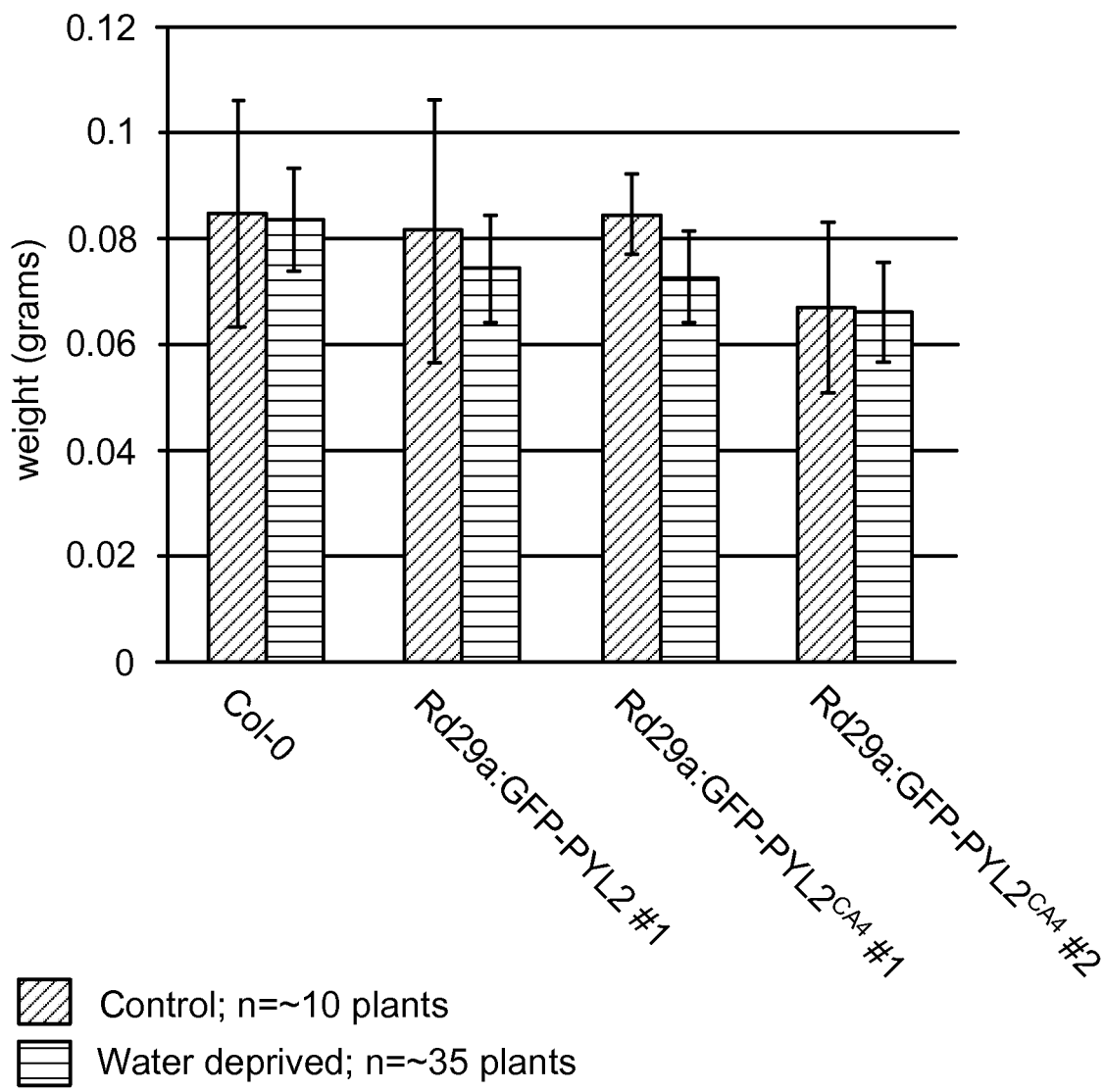

FIG. 25. The RD29A::GFP-PYL2CA4 Transgene does not Affect *Arabidopsis* Dry Mass Accumulation.

Plants used in the water use efficacy experiment described in FIG. 24 (n=~32) and controls (n=10) were dried out and weighed. Graphs plot the averages of values and error bars show one standard deviation.

Figure 26:
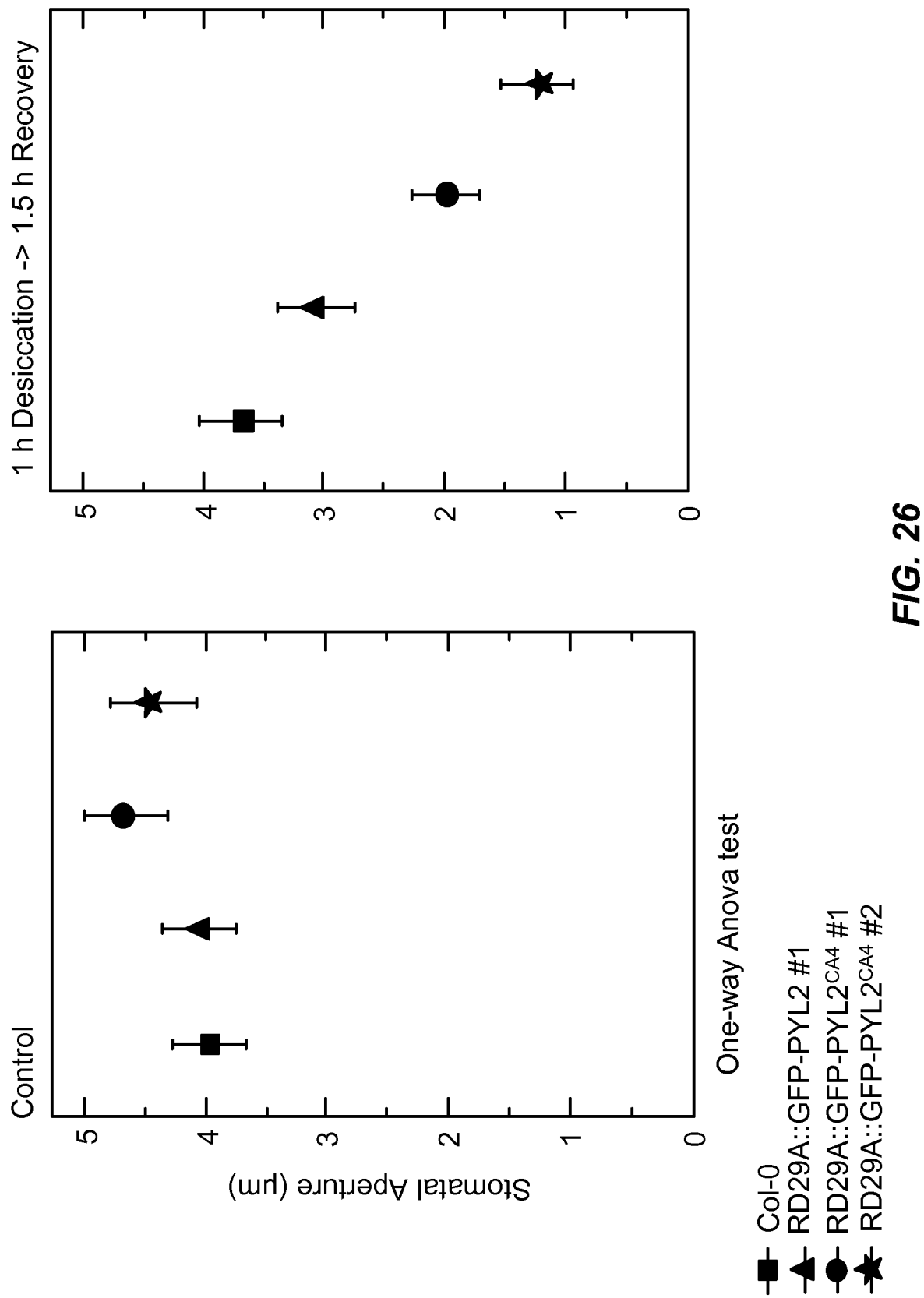

FIG. 26. The RD29A::GFP-PYL2CA4 Transgene Affects Stomatal Aperture after Recovery from Desiccation.

Leaves from four-week-old plants of wild-type Columbia (Col-0), RD29A::GFP-PYL2, or two independent RD29A:: GFP-PYL2$^{CA4}$ transgenic lines were severed and dried under light for one hour, then plants were rehydrated for 90 minutes. Controls were grown for 24 hours under high humidity. Stomatal morphologies of 4 leaves per genotype were captured by molding as described in the example. The aperture of ~100 stomata per genotype was measured and One-way Anova statistical analysis was performed on the resulting measurements. Plots indicate the stomatal aperture means (in μm) with 95% confidence intervals plotted on the error bars.

DEFINITIONS

The term "PYR/PYL receptor polypeptide" refers to a protein characterized in part by the presence of one or more or all of a polyketide cyclase domain 2 (PF10604), a polyketide cyclase domain 1 (PF03364), and a Bet V I domain (PF03364), which in wild-type form mediates abscisic acid (ABA) and ABA analog signaling. A wide variety of PYR/PYL receptor polypeptide sequences are known in the art. In some embodiments, a PYR/PYL receptor polypeptide comprises a polypeptide that is substantially identical to PYR1 (SEQ ID NO:1), PYL1 (SEQ ID NO:2), PYL2 (SEQ ID NO:3), PYL3 (SEQ ID NO:4), PYL4 (SEQ ID NO:5), PYL5 (SEQ ID NO:6), PYL6 (SEQ ID NO:7), PYL7 (SEQ ID NO:8), PYL8 (SEQ ID NO:9), PYL9 (SEQ ID NO:10), PYL10 (SEQ ID NO:11), PYL11 (SEQ ID NO:12), PYL12 (SEQ ID NO:13), or PYL13 (SEQ ID NO:14), or to any of SEQ ID NOs:15-155.

The term "ligand-binding pocket" refers to an amino acid residue of a PYR/PYL receptor polypeptide which is located within 5 Å of the ligand ABA, or a water molecule that hydrogen bonds to ABA, when ABA is bound to the PYR/PYL receptor polypeptide. Proximity of an amino acid residue to ABA when ABA is bound to a PYR/PYL receptor can be determined, e.g., by protein crystallography.

The term "type 2 protein phosphatase binding interface" or "PP2C binding interface" refers to an amino acid residue of a PYR/PYL receptor polypeptide which is located within 5 Å of PP2C when ABA, the PYR/PYL receptor polypeptide, and the PP2C are bound in a ternary complex. Proximity of an amino acid residue to PP2C when the PP2C is bound to a PYR/PYL receptor can be determined, e.g., by protein crystallography.

A "wild-type PYR/PYL receptor polypeptide" refers to a naturally occurring PYR/PYL receptor polypeptide that mediates abscisic acid (ABA) and ABA analog signaling.

A "mutated PYR/PYL receptor polypeptide" refers to a PYR/PYL receptor polypeptide that is a variant from a naturally-occurring (i.e., wild-type) PYR/PYL receptor polypeptide. As used herein, a mutated PYR/PYL receptor polypeptide comprises one, two, three, four, or more amino acid substitutions relative to a corresponding wild-type PYR/PYL receptor polypeptide. In this context, a "mutated" polypeptide can be generated by any method for generating non-wild type nucleotide sequences. In some embodiments, a mutated PYR/PYL receptor polypeptide is "constitutively active." As used herein, "constitutively active" refers to a PYR/PYL receptor that can bind to a type 2 protein phosphatase (PP2C) in the absence of ABA and/or inhibit the activity of the PP2C in the absence of ABA.

The phrase "significantly inhibits the activity of a type 2 protein phosphatase (PP2C)," as used herein, means that the activity level of a PP2C that is contacted with a mutated PYR/PYL receptor polypeptide in the absence of abscisic acid is substantially decreased relative to the activity level of a PP2C in the absence of abscisic acid. In some embodiments, the activity level of a PP2C that is contacted with a mutated PYR/PYL receptor polypeptide in the absence of abscisic acid is substantially decreased when it is decreased by at least about 10%, at least 20%, 30%, 40%, 50%, 60%, 70%, 80%, 90% or more relative to the activity level of a PP2C in the absence of abscisic acid. In some embodiments, a constitutively active PYR/PYL receptor of the present invention significantly inhibits PP2C activity (e.g., inhibits at least 10%, 20%, 30%, 40%, 50%, 60%, 70%, 80%, 90% or more of PP2C activity) at a receptor/PP2C molar ratio of about 1:1, about 1:2, about 1:3, or about 1:4.

An "amino acid substitution" refers to replacing the naturally occurring amino acid residue in a given position (e.g., the naturally occurring amino acid residue that occurs in a wild-type PYR/PYL receptor polypeptide) with an amino acid residue other than the naturally-occurring residue. For example, the naturally occurring amino acid residue at position 60 of the wild-type PYR1 receptor polypeptide sequence (SEQ ID NO:1) is histidine (H60); accordingly, an amino acid substitution at H60 refers to replacing the naturally occurring histidine with any amino acid residue other than histidine.

Figure 1:
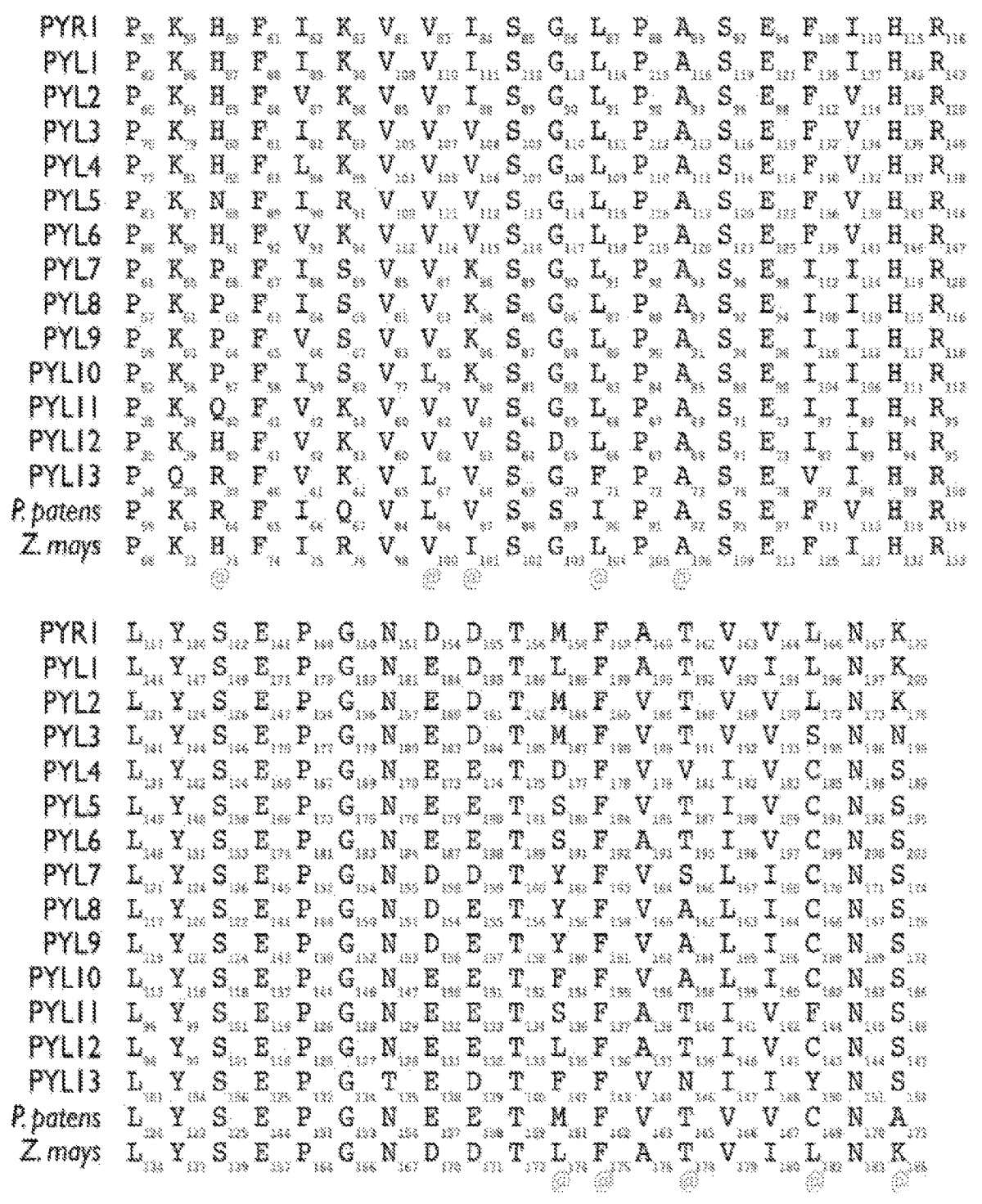

An amino acid residue "corresponding to an amino acid residue [X] in [specified sequence]," or an amino acid substitution "corresponding to an amino acid substitution [X] in [specified sequence]" refers to an amino acid in a polypeptide of interest that aligns with the equivalent amino acid of a specified sequence. Generally, as described herein, the amino acid corresponding to a position of a specified PYR/PYL receptor polypeptide sequence can be determined using an alignment algorithm such as BLAST. In some embodiments of the present invention, "correspondence" of amino acid positions is determined by aligning to a region of the PYR/PYL receptor polypeptide comprising SEQ ID NO:1, as discussed further herein. When a PYR/PYL receptor polypeptide sequence differs from SEQ ID NO:1 (e.g., by changes in amino acids or addition or deletion of amino acids), it may be that a particular mutation associated with constitutive activity of the PYR/PYL receptor will not be in the same position number as it is in SEQ ID NO:1. For example, amino acid position V87 of PYL2 (SEQ ID NO:3) aligns with amino acid position V83 of PYR1 (SEQ ID NO:1), as can be readily illustrated in an alignment of the two sequences. In this example, amino acid position 87 in SEQ ID NO:3 corresponds to position 83 in SEQ ID NO:1. Examples of corresponding positions are shown in FIG. 1.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantial identity" or "substantially identical," used in the context of two nucleic acids or polypeptides, refers to a sequence that has at least 70% sequence identity with a reference sequence. Alternatively, percent identity can be any integer from 70% to 100%. In some embodiments, a sequence is substantially identical to a reference sequence if the sequence has at least 70%, 75%, 80%, 85%, 90%, 91%, 92%, 93%, 94%, 95%, 96%, 97%, 98%, or 99% sequence identity to the reference sequence as determined using the methods described herein; preferably BLAST using standard parameters, as described below. Embodiments of the present invention provide for nucleic acids encoding polypeptides that are substantially identical to any of SEQ ID NO:1-155.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=-2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

The term "promoter," as used herein, refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "plant promoter" is a promoter capable of initiating transcription in plant cells. A "constitutive promoter" is one that is capable of initiating transcription in nearly all tissue types, whereas a "tissue-specific promoter" initiates transcription only in one or a few particular tissue types.

A polynucleotide sequence is "heterologous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

An "expression cassette" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, or sense suppression) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence.

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid, and hemizygous.

DETAILED DESCRIPTION OF THE INVENTION

I. Introduction

The present invention is based, in part, on the discovery that combinations of mutations in PYR/PYL receptor polypeptides result in constitutively active forms of the PYR/PYL receptor. PYR/PYL receptor can be classified into three classes on the basis of sequence similarity, ABA sensitivity, oligomeric state, and level of basal activation. PYR1, PYL1, PYL2, PYL3, and PYL4 are dimeric in solution, display low basal activation, and require higher levels of ABA to elicit complete PP2C inhibition in comparison to other PYLs. PYL5, PYL6, PYL7, PYL8, and PYL9 are monomeric in solution, require lower ABA concentrations to inhibit PP2C activity, and possess elevated basal activity in comparison to PYR1-PYL4. PYL10, PYL11, PYL12, and PYL13 are also monomeric in solution, but display much higher basal activation than PYR1-PYL9. Dimeric PYR/PYL receptor proteins do not substantially inhibit type 2 protein phosphatase (PP2C) activity in the absence of abscisic acid (ABA), as ABA is needed to stabilize the receptor in a form that allows high-affinity binding to the PP2C.

In principle, receptor mutations that allow high affinity binding to and inhibition of the PP2Cs in the absence of an agonist should activate the ABA signaling pathway in an ABA-independent form. These forms of mutant receptors are referred to as "constitutively active" forms. However, although some PYL proteins, such as PYL10, have been reported to have higher basal activation in comparison to PYR1, no receptor or variant has previously been reported that shows full constitutively active activity. The present invention surprisingly demonstrates PYR/PYL receptors that possess full constitutively active properties and demonstrates their utility for activating ABA signaling and stress tolerance in transgenic plants.

Constitutively active PYR/PYL receptor mutations are beneficial in comparison to generic chemical agonists (such as ABA) because constitutively active mutations allow single receptors to be activated selectively. Because the PYR/PYL receptors reside in a relatively large gene family (14 members in *Arabidopsis*), selective activation of single receptors by constitutively active mutations can allow responses controlled by distinct family members to be specifically controlled, in contrast to general activation of signaling by ABA or general agonists, which activate a wider range of receptors. Selective action of PYR/PYL receptors may avoid the undesirable side effects of general activation, such as chlorosis, and may enable the myriad desirable and undesirable side effects to be disentangled and controlled with specificity.

II. Constitutively Active PYR/PYL Receptor Polypeptides

In one aspect, the present invention provides for PYR/PYL receptor polypeptides comprising one or more amino acid substitutions in a ligand-binding pocket and/or a type 2 protein phosphatase (PP2C) binding interface, wherein the PYR/PYL receptor binds to PP2C in the absence of abscisic acid, as well as polynucleotides encoding PYR/PYL receptor polypeptides comprising one or more amino acid substitutions wherein the PYR/PYL receptor binds to PP2C in the absence of abscisic acid; expression cassettes and expression vectors comprising polynucleotides encoding PYR/PYL receptor polypeptides comprising one or more amino acid substitutions wherein the PYR/PYL receptor binds to PP2C in the absence of abscisic acid; plants comprising PYR/PYL receptor polypeptides comprising one or more amino acid substitutions wherein the PYR/PYL receptor binds to PP2C in the absence of abscisic acid; methods of making plants comprising PYR/PYL receptor polypeptides comprising one or more amino acid substitutions wherein the PYR/PYL receptor binds to PP2C in the absence of abscisic acid.

In some embodiments, the constitutively active PYR/PYL receptor comprises mutations that result in the mutated receptor binding to a PP2C in the absence of ABA. As used herein, a mutated PYR/PYL receptor "binds" a PP2C in the absence of ABA if the mutated PYR/PYL receptor (e.g., a mutated PYR1 receptor) has a higher binding affinity for the PP2C in the absence of ABA than the basal affinity of the corresponding wild-type PYR/PYL receptor (e.g., a wild-type PYR1 as shown in SEQ ID NO:1) for the PP2C in the absence of ABA. In some embodiments, the constitutively active PYR/PYL receptor comprises mutations that result in the mutated receptor significantly inhibiting the activity of the PP2C in a phosphatase assay in the absence of ABA. In some embodiments, the mutated receptor inhibits the activity of the PP2C by at least about 10%, at least about 20%, at least about 30%, at least about 40%, at least about 50%, at least about 60%, at least about 70%, at least about 80% or more in the absence of ABA as compared to a wild-type PYR/PYL receptor in the absence of ABA.

A wide variety of wild-type (naturally occurring) PYR/PYL polypeptide sequences are known in the art. Although PYR1 was originally identified as an abscisic acid (ABA) receptor in *Arabidopsis*, in fact PYR1 is a member of a group of at least 14 proteins (PYR/PYL proteins) in the same protein family in *Arabidopsis* that also mediate ABA signaling. This protein family is also present in other plants (see, e.g., SEQUENCE LISTING) and is characterized in part by the presence of one or more or all of a polyketide cyclase domain 2 (PF10604), a polyketide cyclase domain 1 (PF03364), and a Bet V I domain (PF03364). START/Bet v 1 superfamily domain are described in, for example, Radauer, *BMC Evol. Biol.* 8:286 (2008). In some embodiments, a wild-type PYR/PYL receptor polypeptide comprises any of SEQ ID NOs:1-119. In some embodiments, a wild-type PYR/PYL receptor polypeptide is substantially identical to (e.g., at least 70%, 75%, 80%, 85%, 90%, 91%, 92%, 93%, 94% 95%, 96%, 97%, 98%, or 99% identical to) any of SEQ ID NOs:1-119.

Constitutively active PYR/PYL receptor polypeptides are variants from naturally occurring (i.e., wild-type) PYR/PYL receptor polypeptides, wherein the variant PYR/PYL receptor polypeptide is able to bind to and/or inhibit the activity of a PP2C in the absence of abscisic acid. Constitutively active PYR/PYL receptor polypeptides of the present invention comprise one or more amino acid substitutions in a ligand-binding pocket and/or a type 2 protein phosphatase (PP2C) binding interface of the PYR/PYL receptor polypeptide. In some embodiments, a constitutively active PYR/PYL receptor polypeptide is substantially identical to (e.g., at least 70%, 75%, 80%, 85%, 90%, 91%, 92%, 93%, 94% 95%, 96%, 97%, 98%, or 99% identical to) any of SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, or 155 and comprises 1, 2, 3, 4, or more mutations (e.g., amino acid substitutions) as described herein in the ligand-binding pocket and/or the PP2C binding interface, wherein the mutated PYR/PYL receptor polypeptide binds to and/or inhibits the activity of a type 2 protein phosphatase (PP2C) in the absence of abscisic acid. In some embodiments, the constitutively active PYR/PYL receptor polypeptide comprises one or more amino acid substitutions in the ligand-binding pocket. In some embodiments, the constitutively active PYR/PYL receptor polypeptide comprises one or more amino acid substitutions in the PP2C binding interface. In some embodiments, the constitutively active PYR/PYL receptor polypeptide comprises one or more amino acid substitutions in each of the ligand-binding pocket and the PP2C binding interface. In some embodiments, the constitutively active PYR/PYL receptor polypeptide has the amino acid sequence of any of SEQ ID NOs:120-155 (i.e., any of SEQ ID NO:120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, or 155).

Ligand-Binding Pocket Mutations

PYR/PYL receptor proteins have a conserved START-domain ligand-binding pocket flanked by two loops called the "gate" and the "latch" (Melcher, K. et al., *Nature* 462 (2009)). ABA binds to a PYR/PYL receptor protein at the ligand-binding pocket and ABA binding induces closure of the loops to seal ABA inside the ligand-binding pocket. The ligand-binding pocket of a PYR/PYL receptor polypeptide comprises amino acid residues that are in close proximity (e.g., within about 5 Å) to a PYR/PYL ligand (e.g., ABA) or a ligand-contacting water molecule when the ligand is bound to the PYR/PYL receptor. Table 1 in the Examples section lists the residues that make up the ligand-binding pocket in PYR1; in total, there are 25 residues that make up the PYR1 ligand-binding pocket. The residues of the ligand-binding pocket are also highly conserved among other PYR/PYL family members.

In some embodiments, a mutated PYR/PYL receptor polypeptide of the present invention comprises one or more (e.g., one, two, three, four, five, six, seven, eight, or more) amino acid substitutions in the ligand-binding pocket. In some embodiments, the one or more amino acid substitutions are selected from the amino acid substitutions H60P/G/R/A/W/I/K/V/M, V83F/L/P, L87F, A89W or F159V/A, wherein the amino acid substitutions correspond to positions H60, V83, L87, A89, and F159 in PYR1 as set forth in SEQ ID NO:1. In some embodiments, the one or more amino acid substitutions are selected from H60G/R/A/W/I/K/V/M, V83F/P, L87F, A89W or F159V/A, wherein the amino acid substitutions correspond to positions H60, V83, L87, A89, and F159 in PYR1 as set forth in SEQ ID NO:1. In some embodiments, the one or more amino acid substitutions comprise two amino acid substitutions selected from H60P/G/R/A/W/I/K/V/M and V83F/L/P, wherein the amino acid substitutions correspond to positions H60 and V83 in PYR1 as set forth in SEQ ID NO:1. In some embodiments, the one or more amino acid substitutions comprise two amino acid substitutions selected from the amino acid substitutions H60P/G/R/A/W/I/K/V/M and F159V/A, wherein the amino acid substitutions correspond to positions H60 and F159 in PYR1 as set forth in SEQ ID NO:1. In some embodiments, the one or more amino acid substitutions comprise three amino acid substitutions selected from the amino acid substitutions H60P/G/R/A/W/I/K/V/M, V83F/L/P, and F159V/A, wherein the amino acid substitutions correspond to positions H60, V83, and F159 in PYR1 as set forth in SEQ ID NO:1. In some embodiments, the one or more amino acid substitutions comprise three amino acid substitutions selected from H60P/G/R/A/W/I/K/V/M, V83F/L/P, and A89W, wherein the amino acid substitutions correspond to positions H60, V83, and A89 in PYR1 as set forth in SEQ ID NO:1. In some embodiments, the one or more amino acid substitutions comprise three amino acid substitutions selected from H60P/G/R/A/W/I/K/V/M, A89W, and F159V/A, wherein the amino acid substitutions correspond to positions H60, A89, and F159 in PYR1 as set forth in SEQ ID NO:1.

Any of the mutations described herein can be made in the polypeptides of any of SEQ ID NOs:1-155 or in polypeptides substantially identical to any of SEQ ID NOs:1-155. One of skill in the art will recognize that analogous amino acid substitutions can be made, for example, in PYR/PYL receptors other than PYR1 by aligning the PYR/PYL receptor polypeptide sequence to be mutated with the PYR1 receptor polypeptide sequence as set forth in SEQ ID NO:1. As a non-limiting example, an amino acid substitution in PYL2 that is analogous to the amino acid substitution V83F in PYR1 as set forth in SEQ ID NO:1 can be determined by aligning the amino acid sequences of PYL2 (SEQ ID NO:3) and PYR1 (SEQ ID NO:1) and identifying position V87 in PYL2 as aligning with amino acid position V83 of PYR1 (SEQ ID NO:1). Analogous amino acid positions in PYR/PYL receptors are shown in FIGS. 1 and 8.

In some embodiments, the one or more amino acid substitutions in the ligand-binding pocket result in the mutated PYR/PYL receptor being able to bind to PP2C in the absence of abscisic acid. In some embodiments, the amino acid substitution(s) in the ligand-binding pocket result in the mutated PYR/PYL receptor being able to significantly inhibit the activity of the PP2C in a phosphatase assay in the absence of abscisic acid. In some embodiments, the amino acid substitution(s) in the ligand-binding pocket result in the mutated PYR/PYL receptor polypeptide being able to inhibit the activity of the PP2C by at least 50% in the absence of abscisic acid as compared to the level of PP2C activity of a PP2C that is contacted with a wild-type PYR/PYL receptor polypeptide in the absence of abscisic acid. In some embodiments, the amino acid substitution(s) in the ligand-binding pocket result in the mutated PYR/PYL receptor polypeptide being able to inhibit the activity of the PP2C by at least 50% in the absence of abscisic acid and at a receptor:PP2C molar ratio of about 1:1, about 1:2, about 1:3, or about 1:4.

The extent to which one or more amino acid substitutions in the ligand-binding pocket activates PYR/PYL receptor activity in the absence of ABA (i.e., inhibits PP2C activity) can be quantitatively measured, for example by assaying phosphatase activity in the presence of the PYR/PYL receptor comprising one or more amino acid substitutions and comparing the phosphatase activity to that of a wild-type PYR/PYL receptor. In some embodiments, an activating mutation in the ligand-binding pocket is any mutation (e.g., amino acid substitution) that results in at least 10%, 20%, 30%, 40%, 50%, 60%, 70%, 80%, or 90% or greater inhibition of PP2C activity. In some embodiments, an activating mutation in the ligand-binding pocket is any mutation (e.g., amino acid substitution) that results in at least 10%, 20%, 30%, 40%, 50%, 60%, 70%, 80%, or 90% or greater inhibition of PP2C activity at a receptor/PP2C molar ratio of about 1:1, about 1:2, about 1:3, or about 1:4.

In some embodiments, a mutated PYR/PYL receptor polypeptide of the present invention comprises one or more (e.g., one, two, three or four) amino acid substitutions in the ligand-binding pocket selected from the group consisting of H60P/G, V83F, A89W or F159V, wherein the amino acid substitutions correspond to positions H60, V83, A89, and F159 in PYR1 as set forth in SEQ ID NO:1. As shown in Table 1 below, amino acid substitutions at these positions strongly activate the PYR/PYL receptor in the absence of ABA. In some embodiments, the mutated PYR/PYL receptor polypeptide comprises an amino acid substitution at H60P. In some embodiments, the mutated PYR/PYL receptor polypeptide comprises an amino acid substitution at H60G. In some embodiments, the mutated PYR/PYL receptor polypeptide comprises an amino acid substitution at V83F. In some embodiments, the mutated PYR/PYL receptor polypeptide comprises an amino acid substitution at A89W. In some embodiments, the mutated PYR/PYL receptor polypeptide comprises an amino acid substitution at F159V. In some embodiments, the mutated PYR/PYL receptor polypeptide comprises two, three, four, or more of the amino acid substitutions described above.

PP2C Binding Interface Mutations

PYR/PYL receptor proteins directly bind to type 2 protein phosphatases (PP2Cs) and thus also contain a PP2C binding interface. The PP2C binding interface of a PYR/PYL receptor polypeptide comprises amino acid residues that are in close proximity (e.g., within about 5 Å) to PP2C when PP2C, the PYR/PYL receptor, and ABA are all bound together in a ternary complex. Table 1 in the Examples section lists the residues that make up the PP2C binding interface in PYR1; in total, there are 25 residues that make up the PYR1 PP2C binding interface. The residues of the PP2C binding interface are also highly conserved among other PYR/PYL family members.

In some embodiments, a mutated PYR/PYL receptor polypeptide of the present invention comprises one or more (e.g., one, two, three, four, five, six, seven, eight, nine or more) amino acid substitutions in the PP2C binding interface. In some embodiments, the one or more amino acid substitutions are selected from the amino acid substitutions H60P/G/R/A/W/I/K/V/M, I84Q/E/P/H/K, L87F, A89W, M158T/C/V/I, F159V/A, T162F, L166Y/F, or K170W, wherein the amino acid substitutions correspond to positions H60, I84, L87, A89, M158, F159, T162, L166, and K170 in PYR1 as set forth in SEQ ID NO:1. In some embodiments, the one or more (e.g., one, two, three, four, five, six, seven, eight, nine or more) amino acid substitutions are selected from the amino acid substitutions H60P/G/R/A/W/I/K/V/M, I84Q/E/P/H, L87F, A89W, M158T/C/V/I, F159V/A, T162F, L166Y/F, or K170W, wherein the amino acid substitutions correspond to positions H60, I84, L87, A89, M158, F159, T162, L166, and K170 in PYR1 as set forth in SEQ ID NO:1. In some embodiments, the one or more amino acid substitutions comprise three amino acid substitutions selected from H60P/G/R/A/W/I/K/V/M, M158T/C/V/I, and F159V/A, wherein the amino acid substitutions correspond to positions H60, M158, and F159 in PYR1 as set forth in SEQ ID NO:1. In some embodiments, the one or more amino acid substitutions comprise three amino acid substitutions selected from the amino acid substitutions H60P/G/R/A/W/I/K/V/M, A89W, and F159V/A, wherein the amino acid substitutions correspond to positions H60, A89, and F159 in PYR1 as set forth in SEQ ID NO:1. In some embodiments, the one or more amino acid substitutions comprise four amino acid substitutions selected from H60P/G/R/A/W/I/K/V/M, A89W, M158T/C/V/I, or F159V/A, wherein the amino acid substitutions correspond to positions H60, A89, M158, and F159 in PYR1 as set forth in SEQ ID NO:1.

Any of mutations described herein can be made in the polypeptides of any of SEQ ID NOs:1-155 or in polypeptides substantially identical to any of SEQ ID NOs:1-155. The residues of the PP2C binding interface are highly conserved among the PYR/PYL family members, and thus one of skill in the art will recognize that analogous amino acid substitutions to those described herein for PYR1 can be made in PYR/PYL receptors other than PYR1.

In some embodiments, the one or more amino acid substitutions in the PP2C binding interface result in the mutated PYR/PYL receptor being able to bind to PP2C in the absence of abscisic acid. In some embodiments, the amino acid substitution(s) in the PP2C binding interface result in the mutated PYR/PYL receptor being able to significantly inhibit the activity of the PP2C in a phosphatase assay in the absence of abscisic acid. In some embodiments, the amino acid substitution(s) in the PP2C binding interface result in the mutated PYR/PYL receptor polypeptide being able to inhibit the activity of the PP2C by at least 50% in the absence of abscisic acid as compared to the level of PP2C activity of a PP2C that is contacted with a wild-type PYR/PYL receptor polypeptide in the absence of abscisic acid. In some embodiments, the amino acid substitution(s) in the PP2C binding interface result in the mutated PYR/PYL receptor polypeptide being able to inhibit the activity of the PP2C by at least 50% in the absence of abscisic acid and at a receptor:PP2C molar ratio of about 1:1, about 1:2, about 1:3, or about 1:4.

The extent to which one or more amino acid substitutions in the PP2C binding interface activate PYR/PYL receptor activity in the absence of ABA (i.e., inhibits PP2C activity) can be quantitatively measured, for example by assaying phosphatase activity in the presence of the PYR/PYL receptor comprising one or more amino acid substitutions and comparing the phosphatase activity to that of a wild-type PYR/PYL receptor. In some embodiments, an activating mutation in the PP2C binding interface is any mutation (e.g., amino acid substitution) that results in at least 10%, 20%, 30%, 40%, 50%, 60%, 70%, 80%, or 90% or greater inhibition of PP2C activity. In some embodiments, an activating mutation in the PP2C binding interface is any mutation (e.g., amino acid substitution) that results in at least 10%, 20%, 30%, 40%, 50%, 60%, 70%, 80%, or 90% or greater inhibition of PP2C activity at a receptor/PP2C molar ratio of about 1:1, about 1:2, about 1:3, or about 1:4.

In some embodiments, a mutated PYR/PYL receptor polypeptide of the present invention comprises one or more amino (e.g., one, two, three, four, five, or six) acid substitutions in the PP2C binding interface selected from the group consisting of H60P/G, I84Q, A89W, M158T/C, F159V, or K170W, wherein the amino acid substitutions correspond to positions H60, I84, A89, M158, F159, and K170 in PYR1 as set forth in SEQ ID NO:1. As shown in Table 1 below, amino acid substitutions at these positions strongly activate the PYR/PYL receptor in the absence of ABA. In some embodiments, the mutated PYR/PYL receptor polypeptide comprises an amino acid substitution at H60P. In some embodiments, the mutated PYR/PYL receptor polypeptide comprises an amino acid substitution at H60G. In some embodiments, the mutated PYR/PYL receptor polypeptide comprises an amino acid substitution at I84Q. In some embodiments, the mutated PYR/PYL receptor polypeptide comprises an amino acid substitution at A89W. In some embodiments, the mutated PYR/PYL receptor polypeptide comprises an amino acid substitution at M158T. In some embodiments, the mutated PYR/PYL receptor polypeptide comprises an amino acid substitution at M158C. In some embodiments, the mutated PYR/PYL receptor polypeptide comprises an amino acid substitution at F159V. In some embodiments, the mutated PYR/PYL receptor polypeptide comprises an amino acid substitution at K170W. In some embodiments, the mutated PYR/PYL receptor polypeptide comprises two, three, four, or more of the amino acid substitutions described above.

In some embodiments, a mutated PYR/PYL receptor polypeptide of the present invention comprises one or more (e.g., one, two, three, four, or five) amino acid substitutions in the PP2C binding interface selected from the group consisting of H60P, A89W, M158I, F159V, or K170W, wherein the amino acid substitutions correspond to positions H60, A89, M158, F159, and K170 in PYR1 as set forth in SEQ ID NO:1. In some embodiments, the mutated PYR/PYL receptor polypeptide comprises two, three, four, or five of the amino acid substitutions described above. For example, in some embodiments, the mutated PYR/PYL receptor polypeptide comprises two amino acid substitutions corresponding to H60P and F159V, or H60P and A89W, or A89W and F159V. In some embodiments, the mutated PYR/PYL receptor polypeptide comprises three amino acid substitutions corresponding to H60P, A89W and F159V, or H60P, M158I and F159V. In some embodiments, the mutated PYR/PYL receptor polypeptide comprises four amino acid substitutions corresponding to H60P, A89W, M158I and F159V.

Combinations of Ligand-Binding Pocket and PP2C Binding Interface Mutations

In some embodiments, a mutated PYR/PYL receptor polypeptide of the present invention comprises one or more amino acid substitutions in each of the ligand-binding pocket and the PP2C binding interface. In some embodiments, the one or more amino acid substitutions in each of the ligand-pocket and the PP2C binding interface are selected from H60P/G/R/A/W/I/K/V/M, V83F/L/P, I84Q/E/P/H/K, L87F, A89W, M158T/C/V/I, F159V/A, T162F, L166Y/F, and K170W, wherein the amino acid substitutions correspond to positions H60, V83, I84, L87, A89, M158, F159, T162, L166, and K170 in PYR1 as set forth in SEQ ID NO:1. In some embodiments, the mutated PYR/PYL receptor polypeptide comprises two, three, four, or more amino acid substitutions selected from H60P/G/R/A/W/I/K/V/M, V83F/L/P, I84Q/E/P/H/K, L87F, A89W, M158T/C/V/I, F159V/A, T162F, L166Y/F, and K170W, wherein the amino acid substitutions correspond to positions H60, V83, I84, L87, A89, M158, F159, T162, L166, and K170 in PYR1 as set forth in SEQ ID NO:1. Any of mutations described herein can be made in the polypeptides of any of SEQ ID NOs:1-155 or in polypeptides substantially identical to any of SEQ ID NOs:1-155. The residues of the ligand-binding pocket and the PP2C binding interface are highly conserved among the PYR/PYL family members, and thus one of skill in the art will recognize that analogous amino acid substitutions to those described herein for PYR1 can be made in PYR/PYL receptors other than PYR1.

In some embodiments, an amino acid substitution made in the ligand-binding pocket can be the same amino acid substitution as the amino acid substitution made in the PP2C binding interface, as some amino acid residues in PYR/PYL are able to contact both ABA and a PP2C when the ABA, PP2C, and PYR/PYL receptor are complexed together. Table 1 below lists amino acid residues of PYR/PYL, numbered with respect to PYR1, that make contact with both the ligand-binding pocket and the PP2C binding interface. Thus, in some embodiments, a mutated PYR/PYL receptor polypeptide of the present invention comprises one or more amino acid substitutions in each of the ligand-binding pocket and the PP2C binding interface, wherein the one or more amino acid substitutions are selected from the amino acid substitutions H60P/G/R/A/W/I/K/V/M, L87F, A89W, and F159V/A, wherein the amino acid substitutions correspond to positions H60, L87, A89, and F159 in PYR1 as set forth in SEQ ID NO:1.

In some embodiments, a mutated PYR/PYL receptor polypeptide of the present invention comprises three mutations selected from H60P, V83F, A89W, M158I, F159V, T162F, and/or K170W, wherein the amino acid substitutions correspond to positions H60, V83, I84, A89, M158, F159, T162, and/or K170 in PYR1 as set forth in SEQ ID NO:1. In some embodiments, the three mutations are selected from amino acid substitutions corresponding to positions (i) H60P, V83F, and A89W; (ii) H60P, V83F, and F159V; (iii) H60P, A89W, and F159V; (iv) H60P, V83F, and M158I; and (v) H60P, M158I, and F159V of SEQ ID NO:1.

In some embodiments, a mutated PYR/PYL receptor polypeptide of the present invention comprises four mutations selected from H60P, V83F, A89W, M158I, F159V, T162F, and/or K170W, wherein the amino acid substitutions correspond to positions H60, V83, I84, A89, M158, F159, T162, and/or K170 in PYR1 as set forth in SEQ ID NO:1. In some embodiments, the four mutations are selected from amino acid substitutions corresponding to positions (i) H60P, V83F, A89W, and F159V; (ii) H60P, V83F, M158I, and F159V; (iii) H60P, A89W, M158I, and F159V; (iv) H60P, V83F, F159V, and K170W; (v) H60P, V83F, M158I, and K170W; and (vi) V83F, M158I, F159V, and K170W of SEQ ID NO:1. Examples of exemplary mutations are shown in FIG. 17.

Embodiments of the present invention provide for use of the above proteins and/or nucleic acid sequences, encoding such polypeptides, in the methods and compositions (e.g., expression cassettes, plants, etc.) of the present invention. The isolation of a polynucleotide sequence encoding a plant wild-type PYR/PYL receptor (e.g., from plants where PYR/PYL sequences have not yet been identified) may be accomplished by a number of techniques. For instance, oligonucleotide probes based on the PYR/PYL coding sequences disclosed (e.g., as listed in the SEQUENCE LISTING) here can be used to identify the desired wild-type PYR/PYL gene in a cDNA or genomic DNA library. To construct genomic libraries, large segments of genomic DNA are generated by random fragmentation, e.g., using restriction endonucleases, and are ligated with vector DNA to form concatemers that can be packaged into the appropriate vector. To prepare a cDNA library, mRNA is isolated from the desired tissue, such as a leaf from a particular plant species, and a cDNA library containing the gene transcript of interest is prepared from the mRNA. Alternatively, cDNA may be prepared from mRNA extracted from other tissues in which PYR/PYL gene is expressed.

The cDNA or genomic library can then be screened using a probe based upon the sequence of a PYR/PYL gene disclosed here. Probes may be used to hybridize with genomic DNA or cDNA sequences to isolate homologous genes in the same or different plant species. Alternatively, antibodies raised against a polypeptide can be used to screen an mRNA expression library.

Alternatively, the nucleic acids encoding PYR/PYL can be amplified from nucleic acid samples using amplification techniques. For instance, polymerase chain reaction (PCR) technology can be used to amplify the coding sequences of PYR/PYL directly from genomic DNA, from cDNA, from genomic libraries or cDNA libraries. PCR and other in vitro amplification methods may also be useful, for example, to clone polynucleotide sequences encoding PYR/PYL to be expressed, to make nucleic acids to use as probes for detecting the presence of the desired mRNA in samples, for nucleic acid sequencing, or for other purposes. For a general overview of PCR see *PCR Protocols: A Guide to Methods and Applications* (Innis, M., Gelfand, D., Sninsky, J. and White, T., eds.), Academic Press, San Diego (1990). Appropriate primers and probes for identifying sequences from plant tissues are generated from comparisons of the sequences provided here with other related genes.

In some embodiments, the partial or entire genome of a number of plants has been sequenced and open reading frames identified. By a BLAST search, one can identify the coding sequence for wild-type PYR/PYL in various plants.

III. Methods of Making Constitutively Active PYR/PYL Receptor Polypeptides

In another aspect, the present invention provides for methods of making PYR/PYL receptor polypeptides comprising one or more amino acid substitutions in a ligand-binding pocket and/or a type 2 protein phosphatase (PP2C) binding interface, wherein the PYR/PYL receptor binds to PP2C in the absence of abscisic acid. In some embodiments, the method comprises mutagenizing a wild-type PYR/PYL receptor and determining whether the mutagenized PYR/PYL receptor significantly inhibits the activity of a PP2C in a phosphatase assay in the absence of abscisic acid.

Mutated PYR/PYL receptor polypeptides can be constructed by mutating the DNA sequences that encode the corresponding wild-type PYR/PYL receptor polypeptide (e.g., a wild-type PYR/PYL polypeptide of any of SEQ ID NOs:1-119 or a corresponding variant from which the mutant PYR/PYL receptor polypeptide of the invention is derived), such as by using techniques commonly referred to as site-directed mutagenesis. Nucleic acid molecules encoding the wild-type PYR/PYL receptor polypeptide can be mutated by a variety of polymerase chain reaction (PCR) techniques well-known to one of ordinary skill in the art. (See, e.g., PCR Strategies (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, NY, 1990).

As a non-limiting example, mutagenesis may be accomplished using site-directed mutagenesis, in which point mutations, insertions, or deletions are made to a DNA template. Kits for site-directed mutagenesis are commercially available, such as the QuikChange Site-Directed Mutagenesis Kit (Stratagene). Briefly, a DNA template to be mutagenized is amplified by PCR according to the manufacturer's instructions using a high-fidelity DNA polymerase (e.g., Pfu Turbo™) and oligonucleotide primers containing the desired mutation. Incorporation of the oligonucleotides generates a mutated plasmid, which can then be transformed into suitable cells (e.g., bacterial or yeast cells) for subsequent screening to confirm mutagenesis of the DNA.

As another non-limiting example, mutagenesis may be accomplished by means of error-prone PCR amplification (ePCR), which modifies PCR reaction conditions (e.g., using error-prone polymerases, varying magnesium or manganese concentration, or providing unbalanced dNTP ratios) in order to promote increased rates of error in DNA replication. Kits for ePCR mutagenesis are commercially available, such as the GeneMorph® PCR Mutagenesis kit (Stratagene) and Diversify® PCR Random Mutagenesis Kit (Clontech). Briefly, DNA polymerase (e.g., Taq polymerase), salt (e.g., MgCl2, MgSO4, or MnSO4), dNTPs in unbalanced ratios, reaction buffer, and DNA template are combined and subjected to standard PCR amplification according to manufacturer's instructions. Following ePCR amplification, the reaction products are cloned into a suitable vector to construct a mutagenized library, which can then be transformed into suitable cells (e.g., yeast cells) for subsequent screening (e.g., via a two-hybrid screen) as described below.

Alternatively, mutagenesis can be accomplished by recombination (i.e. DNA shuffling). Briefly, a shuffled mutant library is generated through DNA shuffling using in vitro homologous recombination by random fragmentation of a parent DNA followed by reassembly using PCR, resulting in randomly introduced point mutations. Methods of performing DNA shuffling are known in the art (see, e.g., Stebel, S. C. et al., *Methods Mol Biol.* 352:167-190 (2007)).

Optionally, multiple rounds of mutagenesis may be performed in order to improve the efficiency of mutant proteins isolated. Thus, in some embodiments, PYR/PYL mutants isolated from ePCR and subsequent screening may be pooled and used as templates for later rounds of mutagenesis.

IV. Screening for Constitutively Active PYR/PYL Receptor Polypeptides

In some embodiments, mutated PYR/PYL receptor polypeptides are screened to determine whether the mutated PYR/PYL receptor is activated in the absence of ABA. In some embodiments, whether a mutated PYR/PYL receptor is activated in the absence of ABA is determined by measuring whether the mutated receptor significantly inhibits the activity of a PP2C in a phosphatase assay in the absence of ABA. In some embodiments, a mutated receptor is said to be activated in the absence of ABA (i.e., constitutively active) if the mutated receptor inhibits the activity of the PP2C by at least about 10%, at least about 20%, at least about 30%, at least about 40%, at least about 50%, at least about 60%, at least about 70%, at least about 80% or more in the absence of ABA as compared to a wild-type PYR/PYL receptor in the absence of ABA. In some embodiments, a mutated receptor is activated in the absence of ABA (i.e., constitutively active) if the mutated receptor inhibits the activity of the PP2C by at least about 10%, at least about 20%, at least about 30%, at least about 40%, at least about 50%, at least about 60%, at least about 70%, at least about 80% or more in the absence of ABA as compared to a wild-type PYR/PYL receptor in the absence of ABA when the receptor and PP2C are present at a receptor/PP2C molar ratio of about 1:1, about 1:2, about 1:3, or about 1:4.

A number of different screening protocols can be used to screen for constitutively active PYR/PYL receptors. Screening can take place using isolated, purified or partially purified reagents. In some embodiments, purified or partially purified PYR/PYL polypeptide can be used.

Alternatively, cell-based or plant-based methods of screening can be used. For example, cells that naturally express a wild-type PYR/PYL receptor polypeptide or that recombinantly express a wild-type or mutated PYR/PYL receptor polypeptide can be used. In some embodiments, the cells used are plant cells, animal cells, bacterial cells, fungal cells, including but not limited to yeast cells, insect cells, or mammalian cells. In general terms, the screening methods involve comparing the activity of a mutated PYR/PYL receptor polypeptide to the activity of a wild-type PYR/PYL receptor polypeptide in the absence of ABA, e.g., by comparing ABA-regulated gene expression in the wild-type and mutant PYR/PYL receptor-expressing cells or plants. In some embodiments, the PYR/PYL receptor polypeptide can be expressed in a cell or a plant that is deficient for ABA signaling (e.g., the aba2 mutant, which is deficient for aldehyde oxidase, an enzyme necessary for ABA biosynthesis), and the level of expression of genes downstream of ABA can be compared to the level of expression of the same genes in a wild-type cell or plant expressing the PYR/PYL receptor polypeptide. In some embodiments, the PYR/PYL receptor polypeptide can be expressed in a cell or a plant that is deficient for ABA signaling and the plant evaluated for any phenotype that results from reduced ABA levels (including but not limited to wiltiness, increased sensitivity to multiple abiotic stresses, and non-dormant seeds), then the phenotype can be compared to the phenotype of a wild-type cell or plant expressing the PYR/PYL receptor polypeptide.

One exemplary assay involves testing whether a mutated PYR/PYL receptor can bind to a type 2 protein phosphatase (PP2C) (e.g., Homology to ABI1 (HAB1)) in the absence of ABA. Binding assays can involve contacting a mutated PYR/PY1 receptor polypeptide with a PP2C and allowing sufficient time for the PYR/PYL receptor and PP2C to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. Other binding assays involve the use of mass spectrometry or NMR techniques to identify molecules bound to the PYR/PYL polypeptide. The PYR/PYL polypeptide protein utilized in such assays can be naturally expressed, cloned or synthesized.

In some embodiments, mammalian or yeast two-hybrid approaches (see, e.g., Bartel, P. L. et. al. *Methods Enzymol*, 254:241 (1995)) can be used to identify polypeptides or other molecules that interact or bind when expressed together in a cell. In some embodiments, a constitutively active PYR/PYL polypeptide is identified in a two-hybrid assay between a PYR/PYL polypeptide and a PP2C polypeptide, wherein the PYR/PYL polypeptide and the PP2C bind in the absence of ABA. A wild-type PYR/PYL polypeptide, which does not bind PP2C in the absence of ABA, can be used as a control.

In another exemplary assay, the level of basal activity of a mutated PYR/PYL receptor polypeptide (i.e., level of activity in the absence of ABA) can be determined using an enzymatic phosphatase assay, in which the PYR/PYL receptor and PP2C are incubated in the absence of ABA. In this type of assay, a decrease in phosphatase activity in the absence of ABA is indicative of an activated (constitutively active) PYR/PYL receptor. A decrease in phosphatase activity can be determined and quantified using any detection reagent known in the art, e.g., a colorimetric detection reagent such as para-nitrophenylphosphate.

Constitutively active PYR/PYL receptor polypeptides that are initially identified by any of the foregoing screening methods can be further tested to validate the apparent activity and/or determine other biological effects of the constitutively active PYR/PYL receptor polypeptide. In some cases, the PYR/PYL receptor polypeptide is tested for the ability to affect plant stress (e.g., drought tolerance and/or high salt tolerance), seed germination, or another phenotype affected by ABA. A number of such assays and phenotypes are known in the art and can be employed according to the methods of the invention.

V. Recombinant Expression Vectors

Once a polynucleotide encoding a mutated PYR/PYL receptor polypeptide is obtained, it can also be used to prepare an expression cassette for expressing the mutated PYR/PYL receptor polypeptide in a transgenic plant, directed by a heterologous promoter. Increased expression of mutated PYR/PYL polynucleotide is useful, for example, to produce plants that selectively activate PYR/PYL receptors, thus enhancing stress tolerance.

Any of a number of means well known in the art can be used to drive mutated PYR/PYL activity or expression in plants. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, the mutated PYR/PYL polynucleotide can be expressed specifically in certain cell and/or tissue types within one or more organs (e.g., guard cells in leaves using a guard cell-specific promoter). Alternatively, the mutated PYR/PYL polynucleotide can be expressed constitutively (e.g., using the CaMV 35S promoter).

To use a polynucleotide sequence for a mutated PYR/PYL receptor polypeptide in the above techniques, recombinant DNA vectors suitable for transformation of plant cells are prepared. Techniques for transforming a wide variety of higher plant species are well known and described in the technical and scientific literature. See, e.g., Weising et al. *Ann. Rev. Genet.* 22:421-477 (1988). A DNA sequence coding for the mutated PYR/PYL receptor polypeptide preferably will be combined with transcriptional and translational initiation regulatory sequences which will direct the transcription of the sequence from the gene in the intended tissues of the transformed plant.

For example, a plant promoter fragment may be employed to direct expression of the mutated PYR/PYL polynucleotide in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the mutated PYR/PYL receptor protein in a specific tissue (tissue-specific promoters) or may be otherwise under more precise environmental control (inducible promoters). Examples of tissue-specific promoters under developmental control include promoters that initiate transcription only in certain tissues, such as leaves or guard cells (including but not limited to those described in WO 2005/085449; U.S. Pat. No. 6,653,535; Li et al., *Sci China C Life Sci.* 2005 April; 48(2):181-6; Husebye, et al., *Plant Physiol*, April 2002, Vol. 128, pp. 1180-1188; and Plesch, et al., *Gene*, Volume 249, Number 1, 16 May 2000, pp. 83-89(7)). Examples of environmental conditions that may affect transcription by inducible promoters include anaerobic conditions, elevated temperature, or the presence of light.

If proper protein expression is desired, a polyadenylation region at the 3'-end of the coding region should be included. The polyadenylation region can be derived from a naturally occurring PYR/PYL gene, from a variety of other plant genes, or from T-DNA.

The vector comprising the sequences (e.g., promoters or PYR/PYL coding regions) will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

In some embodiments, the mutated PYR/PYL nucleic acid sequence is expressed recombinantly in plant cells. A variety of different expression constructs, such as expression cassettes and vectors suitable for transformation of plant cells, can be prepared. Techniques for transforming a wide variety of higher plant species are well known and described in the technical and scientific literature. See, e.g., Weising et al. *Ann. Rev. Genet.* 22:421-477 (1988). A DNA sequence coding for a PYR/PYL protein can be combined with cis-acting (promoter) and trans-acting (enhancer) transcriptional regulatory sequences to direct the timing, tissue type and levels of transcription in the intended tissues of the transformed plant. Translational control elements can also be used.

Embodiments of the present invention also provide for a mutated PYR/PYL nucleic acid operably linked to a promoter which, in some embodiments, is capable of driving the transcription of the PYR/PYL coding sequence in plants. The promoter can be, e.g., derived from plant or viral sources. The promoter can be, e.g., constitutively active, inducible, or tissue specific. In construction of recombinant expression cassettes, vectors, transgenics, of the invention, a different promoters can be chosen and employed to differentially direct gene expression, e.g., in some or all tissues of a plant or animal.

Constitutive Promoters

A fragment can be employed to direct expression of a mutated PYR/PYL nucleic acid in all transformed cells or tissues, e.g., as those of a regenerated plant. The term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a plant generally is widely expressed in a large number of cell and tissue types. Promoters that drive expression continuously under physiological conditions are referred to as "constitutive" promoters and are active under most environmental conditions and states of development or cell differentiation.

A variety of constitutive regulatory elements useful for ectopic expression in a transgenic plant are well known in the art. The cauliflower mosaic virus 35S (CaMV 35S) promoter, for example, is a well-characterized constitutive regulatory element that produces a high level of expression in all plant tissues (Odell et al., *Nature* 313:810-812 (1985)). The CaMV 35S promoter can be particularly useful due to its activity in numerous diverse plant species (Benfey and Chua, *Science* 250:959-966 (1990); Futterer et al., *Physiol. Plant* 79:154 (1990); Odell et al., supra, 1985). A tandem 35S promoter, in which the intrinsic promoter element has been duplicated, confers higher expression levels in comparison to the unmodified 35S promoter (Kay et al., *Science* 236:1299 (1987)). Other useful constitutive regulatory elements include, for example, the cauliflower mosaic virus 19S promoter; the Figwort mosaic virus promoter; and the nopaline synthase (nos) gene promoter (Singer et al., *Plant Mol. Biol.* 14:433 (1990); An, *Plant Physiol.* 81:86 (1986)).

Additional constitutive regulatory elements including those for efficient expression in monocots also are known in the art, for example, the pEmu promoter and promoters based on the rice Actin-1 5' region (Last et al., *Theon. Appl. Genet.* 81:581 (1991); Mcelroy et al., *Mol. Gen. Genet.* 231:150 (1991); Mcelroy et al., *Plant Cell* 2:163 (1990)). Chimeric regulatory elements, which combine elements from different genes, also can be useful for ectopically expressing a nucleic acid molecule encoding a mutated PYR/PYL receptor protein (Comai et al., *Plant Mol. Biol.* 15:373 (1990)).

Other examples of constitutive promoters include the 1'- or 2'-promoter derived from T-DNA of *Agrobacterium tumafaciens* (see, e.g., Mengiste (1997) supra; O'Grady (1995) *Plant Mol. Biol.* 29:99-108); actin promoters, such as the *Arabidopsis* actin gene promoter (see, e.g., Huang (1997) *Plant Mol. Biol.* 1997 33:125-139); alcohol dehydrogenase (Adh) gene promoters (see, e.g., Millar (1996) *Plant Mol. Biol.* 31:897-904); ACT11 from *Arabidopsis* (Huang et al. *Plant Mol. Biol.* 33:125-139 (1996)), Cat3 from *Arabidopsis* (GenBank No. U43147, Zhong et al., *Mol. Gen. Genet.* 251:196-203 (1996)), the gene encoding stearoyl-acyl carrier protein desaturase from *Brassica napus* (Genbank No. X74782, Solocombe et al. *Plant Physiol.* 104:1167-1176 (1994)), GPc1 from maize (GenBank No. X15596, Martinez et al. *J. Mol. Riot* 208:551-565 (1989)), Gpc2 from maize (GenBank No. U45855, Manjunath et al., *Plant Mol. Biol.* 33:97-112 (1997)), other transcription initiation regions from various plant genes known to those of skill. See also Holtorf *Plant Mol. Biol.* 29:637-646 (1995).

Inducible Promoters

Alternatively, a plant promoter may direct expression of the mutated PYR/PYL polynucleotide under the influence of changing environmental conditions or developmental conditions. Examples of environmental conditions that may effect transcription by inducible promoters include anaerobic conditions, elevated temperature, drought, or the presence of light. Such promoters are referred to herein as "inducible" promoters. In some embodiments, an inducible promoter is one that is induced by one or more environmental stressors, including but not limited to, drought, freezing cold, and high salt. For example, the invention can incorporate a drought-specific promoter such as a drought-inducible promoter of maize (e.g., the maize rab17 drought-inducible promoter (Vilardell et al. (1991) *Plant Mol. Biol.* 17:985-993; Vilardell et al. (1994) *Plant Mol. Biol.* 24:561-569)); or alternatively a cold, drought, and high salt inducible promoter from potato (Kirch (1997) *Plant Mol. Biol.* 33:897-909) or from *Arabidopsis* (e.g., the rd29A promoter (Kasuga et al. (1999) *Nature Biotechnology* 17:287-291). Other environmental stress-inducible promoters include promoters from the following genes: Rab21, Wsi18, Lea3, Uge1, Dip1, and R1G1B in rice (Yi et al. (2010) *Planta* 232:743-754).

In some embodiments, a plant promoter is a stress-inducible promoter (e.g., a drought-, cold-, or salt-inducible promoter) that comprises a dehydration-responsive element (DRE) and/or an ABA-responsive element (ABRE), including but not limited to the rd29A promoter.

Alternatively, plant promoters which are inducible upon exposure to plant hormones, such as auxins, are used to express the mutated PYR/PYL polynucleotide. For example, the invention can use the auxin-response elements E1 promoter fragment (AuxREs) in the soybean (*Glycine max* L.) (Liu (1997) *Plant Physiol.* 115:397-407); the auxin-responsive *Arabidopsis* GST6 promoter (also responsive to salicylic acid and hydrogen peroxide) (Chen (1996) *Plant J.* 10: 955-966); the auxin-inducible parC promoter from tobacco (Sakai (1996) 37:906-913); a plant biotin response element (Streit (1997) *Mol. Plant Microbe Interact.* 10:933-937); and, the promoter responsive to the stress hormone abscisic acid (Sheen (1996) *Science* 274:1900-1902).

Plant promoters inducible upon exposure to chemicals reagents that may be applied to the plant, such as herbicides or antibiotics, are also useful for expressing the mutated PYR/PYL polynucleotide. For example, the maize In2-2 promoter, activated by benzenesulfonamide herbicide safeners, can be used (De Veylder (1997) *Plant Cell Physiol.* 38:568-577); application of different herbicide safeners induces distinct gene expression patterns, including expression in the root, hydathodes, and the shoot apical meristem. A PYR/PYL coding sequence can also be under the control of, e.g., a tetracycline-inducible promoter, e.g., as described with transgenic tobacco plants containing the *Avena sativa* L. (oat) arginine decarboxylase gene (Masgrau (1997) *Plant J.* 11:465-473); or, a salicylic acid-responsive element (Stange (1997) *Plant J.* 11:1315-1324; Uknes et al., *Plant Cell* 5:159-169 (1993); Bi et al., *Plant J.* 8:235-245 (1995)).

Examples of useful inducible regulatory elements include copper-inducible regulatory elements (Mett et al., *Proc.*

Natl. Acad. Sci. USA 90:4567-4571 (1993); Furst et al., Cell 55:705-717 (1988)); tetracycline and chlor-tetracycline-inducible regulatory elements (Gatz et al., Plant J. 2:397-404 (1992); Roder et al., Mol. Gen. Genet. 243:32-38 (1994); Gatz, Meth. Cell Biol. 50:411-424 (1995)); ecdysone inducible regulatory elements (Christopherson et al., Proc. Natl. Acad. Sci. USA 89:6314-6318 (1992); Kreutzweiser et al., Ecotoxicol. Environ. Safety 28:14-24 (1994)); heat shock inducible regulatory elements (Takahashi et al., Plant Physiol. 99:383-390 (1992); Yabe et al., Plant Cell Physiol. 35:1207-1219 (1994); Ueda et al., Mol. Gen. Genet. 250: 533-539 (1996)); and lac operon elements, which are used in combination with a constitutively expressed lac repressor to confer, for example, IPTG-inducible expression (Wilde et al., EMBO J. 11:1251-1259 (1992)). An inducible regulatory element useful in the transgenic plants of the invention also can be, for example, a nitrate-inducible promoter derived from the spinach nitrite reductase gene (Back et al., Plant Mol. Biol. 17:9 (1991)) or a light-inducible promoter, such as that associated with the small subunit of RuBP carboxylase or the LHCP gene families (Feinbaum et al., Mol. Gen. Genet. 226:449 (1991); Lam and Chua, Science 248:471 (1990)).

Tissue-Specific Promoters

Alternatively, the plant promoter may direct expression of the mutated PYR/PYL polynucleotide in a specific tissue (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistols, flowers, or any embryonic tissue, or epidermis or mesophyll. Reproductive tissue-specific promoters may be, e.g., ovule-specific, embryo-specific, endosperm-specific, integument-specific, seed and seed coat-specific, pollen-specific, petal-specific, sepal-specific, or some combination thereof. In some embodiments, the promoter is cell-type specific, e.g., guard cell-specific.

Epidermal-specific promoters include, for example, the Arabidopsis LTP1 promoter (Thoma et al. (1994) Plant Physiol. 105(1):35-45), the CER1 promoter (Aarts et al. (1995) Plant Cell 7:2115-27), and the CER6 promoter (Hooker et al. (2002) Plant Physiol 129:1568-80), and the orthologous tomato LeCER6 (Vogg et al. (2004) J. Exp Bot. 55:1401-10).

Guard cell-specific promoters include, for example, the DGP1 promoter (Li et al. (2005) Science China C Life Sci. 48:181-186).

Other tissue-specific promoters include seed promoters. Suitable seed-specific promoters are derived from the following genes: MAC1 from maize (Sheridan (1996) Genetics 142:1009-1020); Cat3 from maize (GenBank No. L05934, Abler (1993) Plant Mol. Biol. 22:10131-1038); vivparous-1 from Arabidopsis (Genbank No. U93215); atmyc1 from Arabidopsis (Urao (1996) Plant Mol. Biol. 32:571-57; Conceicao (1994) Plant 5:493-505); napA from Brassica napus (GenBank No. J02798, Josefsson (1987) JBL 26:12196-1301); and the napin gene family from Brassica napus (Sjodahl (1995) Planta 197:264-271).

A variety of promoters specifically active in vegetative tissues, such as leaves, stems, roots and tubers, can also be used to express polynucleotides encoding mutated PYR/PYL receptor polypeptides. For example, promoters controlling patatin, the major storage protein of the potato tuber, can be used, see, e.g., Kim (1994) Plant Mol. Biol. 26:603-615; Martin (1997) Plant J. 11:53-62. The ORF13 promoter from Agrobacterium rhizogenes that exhibits high activity in roots can also be used (Hansen (1997) Mol. Gen. Genet. 254:337-343. Other useful vegetative tissue-specific promoters include: the tarin promoter of the gene encoding a globulin from a major taro (Colocasia esculenta L. Schott) corm protein family, tarin (Bezerra (1995) Plant Mol. Biol. 28:137-144); the curculin promoter active during taro corm development (de Castro (1992) Plant Cell 4:1549-1559) and the promoter for the tobacco root-specific gene TobRB7, whose expression is localized to root meristem and immature central cylinder regions (Yamamoto (1991) Plant Cell 3:371-382).

Leaf-specific promoters, such as the ribulose biphosphate carboxylase (RBCS) promoters, can also be used. For example, the tomato RBCS1, RBCS2 and RBCS3A genes are expressed in leaves and light-grown seedlings, only RBCS1 and RBCS2 are expressed in developing tomato fruits (Meier (1997) FEES Lett. 415:91-95). A ribulose bisphosphate carboxylase promoters expressed almost exclusively in mesophyll cells in leaf blades and leaf sheaths at high levels, described by Matsuoka (1994) Plant J. 6:311-319, can be used. Another leaf-specific promoter is the light harvesting chlorophyll a/b binding protein gene promoter, see, e.g., Shiina (1997) Plant Physiol. 115:477-483; Casal (1998) Plant Physiol. 116:1533-1538. The Arabidopsis thaliana myb-related gene promoter (Atmyb5) described by Li (1996) FEBS Lett. 379:117-121, is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize by Busk (1997) Plant J. 11:1285-1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio (1996) Cell 86:423-433; and, Long (1996) Nature 379:66-69; can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto (1995) Plant Cell. 7:517-527). Also useful are kn1-related genes from maize and other species which show meristem-specific expression, see, e.g., Granger (1996) Plant Mol. Biol. 31:373-378; Kerstetter (1994) Plant Cell 6:1877-1887; Hake (1995) Philos. Trans. R. Soc. Lond. B. Biol. Sci. 350:45-51. For example, the Arabidopsis thaliana KNAT1 promoter (see, e.g., Lincoln (1994) Plant Cell 6:1859-1876).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, the mutated PYR/PYL polynucleotide is expressed through a transposable element. This allows for constitutive, yet periodic and infrequent expression of the constitutively active polypeptide. The invention also provides for use of tissue-specific promoters derived from viruses including, e.g., the tobamovirus subgenomic promoter (Kumagai (1995) *Proc. Natl. Acad. Sci. USA* 92:1679-1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) *Plant Mol. Biol.* 31:1129-1139).

VI. Production of Transgenic Plants

In another aspect, the present invention provides for transgenic plants comprising recombinant expression cassettes for expressing a constitutively active PYR/PYL receptor protein as described herein in a plant. In some embodiments, a transgenic plant is generated that contains a complete or partial sequence of a polynucleotide that is derived from a species other than the species of the transgenic plant. It should be recognized that transgenic plants encompass the plant or plant cell in which the expression cassette is introduced as well as progeny of such plants or plant cells that contain the expression cassette, including the progeny that have the expression cassette stably integrated in a chromosome.

A recombinant expression vector comprising a PYR/PYL coding sequence driven by a heterologous promoter may be introduced into the genome of the desired plant host by a variety of conventional techniques. For example, the DNA construct may be introduced directly into the genomic DNA of the plant cell using techniques such as electroporation and microinjection of plant cell protoplasts, or the DNA construct can be introduced directly to plant tissue using ballistic methods, such as DNA particle bombardment. Alternatively, the DNA construct may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. While transient expression of the constitutively active PYR/PYL receptor is encompassed by the invention, generally expression of construction of the invention will be from insertion of expression cassettes into the plant genome, e.g., such that at least some plant offspring also contain the integrated expression cassette.

Microinjection techniques are also useful for this purpose. These techniques are well known in the art and thoroughly described in the literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example, Horsch et al. *Science* 233:496-498 (1984), and Fraley et al. *Proc. Natl. Acad. Sci. USA* 80:4803 (1983).

Transformed plant cells derived by any of the above transformation techniques can be cultured to regenerate a whole plant that possesses the transformed genotype and thus the desired phenotype such as enhanced abiotic stress resistance. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture*, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987). One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The expression cassettes of the invention can be used to confer abiotic stress resistance on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna,* and, *Zea*. In some embodiments, the plant is selected from the group consisting of rice, maize, wheat, soybeans, cotton, canola, turfgrass, and alfalfa. In some embodiments, the plant is an ornamental plant. In some embodiment, the plant is a vegetable- or fruit-producing plant.

Those of skill will recognize that a number of plant species can be used as models to predict the phenotypic effects of transgene expression in other plants. For example, it is well recognized that both tobacco (*Nicotiana*) and *Arabidopsis* plants are useful models of transgene expression, particularly in other dicots.

In some embodiments, the plants of the invention have enhanced ABA-mediated phenotypes, for example enhanced seed dormancy, as compared to plants that are otherwise identical except for expression of the constitutively active PYR/PYL receptor polypeptide. Those of skill in the art will recognize that ABA is a well-studied plant hormone and that ABA mediates many changes in characteristics, any of which can be monitored to determine changes in phenotype. In some embodiments, an enhanced ABA-mediated phenotype is manifested by altered timing of seed germination or altered stress (e.g., drought, freezing cold, and/or salt) tolerance.

Abiotic stress resistance can assayed according to any of a number of well-known techniques. For example, for drought tolerance, plants can be grown under conditions in which less than optimum water is provided to the plant. Drought resistance can be determined by any of a number of standard measures including turgor pressure, growth, yield, and the like. In some embodiments, a transgenic plant expressing a mutated PYR/PYL receptor as described herein has enhanced drought tolerance if the loss of turgor in the transgenic plant is reduced by at least about 10%, 15%, 20%, 25%, 30%, 40%, 50%, 60%, 70%, 80%, 90%, or more as compared to a non-transgenic control plant over a defined period of time (e.g., over the course of 5, 6, 7, 8, 9, 10, 11, 12, 13, 14 days or more, e.g., 3, 4, 5 weeks or more).

In some embodiments, the enhanced ABA-mediated phenotype is enhanced tolerance to moderate or high salinity. Salinity tolerance can be determined by any of a number of standard measures, including germination, growth, yield, or plant survival, leaf injury, premature loss of chlorophyll, and the like. In some embodiments, transgenic plants expressing a mutated PYR/PYL receptor as described herein have enhanced salt tolerance if the survival of the transgenic plants under moderate-salt or high-salt conditions (e.g., about 50 mM, 100 mM, 150 mM, 200 mM, 250 mM, 300 mM NaCl or higher) is increased by at least about 10%, 15%, 20%, 25%, 30%, 40%, 50%, 60%, 70%, 80%, 90%, or more as compared to a non-transgenic control plant over a defined period of time (e.g., over the course of 5, 6, 7, 8, 9, 10, 11, 12, 13, 14 days or more, e.g., 3, 4, 5 weeks or more).

EXAMPLES

The following examples are offered to illustrate, but not to limit the claimed invention.

Example 1

Saturation Mutagenesis of PYR1 Identifies Activating Mutations that Increase PYR1-PP2C Interactions To define sites that can be mutated to improve interactions between PYR/PYL receptors and PP2Cs, we conducted saturation mutagenesis on 39 residues in PYR1 that normally contact ABA (i.e., are within the ligand-binding pocket of PYR1) and/or PP2Cs (i.e., are within the PP2C binding interface). All 741 single-mutant variants possible at these functionally critical locations were constructed and then assayed for PP2C interactions using a yeast two-hybrid based assay. Saturation mutagenesis is a method that involves the construction of all possible amino acid variants at a given site (i.e., the generation of all 19 substitution mutants per site). We focused mutagenesis efforts on PYR1 because it is a well-characterized member of the PYR/PYL receptor family and has extensive structural data on which to guide mutagenesis studies, although it should be noted that the sites targeted display high sequence conservation among the PYR/PYL receptors (FIG. 1). Moreover, PYR1 is well suited for functional studies because its low basal activity allows its activation status to be studied using a yeast-based two-hybrid assay in which wild-type PYR1 will only bind to the PP2C HAB1 (or other PP2Cs) when the appropriate yeast cells are grown in the presence of ABA. Thus, this assay allows mutations that activate PYR1 to be identified as those that stimulate reporter gene expression in the absence of added ABA.

Sites selected for our mutagenesis study were guided by crystallographic data for ABA-bound PYR1 and an ABA-PYR-HAB1 ternary complex (Santiago et al., 2009; Nishimura et al., 2009; Dupeux et al., 2011). Residues within 5 Å of ABA or PP2C were targeted for mutagenesis, with the exception of R116, which forms an architecturally important salt bridge (Santiago et al., 2009; Nishimura et al., 2009). In total, 39 target sites were selected for mutagenesis and ultimately a total of 741 PYR1 mutants were generated by site-directed mutagenesis.

Mutants were created using the QuikChange® site-directed mutagenesis kit (Stratagene) using primers that contain random nucleotides (i.e., NNN) at the target position. In addition, each reaction contained a small amount of M and W codon primers to enrich the frequency of rare codons. Site-directed mutagenesis reactions were conducted on pBD GAL4-PYR1 template (Park et al., 2009), digested with DpnI, and transformed into competent *Escherichia coli* DH5a cells. Plasmid DNA for 96 colonies per site was isolated using Bioneer AccuPrep® Plasmid Mini Extraction Kit (Alameda, Calif.) and sequenced to identify mutants; this typically identified about 13 of the 19 desired mutations per target site. The remaining mutations at each site were constructed with specific mutagenic primers. This process was conducted for all 39 target sites to yield a set of 741 sequence-validated mutant PYR1 clones. The vector template used, pBD-GAL4-PYR1, expresses a GAL4 DNA binding domain (BD)—PYR1 fusion protein when transformed into suitable yeast strains. Mutants were also created using the QuikChange lightning multi-site directed mutagenesis kit (Agilent Technologies, USA), as described in Example 5.

To interrogate the effects of mutations on PP2C interactions, the mutant clones were individually transformed into *S. cerevisiae* strain Y190 containing pACT-HAB1 (Park et al., 2009), which expresses a GAL4 activation domain—HAB1 fusion protein. Yeast transformants were selected for the presence of plasmids on selective SD agar plates lacking Leu and Trp and examined for PP2C interactions by using X-Gal staining to monitor β-gal reporter gene expression levels. 29 of the 741 mutants, located in 10 different residues, increased PYR1-HAB1 interaction in the absence of added ABA (Table 1 and FIG. 2). By increasing PYR-PP2C binding, the identified mutants are expected to increase basal receptor activity. As a control for this expectation and to explore the efficacy of our mutant set, the coding sequences for 8 PYR1 mutants (H60P, V83F, I84Q, A89W, M158I, F159V, T162F, and K170W) were cloned as 6xHis (SEQ ID NO:173) fusion proteins in the vector pET-28a, expressed in *E. coli*, and purified using previously described methods (Park et al., 2009), and then tested for their effects on HAB1 phosphatase activity at different PYR1:PP2C stoichiometry.

Recombinant receptor proteins were produced as follows: Coding sequences were cloned into pET28 yielding 6xHIS (SEQ ID NO:173) fusions proteins and transformed into *E. coli* expression strain BL21. To prepare recombinant protein, 1 ml of an overnight culture was inoculated to 50 ml TB (1.2% peptone, 2.4% yeast extract, 72 mM K2HPO4, 17 mM KH2PO4, and 0.4% glycerol 1) and was grown for additional 2 hours at 30° C. with shaking Protein expression was induced by addition of IPTG to 1 mM. Cells were harvested 6 hr later by centrifugation for 15 min at 5000xg and the pellet was resuspended in 5 ml of the Buffer A (50 mM NaH2PO4, 300 mM NaCl) containing 10 mM imidazole, pH 8.0). Cells were stored at −80° C. before purification. After thawing, cells were sonicated on ice five times for 30 sec with 30 sec resting intervals. A cleared lysate was obtained after centrifugation at 12,000xg for 10 min and applied to 1 ml of Ni-NTA column (Qiagen) and washed with 20 column volumes of Buffer A containing 30 mM imidazole. Bound protein was eluted with 10 ml of Buffer A with 250 mM imidazole. The elutate was dialyzed against TBS. The purified recombinant proteins were then used together with recombinant phosphatases in receptor assays. In these assays, receptor activity is indicated by inhibition of phosphatase activity, as inferred from initial reaction velocities for GST-HAB1 mediated hydrolysis of the synthetic phosphatase substrate pNPP. Reactions contained 600 nM GST-HAB1 and either 0, 600, 1200, 2400 or 4800 nM 6xHis-PYR1 or variants in a reaction buffer consisting of 33 mM Tris-OAc, pH 7.9, 66 mM KOAc, 0.1% BSA, 25 mM Mn(OAc)2, 50 mM pNPP. To infer the level of receptor activation with respect to fully activated wild type receptor, control reactions were also conducted using saturating levels of (+)-ABA (10 μM), and 600 nM wild type PYR1 and HAB1. Immediately after mixing proteins and substrates, reactions were monitored for hydrolysis of pNPP at $A_{405}$ at ~10 second intervals over 20 minutes using a Wallac plate reader. Reaction progressions were plotted, initial velocities calculated and converted to specific activities using a standard curve for 4-nitrophenol made in the same buffer system volumes/plate reader used for enzymatic reaction measurements. The values shown are expressed as %-control phosphatase activity levels as measured in the absence of receptor protein. The average specific activity level of GST-HAB1 utilized in our experiments was 4000 μmol/min/mg, when assayed on the phosphatase substrate pNPP in the absence of PYR1 or other receptors, as described using the methods above.

As shown in FIG. 2, FIG. 15 and FIG. 17, each of the activating mutants increased basal receptor activity in comparison to wild-type PYR1. These results demonstrate that the PP2C binding reported using the Y2H assay faithfully reflects differences in basal receptor activation status. Thus, our mutagenesis strategy has systematically defined a comprehensive set of mutations that can be used to improve PYR/PYL-PP2C interactions and increase basal receptor activation levels. We note that to date, full CA mutants have not been described for any ABA receptor and that PYL6 and PYL10, which have high basal activities (Melcher K, et al. (2010); Hao Q, et al. (2011) *Mol Cell* 42 (5):662-672), are not full CA receptors (See FIG. 14 and FIG. 17).

TABLE 1

Mutation sites and strength of activating mutations identified

| Residue | Contact Type | Activating Mutations Defined | Strength of Activating Mutations +++ | ++ | + |
|---|---|---|---|---|---|
| P55 | LIG | | | | |
| K59 | LIG | | | | |
| H60 | LIG + PPI | P, G, R, A, W, I, K, V, M | P, G | R, A | W, I, K, V, M |
| F61 | LIG + PPI | | | | |
| I62 | LIG + PPI | | | | |
| K63 | PPI | | | | |
| V81 | LIG | | | | |
| V83 | LIG | F, L, P | F | L | P |
| I84 | PPI | Q, E, P, H, K | Q | E, P, H | K |
| S85 | PPI | | | | |
| G86 | PPI | | | | |
| L87 | LIG + PPI | F | | F | |
| P88 | LIG + PPI | | | | |
| A89 | LIG + PPI | W | W | | |
| S92 | LIG | | | | |
| E94 | LIG | | | | |
| F108 | LIG | | | | |
| I110 | LIG | | | | |
| H115 | LIG + PPI | | | | |
| R116 | LIG + PPI | | | | |
| L117 | LIG + PPI | | | | |
| Y120 | LIG | | | | |
| S122 | LIG | | | | |
| E141 | LIG | | | | |
| P148 | PPI | | | | |
| G150 | PPI | | | | |
| N151 | PPI | | | | |
| D154 | PPI | | | | |
| D155 | PPI | | | | |
| T156 | PPI | | | | |
| M158 | PPI | T, C, V, I | T, C | V | I |
| F159 | LIG + PPI | V, A | V | | A |
| A160 | LIG | | | | |
| T162 | PPI | F | F | | |
| V163 | LIG + PPI | | | | |
| V164 | LIG | | | | |

TABLE 1-continued

Mutation sites and strength of activating mutations identified

| Residue | Contact Type | Activating Mutations Defined | Strength of Activating Mutations +++ | ++ | + |
|---|---|---|---|---|---|
| L166 | PPI | Y, F | | | Y, F |
| N167 | LIG | | | | |
| K170 | PPI | W | W | | |

LIG = Ligand-binding pocket residue
PPI = PP2C binding interface residue
LIG + PPI = Ligand-binding pocket residue and PP2C binding interface residue With the exception of mutations at V83, all of the activating mutations tested in FIG. 2 are located in residues that lie at the PYR1-PP2C or PYR1-PYR1 interaction interfaces. Residue V83 is located on the edge of the "gate" loop, and its hydrophobic side chain points into the ABA binding pocket and forms close contact with ABA in ABA-bound receptor structures. We hypothesize that the activating mutations at this site may mimic ligand occupancy and consequently stabilize the closed form of the gate. Another gate residue, L87, can also be mutated to result in receptor activation. Residue M158 is located in the pore that interacts with the PP2C tryptophan lock residue and is also positioned to directly stabilize PYR/PYL-PP2C interactions.

Example 2

Strong Constitutively Active Receptors can be Engineered by Combining Activating Mutations To establish that the activating mutations can be combined to further enhance receptor activation, we constructed a triple mutant (H60P, V83F, F159V) called PYR1$^{CA3}$ and a quadruple mutant (H60P, V83F, F159V, M158I) called PYR1$^{CA4}$ using the Quickchange Lightening multi-site directed mutagenesis kit (Agilent; USA). The mutant clones were sequence validated and recombinant proteins produced in *E. coli* and utilized in PP2C assays as described above. As shown in FIG. 3, both the triple and quadruple mutants dramatically increased basal PYR1 activity relative to wild-type PYR1. Importantly, the constitutively active (CA) alleles interact with ABI1 and ABI2, in addition to HAB1, demonstrating that their constitutive activity is not restricted to particular PP2Cs within the groups of ABA-regulated phosphatases. This demonstrates that single activating mutations can be combined to create mutant proteins with enhanced basal activation levels.

Additional quadruple mutants PYR1$^{CA4B}$ (V83F, M158I, F159V, K170W) and PYR1$^{CA4C}$ (H60P, A89W, M158I, F159V) were constructed to enhance receptor activation. As shown in FIG. 9, FIG. 16, and FIG. 17, both the PYR1$^{CA4B}$ and PYR1$^{CAc}$ mutants dramatically increased basal PYR1 activity relative to wild-type PYR1. Thus, combinations of four single activating mutations can be combined to create mutant proteins with enhanced basal activation levels.

Example 3

Activating Mutations Function in Diverse PYR/PYL Receptors

As described previously, the sites that can be mutated to activate PYR1 are highly conserved across the PYR/PYL receptor family (FIG. 1) and it is therefore expected that the activating mutations identified in PYR1 can be used to activate other receptors. To test this hypothesis, mutations homologous to the PYR1 triple or quadruple mutants described in Example 2 were introduced into PYL2 to generate the mutants PYL2$^{CA3}$ (H65P, V87F, F165V) and PYL2$^{CA4}$ (H65P, V87F, M164I, F165V). The mutations were also introduced into PYL9 to create the PYL9$^{CA4}$ mutant (V85F, Y160I, F161V) using the Lightening multi-site directed mutagenesis kit. Recombinant proteins were produced as described above in Example 2. As shown in FIG. 4, the mutant proteins were highly activated in the absence of ABA in comparison to wild-type PYL2 or PYL9, demonstrating that activating mutations can be transplanted into other receptors in the ABA receptor family. As observed with PYR1 CA alleles, the PYL2 and PYL9 CA alleles are active towards multiple PP2Cs (FIG. 4).

Further, mutations homologous to the quadruple mutant CA4C described above were introduced into PYL2 to create the PYL2$^{CA4C}$ mutant (H65P, A93W, M164I, F165V). The homologous mutations were also introduced into PYL9 to create the PYL9$^{CA4C}$ mutant (A91W, Y160I, F161V) as described above. As shown in FIG. 16 and FIG. 17, the mutant proteins were highly activated in the absence of ABA in comparison to wild-type PYL2 or PYL9. Thus, combining a small number of specific partially-activating mutations enables full activation of diverse receptors, despite only 55% and 49% amino acid sequence identity between PYL2-PYR1 and PYL9-PYR1 respectively.

Example 4

In Planta Activation of ABA Signaling by Constitutively Active Receptors

The activating mutations identified by our work are expected to increase ABA signaling above basal levels when expressed in plants. Such activation can be quantified in a number of ways, including analyses of ABA-regulated gene expression and characterization of ABA-mediated physiological responses in transgenic plants expressing the constitutively active or control wild-type receptor proteins. We therefore made two sets of transgenic plants expressing wild-type PYL2 or PYL2$^{CA3}$ in either the wild-type Columbia background or an aba2-1 mutant background. The aba2 mutant is defective in ABA aldehyde oxidase, an enzyme necessary for ABA biosynthesis. The aba2 mutant possesses a number of phenotypes that result from reduced ABA levels, including wiltiness, increased sensitivity to multiple abiotic stresses, and non-dormant seeds. In addition, its seed germination does not require gibberellin (GA) biosynthesis, unlike the wild-type which requires GA for germination. As a result, aba2 mutants are resistant to the effects of GA biosynthesis inhibitors (such as paclobutrazole). If PYL2$^{CA3}$ effectively activates ABA signaling, it should be able to suppress the effects of ABA depletion in the aba2 mutant and affect ABA regulated gene expression in both the wild-type and aba2 strains.

To create the desired transgenic plants, the coding sequences of PYL2 and PYL2$^{CA3}$ were cloned into a modified version of the vector pEGAD to create 35S-driven GFP-PYL fusion proteins. Prior work has demonstrated that N-terminal GFP fusion tags do not interfere with PYL receptor function (Park et al., 2009); the virtue of using a GFP tag is that it enables rapid monitoring of fusion protein levels in transgenic plants as well as lines that display transgene silencing. The constructs created were sequence validated and then introduced into Columbia or the aba2-1 mutant using *agrobacterium*-mediated transformation via the floral dip method. For each genotype constructed, approximately 40 primary transgenic plants were identified by glufosinate resistance or GFP expression in T1 seedlings, and single-insertion homozygous lines were then isolated from the progeny of 10 T1 lines; two independent PYL2$^{CA3}$ single insertion lines were characterized. Interestingly, we observed that all of the PYL2$^{CA3}$ transgenics obtained in both the wild-type and aba2 backgrounds displayed detectable GFP expression in developing and imbibed seeds, but undetectable expression after germination stages. Our inability to recover PYL2$^{CA3}$ transgenics with post-germination expression from a total of greater than 80 lines analyzed suggests that there may have been selection against high-level transgene expression after germination; this was not observed for wild-type PYL2 overexpressing transgenics, suggesting that selection acted specifically against the PYL2$^{CA3}$ allele, possibly indicating toxicity of the CA3 allele in adult plants when expressed under the constitutive 35S promoter.

To investigate the effects of the PYL2$^{CA3}$ allele, we performed a number of physiological assays on wild-type and aba2-1 genotypes. Columbia (Col), 35S::PYL2, and 35S::PYL2$^{CA3}$ seed samples were divided into two portions; one portion was stratified on ⅓ MS plates for 6 days at 4° C. and the second portion was plated six days later ⅓ MS plates. Both samples were the transferred to room temperature (23° C.) and incubated in darkness. A seed was scored as positive for germination if it possessed a radical at least ½ the length of the seed. Each experiment was performed in triplicate and each point plotted represents the average of tests conducted using 40 to 70 seeds. As shown in FIG. 5 and FIG. 11, in the wild-type Columbia background, overexpression of the PYL2$^{CA3}$, but not wild-type PYL2, induces a state of hyperdormancy in seeds as indicated by the stratification dependent germination of PYL2$^{CA3}$ lines. Seed dormancy is induced by ABA and it is well established that mutants with increased ABA sensitivity have higher seed dormancy; for example, the enhanced response to aba1 (era1) mutation shows a similar stratification requirement (Cutler et al., 1996). Thus, overexpression of PYL2$^{CA3}$ activates the ABA-regulated seed dormancy pathway.

To investigate if other ABA responses are affected in the PYL2$^{CA3}$ lines, we profiled the expression levels of several ABA-regulated genes using quantitative RT-PCR (qRT-PCR). For these experiments, seeds of Col, 35S::PYL2, and two independent 35S:: PYL2$^{CA3}$ transgenic lines were imbibed for 32 hours in either water or 5 μM ABA at room temperature under continuous illumination, after which RNA was isolated using Concert™ Plant RNA Reagent and utilized in qRT-PCR reactions using primers for the ABA-regulated genes Em6 (At2g40170), LEA (At2g21490), and Rd29b (At5g52300). Biological duplicates with triple technical replicate measurements were conducted and gene expression levels were determined. For qRT-PCR analyses of gene expression, cDNA was generated from 5 μg of total RNA using superscript reverse transcriptase II (Invitrogen), in a reaction mixture containing a oligo-dT$_{20}$ (SEQ ID NO:174) and ribosomal RNA primer (5'-ACATCTAAGGGCATCACAGAC-3'; SEQ ID NO:175). Real-time quantitative PCR analysis was performed by ΔΔCt method of relative quantification. PCR mixtures contained 2 μl of cDNA, 7.5 μl of 2× Maxima® SYBR grean/Fluorescein qPCR master mix (2×) (Fermentas) and 330 nM of each gene-specific primer in a final volume of 15 μl. The RT-PCRs were done using BioRad CFX96 Real-Time System and BioRad CFX Manager software (BioRad). PCRs were performed under the following conditions: 3 min at 95° C., and 40 cycles of 10 s at 95° C., 10 s at 55° C. and 30 s 72° C. in 96-well optical reaction plates (BioRad). The specificity of amplicons was verified by melting curve (disassociation) analysis (60-95° C.) after 40 cycles. Input cDNA was normalized using rRNA primers. The following primers were used to detect specific gene expression levels: Em6 (At2g40170) TCGAAGCTCAACAGCATCTC (SEQ ID NO:176) and ACTGCTCCTTTCGAGTTTGC (SEQ ID NO:177), LEA (At2g21490) CGTCGGTCTGGAAGT-TCATC (SEQ ID NO:178) and TCTTCTTCCTCCTC-CCTCCT (SEQ ID NO:179), Rd29b (At5g52300) ATC-CGAAAACCCATAGTCC (SEQ ID NO:180) and TGGTGGGGAAAGTTAAAGGA (SEQ ID NO:181), and rRNA AAACGGCTACCACATCCAAG (SEQ ID NO:182) and GACTCGAAAGAGCCCGGTAT (SEQ ID NO:183). As shown in FIG. 6 and FIG. 12, two independent PYL2$^{CA3}$ transgenic lines display elevated levels of ABA-regulated genes in the absence of ABA treatment. The expression levels of these genes are comparable (FIG. 6) or elevated (FIG. 12) with respect to the levels observed in wild-type seeds treated with 5 μM ABA. Thus, the PYL2$^{CA3}$ allele causes high-level induction of several ABA-regulated genes, consistent with the conclusion that the PYL2$^{CA3}$ activates ABA signaling in vivo comparable to ABA treatment.

As a further test of the ability of PYL2$^{CA3}$ to activate ABA signaling in vivo, we examined the ability of this allele to revert phenotypes caused by ABA deficiency, reasoning that effective activation of the ABA pathway should suppress phenotypes observed in the aba2 mutant. Since aba2 mutants have greatly reduced ABA levels, the aba2 genetic background provides a stringent test for constitutive activation of signaling, which by definition should be ABA-independent. To test this, we examined the germination of various genotypes on paclobutrazol, an inhibitor of GA biosynthesis. Wild-type seed germination is blocked by paclobutrazol treatment but aba2 mutants germinate due to defects in ABA-induced seed dormancy. We also examined the germination of various genotypes in the presence of NaCl, which, like paclobutrazole, inhibits seed germination in an ABA- and aba2-dependent manner (Gonzalez-Guzman M. et al. (2002) *Plant Cell* 14(8):1833-1846; Leon-Kloosterziel K M, et al. (1996) *Plant J* 10 (4):655-661). Consistent with our observations made in wild-type plants overexpressing PYL2$^{CA3}$, the PYL2$^{CA3}$ transgene suppressed the paclobutrazol and NaCl resistance observed in the aba2 mutants, while overexpression of wild-type PYL2 was unable to suppress this aba2 phenotype (FIG. 7 and FIG. 13). Thus, expression of PYL2$^{CA3}$ in developing seeds is sufficient to activate an ABA-dependent physiological process despite the depleted ABA levels present in the aba2 background. Collectively, our body of data demonstrates that the PYL2$^{CA3}$ is a potent activator of ABA responses in transgenic plants and that activating mutations can be used to modulate ABA signaling in vivo.

Example 5

Methods

Site-Saturation Mutagenesis

Mutants were created using one of two methods. About half the mutants were made using the QuikChange site-directed mutagenesis kit (Stratagene, USA) using primers that contain random nucleotides (i.e., NNN) at target position (see Table 2 for a list of all mutagenesis primer sequences used). 20 μL mutagenesis reactions were conducted using pBD GAL4-PYR1 template (Park et al. (2009) *Science* 324 (5930):1068-1071), as per the manufacturers' instructions, containing 10 pmol NNN primer and 0.5 pmol each of M- and W-encoding primers, which were added to enrich the frequency of rare codons. Plasmid DNA for 96 colonies per site was isolated using Bioneer AccuPrep® Plasmid Mini Extraction Kit (Alameda, Calif.) and sequenced to identify mutants, which identified on average 12 of the 19 desired mutations per target site per 96 clones sequenced. In the second mutagenesis method we made mutations using the QuikChange lightning multi-site directed mutagenesis kit (Agilent Technologies, USA) using a phosphorylated primer that instead of NNN at the mutagenesis target site contained the sequence NNK, which reduces degeneracy (Kretz K A, et al. (2004) *Methods Enzymol* 388:3-11). Plasmid DNA for 96 colonies per site was isolated using Beckman Multimek 96 robot and Perfectprep Vac kit (5 Prime Inc., USA) and sequenced, which identified 14 of the 19 desired mutations per 96 clones sequenced on average. Mutations not identified by sequencing of random clones were constructed with specifically designed mutagenic primers using the QuickChange® lightning multi-site directed mutagenesis kit (Agilent Technologies, USA). This process was conducted for all 39 target sites to ultimately yield a set of 741 sequence-validated mutant PYR1 clones.

TABLE 2

Mutagenesis primers

| Primer name | Primer sequence | SEQ ID NO |
|---|---|---|
| pyl2A93W | CTCCGGCCTCCCAtggTCAACCAGTACCGAGC | 184 |
| pyl2A93W+ | CTCCGGCCTCCCATGGTCAACCAGTACCGAGC | 184 |
| pyl2V87F | CAGAGAAGTGACCtttATCTCCGGCCTCCC | 185 |
| pyl2V87F+ | CAGAGAAGTGACCTTTATCTCCGGCCTCCC | 185 |
| PYR1R116# | CATCGGAGGCGAACATnnkCTGACGAATTACAAATCCg | 186 |
| PYR1R116E | CATCGGAGGCGAACATGAGCTGACGAATTACAAATCCg | 187 |
| PYR1R116E | CATCGGAGGCGAACATGAGCTGACGAATTACAAATCCg | 187 |
| PYR1R116H | CATCGGAGGCGAACATCATCTGACGAATTACAAATCCg | 188 |
| PYR1R116H | CATCGGAGGCGAACATCATCTGACGAATTACAAATCCg | 188 |

TABLE 2-continued

Mutagenesis primers

| Primer name | Primer sequence | SEQ ID NO |
|---|---|---|
| PYR1R116I | CATCGGAGGCGAACATATTCTGACGAATTACAAATCCg | 189 |
| PYR1R116I | CATCGGAGGCGAACATATTCTGACGAATTACAAATCCg | 189 |
| PYR1R116T | CATCGGAGGCGAACATACCCTGACGAATTACAAATCCg | 190 |
| PYR1R116T | CATCGGAGGCGAACATACCCTGACGAATTACAAATCCg | 190 |
| PYR1R116Y | CATCGGAGGCGAACATTATCTGACGAATTACAAATCCg | 191 |
| PYR1R116Y | CATCGGAGGCGAACATTATCTGACGAATTACAAATCCg | 191 |
| PYL2E147K | CACGGTGGTTCTTaAATCTTACACCGTTGATATTCc | 192 |
| PYL2E147L | CACGGTGGTTCTTTTATCTTACACCGTTGATATTCc | 193 |
| PYL2E98D | CCTCAACCAGTACCGAtCGGCTTGAGTTCGTC | 194 |
| pyl2F165V+ | GAGGAAGACACTAAAATGGTTGTGGACACTGTCGTC | 195 |
| pyl2F165V+ | GAGGAAGACACTAAAATGGTTGTGGACACTGTCGTC | 195 |
| pyl2H60P+ | cCGAACGCTACAAACcCTTTGTAAAAGGTGCc | 196 |
| PYL2H65P+ | CCGAACGCTACAAACCCTTTGTAAAAGGTGCC | 196 |
| PYL2K64L | CAACCCCGAACGCTACTTACACTTTGTAAAAGGTGC | 197 |
| pyl2m158I, f159v+ | CAGAGGAAGACACTAAAATcGTTGTGGACACTGTCG | 198 |
| PYL2V85I | GGAAGCGTCAGAGAAatcACCGTAATCTCCGGCC | 199 |
| PYL9A91W+ | TGTTAAATCTGGTCTTCCTTGGACAACATCTACTGAGAG | 200 |
| PYL9 A91WV85F+ | GCAGTCTTAGAGAAGTCAATTTTAAATCTGGTCTTCCTTGGACAACATCTACTGAGAG | 201 |
| PYL9F161V+ | GATGAGACTTGCTACGTTGTTGAAGCACTTATCAG | 202 |
| PYL9V85F+ | GTCTTAGAGAAGTCAATTTTAAATCTGGTCTTCCTG | 203 |
| PYR1A160# | GGATGATACTCGTATGTTTnnkGATACGGTTGTGAAGC | 204 |
| PYR1A160E | GGATGATACTCGTATGTTTgagGATACGGTTGTGAAGC | 205 |
| PYR1A160H | GGATGATACTCGTATGTTTcatGATACGGTTGTGAAGC | 206 |
| PYR1A160K | GGATGATACTCGTATGTTTaaaGATACGGTTGTGAAGC | 207 |
| PYR1A160N | GGATGATACTCGTATGTTTaatGATACGGTTGTGAAGC | 208 |
| PYR1A160Q | GGATGATACTCGTATGTTTcaaGATACGGTTGTGAAGC | 209 |
| PYR1A160T | GGATGATACTCGTATGTTTactGATACGGTTGTGAAGC | 210 |
| PYR1A89M+ | CATCAGTGGATTACCGATGAACACATCAACGGAAAG | 211 |
| pyr1a89N+ | catcagtggattaccgAACaacacatcaacggaaag | 212 |
| PYR1A89NNN- | CTTTCCGTTGATGTGTTNNNCGGTAATCCACTGATG | 213 |
| PYR1A89NNN+ | CATCAGTGGATTACCGNNNAACACATCAACGGAAAG | 214 |
| PYR1A89W+ | CATCAGTGGATTACCGTGGAACACATCAACGGAAAG | 215 |
| pyr1a89Y+ | catcagtggattaccgTACaacacatcaacggaaag | 216 |
| PYR1D154F | CCGGAAGGTAACTCGGAGTTTGATACTCGTATGTTTGCTG | 217 |
| PYR1D154F | CCGGAAGGTAACTCGGAGTTTGATACTCGTATGTTTGCTG | 217 |
| PYR1D154I | CCGGAAGGTAACTCGGAGATTGATACTCGTATGTTTGCTG | 218 |

TABLE 2-continued

Mutagenesis primers

| Primer name | Primer sequence | SEQ ID NO |
|---|---|---|
| PYR1D154I | CCGGAAGGTAACTCGGAGATTGATACTCGTATGTTTGCTG | 218 |
| PYR1D154M | CCGGAAGGTAACTCGGAGATGGATACTCGTATGTTTGCTG | 219 |
| PYR1D154M | CCGGAAGGTAACTCGGAGATGGATACTCGTATGTTTGCTG | 219 |
| PYR1D154Y | CCGGAAGGTAACTCGGAGTATGATACTCGTATGTTTGCTG | 220 |
| PYR1D155# | GGAAGGTAACTCGGAGGATnnkACTCGTATGTTTGCTGATAC | 221 |
| PYR1D155E | GGAAGGTAACTCGGAGGATgaaACTCGTATGTTTGCTGATAC | 222 |
| PYR1D155H | GGAAGGTAACTCGGAGGATcatACTCGTATGTTTGCTGATAC | 223 |
| PYR1D155P | GGAAGGTAACTCGGAGGATcctACTCGTATGTTTGCTGATAC | 224 |
| PYR1D155T | GGAAGGTAACTCGGAGGATactACTCGTATGTTTGCTGATAC | 225 |
| pyr1e141f+ | ggacggtggttttgttttcttacgtcgttgatatgc | 226 |
| pyr1e141g+ | ggacggtggttttgggatcttacgtcgttgatatgc | 227 |
| pyr1e141k+ | ggacggtggttttgaaatcttacgtcgttgatatgc | 228 |
| pyr1e141L+ | ggacggtggttttgttgtcttacgtcgttgatatgc | 229 |
| PYR1E141M+ | GGACGGTGGTTTTGATGTCTTACGTCGTTGATATGC | 230 |
| PYR1E141NNN- | GCATATCAACGACGTAAGANNNCAAAACCACCGTCC | 231 |
| PYR1E141NNN+ | GGACGGTGGTTTTGNNNTCTTACGTCGTTGATATGC | 232 |
| pyr1e141s+ | ggacggtggttttgtcatcttacgtcgttgatatgc | 233 |
| PYR1E141W+ | GGACGGTGGTTTTGTGGTCTTACGTCGTTGATATGC | 234 |
| pyr1e94C+ | gcgaacacatcaacgTGTagactcgatatactcg | 235 |
| pyr1e94D+ | gcgaacacatcaacggatagactcgatatactcg | 236 |
| pyr1e94F+ | gcgaacacatcaacgttcagactcgatatactcg | 237 |
| pyr1e94I+ | gcgaacacatcaacgATAagactcgatatactcg | 238 |
| PYR1E94M+ | GCGAACACATCAACGATGAGACTCGATATACTCG | 239 |
| PYR1E94NNN- | CGAGTATATCGAGTCTNNNCGTTGATGTGTTCGC | 240 |
| PYR1E94NNN+ | GCGAACACATCAACGNNNAGACTCGATATACTCG | 241 |
| pyr1e94R+ | gcgaacacatcaacgcgAagactcgatatactcg | 242 |
| PYR1E94W+ | GCGAACACATCAACGTGGAGACTCGATATACTCG | 243 |
| pyr1e94Y+ | gcgaacacatcaacgTATagactcgatatactcg | 244 |
| pyr1f108c+ | ggagagttaccggatgcagtatcatcggagg | 245 |
| pyr1f108d+ | ggagagttaccggagacagtatcatcggagg | 246 |
| pyr1f108e+ | ggagagttaccggagagagtatcatcggagg | 247 |
| pyr1f108k+ | ggagagttaccggaaagagtatcatcggagg | 248 |
| PYR1F108M+ | GGAGAGTTACCGGAATGAGTATCATCGGAGG | 249 |
| PYR1F108NNN- | CCTCCGATGATACTNNNTCCGGTAACTCTCC | 250 |
| PYR1F108NNN+ | GGAGAGTTACCGGANNNAGTATCATCGGAGG | 251 |

TABLE 2-continued

Mutagenesis primers

| Primer name | Primer sequence | SEQ ID NO |
|---|---|---|
| pyr1f108t+ | ggagagttaccggaaccagtatcatcggagg | 252 |
| PYR1F108W+ | GGAGAGTTACCGGATGGAGTATCATCGGAGG | 253 |
| pyr1f159a+ | ggatgatactcgtatggctgctgatacggttg | 254 |
| pyr1f159d+ | ggatgatactcgtatggatgctgatacggttg | 255 |
| pyr1f159e+ | ggatgatactcgtatggaagctgatacggttg | 256 |
| pyr1f159h+ | ggatgatactcgtatgcatgctgatacggttg | 257 |
| pyr1f159L+ | ggatgatactcgtatgttagctgatacggttg | 258 |
| PYR1F159M+ | GGATGATACTCGTATGATGGCTGATACGGTTG | 259 |
| PYR1F159NNN- | CAACCGTATCAGCNNNCATACGAGTATCATCC | 260 |
| PYR1F159NNN+ | GGATGATACTCGTATGNNNGCTGATACGGTTG | 261 |
| pyr1f159t+ | ggatgatactcgtatgactgctgatacggttg | 262 |
| PYR1F159V+ | ggatgatactcgtatggttgctgatacggttg | 263 |
| PYR1F159W+ | GGATGATACTCGTATGTGGGCTGATACGGTTG | 264 |
| pyr1f61d+ | gacaaaccacaaacatacaaacgacatcaaatcctgctccgtcg | 265 |
| pyr1f61e+ | gacaaaccacaaacatacaaacgagatcaaatcctgctccgtcg | 266 |
| pyr11f61h+ | gacaaaccacaaacatacaaacaccatcaaatcctgctccgtcg | 267 |
| PYR1F61M+ | GACAAACCACAAACATACAAACACATGATCAAATCCTGCTCCGTCG | 268 |
| PYR1F61NNN- | CGACGGAGCAGGATTTGATNNNGTGTTTGTATGTTTGTGGTTTGTC | 269 |
| PYR1F61NNN+ | GACAAACCACAAACATACAAACACNNNATCAAATCCTGCTCCGTCG | 270 |
| pyr1f61q+ | gacaaaccacaaacatacaaacaccaaatcaaatcctgctccgtcg | 271 |
| pyr1f61s+ | gacaaaccacaaacatacaaacactccatcaaatcctgctccgtcg | 272 |
| PYR1F61W+ | GACAAACCACAAACATACAAACACTGGATCAAATCCTGCTCCGTCG | 273 |
| PYR1G150E | cGTCGTTGATATGCCGGAAGAGAACTCGGAGGATGATACtc | 274 |
| PYR1G150F | cGTCGTTGATATGCCGGAATTTAACTCGGAGGATGATACtc | 275 |
| PYR1G150F | cGTCGTTGATATGCCGGAATTTAACTCGGAGGATGATACtc | 275 |
| PYR1G150I | cGTCGTTGATATGCCGGAAATTAACTCGGAGGATGATACtc | 276 |
| PYR1G150N | cGTCGTTGATATGCCGGAAaatAACTCGGAGGATGATACtc | 277 |
| PYR1G150T | cGTCGTTGATATGCCGGAAACTAACTCGGAGGATGATACtc | 278 |
| PYR1G150Y | cGTCGTTGATATGCCGGAATATAACTCGGAGGATGATACtc | 279 |
| PYR1G86# | GACGTGATCGTCATCAGTnnkTTACCGGCGAACACATC | 280 |
| pyr1H115D+ | catcggaggcgaagataggctgacgaattac | 281 |
| pyr1H115e+ | catcggaggcgaagagaggctgacgaattac | 282 |
| pyr1H115i+ | catcggaggcgaaattaggctgacgaattac | 283 |
| PYR1H115M+ | CATCGGAGGCGAAATGAGGCTGACGAATTAC | 284 |
| pyr1H115n+ | catcggaggcgaaaataggctgacgaattac | 285 |
| PYR1H115NNN- | GTAATTCGTCAGCCTNNNTTCGCCTCCGATG | 286 |

TABLE 2-continued

Mutagenesis primers

| Primer name | Primer sequence | SEQ ID NO |
|---|---|---|
| PYR1H115NNN+ | CATCGGAGGCGAANNNAGGCTGACGAATTAC | 287 |
| PYR1H115W+ | CATCGGAGGCGAATGGAGGCTGACGAATTAC | 288 |
| pyr1h60N+ | GACAAACCACAAACATACAAAAACTTCATCAAATCCTGCTCCGTCG | 289 |
| pyr1h60S+ | GACAAACCACAAACATACAAATCCTTCATCAAATCCTGCTCCGTCG | 290 |
| pyr1I110E+ | gttaccggattcagtGAGatcggaggcgaac | 291 |
| PYR1I110M+ | GTTACCGGATTCAGTATGATCGGAGGCGAAC | 292 |
| PYR1I110NNN- | GTTCGCCTCCGATNNNACTGAATCCGGTAAC | 293 |
| PYR1I110NNN+ | GTTACCGGATTCAGTNNNATCGGAGGCGAAC | 294 |
| PYR1I110W+ | GTTACCGGATTCAGTTGGATCGGAGGCGAAC | 295 |
| PYR1I62c+ | ccacaaacatacaaacacttcTGCaaatcctgctccgtcgaac | 296 |
| PYR1I62H+ | ccacaaacatacaaacacttccATaaatcctgctccgtcgaac | 297 |
| PYR1I62M+ | CCACAAACATACAAACACTTCATGAAATCCTGCTCCGTCGAAC | 298 |
| PYR1I62n+ | ccacaaacatacaaacacttcAACaaatcctgctccgtcgaac | 299 |
| PYR1I62NNN- | GTTCGACGGAGCAGGATTTNNNGAAGTGTTTGTATGTTTGTGG | 300 |
| PYR1I62NNN+ | CCACAAACATACAAACACTTCNNNAAATCCTGCTCCGTCGAAC | 301 |
| PYR1I62W+ | CCACAAACATACAAACACTTCTGGAAATCCTGCTCCGTCGAAC | 302 |
| PYR1I62Y+ | ccacaaacatacaaacacttcTATaaatcctgctccgtcgaac | 303 |
| pyr1I82# | ACGCGCGACGTGnnkGTCATCAGTGGATTACCGg | 304 |
| PYR1I84# | GCGACGTGATCGTCnkkAGTGGATTACCGGCG | 305 |
| PYR1K170# | GTTGTGAAGCTTAATTTGCAGnnkCTCGCGACGGTTGC | 306 |
| PYR1K170C | GTTGTGAAGCTTAATTTGCAGtgtCTCGCGACGGTTGC | 307 |
| PYR1K170F | GTTGTGAAGCTTAATTTGCAGtttCTCGCGACGGTTGC | 308 |
| PYR1K170H | GTTGTGAAGCTTAATTTGCAGcatCTCGCGACGGTTGC | 309 |
| PYR1K170I | GTTGTGAAGCTTAATTTGCAGataCTCGCGACGGTTGC | 310 |
| pyr1k170w+ | GAAGCTTAATTTGCAGtggCTCGCGACGGTTGCTG | 311 |
| PYR1K59D+ | caaaccacaaacatacGATcacttcatcaaatcctgc | 312 |
| PYR1K59E+ | caaaccacaaacatacGAAcacttcatcaaatcctgc | 313 |
| PYR1K59L+ | caaaccacaaacataccttcacttcatcaaatcctgc | 314 |
| PYR1K59M+ | CAAACCACAAACATACATGCACTTCATCAAATCCTGC | 315 |
| PYR1K59N+ | caaaccacaaacatacAATcacttcatcaaatcctgc | 316 |
| PYR1K59NNN+ | CAAACCACAAACATACNNNCACTTCATCAAATCCTGC | 317 |
| PYR1K59Q+ | caaaccacaaacatacCAAcacttcatcaaatcctgc | 318 |
| PYR1K59W+ | CAAACCACAAACATACTGGCACTTCATCAAATCCTGC | 319 |
| pyr1K63# | CATACAAACACTTCATCnnkTCCTGCTCCGTCG | 320 |

TABLE 2-continued

Mutagenesis primers

| Primer name | Primer sequence | SEQ ID NO |
|---|---|---|
| pyr1K63A | CATACAAACACTTCATCGCATCCTGCTCCGTCG | 321 |
| pyr1K63A | CATACAAACACTTCATCGCATCCTGCTCCGTCG | 321 |
| pyr1K63D | CATACAAACACTTCATCGACTCCTGCTCCGTCG | 322 |
| pyr1K63D | CATACAAACACTTCATCGACTCCTGCTCCGTCG | 322 |
| pyr1K63F | CATACAAACACTTCATCTTTTCCTGCTCCGTCG | 323 |
| pyr1K63F | CATACAAACACTTCATCTTTTCCTGCTCCGTCG | 323 |
| pyr1K63H | CATACAAACACTTCATCCACTCCTGCTCCGTCG | 324 |
| pyr1K63H | CATACAAACACTTCATCCACTCCTGCTCCGTCG | 324 |
| pyr1K63R | CATACAAACACTTCATCAGATCCTGCTCCGTCG | 325 |
| pyr1K63R | CATACAAACACTTCATCAGATCCTGCTCCGTCG | 325 |
| pyr1K63T | CATACAAACACTTCATCACATCCTGCTCCGTCG | 326 |
| pyr1K63T | CATACAAACACTTCATCACATCCTGCTCCGTCG | 326 |
| pyr1L117A+ | ggaggcgaacataggGCGacgaattacaaatccg | 327 |
| pyr1L117D+ | ggaggcgaacataggGATacgaattacaaatccg | 328 |
| pyr1L117E+ | ggaggcgaacataggGAGacgaattacaaatccg | 329 |
| PYR1L117M+ | GGAGGCGAACATAGGATGACGAATTACAAATCCG | 330 |
| pyr1L117N+ | ggaggcgaacataggAACacgaattacaaatccg | 331 |
| PYR1L117NNN- | CGGATTTGTAATTCGTNNNCCTATGTTCGCCTCC | 332 |
| PYR1L117NNN+ | GGAGGCGAACATAGGNNNACGAATTACAAATCCG | 333 |
| PYR1L117W+ | GGAGGCGAACATAGGTGGACGAATTACAAATCCG | 334 |
| PYR1L166# | CTGATACGGTTGTGAAGnnkAATTTGCAGAAACTCGCGACG | 335 |
| PYR1L166E | CTGATACGGTTGTGAAGgaaAATTTGCAGAAACTCGCGACG | 336 |
| PYR1L166H | CTGATACGGTTGTGAAGcatAATTTGCAGAAACTCGCGACG | 337 |
| PYR1L166P | CTGATACGGTTGTGAAGcctAATTTGCAGAAACTCGCGACG | 338 |
| PYR1L166Q | CTGATACGGTTGTGAAGcaaAATTTGCAGAAACTCGCGACG | 339 |
| PYR1L166Y | CTGATACGGTTGTGAAGtatAATTTGCAGAAACTCGCGACG | 340 |
| PYR1L87# | GTGATCGTCATCAGTGGAnnkCCGGCGAACACATCAAC | 341 |
| PYR1M158D | CGGAGGATGATACTCGTGACTTTGCTGATACGGTTGTGAAGC | 342 |
| PYR1M158F | CGGAGGATGATACTCGTTTCTTTGCTGATACGGTTGTGAAGC | 343 |
| PYR1M158H | CGGAGGATGATACTCGTCACTTTGCTGATACGGTTGTGAAGC | 344 |
| pyr1m158I+ | CGGAGGATGATACTCGTattTTTGCTGATACGGTTG | 345 |
| PYR1M158N | CGGAGGATGATACTCGTAACTTTGCTGATACGGTTGTGAAGC | 346 |
| PYR1M158Q | CGGAGGATGATACTCGTCAGTTTGCTGATACGGTTGTGAAGC | 347 |
| PYR1M158Y | CGGAGGATGATACTCGTTATTTTGCTGATACGGTTGTGAAGC | 348 |

TABLE 2-continued

Mutagenesis primers

| Primer name | Primer sequence | SEQ ID NO |
|---|---|---|
| PYR1N151F | CGTTGATATGCCGGAAGGTTTCTCGGAGGATGATACTCg | 349 |
| PYR1N151F | CGTTGATATGCCGGAAGGTTTCTCGGAGGATGATACTCg | 349 |
| PYR1N151H | CGTTGATATGCCGGAAGGTCACTCGGAGGATGATACTCg | 350 |
| PYR1N151I | CGTTGATATGCCGGAAGGTATCTCGGAGGATGATACTCg | 351 |
| PYR1N151M | CGTTGATATGCCGGAAGGTATGTCGGAGGATGATACTCg | 352 |
| PYR1N151V | CGTTGATATGCCGGAAGGTGTCTCGGAGGATGATACTCg | 353 |
| PYR1N151Y | CGTTGATATGCCGGAAGGTTACTCGGAGGATGATACTCg | 354 |
| pyr1N167a+ | gatacggttgtgaagcttgctttgcagaaactcgcg | 355 |
| pyr1N167c+ | gatacggttgtgaagctttgtttgcagaaactcgcg | 356 |
| pyr1N167d+ | gatacggttgtgaagcttgatttgcagaaactcgcg | 357 |
| pyr1N167e+ | gatacggttgtgaagcttgaattgcagaaactcgcg | 358 |
| pyr1N167g+ | gatacggttgtgaagcttggtttgcagaaactcgcg | 359 |
| PYR1N167M+ | GATACGGTTGTGAAGCTTATGTTGCAGAAACTCGCG | 360 |
| PYR1N167NNN- | CGCGAGTTTCTGCAANNNAAGCTTCACAACCGTATC | 361 |
| PYR1N167NNN+ | GATACGGTTGTGAAGCTTNNNTTGCAGAAACTCGCG | 362 |
| pyr1N167p+ | gatacggttgtgaagcttcctttgcagaaactcgcg | 363 |
| pyr1N167s | gatacggttgtgaagctttctttgcagaaactcgcg | 364 |
| pyr1N167t+ | gatacggttgtgaagcttactttgcagaaactcgcg | 365 |
| PYR1N167W+ | GATACGGTTGTGAAGCTTTGGTTGCAGAAACTCGCG | 366 |
| PYR1P148# | CTTACGTCGTTGATATGnnkGAAGGTAACTCGGAGGATG | 367 |
| PYR1P55c+ | cgtacGAcgattcgacaaatgtcaaacatacaaacacttcatc | 368 |
| PYR1P55h+ | cgtacGAcgattcgacaaaccacaaacatacaaacacttcatc | 369 |
| PYR1P55i+ | cgtacGAcgattcgacaaaatacaaacatacaaacacttcatc | 370 |
| PYR1P55k+ | cgtacGAcgattcgacaaaaagcaaacatacaaacacttcatc | 371 |
| PYR1P55M+ | CGTACGACGATTCGACAAAATGCAAACATACAAACACTTCATC | 372 |
| PYR1P55NNN- | GATGAAGTGTTTGTATGTTTGNNNTTTGTCGAATCGTCGTACG | 373 |
| PYR1P55NNN+ | CGTACGACGATTCGACAAANNNCAAACATACAAACACTTCATC | 374 |
| PYR1P55v+ | cgtacGAcgattcgacaaagtacaaacatacaaacacttcatc | 375 |
| PYR1P55W+ | CGTACGACGATTCGACAAATGGCAAACATACAAACACTTCATC | 376 |
| PYR1P55y+ | cgtacGAcgattcgacaaatatcaaacatacaaacacttcatc | 377 |
| Pyr1p88a+ | gtcatcagtggattaGCGgcgaacacatcaacg | 378 |
| Pyr1p88D+ | gtcatcagtggattagatgcgaacacatcaacg | 379 |
| Pyr1p88g+ | gtcatcagtggattaggggcgaacacatcaacg | 380 |
| Pyr1p88K+ | gtcatcagtggattaaaggcgaacacatcaacg | 381 |
| PYR1P88M+ | GTCATCAGTGGATTAATGGCGAACACATCAACG | 382 |

TABLE 2-continued

Mutagenesis primers

| Primer name | Primer sequence | SEQ ID NO |
|---|---|---|
| PYR1P88NNN- | CGTTGATGTGTTCGCNNNTAATCCACTGATGAC | 383 |
| PYR1P88NNN+ | GTCATCAGTGGATTANNNGCGAACACATCAACG | 384 |
| PYR1P88W+ | GTCATCAGTGGATTATGGGCAACACATCAACG | 385 |
| Pyr1p88y+ | gtcatcagtggattaTATgcgaacacatcaacg | 386 |
| PYR1S122# | GGCTGACGAATTACAAAnnkGTTACGACGGTGCATCG | 387 |
| PYR1S122E | GGCTGACGAATTACAAAgaaGTTACGACGGTGCATCG | 388 |
| PYR1S122I | GGCTGACGAATTACAAAatcGTTACGACGGTGCATCG | 389 |
| PYR1S122K | GGCTGACGAATTACAAAaaaGTTACGACGGTGCATCG | 390 |
| PYR1S122W | GGCTGACGAATTACAAAtggGTTACGACGGTGCATCG | 391 |
| PYR1S85# | CGACGTGATCGTCATCnnkGGATTACCGGCGAACAC | 392 |
| pyr1s92D+ | ccggcgaacacagatacggaaagactcg | 393 |
| pyr1s92G+ | ccggcgaacacaggaacggaaagactcg | 394 |
| pyr1s92K+ | ccggcgaacacaaagacggaaagactcg | 395 |
| PYR1S92M+ | CCGGCGAACACAATGACGGAAAGACTCG | 396 |
| PYR1S92NNN- | CGAGTCTTTCCGTNNNTGTGTTCGCCGG | 397 |
| PYR1S92NNN+ | CCGGCGAACACANNNACGGAAAGACTCG | 398 |
| PYR1S92W+ | CCGGCGAACACATGGACGGAAAGACTCG | 399 |
| pyr1s92y+ | ccggcgaacacaTATacggaaagactcg | 400 |
| PYR1T156# | GAAGGTAACTCGGAGGATGATnnkCGTATGTTTGCTGATACG | 401 |
| PYR1T156A | GAAGGTAACTCGGAGGATGATgctCGTATGTTTGCTGATACG | 402 |
| PYR1T156H | GAAGGTAACTCGGAGGATGATcatCGTATGTTTGCTGATACG | 403 |
| PYR1T156K | GAAGGTAACTCGGAGGATGATaaaCGTATGTTTGCTGATACG | 404 |
| PYR1T156N | GAAGGTAACTCGGAGGATGATaatCGTATGTTTGCTGATACG | 405 |
| PYR1T156Q | GAAGGTAACTCGGAGGATGATcaaCGTATGTTTGCTGATACG | 406 |
| PYR1T156Y | GAAGGTAACTCGGAGGATGATtatCGTATGTTTGCTGATACG | 407 |
| PYR1T162# | CTCGTATGTTTGCTGATnnkGTTGTGAAGCTTAATTTGCAGA | 408 |
| PYR1T162F | CTCGTATGTTTGCTGATtttGTTGTGAAGCTTAATTTGCAGA | 409 |
| PYR1T162I | CTCGTATGTTTGCTGATattGTTGTGAAGCTTAATTTGCAGA | 410 |
| PYR1T162Y | CTCGTATGTTTGCTGATtatGTTGTGAAGCTTAATTTGCAGA | 411 |
| PYR1V163M+ | CGTATGTTTGCTGATACGATGGTGAAGCTTAATTTGCAGAAACTCGC | 412 |
| PYR1V163NNN- | GCGAGTTTCTGCAAATTAAGCTTCACNNNCGTATCAGCAAACATACG | 413 |
| PYR1V163NNN+ | CGTATGTTTGCTGATACGNNNGTGAAGCTTAATTTGCAGAAACTCGC | 414 |

TABLE 2-continued

Mutagenesis primers

| Primer name | Primer sequence | SEQ ID NO |
|---|---|---|
| PYR1V163W+ | CGTATGTTTGCTGATACGTGGGTGAAGCTTAATTTGCAGAAACTCGC | 415 |
| PYR1V164# | CGTATGTTTGCTGATACGGTTnnkAAGCTTAATTTGCAG | 416 |
| PYR1V164A | CGTATGTTTGCTGATACGGTTgcgAAGCTTAATTTGCAG | 417 |
| PYR1V164D | CGTATGTTTGCTGATACGGTTgacAAGCTTAATTTGCAG | 418 |
| PYR1V164K | CGTATGTTTGCTGATACGGTTaagAAGCTTAATTTGCAG | 419 |
| PYR1V164N | CGTATGTTTGCTGATACGGTTaatAAGCTTAATTTGCAG | 420 |
| PYR1V164W | CGTATGTTTGCTGATACGGTTtggAAGCTTAATTTGCAG | 421 |
| PYR1V164Y | CGTATGTTTGCTGATACGGTTtatAAGCTTAATTTGCAG | 422 |
| PYR1V81c+ | gatgcacgcgcgactgtatcgtcatcagtg | 423 |
| PYR1V81e+ | gatgcacgcgcgacgagatcgtcatcagtg | 424 |
| PYR1V81I+ | gatgcacgcgcgacatcatcgtcatcagtg | 425 |
| PYR1V81M+ | GATGCACGCGCGACATGATCGTCATCAGTG | 426 |
| PYR1V81NNN- | CACTGATGACGATNNNGTCGCGCGTGCATC | 427 |
| PYR1V81NNN+ | GATGCACGCGCGACNNNATCGTCATCAGTG | 428 |
| PYR1V81W+ | GATGCACGCGCGACTGGATCGTCATCAGTG | 429 |
| PYR1V81y+ | gatgcacgcgcgactatatcgtcatcagtg | 430 |
| PYR1V83c+ | cgcgcgacgtgatctgcatcagtggattacc | 431 |
| PYR1V83d+ | cgcgcgacgtgatcgacatcagtggattacc | 432 |
| PYR1V83e+ | cgcgcgacgtgatcgagatcagtggattacc | 433 |
| PYR1V83F+ | cgcgcgacgtgatctttatcagtggattacc | 434 |
| PYR1V83k+ | cgcgcgacgtgatcaagatcagtggattacc | 435 |
| PYR1V83M+ | CGCGCGACGTGATCATGATCAGTGGATTACC | 436 |
| PYR1V83NNN- | GGTAATCCACTGATNNNGATCACGTCGCGCG | 437 |
| PYR1V83NNN+ | CGCGCGACGTGATCNNNATCAGTGGATTACC | 438 |
| PYR1V83q+ | cgcgcgacgtgatccaaatcagtggattacc | 439 |
| PYR1V83W+ | CGCGCGACGTGATCTGGATCAGTGGATTACC | 440 |
| PYR1V83y+ | cgcgcgacgtgatctacatcagtggattacc | 441 |
| pyr1y120A+ | cataggctgacgaatGCCaaatccgttacgacg | 442 |
| pyr1y120C+ | cataggctgacgaatTGTaaatccgttacgacg | 443 |
| pyr1y120E+ | cataggctgacgaatGAGaaatccgttacgacg | 444 |
| pyr1y120G+ | cataggctgacgaatGGCaaatccgttacgacg | 445 |
| pyr1y120H+ | cataggctgacgaatCACaaatccgttacgacg | 446 |
| PYR1Y120M+ | CATAGGCTGACGAATATGAAATCCGTTACGACG | 447 |
| PYR1Y120NNN- | CGTCGTAACGGATTTNNNATTCGTCAGCCTATG | 448 |
| PYR1Y120NNN+ | CATAGGCTGACGAATNNNAAATCCGTTACGACG | 449 |
| pyr1y120P+ | cataggctgacgaatCCCaaatccgttacgacg | 450 |

TABLE2-continued

Mutagenesis primers

| Primer name | Primer sequence | SEQ ID NO |
|---|---|---|
| pyr1y120Q+ | cataggctgacgaatCAGaaatccgttacgacg | 451 |
| PYR1Y120W+ | CATAGGCTGACGAATTGGAAATCCGTTACGACG | 452 |

Yeast-Based Receptor Activation Assays

Mutant pBD GAL-PYR1 clones were individually transformed into S. cerevisiae strain Y190 containing pACT-HAB1 (Park et al., 2009), which expresses a GAL4 activation domain—HAB1 fusion protein. Yeast transformants were selected for the presence of plasmids on synthetic dextrose (SD) agar plates lacking Leu and Trp (SD-LT) and examined for PP2C interactions by using X-gal staining to monitor β-gal reporter gene expression levels. Individual clones were arrayed into 96 well plates and then spotted onto SD-LT lawn (i.e. one-well) plates. Each assay plate contained 95 mutant clones and one wild type PYR1 control clone. Plates were stained by the chloroform overlay X-gal method after 2 days incubation at 30° C. Each assay plate was tested least three times and the activating mutations shown in FIG. 1 were observed as X-gal+ in all three separate experiments.

In Vitro Receptor Activation Assays

Full length ABI1 and ABI2 were cloned into a modified pSUMO vector (LifeSensors Inc, USA) vector yielding 6×His-SUMO fusion proteins; GST-HAB1 was expressed and purified as previously described (Park et al., 2009). Mutant receptors were cloned into pET28 yielding 6×His-fusion proteins. Clones were transformed into E. coli expression strain BL21 (DE3) pLysS and recombinant proteins prepared as follows: 1 ml of an overnight culture was inoculated in to 200 ml TB (for receptors) or 200 ml LB (for PP2Cs). The cultures were pre-incubated 2 hours at 30° C. and, for PP2C expression, media was supplemented with 4 mM $MnCl_2$ one hour after inoculation. After pre-incubation, IPTG was added (1 mM) and cells were induced at 15° C. for 16 hours, after which they were collected by centrifugation, resuspended in 5 ml Buffer A (50 mM $NaH_2PO_4$, 300 mM NaCl) +10 mM imidazole, pH 8.0 and stored at −80° C. For purification, cells were thawed, sonicated on ice (60 seconds) and a cleared lysate was then applied a 1 ml-bed volume column of Ni-NTA (Qiagen, USA), washed with 20 column volumes of Buffer A+30 mM imidazole and bound protein eluted with 1 ml of Buffer A+250 mM imidazole. For receptors, the elutate was dialyzed against TBS and for PP2Cs, fusion proteins were desalted by passage over a Sephadex G50 column.

The purified receptors and phosphatases were then used in receptor assays where receptor activation is indicated by inhibition of phosphatase activity, as inferred from initial reaction velocities for PP2C-mediated hydrolysis of the synthetic phosphatase substrate pNPP in reactions containing 600 nM PP2C and either 0, 600, 1200, 2400 or 4800 nM receptor. The receptor assay buffer consisted of 33 mM Tris-OAc, pH 7.9, 66 mM KOAc, 0.1% BSA, 25 mM $Mn(OAc)_2$, 0.1%13-ME and 50 mM pNPP. Immediately after mixing proteins and substrates, reactions were monitored for hydrolysis of pNPP at $A_{405}$ at ~2 minutes intervals using a Wallac plate reader. Reaction progressions were plotted, initial velocities calculated and converted to specific activities by comparison to a standard curve for 4-nitrophenol made in the same buffer system. PP2C activity values shown in figures are expressed as %-control phosphatase activity levels, as measured under identical reaction conditions in the absence of receptor protein. The average specific activity level of GST-HAB1, 6×His-SUMO-ABI1 and 6×His-SUMO-ABI2 utilized in our experiments was 4500 (GST-PP2C) or 2500 (SUMO-PP2C) μmol/min/mg, when assayed using the phosphatase substrate pNPP in the absence of PYR1 or other receptors.

Transgenic Plants

To create the desired transgenic plants, the coding sequences of PYL2, PYL2$^{C43}$ and PYL2$^{C44}$ were cloned into a modified version of the pEGAD (Cutler S R et al (2000) Proc Natl Acad Sci USA 97(7):3718-3723) to create 35S-driven GFP-receptor fusion proteins. Prior work has demonstrated that an N-terminal GFP fusion tags does not interfere with PYR1 function in vivo (Park et al., 2009). The constructs were sequence validated and then introduced into Columbia or the aba2-1 mutant using agrobacterium-mediated transformation via the floral dip method (Clough S J & Bent A F (1998) Plant J 16(6):735-743). For each genotype constructed, approximately 40 primary transgenic plants were identified by virtue glufosinate resistance or GFP expression in T1 seedlings, and single-insertion homozygous lines were then isolated from the progeny of 10 T1 lines.

Seed Assays

In order to assay dormancy of seeds for Columbia, 35S::GFP-PYL2, and 35S::GFP-PYL2$^{C43}$ were divided into two portions and surface sterilized using chlorine gas (prepared in situ using bleach and HCl). One portion was stratified on ⅓ MS agar plates for 6 days at 4° C. in darkness and the second portion, which was maintained at room temperature, was seeded six days later on the ⅓ MS agar plates; both samples were transferred to a 23° C. light-tight growth chamber and germination scored at 24 hour periods. The homozygous 35S::GFP-PYL2 and 35S::GFP-PYL2"³ seeds used in these experiments were ~5- and ~6-months post-harvest respectively at the time of the experiment shown in FIG. 12.

Germination tests on paclobutrazol (Wako Chemicals, Japan) and NaCl were conducted as following. Columbia, aba2-1, aba2-1; 35S::GFP-PYL2 and aba2-1; 35S::GFP-PYL2"³ seeds were surface sterilized and plated onto ⅓ MS agar media containing 25, 50 or 100 μM paclobutrazol or 0, 50, 200, 250 mM NaCl. Control wells contained ⅓ MS agar and 0.1% DMSO, the carrier solvent for paclobutrazol. The seeds were stratified for four days in darkness and then transferred to continuous illumination at room temperature (23° C.). Germination was assayed after 72 hours; seeds showing radicals at least ½ seed length or greater were scored as positive. Each experiment was performed in triplicate; experiments were performed on seeds that were ~6-months post-harvest.

Quantitative RT-PCR

Wild type or transgenic lines were imbibed for 32 hours in either water or 5 µM ABA at room temperature under continuous illumination, after which RNA was isolated using Concert™ Plant RNA Reagent followed by LiCl$_2$ precipitation and DNase treated using RNase-free DNAse (Ambion). Purified RNA was utilized in qRT-PCR reactions using primers for the ABA-regulated genes Em6 (At2g40170), LEA (At2g21490), and Rd29b (At5g52300). Biological duplicates with triple technical replicate measurements were conducted and gene expression levels were determined. For qRT-PCR analyses of gene expression, cDNA was generated from 5 µg of total RNA using superscript reverse transcriptase II (Invitrogen), in reaction mixture containing a oligo-dT$_{20}$ (SEQ ID NO:174) and ribosomal RNA primer 3404 (−) (5'-ACATCTAA GGGCATCACAGAC-3') (SEQ ID NO:175). Real-time quantitative PCR analysis was performed by ΔΔCt method of relative quantification. PCR mixtures contained 2 µl of cDNA, 7.5 µl of 2× Maxima® SYBR green/Fluorescein qPCR master mix (2×) (Fermentas) and 330 nM of each gene-specific primer in a final volume of 15 µl. The RT-PCRs were done using BioRad CFX96 Real-Time System and BioRad CFX Manager software (BioRad). PCRs were performed under the following conditions: 3 min at 95° C., and 40 cycles of 10 s at 95° C., 10 s at 55° C. and 30 s 72° C. in 96-well optical reaction plates (BioRad). The specificity of amplicons was verified by melting curve (disassociation) analysis (60-95° C.) after 40 cycles. Input cDNA was normalized using rRNA primers. The following primers were used to detect specific gene expression levels: Em6 (At2g40170) tcgaagctcaacagcatctc (SEQ ID NO:176) and actgctccttcgagtttgc (SEQ ID NO:177), LEA (At2g21490) cgtcggtctggaagttcatc (SEQ ID NO:178) and tcttcttcctcctc- cctcct (SEQ ID NO:179), Rd29b (At5g52300) atccgaaaac- ccatagtcc (SEQ ID NO:180) and tggtgggggaaagttaaagga (SEQ ID NO:181) and rRNA aaacggctaccacatccaag (SEQ ID NO:182) and gactcgaaagagcccggtat (SEQ ID NO:183).

We have used saturation mutagenesis to identify a series of mutations in PYR1 that increase its basal activity. Combinations of these mutations led to the rapid construction of a near fully activated PYR1 variant. The activating combinations can be incorporated into diverse PYL receptors to elicit full activation and the PYL2 and PYL9 CA alleles are nearly indistinguishable from wild type receptors examined under saturating ABA levels. When PYL2$^{CA3}$ is expressed in vivo, it activates ABA signaling and enables near complete suppression of 2 separate ABA-mediated seed responses that are deficient in the aba2-1 mutant; this stringent functional test shows that activation of PYL2 is sufficient to activate ABA signaling in vivo and makes an indirect explanation involving the action of ABA on other receptors unlikely.

ABA can normally activate a multiplicity of receptors in the wild type context, and it is not yet clear if different receptors have different sub-functions in ABA signaling. To date, selective ABA receptor activation has only been achieved using pyrabactin, which has strong agonist activity on PYR1 and PYL1 and essentially activates the full complement of ABA-responsive gene transcription in seeds. However, pyrabactin's effects are complicated by its weak partial-agonist/antagonist activity on other receptors like PYL2 (Peterson F C, et al. (2010) Nature Structural and Molecular Biology 17(9):1109-1113; Melcher K, et al. (2010) Nature Structural and Molecular Biology 17(9): 1102-1108) and PYL5 (Hao Q, et al. (2011) Mol Cell 42 (5):662-672). CA alleles have the advantage of avoiding the complication of pharmacological treatments. Activation of PYL2 by the CA3 mutations mimics the effects of ABA-treatment on seeds at the transcript level for three ABA marker genes, suppresses the salt and paclobutrazol sensitivity of aba2-1 mutation and induces hyperdormancy. Together with pyrabactin's previously characterized effects, our data suggest that activation of a single receptor (PYR1 or PYL2) is sufficient to activate signaling in seeds and that multiple receptors need not be activated to elicit an ABA response.

Our efforts have shown that combinations of activating mutations can be incorporated into diverse PYR/PYL receptors to elicit full constitutive activation. As is known to those skilled in the art, constitutively active receptor mutations are valuable because they allow ligand-independent activation of signaling pathways. In the context of PYR/PYL receptors, activating ABA signaling and its associated downstream responses in transgenic plants can be used to improve water use, yield under conditions of stress, and other ABA-regulated traits. Moreover, constitutively active receptor mutations are beneficial in comparison to chemical agonists (such as ABA) because constitutively active mutants allow single receptors to be activated selectively. Since the PYL/PYL receptors reside in a relatively large gene family, selective activation of single receptors by constitutively active mutations allows responses controlled by distinct family members to be specifically activated; this is in contrast to the general activation of signaling elicited by ABA. The value of this is multifold. While ABA is beneficial for inducing stress tolerance, its application often has undesirable side effects such as chlorosis; thus, ABA has side effects that may limit its use. Specific activation of defined receptors by selective agonists or defined constitutively active mutants may enable desirable and undesirable side effects to be disentangled and controlled with specificity. Lastly, tissue specific or regulated expression of constitutively active alleles enables a level of control that cannot be afforded by chemical agonists.

Example 6

RD29A-Driven PYL2$^{CA4}$ Transgenes Induce Minimal Effects on *Arabidopsis* Growth and Germination Under Non-Stressed Conditions As shown in the above examples, constitutive expression of GFP-PYL2$^{CA4}$ from the 35S promoter is associated with a number of undesirable effects, including enhanced seed dormancy. In general, constitutive expression of abiotic stress responses is associated with reduced growth and other physiological effects that reduce yield. Inducible expression can be used to bypass these negative effects. For example, RD29A-driven drought inducible expression of DREB1A, a positively acting transcription factor in the abscisic acid pathway, improves drought tolerance with minimal effects under normal growth conditions, while constitutive 35S-driven DREB1A severely impairs growth (Kasuga et al., 1999). To investigate the efficacy of drought inducible constitutively active receptors for modulating stress tolerance, we generated transgenic *Arabidopsis* plants that express either wild-type PYL2 or a PYL2$^{CA4}$ receptor under the control of the RD29A promoter. The stress tolerance of these plants in relationship to control plants was investigated using both salt stress and drought stress treatments.

To create the desired transgenic plants, we replaced the 35S promoter present in pEGAD (Cutler et al. (2000) *Proc Natl Acad Sci USA* 97:3718-3723) with the *Arabidopsis*

RD29A promoter and then cloned desired PYL2 variants into the modified vector. The RD29A promoter was amplified from *A. thaliana* genomic DNA with the following primers (5'-GAGCTCCCATAGATGCAATTCAAT-CAAAC-3' (SEQ ID NO:453) and 5'-ACCGGT-CAAAGATTTTTTTCTTTCCAATAG-3') (SEQ ID NO:454) and cloned into pEGAD using AgeI and SacI restriction enzymes. The coding sequences of PYL2 and PYL2$^{CA4}$ were cloned into the above vector to create RD29A-driven GFP-receptor fusion proteins henceforth referred to as RD29A::GFP-PYL2 and RD29A::GFP-PYL2$^{CA4}$. The constructs were sequence validated and then introduced into Columbia wild-type background by *Agrobacterium*-mediated transformation using the floral dip method (Clough et al. 1998). For each genotype constructed, approximately 25 primary transgenic plants were identified by virtue of glufosinate resistance and/or GFP expression in T1 seedlings, and single-insertion homozygous lines were then identified from the T2 and T3 progeny of the primary T1 lines.

Given that 35S:PYL2$^{CA3}$ lines have dramatically enhanced seed dormancy in comparison to wild-type plants, we first sought to establish if the RD29A::GFP-PYL2 or RD29A::GFP-PYL2$^{CA4}$ constructs affected seed dormancy. The CA4 construct was chosen because of its greater degree of constitutive activity relative to the CA3 construct (see, e.g., FIG. 17) and thus is expected to affect ABA responses more strongly than the CA3 mutation. GFP fusion proteins were utilized to facilitate selection and analysis of transgenic plants. We note that it has previously been shown that a 35S::GFP-PYL1 construct is sufficient to rescue the pyrabactin insensitivity of the pyr1-1 mutant, which indicates that the GFP tag is not likely to impair PYR1 or PYL2 protein function (Park et al. 2009). In order to assay dormancy of different genotypes, seeds for wild-type Columbia, RD29A::GFP-PYL2, and two independent RD29A::GFP-PYL2$^{CA4}$ transgenics (lines #1 and #2) were divided in two aliquots and dry-surface sterilized for two hours using chlorine gas (prepared in situ by mixing commercial bleach and 12N HCl). One portion of sterilized seeds was stratified on ⅓ MS agar plats for 5 days at 4° C. in darkness and the second portion, which was maintained dry at room temperature, was seeded six days later on the ⅓ MS agar plates; both samples were transferred to a 23° C. light-tight growth chamber and germination scored at 24 hour intervals. As shown in FIG. 18, RD29A-driven expression of the PYL2$^{CA4}$ transgene was associated with a modest enhancement of seed dormancy that varies in severity between the 2 lines characterized. This variation suggests that appropriate selection of transgenic lines can be used to mitigate the severity of the seed effect. The mild seed phenotype observed is consistent with documented expression of the RD29A promoter during seed development in public microarray databases (Schmid et al., 2005). Nonetheless, the effects of the transgene on seed dormancy are minor when using the inducible promoter in comparison to that observed with the 35S-driven PYL2$^{CA3}$ variant.

To further investigate the effects of the RD29A-driven PYL2$^{CA4}$ constructs, we characterized the whole plant phenotypes at flowering. As shown in FIG. 19, minimal effects on whole plant growth are observed. The effect of the transgenes on whole plant fertility was also examined. As shown in FIG. 20, none of the transgenic plants characterized possessed significant differences in silique length or number, which are proxies for seed yield. Thus, RD29A-driven expression of PYL2 or PYL2$^{CA4}$ proteins is associated with minimal effects on plant yield and physiology under non-stressed conditions.

Example 7

The RD29A Promoter Drives Drought-Inducible Expression of PYL Proteins

To confirm that the transgenic plants constructed express PYL proteins appropriately in response to stress, mature rosette leaves of 4 week old plants grown under short days for the RD29A::GFP-PYL2 and two independent RD29A::GFP-PYL2$^{CA4}$ transgenic genotypes were detached and allowed to dry for 4 hours. Proteins were subsequently extracted in TBS buffer (10 mM Tris-Cl (pH 7.4), 150 mM NaCl) supplemented with 1% protease inhibitor mixture (Sigma-Aldrich, USA). 20 µg total protein was then separated on a 10% acrylamide (wt/vol) SDS/PAGE gel and then blotted onto nitrocellulose membranes and probed with monoclonal anti-GFP (Clontech, USA) or anti-α-tubulin (Sigma-Aldrich, USA) antibody at 1:10,000 dilution. An anti-mouse-HRP (1:10,000) conjugate was used as a secondary antibody and ECL (GE Healthcare, USA) was then used to visualize immunoreactive protein. As shown in FIG. 21, RD29A-driven PYL proteins were expressed at high levels in response to dehydration and had lower basal levels in the absence of stress, consistent with the previously characterized induction of the RD29A promoter after desiccation (Yamaguchi-Shinozaki et al., 1992). Thus, the RD29A-driven PYL2 constructs induce PYL2 proteins in a stress-inducible manner in mature *Arabidopsis* plants, as expected.

Example 8

*Arabidopsis* Plants Expressing RD29A-Driven PYR1CA4 or PYL2CA4 Receptors Possess Improved Salt Tolerance ABA plays a well-recognized role in mediating salt tolerance (Zhu, 2002). We therefore sought to examine if *Arabidopsis* plants expressing RD29A-driven PYR1, PYL2, PYR1$^{CA4}$, or PYL2$^{CA4}$ variants can enhance *Arabidopsis* salt tolerance. RD29A-driven PYR1 and PYR1$^{CA4}$ transgenic plants were constructed using methods described in Example 6 for analogous PYL2 constructs. Salinity sensitivity assays of wild-type and transgenic materials were conducted as follows: seedlings of the wild-type Columbia, RD29A::GFP-PYR1, two independent RD29A::GFP-PYR1$^{CA4}$, RD29A::GFP-PYL2, or two independent RD29A::GFP-PYL2$^{CA4}$ lines were sown and germinated in BD Falcon 100×15 mm disposable square integrid petri dishes on a general growth media consisting of 0.5% Murashige and Skoog Basal Salt Mixture (MS), 0.5% sucrose, and 0.5% Gelzan™ agar and 100 mg/ml carboxyline antimicrobial agent. A sterile 80×80 mm nylon mesh was placed on top of 25 ml molten media. The nylon mesh used contains 1000 micron square openings, 59% open area, and a 515 micron thread diameter (obtained from Small Parts, USA). These mesh coverings enable facile transfer of seedlings from low salinity to high salinity petri plates. Nine sterilized seeds were sown evenly over 10×10 mesh square units, stratified in darkness at 4° C. for 5 days and then exposed to continuous light at room temperature. Seven days later, seedlings were transferred to plates containing 100 mM NaCl plus the general growth media to induce expression of the RD29A promoter. Following transgene induction, seedlings were transferred to 250 mM NaCl plates and seedling survival rates were scored 14 days after transfer to the high-salt plates. As shown in FIG. 22A, RD29A::GFP-PYR1$^{C44}$ and RD29A::GFP-PYL2$^{C44}$ transgenic plants displayed significant improvements in survival under high salinity conditions in comparison to both wild-type and RD29A::GFP-PYR1 and RD29A::GFP-PYL2 transgenic plants. Quantification of the survival rates of the PYR1 (FIG. 22B) and PYL2 (FIG. 22C) series of transgenic plants revealed significant improvements in salt tolerance of the CA expressing transgenic lines. To confirm that the 100 mM NaCl treatment effectively induced expression of the various PYR1 and PYL2 proteins, qRT-PCR assays were performed on seedlings after transfer to 100 mM NaCl. Seeding tissues were harvested in three hour intervals post-transfer (0, 3, and 6 hours post-transfer), and RNA isolated using Concert™ Plant RNA Reagent was DNase treated using RNase-free DNase (Ambion, USA). Purified RNA was then utilized in qRT-PCR reactions using oligonucleotide primers for the ABA-regulated genes RAB18 (At5g66400) and RD29B (At5g52300). Biological triplicate and triple technical replicate measurements were conducted. For qRT-PCR analyses of gene expression, cDNA was generated from 2 µg of total RNA using Superscript Reverse Transcriptase III (Invitrogen, USA) in a reaction mixture containing an oligo-dT20 (SEQ ID NO:174) primer. Real-time quantitative PCR analysis was performed by ΔΔCt method of relative quantification. PCR mixtures contained 2 µl of cDNA, 7.5 µl of 2× Maxima® SYBR green/Fluorescein qPCR master mix (2×) (Fermentas) and 330 nM of each gene-specific primer in a final reaction volume of 15 µl. The RT-PCRs were performed using BioRad CFX Manager software (BioRad, USA). PCRs were performed under the following conditions: 3 min at 95° C., followed by 40 cycles of 10 s at 95° C., 10 s at 55° C. and 30 s at 72° C. in 96-well optical reaction plates (BioRad). The specificity of amplicons was verified by melting curve (disassociation) analysis (60-95° C.) after 40 cycles. Input cDNA was normalized using rRNA primers. As shown in FIG. 23, heightened expression of ABA-responsive genes was observed in the RD29A::GFP-PYL2$^{C44}$ line #1 in comparison to wild-type and RD29A::GFP-PYL2 transgenic plants. Thus, RD29A-driven expression of PYR1$^{C44}$ or PYL2$^{C44}$ is associated with a heightened ABA response and improved salt tolerance in *Arabidopsis* seedlings.

Example 9

RD29A-Driven PYL2$^{C44}$ Receptors Improve *Arabidopsis* Drought Tolerance

To investigate if RD29A-driven expression of PYL2$^{C44}$ enhances drought tolerance, mature plants of either the Columbia wild-type, RD29A::GFP-PYL2, or two independent RD29A::GFP-PYL2$^{C44}$ transgenic genotypes were subjected to water deprivation experiments and water loss monitored two weeks post-water deprivation. The experiments were conducted as follows: seedlings of each genotype were individually transferred to hydrated Jiffy-7 peat pellet soil and grown to maturity (~6 weeks) in short day conditions (8/16 light dark) with regular watering; ~40 plants per genotype were characterized. Once mature, pots were sealed using a combination of polyvinyl-chloride and Parafilm to minimize non-transpirational water loss. The lower half of the pot was sealed with polyvinyl-chloride wrap while the upper half was sealed with Parafilm. Control well-watered plants (~10 plants per genotype) were grown alongside treated specimens. Plants were photographed and weighed weekly throughout the course of the experiment. At the completion of the experiment, each pot (containing plant biomass and soil) was oven-dried and weighed to determine the dry weight of each pot, which was then used to infer the water content measured throughout the course of the water deprivation experiment. The plants were additionally scored visually for leaf collapse (i.e., loss of turgor), which is an indication of drought stress. Aerial plant dry mass was additionally measured for both control and experimental plants at the cessation of the experiment. As shown in FIG. 24A, RD29A::GFP-PYL2$^{C44}$ transgenic plants better survived 2 weeks of water deprivation than did either the Columbia wild-type or RD29A::GFP-PYL2 genotypes, as evidenced by reduced turgor loss. Additionally, quantification of water retention revealed that the RD29A::GFP-PYL2$^{C44}$ transgenic plants better retained water over the 2 weeks of water deprivation than did either the Columbia wild-type or RD29A::GFP-PYL2 genotypes. This improvement in stress tolerance cannot be attributed to a difference in plant size, as the dry weights of control and water-stressed plants did not significantly differ, as shown in FIG. 25. Thus, drought inducible expression of the PYL2$^{C44}$ receptor enhances *Arabidopsis* drought tolerance.

Example 10

The RD29A::GFP-PYL2$^{C44}$ Transgene Affects Stomatal Aperture after Recovery from Desiccation Given the importance of stomatal aperture to transpiration and water use, we sought to examine if the drought-induced expression of PYL2$^{C44}$ driven by the RD29A promoter affected stomatal aperture. To investigate this, we examined the aperture of stomata in plants after recovery from desiccation. Plants from the Columbia, RD29A::GFP-PYL2, or RD29A::GFP-PYL2$^{C44}$ transgenic genotypes were severed and dried for one hour to enable induction of the RD29A promoter. Plants were then rehydrated for 90 minutes after which stomatal morphologies of 4 leaves per genotype were captured by molding onto Suzuki's Universal Micro-Printing (SUMP) plates (SUMP Laboratory, Tokyo). The stomatal impressions were images using a TM1000 Hitachi Tabletop SEM at X1200 magnification (~100 stomata per genotype). As shown in FIG. 26, the RD29A::GFP-PYL2$^{C44}$ transgenics had reduced stomatal aperture in comparison to wild-type and RD29A::GFP-PYL2 plants.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated nucleic acid comprising a polynucleotide encoding a mutated PYR/PYL receptor polypeptide comprising one or more amino acid substitutions in a ligand-binding pocket as compared to a wild-type PYR/PYL receptor polypeptide, wherein the mutated PYR/PYL receptor binds to a type 2 protein phosphatase (PP2C) in the absence of abscisic acid, wherein:
the mutated PYR/PYL receptor polypeptide comprises amino acid substitutions corresponding to the amino acid substitutions H60P, V83F, and F159V in PYR1 as set forth in SEQ ID NO:1; or
the mutated PYR/PYL receptor polypeptide comprises amino acid substitutions corresponding to the amino acid substitutions H60P, V83F, M158I, and F159V in PYR1 as set forth in SEQ ID NO:1; or
the mutated PYR/PYL receptor polypeptide comprises amino acid substitutions corresponding to the amino acid substitutions V83F, M158I, F159V, and K170W in PYR1 as set forth in SEQ ID NO:1; and
wherein further substitutions if any, correspond to positions of amino acid residues described in Table 1.

2. The isolated nucleic acid of claim 1, wherein the mutated PYR/PYL receptor polypeptide comprises amino acid substitutions corresponding to the amino acid substitutions H60P, V83F, and F159V in PYR1 as set forth in SEQ ID NO:1.

3. The isolated nucleic acid of claim 1, wherein the mutated PYR/PYL receptor polypeptide comprises amino acid substitutions corresponding to the amino acid substitutions H60P, V83F, M158I, and F159V in PYR1 as set forth in SEQ ID NO:1.

4. The isolated nucleic acid of claim 1, wherein the mutated PYR/PYL receptor polypeptide comprises amino acid substitutions corresponding to the amino acid substitutions V83F, M158I, F159V, and K170W in PYR1 as set forth in SEQ ID NO:1.

5. The isolated nucleic acid of claim 1, wherein the mutated PYR/PYL receptor polypeptide inhibits the activity of the PP2C by at least 50% in the absence of abscisic acid as compared to the level of PP2C activity of a PP2C that is contacted with a wild-type PYR/PYL receptor polypeptide in the absence of abscisic acid.

6. The isolated nucleic acid of claim 1, wherein the mutated PYR/PYL receptor polypeptide comprises the amino acid sequence of any of SEQ ID NOs: 149, 150, 152, 153, or 155.

7. The isolated nucleic acid of claim 5, wherein the PP2C is HAB1.

8. An expression cassette comprising a promoter operably linked to the polynucleotide of claim 1, wherein introduction of the expression cassette into a plant results in the plant having a PYR/PYL receptor that binds to a type 2 protein phosphatase (PP2C) in the absence of abscisic acid.

9. The expression cassette of claim 8, wherein the promoter is heterologous to the polynucleotide.

10. The expression cassette of claim 8, wherein the promoter is inducible.

11. The expression cassette of claim 9, wherein the promoter is a stress-inducible promoter.

12. The expression cassette of claim 8, wherein the promoter is tissue-specific.

13. The expression cassette of claim 8, wherein introduction of the expression cassette into a plant results in the plant having significantly inhibited PP2C activity in the absence of abscisic acid as compared to a plant lacking the expression cassette.

14. An expression vector comprising the expression cassette of claim 8.

15. A plant comprising the expression cassette of claim 8.

16. A plant cell from the plant of claim 15, wherein the plant cell comprises the expression cassette.

17. A seed, flower, leaf, fruit, processed food, or food ingredient from the plant of claim 15, wherein the seed, flower, leaf, fruit, processed food, or food ingredient comprises the expression cassette.

18. A method of producing a plant having significantly inhibited activity of a type 2 protein phosphatase (PP2C) in the absence of abscisic acid, the method comprising: introducing the expression cassette of claim 8 into a plurality of plants; and selecting a plant that expresses the polynucleotide from the plurality of plants.

* * * * *